US012767730B2

(12) United States Patent
He et al.

(10) Patent No.: US 12,767,730 B2
(45) Date of Patent: Oct. 20, 2026

(54) GUCY2C BINDING MOLECULES AND USES THEREOF

(71) Applicant: PARASOL BIOTECH LTD., Hefei (CN)

(72) Inventors: Ling He, Xian (CN); Lin Wang, Hefei (CN); Wei Wang, Hefei (CN)

(73) Assignee: SHENZHEN WONDERCEL BIOTECHNOLOGY LIMITED, Shenzhen (CN)

(*) Notice: Subject to any disclaimer, the term of this patent is extended or adjusted under 35 U.S.C. 154(b) by 595 days.

(21) Appl. No.: 18/265,779

(22) PCT Filed: Dec. 16, 2021

(86) PCT No.: PCT/CN2021/138845
§ 371 (c)(1),
(2) Date: Jun. 7, 2023

(87) PCT Pub. No.: WO2022/127871
PCT Pub. Date: Jun. 23, 2022

(65) Prior Publication Data

US 2024/0059794 A1 Feb. 22, 2024

(30) Foreign Application Priority Data

Dec. 17, 2020 (WO) ................ PCT/CN2020/137164

(51) Int. Cl.
*C07K 16/40* (2006.01)
*A61K 40/11* (2025.01)
(Continued)

(52) U.S. Cl.
CPC .............. *C07K 16/40* (2013.01); *A61K 40/11* (2025.01); *A61K 40/31* (2025.01);
(Continued)

(58) Field of Classification Search
CPC ................ C07K 16/40; C07K 14/7051; C07K 14/70517; C07K 14/70578;
(Continued)

(56) References Cited

U.S. PATENT DOCUMENTS

| | | | |
|---|---|---|---|
| 9,662,405 | B2 | 5/2017 | Waldman et al. |
| 2013/0315923 | A1 | 11/2013 | Waldman et al. |

(Continued)

FOREIGN PATENT DOCUMENTS

| | | | |
|---|---|---|---|
| CL | 2023001666 A1 | 1/2024 | |
| CN | 104395470 A | 3/2015 | |

(Continued)

OTHER PUBLICATIONS

Bathula, N.V., et al.(2021) Nanobodies: The future of antibody-based immune therapeutics Cancer biotherapy and radiopharmaceuticals 36; 109-122 (Year: 2021).*

(Continued)

*Primary Examiner* — Scarlett Y Goon
*Assistant Examiner* — Audrey L Buttice
(74) *Attorney, Agent, or Firm* — Panitch Schwarze Belisario & Nadel LLP

(57) ABSTRACT

Provided are single domain antibodies that bind to GUCY2C, and chimeric antigen receptors comprising same. Further provided are engineered immune effector cells (such as T cells) comprising the chimeric antigen receptors. Pharmaceutical compositions, kits and methods of treating a disease or disorder are also provided.

31 Claims, 8 Drawing Sheets

Specification includes a Sequence Listing.

(51) Int. Cl.

| | |
|---|---|
| ***A61K 40/31*** | (2025.01) |
| ***A61K 40/42*** | (2025.01) |
| ***A61P 35/00*** | (2006.01) |
| ***C07K 14/705*** | (2006.01) |
| ***C12N 5/0783*** | (2010.01) |

(52) U.S. Cl.

CPC ...... *A61K 40/4244* (2025.01); *A61K 40/4253* (2025.01); *A61P 35/00* (2018.01); *C07K 14/7051* (2013.01); *C07K 14/70517* (2013.01); *C07K 14/70578* (2013.01); *C12N 5/0636* (2013.01); *A61K 2239/31* (2023.05); *A61K 2239/38* (2023.05); *A61K 2239/50* (2023.05); *C07K 2317/22* (2013.01); *C07K 2317/24* (2013.01); *C07K 2317/569* (2013.01); *C07K 2319/02* (2013.01); *C07K 2319/03* (2013.01); *C07K 2319/70* (2013.01); *C12N 2510/00* (2013.01)

(58) Field of Classification Search

CPC ............ C07K 2317/22; C07K 2317/24; C07K 2317/569; C07K 2319/02; C07K 2319/03; C07K 2319/70; A61K 40/11; A61K 40/31; A61K 40/4244; A61K 40/4253; A61K 2239/31; A61K 2239/38; A61K 2239/50; A61K 39/001164; A61K 2039/505; A61P 35/00; C12N 5/0636; C12N 2510/00; C12Y 406/01002

See application file for complete search history.

(56) References Cited

U.S. PATENT DOCUMENTS

| | | | |
|---|---|---|---|
| 2016/0030595 | A1 | 2/2016 | Waldman et al. |
| 2020/0010566 | A1 | 1/2020 | Chang et al. |
| 2020/0172865 | A1 | 6/2020 | Pu et al. |

FOREIGN PATENT DOCUMENTS

| | | | | |
|---|---|---|---|---|
| JP | 2018525033 | A | 9/2018 | |
| WO | WO-2009080764 | A2 * | 7/2009 | ........... C07K 16/283 |
| WO | WO 2013163633 | A1 | 10/2013 | |
| WO | 2017025038 | A1 | 2/2017 | |
| WO | 2019014891 | A1 | 1/2019 | |
| WO | WO 2019135159 | A2 | 7/2019 | |
| WO | 2019178580 | A1 | 9/2019 | |
| WO | 2022123316 | A1 | 6/2022 | |

OTHER PUBLICATIONS

Hoey, R.J., et al.(2019) Structure and development of single domain antibodies as modules for therapeutics and diagnostics Experimental biology and medicine 244; 1568-1576 (Year: 2019).*

Rojas, G. (2022) Understanding and Modulating Antibody Fine Specificity: Lessons from Combinatorial Biology Antibodies 11(48); 1-22 (Year: 2022).*

Carrithers et al., 1996, "Guanylyl cyclase C is a selective marker for metastatic colorectal tumors in human extraintestinal tissues," Proc. Natl. Acad. Sci. USA, 93(25):14827-14832.

International Searching Authority, International Search Report and Written Opinion for International Patent Application No. PCT/CN2021/138845 (Pub No. WO 2022127871) mailed Mar. 16, 2022 (12 pages).

Magee et al., 2016, "GUCY2C-directed CAR-T cells oppose colorectal cancer metastases without autoimmunity," Oncoimmunology, 5(10):e1227897 (10 pages).

Magee et al., 2018, "Human GUCY2C-Targeted Chimeric Antigen Receptor (CAR)-Expressing T Cells Eliminate Colorectal Cancer Metastases," Cancer Immunol. Res., 6(5):509-516.

Moradi et al., 2020, "Nanobody-based therapeutics against colorectal cancer: Precision therapies based on the personal mutanome profile and tumor neoantigens," Pharmacol. Res., 156:104790 (15 pages).

Rappaport et al., 2020, "An update on guanylyl cyclase C in the diagnosis, chemoprevention, and treatment of colorectal cancer," Expert Rev. Clin. Pharmacol., 13(10):1125-1137.

Waldman et al., 2018, "Guanylate cyclase-C as a therapeutic target in gastrointestinal disorders," Gut., 67(8):1543-1552.

Davies et al., "Affinity improvement of single antibody VH domains: residues in all three hypervariable regions affect antigen binding," Immunotechnology, Elsevier Science Publishers BV, NL, vol. 2, No. 3, pp. 169-179 (1996).

Divya et al., "A Novel GUCY2C-CD3 T-Cell Engaging Bispecific Construct (PF-07062119) for the Treatment of Gastrointestinal Cancers," Cancer Research, vol. 26, No. 9, pp. 2188-2202 (2020).

Dondelinger et al., "Understanding the Significance and Implications of Antibody Numbering and Antigen-Binding Surface/Residue Definition," Frontiers in Immunology, vol. 9, pp. 1-15 (2018).

Extended European Search Report issued on Mar. 27, 2025, by the European Patent Office in corresponding EP Application No. 21905797.3.

Hassanzadeh-Ghassabeh et al., "Nanobodies and their potential applications," Nanomedicine, vol. 8, No. 6, pp. 1013-1026 (2013).

Hock et al., "Development of a Perfusion Bioreactor Platform for High-Density Suspension Hek293 Cells," Molecular Therapy, vol. 28, No. 4S1, p. 380, Abstract 870 (2020).

Koide et al., "Exploring the capacity of minimalist protein interfaces: interface energetics and affinity maturation to picomolar KD of a single-domain antibody with a flat paratope," Journal of Molecular Biology, vol. 373, No. 4, pp. 941-953 (2007).

Leow et al., "Single Domain Antibodies as New Biomarker Detectors," Diagnostics, vol. 4, No. 52, pp. 1-33 (2017).

Li et al., "1304. Novel CoupledCARTM Technology for Treating Colorectal Cancer," 2020 ASGCT Annual Meeting Abstracts, Molecular Therapy, vol. 28, No. 4S1, p. 555 (2020).

Office Action issued on Dec. 15, 2025, by the Vietnam Intellectual Property Office in corresponding VN Application No. 1-2023-04685, and English translation of the Office Action (4 pages).

Office Action issued on Dec. 2, 2025, by the Japanese Patent Office in corresponding JP Application No. 2023-537253, and English translation of the Office Action (15 pages).

Office Action issued on Jul. 11, 2025, by the Chilean Patent Office in corresponding CL Application No. 202301665 (53 pages).

Office Action issued on Jun. 3, 2025, by the Saudi Authority for Intellectual Property in corresponding SA Application No. 523441130, and English translation of the Office Action (12 pages).

Office Action issued on Mar. 28, 2025, by the Vietnam Intellectual Property Office in corresponding VN Application No. 1-2023-04685, and English translation of the Office Action (4 pages).

Office Action issued on Sep. 26, 2024, by the Chilean Patent Office in corresponding CL Application No. 202301665 (23 pages).

Tiller et al., "Facile Affinity Maturation of Antibody Variable Domains Using Natural Diversity Mutagenesis," Frontiers in Immunology, vol. 8, No. 986, pp. 1-16 (2017).

Vincke et al., "General strategy to humanize a camelid single-domain antibody and identification of a universal humanized nanobody scaffold," The Journal of Biological Chemistry, vol. 284, No. 5, pp. 3273-3284 (2009).

Wagner et al., "A Two-Step Approach for the Design and Generation of Nanobodies," International Journal of Molecular Sciences, vol. 19, No. 3444, pp. 1-16 (2018).

Winkler et al., "Changing the antigen binding specificity by single point mutations of an anti-p24 (HIV-1) antibody," Journal of Immunology, vol. 165, No. 8, pp. 4505-4514 (2000).

Yau et al., "Affinity maturation of a VHH by mutational hotspot randomization," Journal of Immunological Methods, vol. 297, Nos. 1-2, pp. 213-224 (2005).

Zavrtanik et al., "Structural Basis of Epitope Recognition by Heavy-Chain Camelid Antibodies,"430, No. 21, pp. 4369-4386 (2018).

* cited by examiner

GUCY2C BINDING MOLECULES AND USES THEREOF

CROSS REFERENCE TO RELATED APPLICATIONS

This application is a U.S. National Stage Application under 35 U.S.C. § 371 of International Patent Application No. PCT/CN2021/138845, filed on Dec. 16, 2021, which claims priority to International Patent Application No. PCT/CN2020/137164, filed on Dec. 17, 2020, the disclosure of each of which is incorporated by reference herein in its entirety and for all purposes.

SEQUENCE LISTING

This application incorporates by reference in its entirety the Computer Readable Form (CRF) of a Sequence Listing in ASCII text format submitted via EFS-Web. The Sequence Listing text file submitted via EFS-Web is entitled "14687-002-999 SEQ LISTING.txt", was created on Jun. 2, 2023 and is 69,944 bytes in size.

1. FIELD

The present disclosure relates to anti-GUCY2C single domain antibodies, chimeric antigen receptors, engineered immune effector cells, and methods of use thereof. The present disclosure further relates to activation and expansion of cells for therapeutic uses, especially to chimeric antigen receptor-based T cell immunotherapies.

2. BACKGROUND

Colorectal cancer is one of the most common types of cancer globally, accounting for about 10% of all tumor cases and 8.5% of all cancer deaths. The incidence of colorectal cancer gradually tends to be younger, and the number of patients younger than 40 years accounts for 2%-8% of all colorectal cancer patients. At present, the treatment of colorectal cancer is based on the combination of surgery, radiotherapy and chemotherapy. Most early-stage patients have a good prognosis after treatment with traditional therapies, but for colorectal cancer patients with metastases, the prognosis is poor and the 5-year survival rate is very low. The current treatment can not eliminate the latent residual tumor cells or inhibit the growth of metastases. Chimeric antigen receptor T (CAR-T) cell therapy is an emerging and promising cancer immunotherapy.

The unbalanced homeostasis of colonic epithelial cells which promotes the generation of intestinal tumors is caused by lack of Guanylate cyclase C (GUCY2C; GCC) ligand (Waldman, S. A. and M. Camilleri, Gut, 67(8): 1543-1552 (2018)). GUCY2C is a member of the guanylate cyclase receptor family of N-linked glycoproteins, and is an intestinal tissue-specific polypeptide. It is expressed in epithelial cells which located in the intestinal mucosa of the small intestine to the rectum, but not in normal stomach and esophagus tissues. GUCY2C receptors may regulate the proliferation and differentiation of small intestinal mucosal epithelial cells through cyclic guanine phosphate (cGMP)-dependent mechanisms. It has been shown that GUCY2C is stably expressed in primary colorectal cancer cells, and the expression of GUCY2C in metastatic colorectal cancer cells is 2-10 times greater than normal intestinal epithelial cells (Carrithers et al., Proceedings of the National Academy of Sciences, 93(25): 14827-14832 (1996)), making GUCY2C is potential target for treating colorectal cancer. There is a need for improved GUCY2C-binding molecules and engineered GUCY2C-targeting cells in the art, for example, for use in more effective or efficient CAR-T therapies.

3. SUMMARY

In one aspect, provided herein is an anti-GUCY2C single domain antibody (sdAb) comprising: (i) a CDR1 comprising an amino acid sequence of $X_1YGMX_2$, wherein $X_1$ is A, I or V, and $X_2$ is D or G (SEQ ID NO: 64); (ii) a CDR2 comprising an amino acid sequence of $X_3IX_4LSGRX_5X_6YX_7DAVX_8G$, wherein $X_3$ is A, S or T; $X_4$ is F, W or Y; $X_5$ is S or T; $X_6$ is E, N or T; $X_7$ is A, S or T; and $X_8$ is K or Q (SEQ ID NO: 65); and (iii) a CDR3 comprising an amino acid sequence of $GX_9X_{10}TAX_{11}SX_{12}RQY$, wherein $X_9$ is A, E or P; $X_{10}$ is P or T; $X_{11}$ is S or T; and $X_{12}$ is G or V (SEQ ID NO: 66).

In some embodiments, the CDR1 comprises an amino acid sequence selected from a group consisting of SEQ ID NOs: 19 to 26; the CDR2 comprises an amino acid sequence selected from a group consisting of SEQ ID NOs: 27 to 34; and the CDR3 comprises an amino acid sequence selected from a group consisting of SEQ ID NOs: 35 to 42.

In some embodiments, the anti-GUCY2C sdAb provided herein comprises (i) a CDR1 comprising the amino acid sequence of SEQ ID NO: 19; a CDR2 comprising the amino acid sequence of SEQ ID NO: 27; and a CDR3 comprising the amino acid sequence of SEQ ID NO: 35; (ii) a CDR1 comprising the amino acid sequence of SEQ ID NO: 20; a CDR2 comprising the amino acid sequence of SEQ ID NO: 28; and a CDR3 comprising the amino acid sequence of SEQ ID NO: 36; (iii) a CDR1 comprising the amino acid sequence of SEQ ID NO: 21; a CDR2 comprising the amino acid sequence of SEQ ID NO: 29; and a CDR3 comprising the amino acid sequence of SEQ ID NO: 37; (iv) a CDR1 comprising the amino acid sequence of SEQ ID NO: 22; a CDR2 comprising the amino acid sequence of SEQ ID NO: 30; and a CDR3 comprising the amino acid sequence of SEQ ID NO: 38; (v) a CDR1 comprising the amino acid sequence of SEQ ID NO: 23; a CDR2 comprising the amino acid sequence of SEQ ID NO: 31; and a CDR3 comprising the amino acid sequence of SEQ ID NO: 39; (vi) a CDR1 comprising the amino acid sequence of SEQ ID NO: 24; a CDR2 comprising the amino acid sequence of SEQ ID NO: 32; and a CDR3 comprising the amino acid sequence of SEQ ID NO: 40; (vii) a CDR1 comprising the amino acid sequence of SEQ ID NO: 25; a CDR2 comprising the amino acid sequence of SEQ ID NO: 33; and a CDR3 comprising the amino acid sequence of SEQ ID NO: 41; or (viii) a CDR1 comprising the amino acid sequence of SEQ ID NO: 26; a CDR2 comprising the amino acid sequence of SEQ ID NO: 34; and a CDR3 comprising the amino acid sequence of SEQ ID NO: 42.

In some embodiments, provided herein is an anti-GUCY2C single domain antibody (sdAb) comprising (i) a CDR1, a CDR2, and a CDR3 having the amino acid sequences of the CDR1, CDR2, and CDR3, respectively, as set forth in SEQ ID NO: 3; (ii) a CDR1, a CDR2, and a CDR3 having the amino acid sequences of the CDR1, CDR2, and CDR3, respectively, as set forth in SEQ ID NO: 4; (iii) a CDR1, a CDR2, and a CDR3 having the amino acid sequences of the CDR1, CDR2, and CDR3, respectively, as set forth in SEQ ID NO: 5; (iv) a CDR1, a CDR2, and a CDR3 having the amino acid sequences of the CDR1, CDR2, and CDR3, respectively, as set forth in SEQ ID NO: 6; (v) a CDR1, a CDR2, and a CDR3 having the amino acid sequences of the CDR1, CDR2, and CDR3, respectively, as set forth in SEQ ID NO: 7; (vi) a CDR1, a CDR2, and a CDR3 having the amino acid sequences of the CDR1, CDR2, and CDR3, respectively, as set forth in SEQ ID NO: 8; (vii) a CDR1, a CDR2, and a CDR3 having the amino acid sequences of the CDR1, CDR2, and CDR3, respectively, as set forth in SEQ ID NO: 9; or (viii) a CDR1, a CDR2, and a CDR3 having the amino acid sequences of the CDR1, CDR2, and CDR3, respectively, as set forth in SEQ ID NO: 10. In some embodiments, the CDR1, CDR2 or CDR3 are determined according to the Kabat numbering scheme, the IMGT numbering scheme, the AbM numbering scheme, the Chothia numbering scheme, the Contact numbering scheme, or a combination thereof.

In some embodiments, the sdAb provided herein further comprises one or more FR regions as set forth in any one of SEQ ID NOs: 3 to 10.

In some embodiments, the anti-GUCY2C sdAb provided herein comprises the amino acid sequence of any one of SEQ ID NOs: 3 to 10. In some embodiments, the anti-GUCY2C sdAb provided herein comprises or consists of an amino acid sequence having at least 75%, 80%, 85%, 90%, 95%, 96%, 97%, 98%, 99%, or more sequence identity with the sequence of any one of SEQ ID NOs: 3 to 10.

In some embodiments, the anti-GUCY2C sdAb is a camelid sdAb. In other embodiments, the anti-GUCY2C sdAb is a humanized sdAb.

In some embodiments, the anti-GUCY2C sdAb is genetically fused or chemically conjugated to an agent.

In yet another aspect, provided herein is a chimeric antigen receptor (CAR), comprising (a) an extracellular antigen binding domain comprising the anti-GUCY2C sdAb provided herein, (b) a transmembrane domain; and (c) an intracellular signaling domain.

In some embodiments, the extracellular antigen binding domain further comprises one or more additional antigen binding domain(s). In some embodiments, the transmembrane domain is derived from a molecule selected from a group consisting of CD8α, CD4, CD28, CD137, CD80, CD86, CD152, and PD1. In some embodiments, the transmembrane domain is derived from CD8α.

In some embodiments, the intracellular signaling domain comprises a primary intracellular signaling domain of an immune effector cell. In some embodiments, the primary intracellular signaling domain is derived from CD3ζ.

In other embodiments, the intracellular signaling domain further comprises a co-stimulatory signaling domain. In some embodiments, the co-stimulatory signaling domain is derived from a co-stimulatory molecule selected from the group consisting of CD27, CD28, CD137 (4-1BB), OX40, CD30, CD40, CD3, LFA-1, CD2, CD7, LIGHT, NKG2C, B7-H3, ligands of CD83 and combinations thereof. In some embodiments, the co-stimulatory signaling domain is derived from CD137.

In some embodiments, the CAR provided herein further comprises a hinge domain located between the C-terminus of the extracellular antigen binding domain and the N-terminus of the transmembrane domain. In some embodiments, the hinge domain is derived from CD8α.

In some embodiments, the CAR provided herein further comprises a signal peptide located at the N-terminus of the polypeptide. In some embodiments, the signal peptide is derived from CD8α.

In some embodiments, provided herein is a chimeric antigen receptor (CAR), comprising (i) an amino acid sequence selected from the group consisting of SEQ ID NOs: 48 to 55; or (ii) an amino acid sequence having at least 75%, 80%, 85%, 90%, 95%, 96%, 97%, 98%, 99%, or more sequence identity with the sequence of any one of SEQ ID NOs: 48 to 55.

In another aspect, provided herein is an isolated nucleic acid comprising a nucleic acid sequence encoding the anti-GUCY2C sdAb provided herein. In some embodiments, the isolated nucleic acid provided herein comprises a nucleic acid sequence of SEQ ID NOs: 11 to 18.

In yet another aspect, provided herein is a vector comprising the isolated nucleic acid encoding the single domain antibodies provided herein.

In yet another aspect, provided herein is an isolated nucleic acid comprising a nucleic acid sequence encoding the CAR provided herein. In some embodiments, the isolated nucleic acid provided herein comprises a nucleic acid sequence of SEQ ID NOs: 56 to 63.

In yet another aspect, provided herein is a vector comprising the isolated nucleic acid encoding the CAR provided herein.

In yet another aspect, provided herein is an engineered immune effector cell, comprising the CAR, the isolated nucleic acid, or the vector provided herein. In some embodiments, the immune effector cell is a T cell.

In yet another aspect, provided herein is a pharmaceutical composition, comprising the anti-GUCY2C sdAb, the engineered immune effector cell, or the vector provided herein, and a pharmaceutically acceptable excipient.

In yet another aspect, provided herein is a method of treating a disease or disorder in a subject, comprising administering to the subject an effective amount of the anti-GUCY2C sdAb, the engineered immune effector cell, or the pharmaceutical composition provided herein. In some embodiments, the disease or disorder is a GUCY2C associated disease or disorder. In some embodiments, the disease or disorder is cancer. In some embodiments, the disease or disorder is colorectal cancer, gastric cancer or esophageal cancer.

4. BRIEF DESCRIPTION OF THE FIGURES

FIG. 1 shows the electrophoresis diagram of the phage antibody library colony. The first lane is DL2000 DNA marker, the last lane is the negative control of the plasmid pComb3XSS, and 1-23 are the phage antibody library monoclonal. 23 monoclones are selected, of which 22 monoclones were positive clones, and the insertion rate was 96%.

Figure 5:
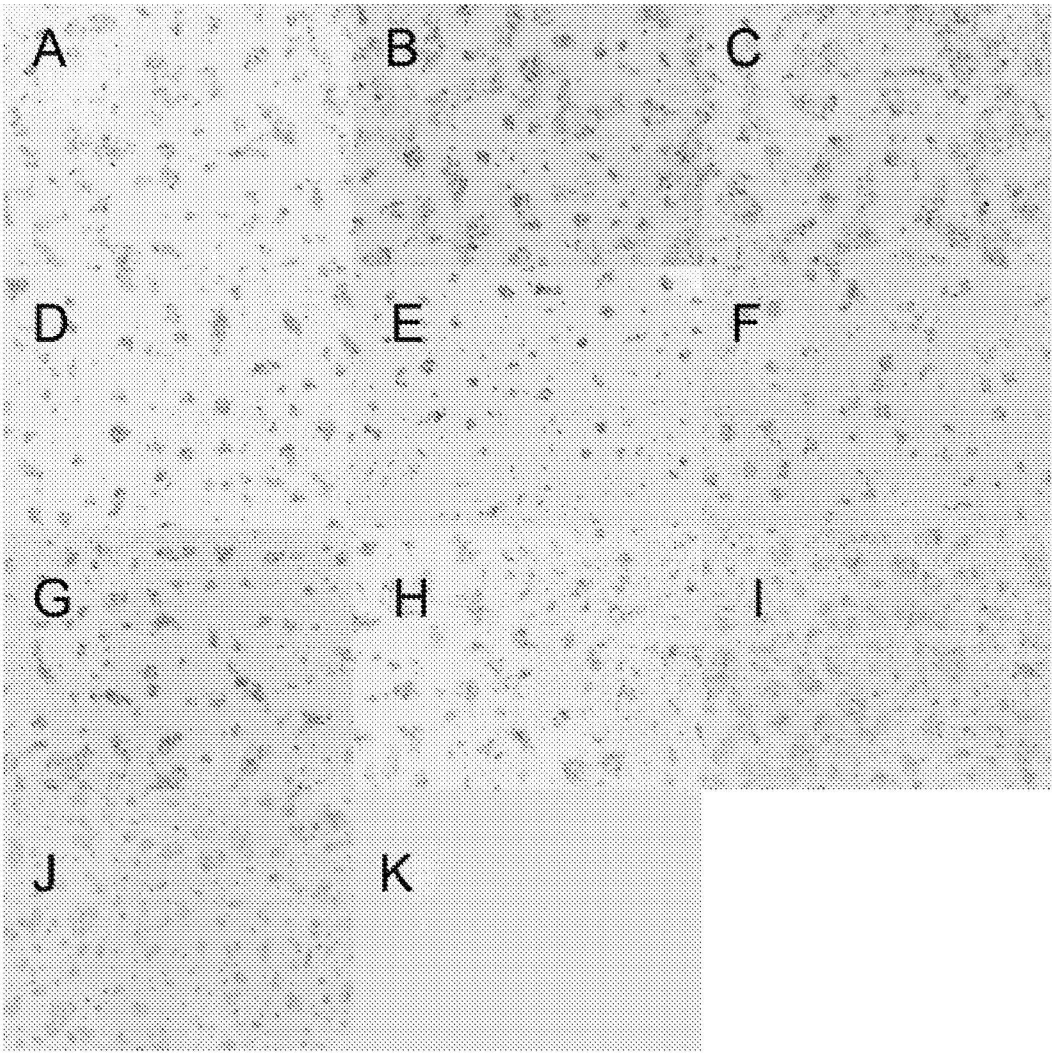

FIG. 5 shows a fluorescence photograph of T84 transfected with GFP and various anti-GUCY2C CAR-T cells which were co-cultured for 24 hours at the effector:target cell ratios of 2:1. The various CAR-T cell lines co-cultured were (A) clone C08, (B) clone C12, (C) clone C13, (D) clone C15, (E) clone C21, (F) clone C27, (G) clone C30, (H) clone C31, (I) T cell, (J) T84 cell only, and (J) T84 cell with cell lysis agent.

Figure 6:
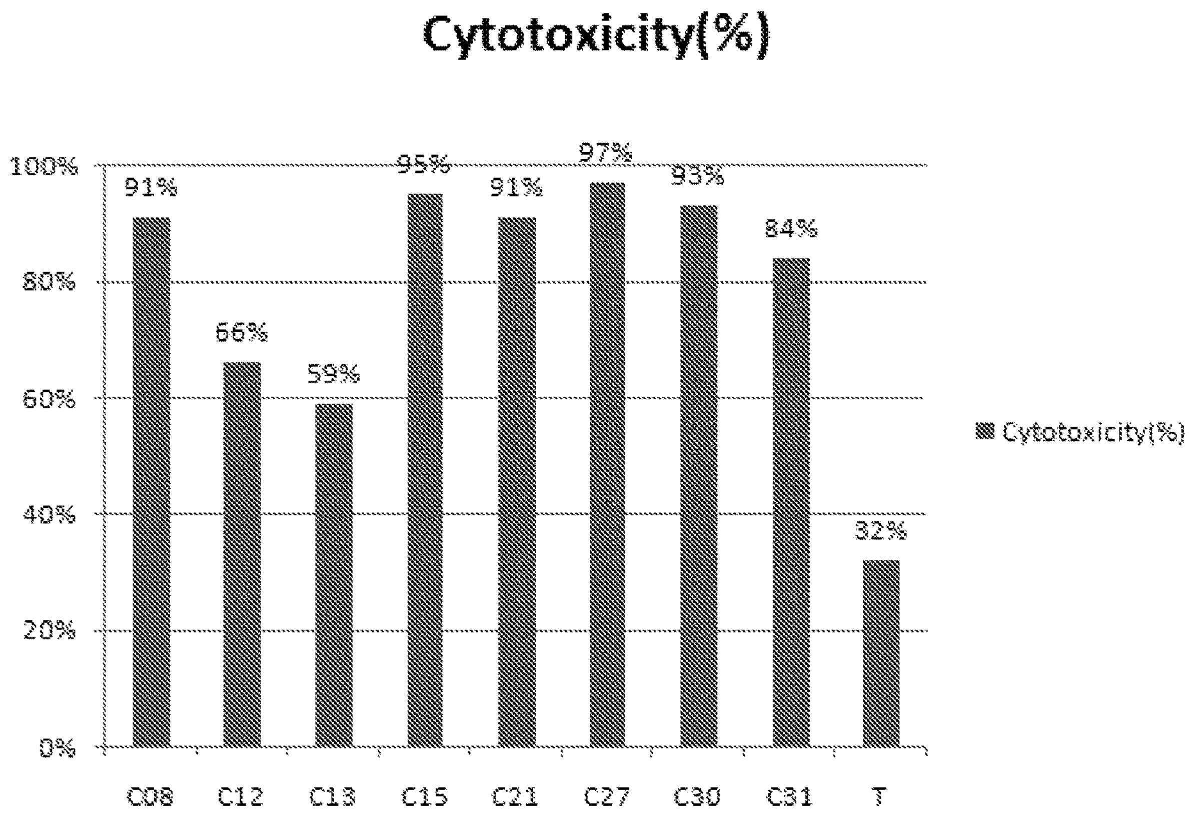

FIG. 6 shows the histogram showing the specific cytolytic activity of various anti-GUCY2C CAR T cells. CAR-T cells and T cells were co-cultured with T84 cells at the effector: target cell ratios of 2:1. The specific cell lysis percentage of T84 cells was calculated at the end of the co-cultured.

Figure 7A:
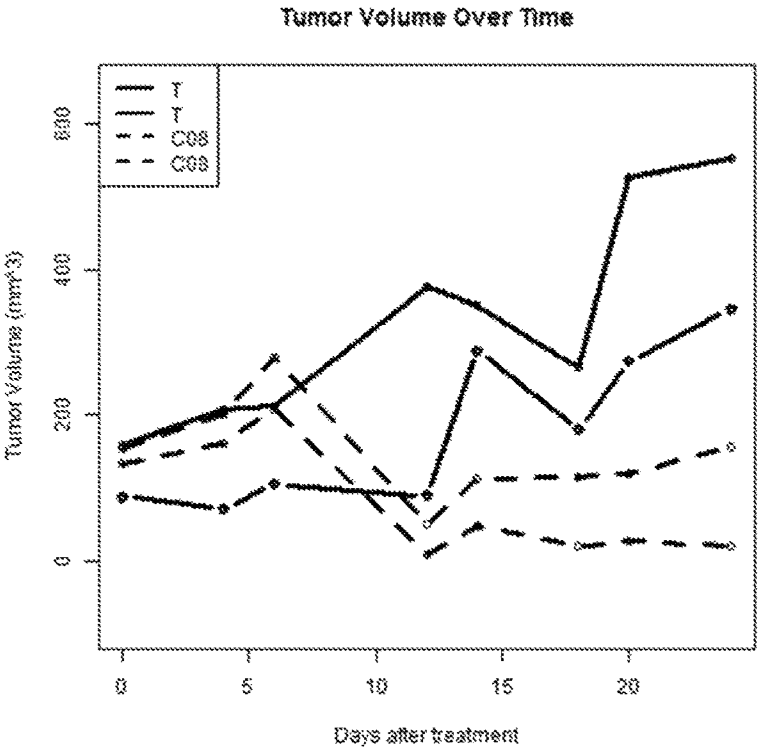
Figure 7B:
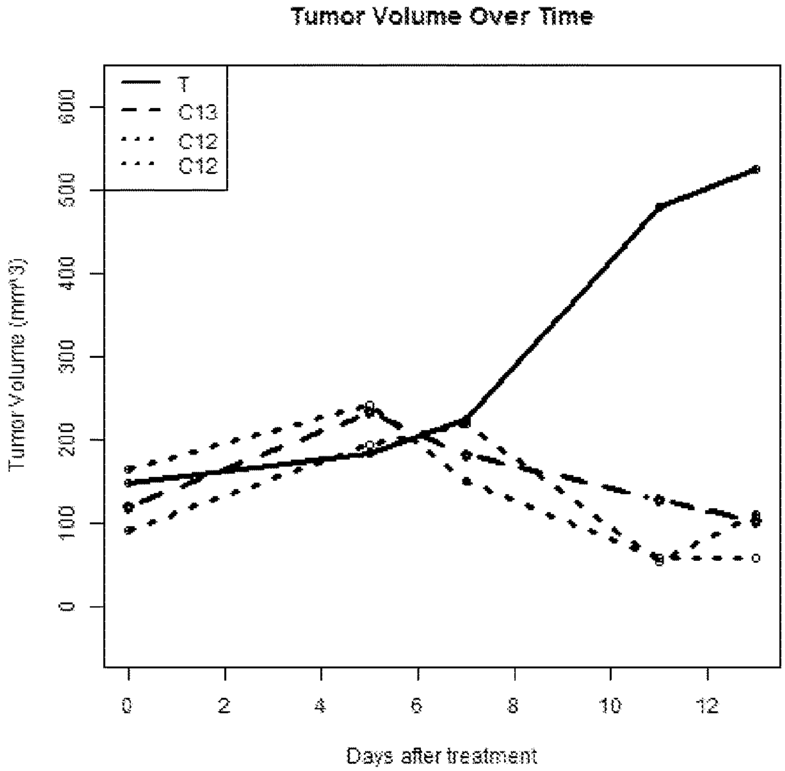
Figure 7C:
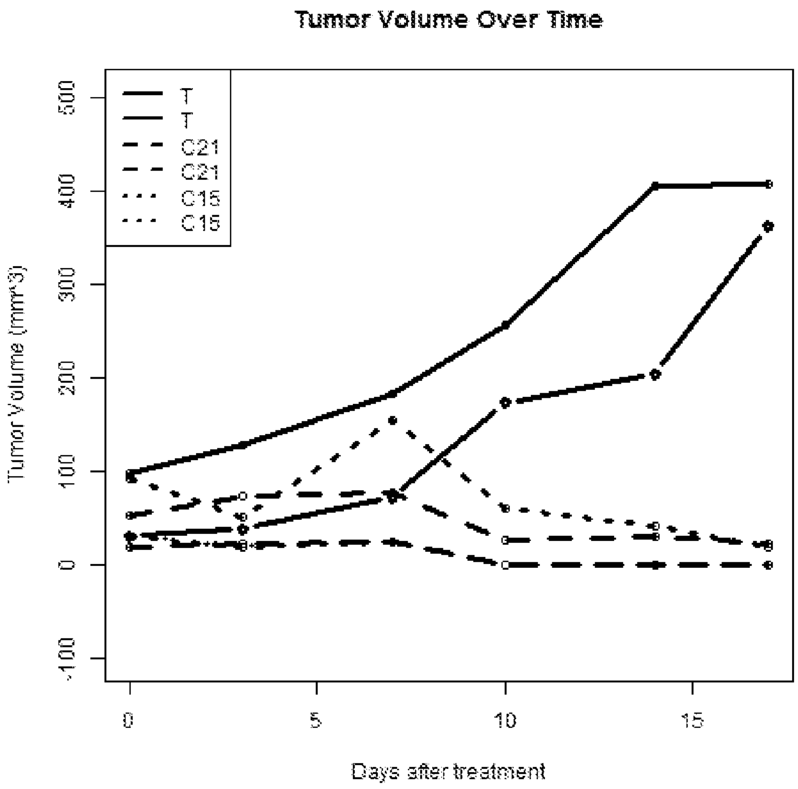

FIG. 7A shows tumor growth after anti-GUCY2C CAR-T treatments in the T84 tumor NCG mouse model. Immunodeficient NCG mice were injected with $5\times10^6$ luciferase expressing T84 colorectal cancer cells via subcutaneous injection and were treated with $3\times10^6$ T cells or clone C08 CAR-T cells on day 14 by tail vein injection. Solid line: T cells injected, dashed line: clone C08 CAR-T cells injected. FIG. 7B shows tumor growth after anti-GUCY2C CAR-T treatments in the T84 tumor NCG mouse model. Immunodeficient NCG mice were injected with $5\times10^6$ luciferase expressing T84 colorectal cancer cells via subcutaneous injection and were treated with $3\times10^6$ T cells, clone C12 CAR-T cells or clone C13 CAR-T cells on day 14 by tail vein injection. Solid line: T cells injected, dotted line: clone C12 CAR-T cells injected, dashed line: clone C13 CAR-T cells injected. FIG. 7C shows tumor growth after anti-GUCY2C CAR-T treatments in the T84 tumor NCG mouse model. Immunodeficient NCG mice were injected with $5\times10^6$ luciferase expressing T84 colorectal cancer cells via subcutaneous injection and were treated with $3\times10^6$ T cells, clone C15 CAR-T cells or clone C21 CAR-T cells on day 14 by tail vein injection. Solid line: T cells injected, dotted line: clone C15 CAR-T cells injected, dashed line: clone C21 CAR-T cells injected.

5. DETAILED DESCRIPTION

The present disclosure is based in part on the novel single domain antibodies (e.g., VHH domains) that bind to GUCY2C, chimeric antigen receptors or engineered cells comprising same, and improved properties thereof.

5.1. Definitions

Techniques and procedures described or referenced herein include those that are generally well understood and/or commonly employed using conventional methodology by those skilled in the art, such as, for example, the widely utilized methodologies described in Sambrook et al., Molecular Cloning: A Laboratory Manual (3d ed. 2001); Current Protocols in Molecular Biology (Ausubel et al. eds., 2003); Therapeutic Monoclonal Antibodies: From Bench to Clinic (An ed. 2009); Monoclonal Antibodies: *Methods and Protocols* (Albitar ed. 2010); and *Antibody Engineering* Vols 1 and 2 (Kontermann and Dübel eds., 2d ed. 2010). Unless otherwise defined herein, technical and scientific terms used in the present description have the meanings that are commonly understood by those of ordinary skill in the art. For purposes of interpreting this specification, the following description of terms will apply and whenever appropriate, terms used in the singular will also include the plural and vice versa. In the event that any description of a term set forth conflicts with any document incorporated herein by reference, the description of the term set forth below shall control.

The term "antibody," "immunoglobulin," or "Ig" is used interchangeably herein, and is used in the broadest sense and specifically covers, for example, monoclonal antibodies (including agonist, antagonist, neutralizing antibodies, full length or intact monoclonal antibodies), antibody compositions with polyepitopic or monoepitopic specificity, polyclonal or monovalent antibodies, multivalent antibodies, multispecific antibodies (e.g., bispecific antibodies so long as they exhibit the desired biological activity), formed from at least two intact antibodies, single chain antibodies, and fragments thereof (e.g., domain antibodies), as described below. An antibody can be human, humanized, chimeric and/or affinity matured, as well as an antibody from other species, for example, mouse, rabbit, llama, etc. The term "antibody" is intended to include a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa), each amino-terminal portion of each chain includes a variable region of about 100 to about 130 or more amino acids, and each carboxy-terminal portion of each chain includes a constant region. See, e.g., *Antibody Engineering* (Borrebaeck ed., 2d ed. 1995); and Kuby, *Immunology* (3d ed. 1997). Antibodies also include, but are not limited to, synthetic antibodies, recombinantly produced antibodies, single domain antibodies including from Camelidae species (e.g., llama or alpaca) or their humanized variants, intrabodies, anti-idiotypic (anti-Id) antibodies, and functional fragments (e.g., antigen-binding fragments) of any of the above, which refers to a portion of an antibody heavy or light chain polypeptide that retains some or all of the binding activity of the antibody from which the fragment was derived. Non-limiting examples of functional fragments (e.g., antigen-binding fragments) include single-chain Fvs (scFv) (e.g., including monospecific, bispecific, etc.), Fab fragments, F(ab') fragments, $F(ab)_2$ fragments, $F(ab')_2$ fragments, disulfide-linked Fvs (dsFv), Fd fragments, Fv fragments, diabody, triabody, tetrabody, and minibody. In particular, antibodies provided herein include immunoglobulin molecules and immunologically active portions of immunoglobulin molecules, for example, antigen-binding domains or molecules that contain an antigen-binding site that binds to an antigen (e.g., one or more CDRs of an antibody). Such antibody fragments can be found in, for example, Harlow and Lane, *Antibodies: A Laboratory Manual* (1989); *Mol. Biology and Biotechnology: A Comprehensive Desk Reference* (Myers ed., 1995); Huston et al., 1993, Cell Biophysics 22:189-224; Pluckthun and Skerra, 1989, Meth. Enzymol. 178:497-515; and Day, *Advanced Immunochemistry* (2d ed. 1990). The antibodies provided herein can be of any class (e.g., IgG, IgE, IgM, IgD, and IgA) or any subclass (e.g., IgG1, IgG2, IgG3, IgG4, IgA1, and IgA2) of immunoglobulin molecule. Antibodies may be agonistic antibodies or antagonistic antibodies. Antibodies may be neither agonistic nor antagonistic.

An "antigen" is a structure to which an antibody can selectively bind. A target antigen may be a polypeptide, carbohydrate, nucleic acid, lipid, hapten, or other naturally occurring or synthetic compound. In some embodiments, the target antigen is a polypeptide. In certain embodiments, an antigen is associated with a cell, for example, is present on or in a cell.

An "intact" antibody is one comprising an antigen-binding site as well as a CL and at least heavy chain constant regions, CH1, CH2 and CH3. The constant regions may include human constant regions or amino acid sequence variants thereof. In certain embodiments, an intact antibody has one or more effector functions.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of the sFv, see Pluckthun in The Pharmacology of Monoclonal Antibodies, vol. 113, Rosenburg and Moore eds., Springer-Verlag, New York, pp. 269-315 (1994).

The term "heavy chain-only antibody" or "HCAb" refers to a functional antibody, which comprises heavy chains, but lacks the light chains usually found in 4-chain antibodies. Camelid animals (such as camels, llamas, or alpacas) are known to produce HCAbs.

"Single domain antibody" or "sdAb" as used herein refers to a single monomeric variable antibody domain and which is capable of antigen binding (e.g., single domain antibodies that bind to GUCY2C). Single domain antibodies include VHH domains as described herein. Examples of single domain antibodies include, but are not limited to, antibodies naturally devoid of light chains such as those from Camelidae species (e.g., llama), single domain antibodies derived from conventional 4-chain antibodies, engineered antibodies and single domain scaffolds other than those derived from antibodies. Single domain antibodies may be derived from any species including, but not limited to mouse, human, camel, llama, goat, rabbit, and bovine. For example, a single domain antibody can be derived from antibodies raised in Camelidae species, for example in camel, llama, dromedary, alpaca and guanaco, as described herein. Other species besides Camelidae may produce heavy chain antibodies naturally devoid of light chain; VHHs derived from such other species are within the scope of the disclosure. In some embodiments, the single domain antibody (e.g., VHH) provided herein has a structure of FR1-CDR1-FR2-CDR2-FR3-CDR3-FR4. Single domain antibodies may be genetically fused or chemically conjugated to another molecule (e.g., an agent) as described herein. Single domain antibodies may be part of a bigger binding molecule (e.g., a multispecific antibody or a chimeric antigen receptor).

The terms "binds" or "binding" refer to an interaction between molecules including, for example, to form a complex. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions, or forces. The strength of the total non-covalent interactions between a single antigen-binding site on an antibody and a single epitope of a target molecule, such as an antigen, is the affinity of the antibody or functional fragment for that epitope. The ratio of dissociation rate ($k_{off}$) to association rate ($k_{on}$) of a binding molecule (e.g., an antibody) to a monovalent antigen ($k_{off}/k_{on}$) is the dissociation constant $K_D$, which is inversely related to affinity. The lower the $K_D$ value, the higher the affinity of the antibody. The value of $K_D$ varies for different complexes of antibody and antigen and depends on both $k_{on}$ and $k_{off}$. The dissociation constant $K_D$ for an antibody provided herein can be determined using any method provided herein or any other method well known to those skilled in the art. The affinity at one binding site does not always reflect the true strength of the interaction between an antibody and an antigen. When complex antigens containing multiple, repeating antigenic determinants, such as a polyvalent antigen, come in contact with antibodies containing multiple binding sites, the interaction of antibody with antigen at one site will increase the probability of a reaction at a second site. The strength of such multiple interactions between a multivalent antibody and antigen is called the avidity.

In connection with the binding molecules described herein terms such as "bind to," "that specifically bind to," and analogous terms are also used interchangeably herein and refer to binding molecules of antigen binding domains that specifically bind to an antigen, such as a polypeptide. A binding molecule or antigen binding domain that binds to or specifically binds to an antigen can be identified, for example, by immunoassays, Octet®, Biacore®, or other techniques known to those of skill in the art. In some embodiments, a binding molecule or antigen binding domain binds to or specifically binds to an antigen when it binds to an antigen with higher affinity than to any cross-reactive antigen as determined using experimental techniques, such as radioimmunoassay (RIA) and enzyme linked immunosorbent assay (ELISA). Typically, a specific or selective reaction will be at least twice background signal or noise and may be more than 10 times background. See, e.g., *Fundamental Immunology* 332-36 (Paul ed., 2d ed. 1989) for a discussion regarding binding specificity. In certain embodiments, the extent of binding of a binding molecule or antigen binding domain to a "non-target" protein is less than about 10% of the binding of the binding molecule or antigen binding domain to its particular target antigen, for example, as determined by fluorescence activated cell sorting (FACS) analysis or RIA. A binding molecule or antigen binding domain that binds to an antigen includes one that is capable of binding the antigen with sufficient affinity such that the binding molecule is useful, for example, as a therapeutic and/or diagnostic agent in targeting the antigen. In certain embodiments, a binding molecule or antigen binding domain that binds to an antigen has a dissociation constant ($K_D$) of less than or equal to 1 μM, 800 nM, 600 nM, 550 nM, 500 nM, 300 nM, 250 nM, 100 nM, 50 nM, 10 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, or 0.1 nM. In certain embodiments, a binding molecule or antigen binding domain binds to an epitope of an antigen that is conserved among the antigen from different species.

In certain embodiments, the binding molecules or antigen binding domains can comprise "chimeric" sequences in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., 1984, Proc. Natl. Acad. Sci. USA 81:6851-55). Chimeric sequences may include humanized sequences.

In certain embodiments, the binding molecules or antigen binding domains can comprise portions of "humanized" forms of nonhuman (e.g., camelid, murine, non-human primate) antibodies that include sequences from human immunoglobulins (e.g., recipient antibody) in which the native CDR residues are replaced by residues from the corresponding CDR of a nonhuman species (e.g., donor antibody) such as camelid, mouse, rat, rabbit, or nonhuman primate having the desired specificity, affinity, and capacity. In some instances, one or more FR region residues of the human immunoglobulin sequences are replaced by corresponding nonhuman residues. Furthermore, humanized antibodies can comprise residues that are not found in the recipient antibody or in the donor antibody. These modifications are made to further refine antibody performance. A humanized antibody heavy or light chain can comprise substantially all of at least one or more variable regions, in which all or substantially all of the CDRs correspond to those of a nonhuman immunoglobulin and all or substantially all of the FRs are those of a human immunoglobulin sequence. In certain embodiments, the humanized antibody will comprise at least a portion of an immunoglobulin constant region (Fc), typically that of a human immunoglobulin. For further details, see, Jones et al., Nature 321: 522-25 (1986); Riechmann et al., Nature 332:323-29 (1988); Presta, Curr. Op. Struct. Biol. 2:593-96 (1992); Carter et al., Proc. Natl. Acad. Sci. USA 89:4285-89 (1992); U.S. Pat. Nos. 6,800,738; 6,719,971; 6,639,055; 6,407,213; and 6,054,297.

In certain embodiments, the binding molecules or antigen binding domains can comprise portions of a "fully human antibody" or "human antibody," wherein the terms are used interchangeably herein and refer to an antibody that comprises a human variable region and, for example, a human constant region. The binding molecules may comprise a single domain antibody sequence. In specific embodiments, the terms refer to an antibody that comprises a variable region and constant region of human origin. "Fully human" antibodies, in certain embodiments, can also encompass antibodies which bind polypeptides and are encoded by nucleic acid sequences which are naturally occurring somatic variants of human germline immunoglobulin nucleic acid sequence. The term "fully human antibody" includes antibodies having variable and constant regions corresponding to human germline immunoglobulin sequences as described by Kabat et al. (See Kabat et al. (1991) *Sequences of Proteins of Immunological Interest*, Fifth Edition, U.S. Department of Health and Human Services, NIH Publication No. 91-3242). A "human antibody" is one that possesses an amino acid sequence which corresponds to that of an antibody produced by a human and/or has been made using any of the techniques for making human antibodies. This definition of a human antibody specifically excludes a humanized antibody comprising non-human antigen-binding residues. Human antibodies can be produced using various techniques known in the art, including phage-display libraries (Hoogenboom and Winter, J. Mol. Biol. 227:381 (1991); Marks et al., J. Mol. Biol. 222:581 (1991)) and yeast display libraries (Chao et al., Nature Protocols 1: 755-68 (2006)). Also available for the preparation of human monoclonal antibodies are methods described in Cole et al., *Monoclonal Antibodies and Cancer Therapy* 77 (1985); Boerner et al., J. Immunol. 147(1):86-95 (1991); and van Dijk and van de Winkel, Curr. Opin. Pharmacol. 5: 368-74 (2001). Human antibodies can be prepared by administering the antigen to a transgenic animal that has been modified to produce such antibodies in response to antigenic challenge, but whose endogenous loci have been disabled, e.g., mice (see, e.g., Jakobovits, Curr. Opin. Biotechnol. 6(5):561-66 (1995); Bruggemann and Taussing, Curr. Opin. Biotechnol. 8(4):455-58 (1997); and U.S. Pat. Nos. 6,075,181 and 6,150,584 regarding XENOMOUSE™ technology). See also, for example, Li et al., Proc. Natl. Acad. Sci. USA 103:3557-62 (2006) regarding human antibodies generated via a human B-cell hybridoma technology.

In certain embodiments, the binding molecules or antigen binding domains can comprise portions of a "recombinant human antibody," wherein the phrase includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse or cow) that is transgenic and/or transchromosomal for human immunoglobulin genes (see, e.g., Taylor, L. D. et al., *Nucl. Acids Res.* 20:6287-6295 (1992)) or antibodies prepared, expressed, created or isolated by any other means that involves splicing of human immunoglobulin gene sequences to other DNA sequences. Such recombinant human antibodies can have variable and constant regions derived from human germline immunoglobulin sequences (See Kabat, E. A. et al. (1991) *Sequences of Proteins of Immunological Interest*, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

In certain embodiments, the binding molecules or antigen binding domains can comprise a portion of a "monoclonal antibody," wherein the term as used herein refers to an antibody obtained from a population of substantially homogeneous antibodies, e.g., the individual antibodies comprising the population are identical except for possible naturally occurring mutations that may be present in minor amounts or well-known post-translational modifications such as amino acid isomerization or deamidation, methionine oxidation or asparagine or glutamine deamidation, each monoclonal antibody will typically recognize a single epitope on the antigen. In specific embodiments, a "monoclonal antibody," as used herein, is an antibody produced by a single hybridoma or other cell. The term "monoclonal" is not limited to any particular method for making the antibody. For example, the monoclonal antibodies useful in the present disclosure may be prepared by the hybridoma methodology first described by Kohler et al., Nature 256:495 (1975), or may be made using recombinant DNA methods in bacterial or eukaryotic animal or plant cells (see, e.g., U.S. Pat. No. 4,816,567). The "monoclonal antibodies" may also be isolated from phage antibody libraries using the techniques described in Clackson et al., Nature 352:624-28 (1991) and Marks et al., J. Mol. Biol. 222:581-97 (1991), for example. Other methods for the preparation of clonal cell lines and of monoclonal antibodies expressed thereby are well known in the art. See, e.g., *Short Protocols in Molecular Biology* (Ausubel et al. eds., 5th ed. 2002).

A typical 4-chain antibody unit is a heterotetrameric glycoprotein composed of two identical light (L) chains and two identical heavy (H) chains. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ and ε isotypes. Each L chain has at the N-terminus, a variable domain (VL) followed by a constant domain (CL) at its other end. The VL is aligned with the VH, and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, for example, *Basic*

*and Clinical Immunology* 71 (Stites et al. eds., 8th ed. 1994); and *Immunobiology* (Janeway et al. eds., $5^{th}$ ed. 2001).

The term "Fab" or "Fab region" refers to an antibody region that binds to antigens. A conventional IgG usually comprises two Fab regions, each residing on one of the two arms of the Y-shaped IgG structure. Each Fab region is typically composed of one variable region and one constant region of each of the heavy and the light chain. More specifically, the variable region and the constant region of the heavy chain in a Fab region are VH and CH1 regions, and the variable region and the constant region of the light chain in a Fab region are VL and CL regions. The VH, CH1, VL, and CL in a Fab region can be arranged in various ways to confer an antigen binding capability according to the present disclosure. For example, VH and CH1 regions can be on one polypeptide, and VL and CL regions can be on a separate polypeptide, similarly to a Fab region of a conventional IgG. Alternatively, VH, CH1, VL and CL regions can all be on the same polypeptide and oriented in different orders as described in more detail the sections below.

The term "variable region," "variable domain," "V region," or "V domain" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable region of the heavy chain may be referred to as "VH." The variable region of the light chain may be referred to as "VL." The term "variable" refers to the fact that certain segments of the variable regions differ extensively in sequence among antibodies. The V region mediates antigen binding and defines specificity of a particular antibody for its particular antigen. However, the variability is not evenly distributed across the 110-amino acid span of the variable regions. Instead, the V regions consist of less variable (e.g., relatively invariant) stretches called framework regions (FRs) of about 15-30 amino acids separated by shorter regions of greater variability (e.g., extreme variability) called "hypervariable regions" that are each about 9-12 amino acids long. The variable regions of heavy and light chains each comprise four FRs, largely adopting a β sheet configuration, connected by three hypervariable regions, which form loops connecting, and in some cases form part of, the β sheet structure. The hypervariable regions in each chain are held together in close proximity by the FRs and, with the hypervariable regions from the other chain, contribute to the formation of the antigen-binding site of antibodies (see, e.g., Kabat et al., *Sequences of Proteins of Immunological Interest* (5th ed. 1991)). The constant regions are not involved directly in binding an antibody to an antigen, but exhibit various effector functions, such as participation of the antibody in antibody dependent cellular cytotoxicity (ADCC) and complement dependent cytotoxicity (CDC). The variable regions differ extensively in sequence between different antibodies. In specific embodiments, the variable region is a human variable region.

The term "variable region residue numbering according to Kabat" or "amino acid position numbering as in Kabat", and variations thereof, refer to the numbering system used for heavy chain variable regions or light chain variable regions of the compilation of antibodies in Kabat et al., supra. Using this numbering system, the actual linear amino acid sequence may contain fewer or additional amino acids corresponding to a shortening of, or insertion into, an FR or CDR of the variable domain. For example, a heavy chain variable domain may include a single amino acid insert (residue 52a according to Kabat) after residue 52 and three inserted residues (e.g., residues 82a, 82b, and 82c, etc. according to Kabat) after residue 82. The Kabat numbering of residues may be determined for a given antibody by alignment at regions of homology of the sequence of the antibody with a "standard" Kabat numbered sequence. The Kabat numbering system is generally used when referring to a residue in the variable domain (approximately residues 1-107 of the light chain and residues 1-113 of the heavy chain) (e.g., Kabat et al., supra). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG 1 EU antibody. Other numbering systems have been described, for example, by AbM, Chothia, Contact, IMGT, and AHon.

The term "heavy chain" when used in reference to an antibody refers to a polypeptide chain of about 50-70 kDa, wherein the amino-terminal portion includes a variable region of about 120 to 130 or more amino acids, and a carboxy-terminal portion includes a constant region. The constant region can be one of five distinct types, (e.g., isotypes) referred to as alpha (α), delta (δ), epsilon (ε), gamma (γ), and mu (μ), based on the amino acid sequence of the heavy chain constant region. The distinct heavy chains differ in size: α, δ, and γ contain approximately 450 amino acids, while μ and c contain approximately 550 amino acids. When combined with a light chain, these distinct types of heavy chains give rise to five well known classes (e.g., isotypes) of antibodies, IgA, IgD, IgE, IgG, and IgM, respectively, including four subclasses of IgG, namely IgG1, IgG2, IgG3, and IgG4.

The term "light chain" when used in reference to an antibody refers to a polypeptide chain of about 25 kDa, wherein the amino-terminal portion includes a variable region of about 100 to about 110 or more amino acids, and a carboxy-terminal portion includes a constant region. The approximate length of a light chain is 211 to 217 amino acids. There are two distinct types, referred to as kappa (κ) or lambda (λ) based on the amino acid sequence of the constant domains.

As used herein, the terms "hypervariable region," "HVR," "Complementarity Determining Region," and "CDR" are used interchangeably. A "CDR" refers to one of three hypervariable regions (H1, H2 or H3) within the non-framework region of the immunoglobulin (Ig or antibody) VH β-sheet framework, or one of three hypervariable regions (L1, L2 or L3) within the non-framework region of the antibody VL β-sheet framework. Accordingly, CDRs are variable region sequences interspersed within the framework region sequences.

CDR regions are well known to those skilled in the art and have been defined by well-known numbering systems. For example, the Kabat Complementarity Determining Regions (CDRs) are based on sequence variability and are the most commonly used (see, e.g., Kabat et al., supra). Chothia refers instead to the location of the structural loops (see, e.g., Chothia and Lesk, J. Mol. Biol. 196:901-17 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software (see, e.g., *Antibody Engineering* Vol. 2 (Kontermann and Dübel eds., 2d ed. 2010)). The "contact" hypervariable regions are based on an analysis of the available complex crystal structures. Another universal numbering system that has been developed and widely adopted is ImMunoGeneTics (IMGT) Information System® (Lafranc et al., Dev. Comp. Immunol. 27(1):55-77 (2003)). IMGT is an integrated information system specializing in immunoglobulins (IG), T-cell receptors (TCR), and major histocompatibility complex (WIC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues are readily identified. This information can be used in grafting and replacement of CDR residues from immunoglobulins of one species into an acceptor framework from, typically, a human antibody. An additional numbering system (AHon) has been developed by Honegger and Pluckthun, J. Mol. Biol. 309: 657-70 (2001). Correspondence between the numbering system, including, for example, the Kabat numbering and the IMGT unique numbering system, is well known to one skilled in the art (see, e.g., Kabat, supra; Chothia and Lesk, supra; Martin, supra; Lefranc et al., supra). The residues from each of these hypervariable regions or CDRs are exemplified in Table 6 below.

tems, or a combination of Kabat and IMGT numbering systems. Therefore, the term such as "a CDR as set forth in a specific VH or VHH" includes any CDR1 as defined by the exemplary CDR numbering systems described above, but is not limited thereby. Once a variable region (e.g., a VHH, VH or VL) is given, those skilled in the art would understand that CDRs within the region can be defined by different numbering systems or combinations thereof.

Hypervariable regions may comprise "extended hypervariable regions" as follows: 24-36 or 24-34 (L1), 46-56 or 50-56 (L2), and 89-97 or 89-96 (L3) in the VL, and 26-35 or 26-35A (H1), 50-65 or 49-65 (H2), and 93-102, 94-102, or 95-102 (H3) in the VH.

The term "constant region" or "constant domain" refers to a carboxy terminal portion of the light and heavy chain which is not directly involved in binding of the antibody to antigen but exhibits various effector function, such as interaction with the Fc receptor. The term refers to the portion of an immunoglobulin molecule having a more conserved amino acid sequence relative to the other portion of the immunoglobulin, the variable region, which contains the antigen binding site. The constant region may contain the CH1, CH2, and CH3 regions of the heavy chain and the CL region of the light chain.

The term "framework" or "FR" refers to those variable region residues flanking the CDRs. FR residues are present, for example, in chimeric, humanized, human, domain antibodies (e.g., single domain antibodies), diabodies, linear antibodies, and bispecific antibodies. FR residues are those variable domain residues other than the hypervariable region residues or CDR residues.

TABLE 6

Exemplary CDRs According to Various Numbering Systems

| Loop | Kabat | AbM | Chothia | Contact | IMGT |
|---|---|---|---|---|---|
| CDR L1 | L24--L34 | L24--L34 | L26--L32 or L24--L34 | L30--L36 | L27--L38 |
| CDR L2 | L50--L56 | L50--L56 | L50--L52 or L50--L56 | L46--L55 | L56--L65 |
| CDR L3 | L89--L97 | L89--L97 | L91--L96 or L89--L97 | L89--L96 | L105-L117 |
| CDR H1 | H31--H35B (Kabat Numbering) | H26--H35B | H26--H32 . . . 34 | H30--H35B | H27--H38 |
| CDR H1 | H31--H35 (Chothia Numbering) | H26--H35 | H26--H32 | H30--H35 | |
| CDR H2 | H50--H65 | H50--H58 | H53--H55 or H52--H56 | H47--H58 | H56--H65 |
| CDR H3 | H95--H102 | H95--H102 | H96--H101 or H95--H102 | H93--H101 | H105-H117 |

The boundaries of a given CDR may vary depending on the scheme used for identification. Thus, unless otherwise specified, the terms "CDR" and "complementary determining region" of a given antibody or region thereof, such as a variable region, as well as individual CDRs (e.g., CDR-H1, CDR-H2) of the antibody or region thereof, should be understood to encompass the complementary determining region as defined by any of the known schemes described herein above. In some instances, the scheme for identification of a particular CDR or CDRs is specified, such as the CDR as defined by the IMGT, Kabat, Chothia, or Contact method. In other cases, the particular amino acid sequence of a CDR is given. It should be noted CDR regions may also be defined by a combination of various numbering systems, e.g., a combination of Kabat and Chothia numbering sys- The term "Fc region" herein is used to define a C-terminal region of an immunoglobulin heavy chain, including, for example, native sequence Fc regions, recombinant Fc regions, and variant Fc regions. Although the boundaries of the Fc region of an immunoglobulin heavy chain might vary, the human IgG heavy chain Fc region is often defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. A "functional Fc region" possesses an "effector function" of a native sequence Fc region. Exemplary "effector functions" include Clq binding; CDC; Fc receptor binding; ADCC; phagocytosis; downregulation of cell surface receptors (e.g., B cell receptor), etc. Such effector functions generally require the Fc region to be combined with a binding region or binding domain (e.g., an antibody variable region or domain) and can be assessed using various assays known to those skilled in the art. A "variant Fc region" comprises an amino acid sequence which differs from that of a native sequence Fc region by virtue of at least one amino acid modification (e.g., substituting, addition, or deletion). In certain embodiments, the variant Fc region has at least one amino acid substitution compared to a native sequence Fc region or to the Fc region of a parent polypeptide, for example, from about one to about ten amino acid substitutions, or from about one to about five amino acid substitutions in a native sequence Fc region or in the Fc region of a parent polypeptide. The variant Fc region herein can possess at least about 80% homology with a native sequence Fc region and/or with an Fc region of a parent polypeptide, or at least about 90% homology therewith, for example, at least about 95% homology therewith.

As used herein, an "epitope" is a term in the art and refers to a localized region of an antigen to which a binding molecule (e.g., an antibody comprising a single domain antibody sequence) can specifically bind. An epitope can be a linear epitope or a conformational, non-linear, or discontinuous epitope. In the case of a polypeptide antigen, for example, an epitope can be contiguous amino acids of the polypeptide (a "linear" epitope) or an epitope can comprise amino acids from two or more non-contiguous regions of the polypeptide (a "conformational," "non-linear" or "discontinuous" epitope). It will be appreciated by one of skill in the art that, in general, a linear epitope may or may not be dependent on secondary, tertiary, or quaternary structure. For example, in some embodiments, a binding molecule binds to a group of amino acids regardless of whether they are folded in a natural three dimensional protein structure. In other embodiments, a binding molecule requires amino acid residues making up the epitope to exhibit a particular conformation (e.g., bend, twist, turn or fold) in order to recognize and bind the epitope.

A "blocking" antibody or an "antagonist" antibody is one that inhibits or reduces a biological activity of the antigen it binds. In some embodiments, blocking antibodies or antagonist antibodies substantially or completely inhibit the biological activity of the antigen.

An "agonist" or activating antibody is one that enhances or initiates signaling by the antigen to which it binds. In some embodiments, agonist antibodies cause or activate signaling without the presence of the natural ligand.

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

The term "specificity" refers to selective recognition of an antigen binding protein (such as a CAR or an sdAb) for a particular epitope of an antigen. Natural antibodies, for example, are monospecific. The term "multispecific" as used herein denotes that an antigen binding protein (such as a CAR or an sdAb) has two or more antigen-binding sites of which at least two bind different antigens. "Bispecific" as used herein denotes that an antigen binding protein (such as aCAR or an sdAb) has two different antigen-binding specificities. The term "monospecific" CAR as used herein denotes an antigen binding protein (such as a CAR or an sdAb) that has one or more binding sites each of which bind the same antigen.

The term "valent" as used herein denotes the presence of a specified number of binding sites in an antigen binding protein (such as a CAR or an sdAb). A natural antibody for example or a full length antibody has two binding sites and is bivalent. As such, the terms "trivalent", "tetravalent", "pentavalent" and "hexavalent" denote the presence of two binding site, three binding sites, four binding sites, five binding sites, and six binding sites, respectively, in an antigen binding protein (such as a CAR or an sdAb).

"Chimeric antigen receptor" or "CAR" as used herein refers to genetically engineered receptors, which can be used to graft one or more antigen specificity onto immune effector cells, such as T cells. Some CARs are also known as "artificial T-cell receptors," "chimeric T cell receptors," or "chimeric immune receptors." In some embodiments, the CAR comprises an extracellular antigen binding domain specific for one or more antigens (such as tumor antigens), a transmembrane domain, and an intracellular signaling domain of a T cell and/or other receptors. "CAR-T cell" refers to a T cell that expresses a CAR.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification. Also included within the definition are, for example, polypeptides containing one or more analogs of an amino acid, including but not limited to, unnatural amino acids, as well as other modifications known in the art. It is understood that, because the polypeptides of this disclosure may be based upon antibodies or other members of the immunoglobulin superfamily, in certain embodiments, a "polypeptide" can occur as a single chain or as two or more associated chains.

"Polynucleotide" or "nucleic acid," as used interchangeably herein, refers to polymers of nucleotides of any length and includes DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. "Oligonucleotide," as used herein, refers to short, generally single-stranded, synthetic polynucleotides that are generally, but not necessarily, fewer than about 200 nucleotides in length. The terms "oligonucleotide" and "polynucleotide" are not mutually exclusive. The description above for polynucleotides is equally and fully applicable to oligonucleotides. A cell that produces a binding molecule of the present disclosure may include a parent hybridoma cell, as well as bacterial and eukaryotic host cells into which nucleic acids encoding the antibodies have been introduced. Unless specified otherwise, the left-hand end of any single-stranded polynucleotide sequence disclosed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences"; sequence regions on the DNA strand having the same sequence as the RNA transcript that are 3' to the 3' end of the RNA transcript are referred to as "downstream sequences."

An "isolated nucleic acid" is a nucleic acid, for example, an RNA, DNA, or a mixed nucleic acids, which is substantially separated from other genome DNA sequences as well as proteins or complexes such as ribosomes and polymerases, which naturally accompany a native sequence. An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, one or more nucleic acid molecules encoding a single domain antibody or an antibody as described herein are isolated or purified. The term embraces nucleic acid sequences that have been removed from their naturally occurring environment, and includes recombinant or cloned DNA isolates and chemically synthesized analogues or analogues biologically synthesized by heterologous systems. A substantially pure molecule may include isolated forms of the molecule. Specifically, an "isolated" nucleic acid molecule encoding a CAR or an sdAb described herein is a nucleic acid molecule that is identified and separated from at least one contaminant nucleic acid molecule with which it is ordinarily associated in the environment in which it was produced.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

As used herein, the term "operatively linked," and similar phrases (e.g., genetically fused), when used in reference to nucleic acids or amino acids, refer to the operational linkage of nucleic acid sequences or amino acid sequence, respectively, placed in functional relationships with each other. For example, an operatively linked promoter, enhancer elements, open reading frame, 5' and 3' UTR, and terminator sequences result in the accurate production of a nucleic acid molecule (e.g., RNA). In some embodiments, operatively linked nucleic acid elements result in the transcription of an open reading frame and ultimately the production of a polypeptide (i.e., expression of the open reading frame). As another example, an operatively linked peptide is one in which the functional domains are placed with appropriate distance from each other to impart the intended function of each domain.

The term "vector" refers to a substance that is used to carry or include a nucleic acid sequence, including for example, a nucleic acid sequence encoding a binding molecule (e.g., an antibody) as described herein, in order to introduce a nucleic acid sequence into a host cell. Vectors applicable for use include, for example, expression vectors, plasmids, phage vectors, viral vectors, episomes, and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like, which are well known in the art. When two or more nucleic acid molecules are to be co-expressed (e.g., both an antibody heavy and light chain or an antibody VH and VL), both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, immunoblotting for expression of gene products, or other suitable analytical methods to test the expression of an introduced nucleic acid sequence or its corresponding gene product. It is understood by those skilled in the art that the nucleic acid molecules are expressed in a sufficient amount to produce a desired product and it is further understood that expression levels can be optimized to obtain sufficient expression using methods well known in the art.

The term "host" as used herein refers to an animal, such as a mammal (e.g., a human).

The term "host cell" as used herein refers to a particular subject cell that may be transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, the term "autologous" is meant to refer to any material derived from the same individual to whom it is later to be re-introduced into the individual.

"Allogeneic" refers to a graft derived from a different individual of the same species.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "pharmaceutically acceptable" as used herein means being approved by a regulatory agency of the Federal or a state government, or listed in *United States Pharmacopeia, European Pharmacopeia*, or other generally recognized Pharmacopeia for use in animals, and more particularly in humans.

"Excipient" means a pharmaceutically-acceptable material, composition, or vehicle, such as a liquid or solid filler, diluent, solvent, or encapsulating material. Excipients include, for example, encapsulating materials or additives such as absorption accelerators, antioxidants, binders, buffers, carriers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. The term "excipient" can also refer to a diluent, adjuvant (e.g., Freunds' adjuvant (complete or incomplete) or vehicle.

In some embodiments, excipients are pharmaceutically acceptable excipients. Examples of pharmaceutically acceptable excipients include buffers, such as phosphate, citrate, and other organic acids; antioxidants, including ascorbic acid; low molecular weight (e.g., fewer than about 10 amino acid residues) polypeptide; proteins, such as serum albumin, gelatin, or immunoglobulins; hydrophilic polymers, such as polyvinylpyrrolidone; amino acids, such as glycine, glutamine, asparagine, arginine, or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN™, polyethylene glycol (PEG), and PLURONICS™. Other examples of pharmaceutically acceptable excipients are described in Remington and Gennaro, *Remington's Pharmaceutical Sciences* (18th ed. 1990).

In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., Lippincott Williams & Wilkins: Philadelphia, P A, 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, F L, 2009. In some embodiments, pharmaceutically acceptable excipients are nontoxic to the cell or mammal being exposed thereto at the dosages and concentrations employed. In some embodiments, a pharmaceutically acceptable excipient is an aqueous pH buffered solution.

In some embodiments, excipients are sterile liquids, such as water and oils, including those of petroleum, animal, vegetable, or synthetic origin, such as peanut oil, soybean oil, mineral oil, sesame oil, and the like. Water is an exemplary excipient when a composition (e.g., a pharmaceutical composition) is administered intravenously. Saline solutions and aqueous dextrose and glycerol solutions can also be employed as liquid excipients, particularly for injectable solutions. An excipient can also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. Compositions can take the form of solutions, suspensions, emulsion, tablets, pills, capsules, powders, sustained-release formulations, and the like. Oral compositions, including formulations, can include standard excipients such as pharmaceutical grades of mannitol, lactose, starch, magnesium stearate, sodium saccharine, cellulose, magnesium carbonate, etc.

Compositions, including pharmaceutical compounds, may contain a binding molecule (e.g., an antibody), for example, in isolated or purified form, together with a suitable amount of excipients.

The term "effective amount" or "therapeutically effective amount" as used herein refers to the amount of a single domain antibody or a therapeutic molecule comprising an agent and the single domain antibody or pharmaceutical composition provided herein which is sufficient to result in the desired outcome.

The terms "subject" and "patient" may be used interchangeably. As used herein, in certain embodiments, a subject is a mammal, such as a non-primate or a primate (e.g., human). In specific embodiments, the subject is a human. In one embodiment, the subject is a mammal, e.g., a human, diagnosed with a disease or disorder. In another embodiment, the subject is a mammal, e.g., a human, at risk of developing a disease or disorder.

"Administer" or "administration" refers to the act of injecting or otherwise physically delivering a substance as it exists outside the body into a patient, such as by mucosal, intradermal, intravenous, intramuscular delivery, and/or any other method of physical delivery described herein or known in the art.

As used herein, the terms "treat," "treatment" and "treating" refer to the reduction or amelioration of the progression, severity, and/or duration of a disease or condition resulting from the administration of one or more therapies. Treating may be determined by assessing whether there has been a decrease, alleviation and/or mitigation of one or more symptoms associated with the underlying disorder such that an improvement is observed with the patient, despite that the patient may still be afflicted with the underlying disorder. The term "treating" includes both managing and ameliorating the disease. The terms "manage," "managing," and "management" refer to the beneficial effects that a subject derives from a therapy which does not necessarily result in a cure of the disease.

The terms "prevent," "preventing," and "prevention" refer to reducing the likelihood of the onset (or recurrence) of a disease, disorder, condition, or associated symptom(s) (e.g., diabetes or a cancer).

As used herein, "delaying" the development of cancer means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of cancer is a method that reduces probability of disease development in a given time frame and/or reduces the extent of the disease in a given time frame, when compared to not using the method. Such comparisons are typically based on clinical studies, using a statistically significant number of individuals. Cancer development can be detectable using standard methods, including, but not limited to, computerized axial tomography (CAT Scan), Magnetic Resonance Imaging (MRI), abdominal ultrasound, clotting tests, arteriography, or biopsy. Development may also refer to cancer progression that may be initially undetectable and includes occurrence, recurrence, and onset.

"GUCY2C associated disease or disorder" as used herein refers to a disease or disorder that comprises a cell or tissue in which GUCY2C is expressed. In some embodiments, GUCY2C associated disease or disorder comprises a cell on which GUCY2C is abnormally expressed. In other embodiments, GUCY2C associated disease or disorder comprises a cell in or on which GUCY2C is deficient.

The terms "about" and "approximately" mean within 20%, within 15%, within 10%, within 9%, within 8%, within 7%, within 6%, within 5%, within 4%, within 3%, within 2%, within 1%, or less of a given value or range.

As used in the present disclosure and claims, the singular forms "a", "an" and "the" include plural forms unless the context clearly dictates otherwise.

It is understood that wherever embodiments are described herein with the term "comprising" otherwise analogous embodiments described in terms of "consisting of" and/or "consisting essentially of" are also provided. It is also understood that wherever embodiments are described herein with the phrase "consisting essentially of" otherwise analogous embodiments described in terms of "consisting of" are also provided.

The term "between" as used in a phrase as such "between A and B" or "between A-B" refers to a range including both A and B.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

5.2. Single Domain Antibodies

5.2.1. Single Domain Antibodies that Bind to GUCY2C

In one aspect, provided herein are single domain antibodies (e.g., VHH domains) capable of binding to GUCY2C.

In some embodiments, the single domain antibodies (e.g., VHH domains) provided herein bind to human GUCY2C. In some embodiments, the anti-GUCY2C single domain antibody provided herein modulates one or more GUCY2C activities. In some embodiments, the anti-GUCY2C single domain antibody provided herein is an antagonist antibody.

In some embodiments, the anti-GUCY2C single domain antibody provided herein binds to GUCY2C (e.g., human GUCY2C) with a dissociation constant ($K_D$) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). A variety of methods of measuring binding affinity are known in the art, any of which can be used for purposes of the present disclosure, including by RIA, for example, performed with the Fab version of an antibody of interest and its antigen (Chen et al., 1999, J. Mol Biol 293:865-81); by biolayer interferometry (BLI) or surface plasmon resonance (SPR) assays by Octet®, using, for example, an Octet® Red96 system, or by Biacore®, using, for example, a Biacore® TM-2000 or a Biacore® TM-3000. An "on-rate" or "rate of association" or "association rate" or "kon" may also be determined with the same biolayer interferometry (BLI) or surface plasmon resonance (SPR) techniques described above using, for example, the Octet® Red96, the Biacore® TM-2000, or the Biacore® TM-3000 system.

In some embodiments, the anti-GUCY2C single domain antibodies provided herein are VHH domains. Exemplary VHH domains provided herein are generated as described below in Section 6, and these VHH domains are referred to as C8, C12, C13, C15, C21, C27, C30 and C31 as also shown in Table 7 below.

Thus, in some embodiments, the single domain antibody provided herein comprises one or more CDR sequences of any one of C8, C12, C13, C15, C21, C27, C30 and/or C31. In some embodiments, provided herein is a single domain antibody that binds to GUCY2C comprising the following structure: FR1-CDR1-FR2-CDR2-FR3-CDR3-FR4, wherein the CDR sequences are selected from those in C8, C12, C13, C15, C21, C27, C30 and/or C31.

In some embodiments, the anti-GUCY2C sdAb provided herein comprises a CDR1 comprising an amino acid sequence of $X_1YGMX_2$, wherein $X_1$ is A, I or V, and $X_2$ is D or G (SEQ ID NO: 64). In some embodiments, the anti-GUCY2C sdAb provided herein comprises a CDR2 comprising an amino acid sequence of $X_3IX_4LSGRX_5X_6YX_7DAVX_8G$, wherein $X_3$ is A, S or T; $X_4$ is F, W or Y; $X_5$ is S or T; $X_6$ is E, N or T; $X_7$ is A, S or T; and $X_8$ is K or Q (SEQ ID NO: 65). In other embodiments, the anti-GUCY2C sdAb provided herein comprises a CDR3 comprising an amino acid sequence of $GX_9X_{10}TAX_{11}SX_{12}RQY$, wherein $X_9$ is A, E or P; $X_{10}$ is P or T; $X_{11}$ is S or T; and $X_{12}$ is G or V (SEQ ID NO: 66).

In some embodiments, the anti-GUCY2C sdAb provided herein comprises a CDR1 comprising an amino acid sequence of $X_1YGMX_2$, wherein $X_1$ is A, I or V, and $X_2$ is D or G (SEQ ID NO: 64); a CDR2 comprising an amino acid sequence of $X_3IX_4LSGRX_5X_6YX_7DAVX_8G$, wherein $X_3$ is A, S or T; $X_4$ is F, W or Y; $X_5$ is S or T; $X_6$ is E, N or T; $X_7$ is A, S or T; and $X_8$ is K or Q (SEQ ID NO: 65); and a CDR3 comprising an amino acid sequence of $GX_9X_{10}TAX_{11}SX_{12}RQY$, wherein $X_9$ is A, E or P; $X_{10}$ is P or T; $X_{11}$ is S or T; and $X_{12}$ is G or V (SEQ ID NO: 66).

TABLE 7

Exemplary Single Domain Antibodies

| Clone ID | VHH Domain (aa) | CDR1 | CDR2 | CDR3 |
|---|---|---|---|---|
| C8 | SEQ ID NO: 3 | SEQ ID NO: 19 | SEQ ID NO: 27 | SEQ ID NO: 35 |
| C12 | SEQ ID NO: 4 | SEQ ID NO: 20 | SEQ ID NO: 28 | SEQ ID NO: 36 |
| C13 | SEQ ID NO: 5 | SEQ ID NO: 21 | SEQ ID NO: 29 | SEQ ID NO: 37 |
| C15 | SEQ ID NO: 6 | SEQ ID NO: 22 | SEQ ID NO: 30 | SEQ ID NO: 38 |
| C21 | SEQ ID NO: 7 | SEQ ID NO: 23 | SEQ ID NO: 31 | SEQ ID NO: 39 |
| C27 | SEQ ID NO: 8 | SEQ ID NO: 24 | SEQ ID NO: 32 | SEQ ID NO: 40 |
| C30 | SEQ ID NO: 9 | SEQ ID NO: 25 | SEQ ID NO: 33 | SEQ ID NO: 41 |
| C31 | SEQ ID NO: 10 | SEQ ID NO: 26 | SEQ ID NO: 34 | SEQ ID NO: 42 |

In some embodiments, there is provided an anti-GUCY2C single domain antibody comprising one, two, or all three CDRs of the amino acid sequence of SEQ ID NO: 3. In some embodiments, there is provided an anti-GUCY2C single domain antibody comprising one, two, or all three CDRs of the amino acid sequence of SEQ ID NO: 4. In some embodiments, there is provided an anti-GUCY2C single domain antibody comprising one, two, or all three CDRs of the amino acid sequence of SEQ ID NO: 5. In some embodiments, there is provided an anti-GUCY2C single domain antibody comprising one, two, or all three CDRs of the amino acid sequence of SEQ ID NO: 6. In some embodiments, there is provided an anti-GUCY2C single domain antibody comprising one, two, or all three CDRs of the amino acid sequence of SEQ ID NO: 7. In some embodiments, there is provided an anti-GUCY2C single domain antibody comprising one, two, or all three CDRs of the amino acid sequence of SEQ ID NO: 8. In some embodiments, there is provided an anti-GUCY2C single domain antibody comprising one, two, or all three CDRs of the amino acid sequence of SEQ ID NO: 9. In some embodiments, there is provided an anti-GUCY2C single domain antibody comprising one, two, or all three CDRs of the amino acid sequence of SEQ ID NO: 10. In some embodiments, the anti-GUCY2C single domain antibody is camelid. In some embodiments, the anti-GUCY2C single domain antibody is humanized. In some embodiments, the anti-GUCY2C single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 3. In some embodiments, the single domain antibody has a CDR2 having an amino acid sequence of the CDR2 as set forth in SEQ ID NO: 3. In other embodiments, the single domain antibody has a CDR3 having an amino acid sequence of the CDR3 as set forth in SEQ ID NO: 3. In some embodiments, the single domain antibody has a CDR1 and a CDR2 having amino acid sequences of the CDR1 and the CDR2 as set forth in SEQ ID NO: 3. In some embodiments, the single domain antibody has a CDR1 and a CDR3 having amino acid sequences of the CDR1 and the CDR3 as set forth in SEQ ID NO: 3. In some embodiments, the single domain antibody has a CDR2 and a CDR3 having amino acid sequences of the CDR2 and the CDR3 as set forth in SEQ ID NO: 3. In some embodiments, the single domain antibody has a CDR1, a CDR2, and a CDR3 having amino acid sequences of the CDR1, the CDR2, and the CDR3 as set forth in SEQ ID NO: 3. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-GUCY2C single domain antibody is camelid. In some embodiments, the anti-GUCY2C single domain antibody is humanized. In some embodiments, the anti-GUCY2C single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 4. In some embodiments, the single domain antibody has a CDR2 having an amino acid sequence of the CDR2 as set forth in SEQ ID NO: 4. In other embodiments, the single domain antibody has a CDR3 having an amino acid sequence of the CDR3 as set forth in SEQ ID NO: 4. In some embodiments, the single domain antibody has a CDR1 and a CDR2 having amino acid sequences of the CDR1 and the CDR2 as set forth in SEQ ID NO: 4. In some embodiments, the single domain antibody has a CDR1 and a CDR3 having amino acid sequences of the CDR1 and the CDR3 as set forth in SEQ ID NO: 4. In some embodiments, the single domain antibody has a CDR2 and a CDR3 having amino acid sequences of the CDR2 and the CDR3 as set forth in SEQ ID NO: 4. In some embodiments, the single domain antibody has a CDR1, a CDR2, and a CDR3 having amino acid sequences of the CDR1, the CDR2, and the CDR3 as set forth in SEQ ID NO: 4. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-GUCY2C single domain antibody is camelid. In some embodiments, the anti-GUCY2C single domain antibody is humanized. In some embodiments, the anti-GUCY2C single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 5. In some embodiments, the single domain antibody has a CDR2 having an amino acid sequence of the CDR2 as set forth in SEQ ID NO: 5. In other embodiments, the single domain antibody has a CDR3 having an amino acid sequence of the CDR3 as set forth in SEQ ID NO: 5. In some embodiments, the single domain antibody has a CDR1 and a CDR2 having amino acid sequences of the CDR1 and the CDR2 as set forth in SEQ ID NO: 5. In some embodiments, the single domain antibody has a CDR1 and a CDR3 having amino acid sequences of the CDR1 and the CDR3 as set forth in SEQ ID NO: 5. In some embodiments, the single domain antibody has a CDR2 and a CDR3 having amino acid sequences of the CDR2 and the CDR3 as set forth in SEQ ID NO: 5. In some embodiments, the single domain antibody has a CDR1, a CDR2, and a CDR3 having amino acid sequences of the CDR1, the CDR2, and the CDR3 as set forth in SEQ ID NO: 5. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-GUCY2C single domain antibody is camelid. In some embodiments, the anti-GUCY2C single domain antibody is humanized. In some embodiments, the anti-GUCY2C single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 6. In some embodiments, the single domain antibody has a CDR2 having an amino acid sequence of the CDR2 as set forth in SEQ ID NO: 6. In other embodiments, the single domain antibody has a CDR3 having an amino acid sequence of the CDR3 as set forth in SEQ ID NO: 6. In some embodiments, the single domain antibody has a CDR1 and a CDR2 having amino acid sequences of the CDR1 and the CDR2 as set forth in SEQ ID NO: 6. In some embodiments, the single domain antibody has a CDR1 and a CDR3 having amino acid sequences of the CDR1 and the CDR3 as set forth in SEQ ID NO: 6. In some embodiments, the single domain antibody has a CDR2 and a CDR3 having amino acid sequences of the CDR2 and the CDR3 as set forth in SEQ ID NO: 6. In some embodiments, the single domain antibody has a CDR1, a CDR2, and a CDR3 having amino acid sequences of the CDR1, the CDR2, and the CDR3 as set forth in SEQ ID NO: 6. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-GUCY2C single domain antibody is camelid. In some embodiments, the anti-GUCY2C single domain antibody is humanized. In some embodiments, the anti-GUCY2C single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 7. In some embodiments, the single domain antibody has a CDR2 having an amino acid sequence of the CDR2 as set forth in SEQ ID NO: 7. In other embodiments, the single domain antibody has a CDR3 having an amino acid sequence of the CDR3 as set forth in SEQ ID NO: 7. In some embodiments, the single domain antibody has a CDR1 and a CDR2 having amino acid sequences of the CDR1 and the CDR2 as set forth in SEQ ID NO: 7. In some embodiments, the single domain antibody has a CDR1 and a CDR3 having amino acid sequences of the CDR1 and the CDR3 as set forth in SEQ ID NO: 7. In some embodiments, the single domain antibody has a CDR2 and a CDR3 having amino acid sequences of the CDR2 and the CDR3 as set forth in SEQ ID NO: 7. In some embodiments, the single domain antibody has a CDR1, a CDR2, and a CDR3 having amino acid sequences of the CDR1, the CDR2, and the CDR3 as set forth in SEQ ID NO: 7. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-GUCY2C single domain antibody is camelid. In some embodiments, the anti-GUCY2C single domain antibody is humanized. In some embodiments, the anti-GUCY2C single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 8. In some embodiments, the single domain antibody has a CDR2 having an amino acid sequence of the CDR2 as set forth in SEQ ID NO: 8. In other embodiments, the single domain antibody has a CDR3 having an amino acid sequence of the CDR3 as set forth in SEQ ID NO: 8. In some embodiments, the single domain antibody has a CDR1 and a CDR2 having amino acid sequences of the CDR1 and the CDR2 as set forth in SEQ ID NO: 8. In some embodiments, the single domain antibody has a CDR1 and a CDR3 having amino acid sequences of the CDR1 and the CDR3 as set forth in SEQ ID NO: 8. In some embodiments, the single domain antibody has a CDR2 and a CDR3 having amino acid sequences of the CDR2 and the CDR3 as set forth in SEQ ID NO: 8. In some embodiments, the single domain antibody has a CDR1, a CDR2, and a CDR3 having amino acid sequences of the CDR1, the CDR2, and the CDR3 as set forth in SEQ ID NO: 8. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-GUCY2C single domain antibody is camelid. In some embodiments, the anti-GUCY2C single domain antibody is humanized. In some embodiments, the anti-GUCY2C single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 9. In some embodiments, the single domain antibody has a CDR2 having an amino acid sequence of the CDR2 as set forth in SEQ ID NO: 9. In other embodiments, the single domain antibody has a CDR3 having an amino acid sequence of the CDR3 as set forth in SEQ ID NO: 9. In some embodiments, the single domain antibody has a CDR1 and a CDR2 having amino acid sequences of the CDR1 and the CDR2 as set forth in SEQ ID NO: 9. In some embodiments, the single domain antibody has a CDR1 and a CDR3 having amino acid sequences of the CDR1 and the CDR3 as set forth in SEQ ID NO: 9. In some embodiments, the single domain antibody has a CDR2 and a CDR3 having amino acid sequences of the CDR2 and the CDR3 as set forth in SEQ ID NO: 9. In some embodiments, the single domain antibody has a CDR1, a CDR2, and a CDR3 having amino acid sequences of the CDR1, the CDR2, and the CDR3 as set forth in SEQ ID NO: 9. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-GUCY2C single domain antibody is camelid. In some embodiments, the anti-GUCY2C single domain antibody is humanized. In some embodiments, the anti-GUCY2C single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 10. In some embodiments, the single domain antibody has a CDR2 having an amino acid sequence of the CDR2 as set forth in SEQ ID NO: 10. In other embodiments, the single domain antibody has a CDR3 having an amino acid sequence of the CDR3 as set forth in SEQ ID NO: 10 (e.g., SEQ ID NO: 3 or 6). In some embodiments, the single domain antibody has a CDR1 and a CDR2 having amino acid sequences of the CDR1 and the CDR2 as set forth in SEQ ID NO: 10. In some embodiments, the single domain antibody has a CDR1 and a CDR3 having amino acid sequences of the CDR1 and the CDR3 as set forth in SEQ ID NO: 10. In some embodiments, the single domain antibody has a CDR2 and a CDR3 having amino acid sequences of the CDR2 and the CDR3 as set forth in SEQ ID NO: 10. In some embodiments, the single domain antibody has a CDR1, a CDR2, and a CDR3 having amino acid sequences of the CDR1, the CDR2, and the CDR3 as set forth in SEQ ID NO: 10. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-GUCY2C single domain antibody is camelid. In some embodiments, the anti-GUCY2C single domain antibody is humanized. In some embodiments, the anti-GUCY2C single domain antibody comprises an acceptor human framework, e.g., a human immunoglobulin framework or a human consensus framework.

In some embodiments, provided herein is a single domain antibody that binds to GUCY2C comprising the following structure: FR1-CDR1-FR2-CDR2-FR3-CDR3-FR4, wherein (i) the CDR1 comprises an amino acid sequence of SEQ ID NO: 19, SEQ ID NO: 20, SEQ ID NO: 21, SEQ ID NO: 22, SEQ ID NO: 23, SEQ ID NO: 24, or SEQ ID NO: 25, SEQ ID NO: 26; (ii) the CDR2 comprises an amino acid sequence of SEQ ID NO: 27, SEQ ID NO: 28, SEQ ID NO: 29, SEQ ID NO: 30, SEQ ID NO: 31, SEQ ID NO: 32, SEQ ID NO: 33, or SEQ ID NO: 34; and/or (iii) the CDR3 comprises an amino acid sequence of SEQ ID NO: 35, SEQ ID NO: 36, SEQ ID NO: 37, SEQ ID NO: 38, SEQ ID NO: 39, SEQ ID NO: 40, SEQ ID NO: 41, or SEQ ID NO: 42. In some embodiments, the anti-GUCY2C single domain antibody is camelid. In some embodiments, the anti-GUCY2C single domain antibody is humanized. In some embodiments, the anti-GUCY2C single domain antibody comprises an acceptor human framework, e.g., a human immunoglobulin framework or a human consensus framework.

In other embodiments, provided herein is a single domain antibody that binds to GUCY2C comprising the following structure: FR1-CDR1-FR2-CDR2-FR3-CDR3-FR4, wherein (i) the CDR1 comprises an amino acid sequence having at least 75%, 80%, 85%, 86%, 87%, 88%, 89%, 90%, 91%, 92%, 93%, 94%, 95%, 96%, 97%, 98%, or 99% sequence identity to SEQ ID NO: 19, SEQ ID NO: 20, SEQ ID NO: 21, SEQ ID NO: 22, SEQ ID NO: 23, SEQ ID NO: 24, or SEQ ID NO: 25, SEQ ID NO: 26; (ii) the CDR2 comprises an amino acid sequence having at least 75%, 80%, 85%, 86%, 87%, 88%, 89%, 90%, 91%, 92%, 93%, 94%, 95%, 96%, 97%, 98%, or 99% sequence identity to SEQ ID NO: 27, SEQ ID NO: 28, SEQ ID NO: 29, SEQ ID NO: 30, SEQ ID NO: 31, SEQ ID NO: 32, SEQ ID NO: 33, or SEQ ID NO: 34; and/or (iii) the CDR3 comprises an amino acid sequence having at least 75%, 80%, 85%, 86%, 87%, 88%, 89%, 90%, 91%, 92%, 93%, 94%, 95%, 96%, 97%, 98%, or 99% sequence identity to SEQ ID NO: 35, SEQ ID NO: 36, SEQ ID NO: 37, SEQ ID NO: 38, SEQ ID NO: 39, SEQ ID NO: 40, SEQ ID NO: 41, or SEQ ID NO: 42. In some embodiments, the anti-GUCY2C single domain antibody is camelid. In some embodiments, the anti-GUCY2C single domain antibody is humanized. In some embodiments, the anti-GUCY2C single domain antibody comprises an acceptor human framework, e.g., a human immunoglobulin framework or a human consensus framework.

In some embodiments, provided herein is an anti-GUCY2C single domain antibody (sdAb) comprising a CDR1 comprising the amino acid sequence of SEQ ID NO: 19; a CDR2 comprising the amino acid sequence of SEQ ID NO: 27; and a CDR3 comprising the amino acid sequence of SEQ ID NO: 35. In some embodiments, the anti-GUCY2C single domain antibody is camelid. In some embodiments, the anti-GUCY2C single domain antibody is humanized. In some embodiments, the anti-GUCY2C single domain antibody comprises an acceptor human framework, e.g., a human immunoglobulin framework or a human consensus framework.

In some embodiments, provided herein is an anti-GUCY2C single domain antibody (sdAb) comprising a CDR1 comprising the amino acid sequence of SEQ ID NO: 20; a CDR2 comprising the amino acid sequence of SEQ ID NO: 28; and a CDR3 comprising the amino acid sequence of SEQ ID NO: 36. In some embodiments, the anti-GUCY2C single domain antibody is camelid. In some embodiments, the anti-GUCY2C single domain antibody is humanized. In some embodiments, the anti-GUCY2C single domain antibody comprises an acceptor human framework, e.g., a human immunoglobulin framework or a human consensus framework.

In some embodiments, provided herein is an anti-GUCY2C single domain antibody (sdAb) comprising a CDR1 comprising the amino acid sequence of SEQ ID NO: 21; a CDR2 comprising the amino acid sequence of SEQ ID NO: 29; and a CDR3 comprising the amino acid sequence of SEQ ID NO: 37. In some embodiments, the anti-GUCY2C single domain antibody is camelid. In some embodiments, the anti-GUCY2C single domain antibody is humanized. In some embodiments, the anti-GUCY2C single domain antibody comprises an acceptor human framework, e.g., a human immunoglobulin framework or a human consensus framework.

In some embodiments, provided herein is an anti-GUCY2C single domain antibody (sdAb) comprising a CDR1 comprising the amino acid sequence of SEQ ID NO: 22; a CDR2 comprising the amino acid sequence of SEQ ID NO: 30; and a CDR3 comprising the amino acid sequence of SEQ ID NO: 38. In some embodiments, the anti-GUCY2C single domain antibody is camelid. In some embodiments, the anti-GUCY2C single domain antibody is humanized. In some embodiments, the anti-GUCY2C single domain antibody comprises an acceptor human framework, e.g., a human immunoglobulin framework or a human consensus framework.

In some embodiments, provided herein is an anti-GUCY2C single domain antibody (sdAb) comprising a CDR1 comprising the amino acid sequence of SEQ ID NO: 23; a CDR2 comprising the amino acid sequence of SEQ ID NO: 31; and a CDR3 comprising the amino acid sequence of SEQ ID NO: 39. In some embodiments, the anti-GUCY2C single domain antibody is camelid. In some embodiments, the anti-GUCY2C single domain antibody is humanized. In some embodiments, the anti-GUCY2C single domain antibody comprises an acceptor human framework, e.g., a human immunoglobulin framework or a human consensus framework.

In some embodiments, provided herein is an anti-GUCY2C single domain antibody (sdAb) comprising a CDR1 comprising the amino acid sequence of SEQ ID NO:

24; a CDR2 comprising the amino acid sequence of SEQ ID NO: 32; and a CDR3 comprising the amino acid sequence of SEQ ID NO: 40. In some embodiments, the anti-GUCY2C single domain antibody is camelid. In some embodiments, the anti-GUCY2C single domain antibody is humanized. In some embodiments, the anti-GUCY2C single domain antibody comprises an acceptor human framework, e.g., a human immunoglobulin framework or a human consensus framework.

In some embodiments, provided herein is an anti-GUCY2C single domain antibody (sdAb) comprising a CDR1 comprising the amino acid sequence of SEQ ID NO: 25; a CDR2 comprising the amino acid sequence of SEQ ID NO: 33; and a CDR3 comprising the amino acid sequence of SEQ ID NO: 41. In some embodiments, the anti-GUCY2C single domain antibody is camelid. In some embodiments, the anti-GUCY2C single domain antibody is humanized. In some embodiments, the anti-GUCY2C single domain antibody comprises an acceptor human framework, e.g., a human immunoglobulin framework or a human consensus framework.

In some embodiments, provided herein is an anti-GUCY2C single domain antibody (sdAb) comprising a CDR1 comprising the amino acid sequence of SEQ ID NO: 26; a CDR2 comprising the amino acid sequence of SEQ ID NO: 34; and a CDR3 comprising the amino acid sequence of SEQ ID NO: 42. In some embodiments, the anti-GUCY2C single domain antibody is camelid. In some embodiments, the anti-GUCY2C single domain antibody is humanized. In some embodiments, the anti-GUCY2C single domain antibody comprises an acceptor human framework, e.g., a human immunoglobulin framework or a human consensus framework.

In some embodiments, the single domain antibody further comprises one or more framework region(s) of C8, C12, C13, C15, C21, C27, C30 and/or C31. In some embodiments, the single domain antibody comprises one or more framework(s) derived from a VHH domain comprising the sequence of SEQ ID NO: 3. In some embodiments, the single domain antibody comprises one or more framework(s) derived from a VHH domain comprising the sequence of SEQ ID NO: 4. In some embodiments, the single domain antibody comprises one or more framework(s) derived from a VHH domain comprising the sequence of SEQ ID NO: 5. In some embodiments, the single domain antibody comprises one or more framework(s) derived from a VHH domain comprising the sequence of SEQ ID NO: 6. In some embodiments, the single domain antibody comprises one or more framework(s) derived from a VHH domain comprising the sequence of SEQ ID NO: 7. In some embodiments, the single domain antibody comprises one or more framework(s) derived from a VHH domain comprising the sequence of SEQ ID NO: 8. In some embodiments, the single domain antibody comprises one or more framework(s) derived from a VHH domain comprising the sequence of SEQ ID NO: 9. In some embodiments, the single domain antibody comprises one or more framework(s) derived from a VHH domain comprising the sequence of SEQ ID NO: 10.

In some embodiments, the single domain antibody provided herein is a humanized single domain antibody.

Framework regions described herein are determined based upon the boundaries of the CDR numbering system. In other words, if the CDRs are determined by, e.g., Kabat, IMGT, or Chothia, then the framework regions are the amino acid residues surrounding the CDRs in the variable region in the format, from the N-terminus to C-terminus: FR1-CDR1-FR2-CDR2-FR3-CDR3-FR4. For example, FR1 is defined as the amino acid residues N-terminal to the CDR1 amino acid residues as defined by, e.g., the Kabat numbering system, the IMGT numbering system, or the Chothia numbering system, FR2 is defined as the amino acid residues between CDR1 and CDR2 amino acid residues as defined by, e.g., the Kabat numbering system, the IMGT numbering system, or the Chothia numbering system, FR3 is defined as the amino acid residues between CDR2 and CDR3 amino acid residues as defined by, e.g., the Kabat numbering system, the IMGT numbering system, or the Chothia numbering system, and FR4 is defined as the amino acid residues C-terminal to the CDR3 amino acid residues as defined by, e.g., the Kabat numbering system, the IMGT numbering system, or the Chothia numbering system.

In some embodiments, there is provided an isolated a i-GUCY2C single domain antibody comprising a VHH domain having the amino acid sequence of SEQ ID NO: 3. In some embodiments, there is provided a polypeptide comprising the amino acid sequence of SEQ ID NO: 3.

In some embodiments, there is provided an isolated anti-GUCY2C single domain antibody comprising a VHH domain having the amino acid sequence of SEQ ID NO: 4. In some embodiments, there is provided a polypeptide comprising the amino acid sequence of SEQ ID NO: 4.

In some embodiments, there is provided an isolated anti-GUCY2C single domain antibody comprising a VHH domain having the amino acid sequence of SEQ ID NO: 5. In some embodiments, there is provided a polypeptide comprising the amino acid sequence of SEQ ID NO: 5.

In some embodiments, there is provided an isolated anti-GUCY2C single domain antibody comprising a domain having the amino acid sequence of SEQ ID NO: 6. In some embodiments, there is provided a polypeptide comprising the amino acid sequence of SEQ ID NO: 6.

In some embodiments, there is provided an isolated anti-GUCY2C single domain antibody comprising a VHH domain having the amino acid sequence of SEQ ID NO: 7. In some embodiments, there is provided a polypeptide comprising the amino acid sequence of SEQ ID NO: 7.

In some embodiments, there is provided an isolated anti-GUCY2C single domain antibody comprising a VHH domain having the amino acid sequence of SEQ ID NO: 8. In some embodiments, there is provided a polypeptide comprising the amino acid sequence of SEQ ID NO: 8.

In some embodiments, there is provided an isolated anti-GUCY2C single domain antibody comprising a VHH domain having the amino acid sequence of SEQ ID NO: 9. In some embodiments, there is provided a polypeptide comprising the amino acid sequence of SEQ ID NO: 9.

In some embodiments, there is provided an isolated anti-GUCY2C single domain antibody comprising a domain having the amino acid sequence of SEQ ID NO: 10. In some embodiments, there is provided a polypeptide comprising the amino acid sequence of SEQ ID NO: 10.

In some embodiments, provided herein is an anti-GUCY2C antibody, or antigen binding fragment thereof, that specifically binds to GUCY2C competitively with any one of the anti-GUCY2C single domain antibodies described herein. In some embodiments, competitive binding may be determined using an ELISA assay. For example, in some embodiments, an antibody is provided that specifically binds to GUCY2C competitively with an anti-GUCY2C single domain antibody comprising the amino acid sequence of SEQ ID NO: 3. In some embodiments, an antibody is provided that specifically binds to GUCY2C competitively with an anti-GUCY2C single domain antibody comprising the amino acid sequence of SEQ ID NO:

4. In some embodiments, an antibody is provided that specifically binds to GUCY2C competitively with an anti-GUCY2C single domain antibody comprising the amino acid sequence of SEQ ID NO: 5. In some embodiments, an antibody is provided that specifically binds to GUCY2C competitively with an anti-GUCY2C single domain antibody comprising the amino acid sequence of SEQ ID NO: 6. In some embodiments, an antibody is provided that specifically binds to GUCY2C competitively with an anti-GUCY2C single domain antibody comprising the amino acid sequence of SEQ ID NO: 7. In some embodiments, an antibody is provided that specifically binds to GUCY2C competitively with an anti-GUCY2C single domain antibody comprising the amino acid sequence of SEQ ID NO: 8. In some embodiments, an antibody is provided that specifically binds to GUCY2C competitively with an anti-GUCY2C single domain antibody comprising the amino acid sequence of SEQ ID NO: 9. In some embodiments, an antibody is provided that specifically binds to GUCY2C competitively with an anti-GUCY2C single domain antibody comprising the amino acid sequence of SEQ ID NO: 10.

In some embodiments, functional epitopes can be mapped, e.g., by combinatorial alanine scanning, to identify amino acids in the GUCY2C protein that are necessary for interaction with anti-GUCY2C single domain antibodies provided herein. In some embodiments, conformational and crystal structure of anti-GUCY2C single domain antibody bound to GUCY2C may be employed to identify the epitopes. In some embodiments, the present disclosure provides an antibody that specifically binds to the same epitope as any of the anti-GUCY2C single domain antibodies provided herein. In some embodiments, an antibody is provided that binds to the same epitope as an anti-GUCY2C single domain antibody comprising the amino acid sequence of SEQ ID NO: 3. In some embodiments, an antibody is provided that binds to the same epitope as an anti-GUCY2C single domain antibody comprising the amino acid sequence of SEQ ID NO: 4. In some embodiments, an antibody is provided that binds to the same epitope as an anti-GUCY2C single domain antibody comprising the amino acid sequence of SEQ ID NO: 5. In some embodiments, an antibody is provided that binds to the same epitope as an anti-GUCY2C single domain antibody comprising the amino acid sequence of SEQ ID NO: 6. In some embodiments, an antibody is provided that binds to the same epitope as an anti-GUCY2C single domain antibody comprising the amino acid sequence of SEQ ID NO: 7. In some embodiments, an antibody is provided that binds to the same epitope as an anti-GUCY2C single domain antibody comprising the amino acid sequence of SEQ ID NO: 8. In some embodiments, an antibody is provided that binds to the same epitope as an anti-GUCY2C single domain antibody comprising the amino acid sequence of SEQ ID NO: 9. In some embodiments, an antibody is provided that binds to the same epitope as an anti-GUCY2C single domain antibody comprising the amino acid sequence of SEQ ID NO: 10.

In certain embodiments, an antibody described herein or an antigen-binding fragment thereof comprises amino acid sequences with certain percent identity relative to any one of antibodies C8, C12, C13, C15, C21, C27, C30 and C31.

The determination of percent identity between two sequences (e.g., amino acid sequences or nucleic acid sequences) can be accomplished using a mathematical algorithm. A non-limiting example of a mathematical algorithm utilized for the comparison of two sequences is the algorithm of Karlin and Altschul, Proc. Natl. Acad. Sci. U.S.A. 87:2264 2268 (1990), modified as in Karlin and Altschul, Proc. Natl. Acad. Sci. U.S.A. 90:5873 5877 (1993). Such an algorithm is incorporated into the NBLAST and XBLAST programs of Altschul et al., J. Mol. Biol. 215:403 (1990). BLAST nucleotide searches can be performed with the NBLAST nucleotide program parameters set, e.g., for score=100, word length=12 to obtain nucleotide sequences homologous to a nucleic acid molecules described herein. BLAST protein searches can be performed with the XBLAST program parameters set, e.g., to score 50, word length=3 to obtain amino acid sequences homologous to a protein molecule described herein. To obtain gapped alignments for comparison purposes, Gapped BLAST can be utilized as described in Altschul et al., Nucleic Acids Res. 25:3389 3402 (1997). Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another non-limiting example of a mathematical algorithm utilized for the comparison of sequences is the algorithm of Myers and Miller, CABIOS 4:11-17 (1998). Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

In some embodiments, there is provided an anti-GUCY2C single domain antibody comprising a VHH domain having at least about any one of 75%, 80%, 85%, 86%, 87%, 88%, 89%, 90%, 91%, 92%, 93%, 94%, 95%, 96%, 97%, 98%, 99%, or 100% sequence identity to an amino acid sequence selected from SEQ ID NOs: 3 to 10. In some embodiments, a sequence having at least about any one of 75%, 80%, 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence, but the anti-GUCY2C single domain antibody comprising that sequence retains the ability to bind to GUCY2C. In some embodiments, a total of 1 to 10 amino acids have been substituted, inserted and/or deleted in an amino acid sequence selected from SEQ ID NOs: 3 to 10. In some embodiments, substitutions, insertions, or deletions occur in regions outside the CDRs (i.e., in the FRs), Optionally, the anti-GUCY2C single domain antibody comprises an amino acid sequence selected from SEQ ID NOs: 3 to 10, including post-translational modifications of that sequence.

In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 3, wherein the single domain antibody binds to GUCY2C.

In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 4, wherein the single domain antibody binds to GUCY2C.

In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 5, wherein the single domain antibody binds to GUCY2C.

In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 6, wherein the single domain antibody binds to GUCY2C.

In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 7, wherein the single domain antibody binds to GUCY2C.

In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 8, wherein the single domain antibody binds to GUCY2C.

In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 9, wherein the single domain antibody binds to GUCY2C.

In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 10, wherein the single domain antibody binds to GUCY2C.

In some embodiments, provided herein is a GUCY2C binding protein comprising any one of the anti-GUCY2C single domain antibodies described above. In some embodiments, the GUCY2C binding protein is a monoclonal antibody, including a camelid, chimeric, humanized or human antibody. In some embodiments, the anti-GUCY2C antibody is an antibody fragment, e.g., a VHH fragment. In some embodiments, the anti-GUCY2C antibody is a full-length heavy-chain only antibody comprising an Fc region of any antibody class or isotype, such as IgG1 or IgG4. In some embodiments, the Fc region has reduced or minimized effector function. In some embodiments, the GUCY2C binding protein is a fusion protein comprising the anti-GUCY2C single domain antibody provided herein. In other embodiments, the GUCY2C binding protein is a multispecific antibody comprising the anti-GUCY2C single domain antibody provided herein. Other exemplary GUCY2C binding molecules are described in more detail in the following sections.

In some embodiments, the anti-GUCY2C antibody (such as anti-GUCY2C single domain antibody) or antigen binding protein according to any of the above embodiments may incorporate any of the features, singly or in combination, as described in Sections 5.2.2 to 5.2.7 below.

5.2.2. Single Domain Antibody Variants

In addition to the single domain antibodies that bind to GUCY2C described herein, it is contemplated that variants of the single domain antibodies that bind to GUCY2C described herein can be prepared. For example, single domain antibody variants can be prepared by introducing appropriate nucleotide changes into the encoding DNA, and/or by synthesis of the desired antibody or polypeptide. Those skilled in the art who appreciate that amino acid changes may alter post-translational processes of the single domain antibody.

Variations may be a substitution, deletion, or insertion of one or more codons encoding the single domain antibody or polypeptide that results in a change in the amino acid sequence as compared with the original antibody or polypeptide. Sites of interest for substitutional mutagenesis include the CDRs and FRs.

Amino acid substitutions can be the result of replacing one amino acid with another amino acid having similar structural and/or chemical properties, such as the replacement of a leucine with a serine, e.g., conservative amino acid replacements. Standard techniques known to those of skill in the art can be used to introduce mutations in the nucleotide sequence encoding a molecule provided herein, including, for example, site-directed mutagenesis and PCR-mediated mutagenesis which results in amino acid substitutions. Insertions or deletions may optionally be in the range of about 1 to 5 amino acids. In certain embodiments, the substitution, deletion, or insertion includes fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, or fewer than 2 amino acid substitutions relative to the original molecule. In a specific embodiment, the substitution is a conservative amino acid substitution made at one or more predicted non-essential amino acid residues. The variation allowed may be determined by systematically making insertions, deletions, or substitutions of amino acids in the sequence and testing the resulting variants for activity exhibited by the parental antibodies.

Amino acid sequence insertions include amino- and/or carboxyl-terminal fusions ranging in length from one residue to polypeptides containing multiple residues, as well as intrasequence insertions of single or multiple amino acid residues. Examples of terminal insertions include an antibody with an N-terminal methionyl residue.

Single domain antibodies generated by conservative amino acid substitutions are included in the present disclosure. In a conservative amino acid substitution, an amino acid residue is replaced with an amino acid residue having a side chain with a similar charge. As described above, families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined. Conservative (e.g., within an amino acid group with similar properties and/or side chains) substitutions may be made, so as to maintain or not significantly change the properties. Exemplary substitutions are shown in the table below.

TABLE 8

Amino Acid Substitutions

| Original Residue | Exemplary Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to similarities in the properties of their side chains (see, e.g., Lehninger, *Biochemistry* 73-75 (2d ed. 1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); and (4) basic: Lys (K), Arg (R), His (H). Alternatively, naturally occurring residues may be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe. For example, any cysteine residue not involved in maintaining the proper conformation of the single domain antibody also may be substituted, for example, with another amino acid, such as alanine or serine, to improve the oxidative stability of the molecule and to prevent aberrant crosslinking. Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g. binding affinity).

Alterations (e.g., substitutions) may be made in CDRs, e.g., to improve antibody affinity. Such alterations may be made in CDR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant antibody or fragment thereof being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. More detailed description regarding affinity maturation is provided in the section below.

In some embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. In some embodiments of the variant VHH sequences provided herein, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells, *Science,* 244:1081-1085 (1989). In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

The variations can be made using methods known in the art such as oligonucleotide-mediated (site-directed) mutagenesis, alanine scanning, and PCR mutagenesis. Site-directed mutagenesis (see, e.g., Carter, Biochem J. 237:1-7 (1986); and Zoller et al., Nucl. Acids Res. 10:6487-500 (1982)), cassette mutagenesis (see, e.g., Wells et al., Gene 34:315-23 (1985)), or other known techniques can be performed on the cloned DNA to produce the single domain antibody variant DNA.

In some embodiments, the single domain antibodies provided herein are chemically modified, for example, by the covalent attachment of any type of molecule to the single domain antibody. The antibody derivatives may include antibodies that have been chemically modified, for example, by glycosylation, acetylation, pegylation, phosphorylation, amidation, derivatization by known protecting/blocking groups, proteolytic cleavage, linkage to a cellular ligand or other protein, or conjugation to one or more immunoglobulin domains (e.g., Fc or a portion of an Fc). Any of numerous chemical modifications may be carried out by known techniques, including, but not limited to, specific chemical cleavage, acetylation, formulation, metabolic synthesis of tunicamycin, etc. Additionally, the antibody may contain one or more non-classical amino acids.

In some embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

When the single domain antibody provided herein is fused to an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in the binding molecules provided herein may be made in order to create variants with certain improved properties.

In other embodiments, when the single domain antibody provided herein is fused to an Fc region, antibody variants provided herein may have a carbohydrate structure that lacks fucose attached (directly or indirectly) to said Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 and US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Patent Application No. US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

The binding molecules comprising a single domain antibody provided herein are further provided with bisected oligosaccharides, e.g., in which a biantennary oligosaccharide attached to the Fc region is bisected by GlcNAc. Such variants may have reduced fucosylation and/or improved ADCC function. Examples of such variants are described, e.g., in WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such variants may have improved CDC function. Such variants are described, e.g., in WO 1997/30087; WO 1998/58964; and WO 1999/22764.

In molecules that comprise the present single domain antibody and an Fc region, one or more amino acid modifications may be introduced into the Fc region, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In some embodiments, the present application contemplates variants that possesses some but not all effector functions, which make it a desirable candidate for applications in which the half life of the binding molecule in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the binding molecule lacks FcγR binding (hence likely lacking ADCC activity), but retains FcRn binding ability. Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96 ® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind Clq and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:

2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Binding molecules with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, a variant comprises an Fc region with one or more amino acid substitutions which improve ADCC, e.g., substitutions at positions 298, 333, and/or 334 of the Fc region (EU numbering of residues). In some embodiments, alterations are made in the Fc region that result in altered (i.e., either improved or diminished) Clq binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Binding molecules with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those molecules comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, *Nature* 322:738-40 (1988); U.S. Pat. Nos. 5,648,260; 5,624,821; and WO 94/29351 concerning other examples of Fc region variants.

In some embodiments, it may be desirable to create cysteine engineered antibodies, in which one or more residues of an antibody are substituted with cysteine residues. In some embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein.

5.2.3. In Vitro Affinity Maturation

In some embodiments, antibody variants having an improved property such as affinity, stability, or expression level as compared to a parent antibody may be prepared by in vitro affinity maturation. Like the natural prototype, in vitro affinity maturation is based on the principles of mutation and selection. Libraries of antibodies are displayed on the surface of an organism (e.g., phage, bacteria, yeast, or mammalian cell) or in association (e.g., covalently or non-covalently) with their encoding mRNA or DNA. Affinity selection of the displayed antibodies allows isolation of organisms or complexes carrying the genetic information encoding the antibodies. Two or three rounds of mutation and selection using display methods such as phage display usually results in antibody fragments with affinities in the low nanomolar range. Affinity matured antibodies can have nanomolar or even picomolar affinities for the target antigen.

Phage display is a widespread method for display and selection of antibodies. The antibodies are displayed on the surface of Fd or M13 bacteriophages as fusions to the bacteriophage coat protein. Selection involves exposure to antigen to allow phage-displayed antibodies to bind their targets, a process referred to as "panning." Phage bound to antigen are recovered and used to infect bacteria to produce phage for further rounds of selection. For review, see, for example, Hoogenboom, Methods. Mol. Biol. 178:1-37 (2002); and Bradbury and Marks, J. Immunol. Methods 290:29-49 (2004).

In a yeast display system (see, e.g., Boder et al., Nat. Biotech. 15:553-57 (1997); and Chao et al., Nat. Protocols 1:755-68 (2006)), the antibody may be fused to the adhesion subunit of the yeast agglutinin protein Aga2p, which attaches to the yeast cell wall through disulfide bonds to Aga1p. Display of a protein via Aga2p projects the protein away from the cell surface, minimizing potential interactions with other molecules on the yeast cell wall. Magnetic separation and flow cytometry are used to screen the library to select for antibodies with improved affinity or stability. Binding to a soluble antigen of interest is determined by labeling of yeast with biotinylated antigen and a secondary reagent such as streptavidin conjugated to a fluorophore. Variations in surface expression of the antibody can be measured through immunofluorescence labeling of either the hemagglutinin or c-Myc epitope tag flanking the single chain antibody (e.g., scFv). Expression has been shown to correlate with the stability of the displayed protein, and thus antibodies can be selected for improved stability as well as affinity (see, e.g., Shusta et al., J. Mol. Biol. 292:949-56 (1999)). An additional advantage of yeast display is that displayed proteins are folded in the endoplasmic reticulum of the eukaryotic yeast cells, taking advantage of endoplasmic reticulum chaperones and quality-control machinery. Once maturation is complete, antibody affinity can be conveniently "titrated" while displayed on the surface of the yeast, eliminating the need for expression and purification of each clone. A theoretical limitation of yeast surface display is the potentially smaller functional library size than that of other display methods; however, a recent approach uses the yeast cells' mating system to create combinatorial diversity estimated to be $10^{14}$ in size (see, e.g., U.S. Pat. Publication 2003/0186374; and Blaise et al., Gene 342:211-18 (2004)).

In ribosome display, antibody-ribosome-mRNA (ARM) complexes are generated for selection in a cell-free system. The DNA library coding for a particular library of antibodies is genetically fused to a spacer sequence lacking a stop codon. This spacer sequence, when translated, is still attached to the peptidyl tRNA and occupies the ribosomal tunnel, and thus allows the protein of interest to protrude out of the ribosome and fold. The resulting complex of mRNA, ribosome, and protein can bind to surface-bound ligand, allowing simultaneous isolation of the antibody and its encoding mRNA through affinity capture with the ligand. The ribosome-bound mRNA is then reverse transcribed back into cDNA, which can then undergo mutagenesis and be used in the next round of selection (see, e.g., Fukuda et al., Nucleic Acids Res. 34:e127 (2006)). In mRNA display, a covalent bond between antibody and mRNA is established using puromycin as an adaptor molecule (Wilson et al., Proc. Natl. Acad. Sci. USA 98:3750-55 (2001)).

As these methods are performed entirely in vitro, they provide two main advantages over other selection technologies. First, the diversity of the library is not limited by the transformation efficiency of bacterial cells, but only by the number of ribosomes and different mRNA molecules present in the test tube. Second, random mutations can be introduced easily after each selection round, for example, by non-proofreading polymerases, as no library must be transformed after any diversification step.

In some embodiments, mammalian display systems may be used.

Diversity may also be introduced into the CDRs of the antibody libraries in a targeted manner or via random introduction. The former approach includes sequentially targeting all the CDRs of an antibody via a high or low level of mutagenesis or targeting isolated hot spots of somatic hypermutations (see, e.g., Ho et al., J. Biol. Chem. 280:607-17 (2005)) or residues suspected of affecting affinity on experimental basis or structural reasons. Diversity may also be introduced by replacement of regions that are naturally diverse via DNA shuffling or similar techniques (see, e.g., Lu et al., J. Biol. Chem. 278:43496-507 (2003); U.S. Pat. Nos. 5,565,332 and 6,989,250). Alternative techniques target hypervariable loops extending into framework-region residues (see, e.g., Bond et al., J. Mol. Biol. 348:699-709 (2005)) employ loop deletions and insertions in CDRs or use hybridization-based diversification (see, e.g., U.S. Pat. Publication No. 2004/0005709). Additional methods of generating diversity in CDRs are disclosed, for example, in U.S. Pat. No. 7,985,840. Further methods that can be used to generate antibody libraries and/or antibody affinity maturation are disclosed, e.g., in U.S. Pat. Nos. 8,685,897 and 8,603,930, and U.S. Publ. Nos. 2014/0170705, 2014/0094392, 2012/0028301, 2011/0183855, and 2009/0075378, each of which are incorporated herein by reference.

Screening of the libraries can be accomplished by various techniques known in the art. For example, single domain antibodies can be immobilized onto solid supports, columns, pins, or cellulose/poly (vinylidene fluoride) membranes/other filters, expressed on host cells affixed to adsorption plates or used in cell sorting, or conjugated to biotin for capture with streptavidin-coated beads or used in any other method for panning display libraries.

For review of in vitro affinity maturation methods, see, e.g., Hoogenboom, Nature Biotechnology 23:1105-16 (2005); Quiroz and Sinclair, Revista Ingeneria Biomedia 4:39-51 (2010); and references therein.

5.2.4. Modifications of Single Domain Antibodies

Covalent modifications of single domain antibodies are included within the scope of the present disclosure. Covalent modifications include reacting targeted amino acid residues of a single domain antibody with an organic derivatizing agent that is capable of reacting with selected side chains or the N- or C-terminal residues of the single domain antibody. Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (see, e.g., Creighton, *Proteins: Structure and Molecular Properties* 79-86 (1983)), acetylation of the N-terminal amine, and amidation of any C-terminal carboxyl group.

Other types of covalent modification of the single domain antibody included within the scope of this present disclosure include altering the native glycosylation pattern of the antibody or polypeptide as described above (see, e.g., Beck et al., Curr. Pharm. Biotechnol. 9:482-501 (2008); and Walsh, Drug Discov. Today 15:773-80 (2010)), and linking the antibody to one of a variety of nonproteinaceous polymers, e.g., polyethylene glycol (PEG), polypropylene glycol, or polyoxyalkylenes, in the manner set forth, for example, in U.S. Pat. Nos. 4,640,835; 4,496,689; 4,301,144; 4,670,417; 4,791,192; or 4,179,337. The single domain antibody that binds to GUCY2C of the disclosure may also be genetically fused or conjugated to one or more immunoglobulin constant regions or portions thereof (e.g., Fc) to extend half-life and/or to impart known Fc-mediated effector functions.

The single chain antibody that binds to GUCY2C of the present disclosure may also be modified to form chimeric molecules comprising the single chain antibody that binds to GUCY2C fused to another, heterologous polypeptide or amino acid sequence, for example, an epitope tag (see, e.g., Terpe, Appl. Microbiol. Biotechnol. 60:523-33 (2003)) or the Fc region of an IgG molecule (see, e.g., Aruffo, *Antibody Fusion Proteins* 221-42 (Chamow and Ashkenazi eds., 1999)). The single chain antibody that binds to GUCY2C may also be used to generate GUCY2C binding chimeric antigen receptor (CAR), as described in more detail below.

Also provided herein are fusion proteins comprising the single chain antibody that binds to GUCY2C of the disclosure and a heterologous polypeptide. In some embodiments, the heterologous polypeptide to which the antibody is genetically fused or chemically conjugated is useful for targeting the antibody to cells having cell surface-expressed GUCY2C.

Also provided herein are panels of antibodies that bind to a GUCY2C antigen. In specific embodiments, the panels of antibodies have different association rates, different dissociation rates, different affinities for a GUCY2C antigen, and/or different specificities for a GUCY2C antigen. In some embodiments, the panels comprise or consist of about 10 to about 1000 antibodies or more. Panels of antibodies can be used, for example, in 96-well or 384-well plates, for assays such as ELISAs.

5.2.5. Humanized Single Domain Antibodies

The single domain antibodies described herein include humanized single domain antibodies. General strategies to humanize single domain antibodies from Camelidae species have been described (see, e.g., Vincke et al., J. Biol. Chem., 284(5):3273-3284 (2009)) and may be useful for producing humanized VHH domains as disclosed herein. The design of humanized single domain antibodies from Camelidae species may include the hallmark residues in the VHH, such as residues 11, 37, 44, 45 and 47 (residue numbering according to Kabat) (Muyldermans, Reviews Mol Biotech 74:277-302 (2001).

Humanized antibodies, such as the humanized single domain antibodies disclosed herein can also be produced using a variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, Molecular Immunology 28(4/5): 489-498 (1991); Studnicka et al., Protein Engineering 7(6): 805-814 (1994); and Roguska et al., PNAS 91:969-973 (1994)), chain shuffling (U.S. Pat. No. 5,565,332), and techniques disclosed in, e.g., U.S. Pat. Nos. 6,407,213, 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678-84 (1997), Roguska et al., Protein Eng. 9(10):895 904 (1996), Couto et al., Cancer Res. 55 (23 Supp):5973s-5977s (1995), Couto et al., Cancer Res.

55(8):1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), each of which is incorporated by reference herein in its entirety.

In some embodiments, single domain antibodies provided herein can be humanized single domain antibodies that bind to GUCY2C, including human GUCY2C. For example, humanized single chain antibodies of the present disclosure may comprise one or more CDRs set forth in SEQ ID NOs: 3 to 10. Various methods for humanizing non-human antibodies are known in the art. For example, a humanized antibody can have one or more amino acid residues introduced into it from a source that is non-human. These non-human amino acid residues are often referred to as "import" residues, which are typically taken from an "import" variable domain. Humanization may be performed, for example, following the method of Jones et al., Nature 321:522-25 (1986); Riechmann et al., Nature 332:323-27 (1988); and Verhoeyen et al., Science 239:1534-36 (1988)), by substituting hypervariable region sequences for the corresponding sequences of a human antibody.

In some cases, the humanized antibodies are constructed by CDR grafting, in which the amino acid sequences of the CDRs of the parent non-human antibody are grafted onto a human antibody framework. For example, Padlan et al. determined that only about one third of the residues in the CDRs actually contact the antigen, and termed these the "specificity determining residues," or SDRs (Padlan et al., FASEB J. 9:133-39 (1995)). In the technique of SDR grafting, only the SDR residues are grafted onto the human antibody framework (see, e.g., Kashmiri et al., Methods 36:25-34 (2005)).

The choice of human variable domains to be used in making the humanized antibodies can be important to reduce antigenicity. For example, according to the so-called "best-fit" method, the sequence of the variable domain of a non-human antibody is screened against the entire library of known human variable-domain sequences. The human sequence that is closest to that of the non-human antibody may be selected as the human framework for the humanized antibody (Sims et al., J. Immunol. 151:2296-308 (1993); and Chothia et al., J. Mol. Biol. 196:901-17 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA 89:4285-89 (1992); and Presta et al., J. Immunol. 151:2623-32 (1993)). In some cases, the framework is derived from the consensus sequences of the most abundant human subclasses, $V_L6$ subgroup I ($V_L6I$) and $V_H$ subgroup III ($V_HIII$). In another method, human germline genes are used as the source of the framework regions.

In an alternative paradigm based on comparison of CDRs, called superhumanization, FR homology is irrelevant. The method consists of comparison of the non-human sequence with the functional human germline gene repertoire. Those genes encoding the same or closely related canonical structures to the murine sequences are then selected. Next, within the genes sharing the canonical structures with the non-human antibody, those with highest homology within the CDRs are chosen as FR donors. Finally, the non-human CDRs are grafted onto these FRs (see, e.g., Tan et al., J. Immunol. 169:1119-25 (2002)).

It is further generally desirable that antibodies be humanized with retention of their affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. These include, for example, WAM (Whitelegg and Rees, Protein Eng. 13:819-24 (2002)), Modeller (Sali and Blundell, J. Mol. Biol. 234:779-815 (1993)), and Swiss PDB Viewer (Guex and Peitsch, Electrophoresis 18:2714-23 (1997)). Inspection of these displays permits analysis of the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Another method for antibody humanization is based on a metric of antibody humanness termed Human String Content (HSC). This method compares the mouse sequence with the repertoire of human germline genes, and the differences are scored as HSC. The target sequence is then humanized by maximizing its HSC rather than using a global identity measure to generate multiple diverse humanized variants (Lazar et al., Mol. Immunol. 44:1986-98 (2007)).

In addition to the methods described above, empirical methods may be used to generate and select humanized antibodies. These methods include those that are based upon the generation of large libraries of humanized variants and selection of the best clones using enrichment technologies or high throughput screening techniques. Antibody variants may be isolated from phage, ribosome, and yeast display libraries as well as by bacterial colony screening (see, e.g., Hoogenboom, Nat. Biotechnol. 23:1105-16 (2005); Dufner et al., Trends Biotechnol. 24:523-29 (2006); Feldhaus et al., Nat. Biotechnol. 21:163-70 (2003); and Schlapschy et al., Protein Eng. Des. Sel. 17:847-60 (2004)).

In the FR library approach, a collection of residue variants are introduced at specific positions in the FR followed by screening of the library to select the FR that best supports the grafted CDR. The residues to be substituted may include some or all of the "Vernier" residues identified as potentially contributing to CDR structure (see, e.g., Foote and Winter, J. Mol. Biol. 224:487-99 (1992)), or from the more limited set of target residues identified by Baca et al. J. Biol. Chem. 272:10678-84 (1997).

In FR shuffling, whole FRs are combined with the non-human CDRs instead of creating combinatorial libraries of selected residue variants (see, e.g., Dall'Acqua et al., Methods 36:43-60 (2005)). A one-step FR shuffling process may be used. Such a process has been shown to be efficient, as the resulting antibodies exhibited improved biochemical and physicochemical properties including enhanced expression, increased affinity, and thermal stability (see, e.g., Damschroder et al., Mol. Immunol. 44:3049-60 (2007)).

The "humaneering" method is based on experimental identification of essential minimum specificity determinants (MSDs) and is based on sequential replacement of non-human fragments into libraries of human FRs and assessment of binding. This methodology typically results in epitope retention and identification of antibodies from multiple subclasses with distinct human V-segment CDRs.

The "human engineering" method involves altering a non-human antibody or antibody fragment by making specific changes to the amino acid sequence of the antibody so as to produce a modified antibody with reduced immunogenicity in a human that nonetheless retains the desirable binding properties of the original non-human antibodies. Generally, the technique involves classifying amino acid residues of a non-human antibody as "low risk," "moderate risk," or "high risk" residues. The classification is performed using a global risk/reward calculation that evaluates the predicted benefits of making particular substitution (e.g., for immunogenicity in humans) against the risk that the substitution will affect the resulting antibody's folding. The particular human amino acid residue to be substituted at a given position (e.g., low or moderate risk) of a non-human antibody sequence can be selected by aligning an amino acid sequence from the non-human antibody's variable regions with the corresponding region of a specific or consensus human antibody sequence. The amino acid residues at low or moderate risk positions in the non-human sequence can be substituted for the corresponding residues in the human antibody sequence according to the alignment. Techniques for making human engineered proteins are described in greater detail in Studnicka et al., Protein Engineering 7:805-14 (1994); U.S. Pat. Nos. 5,766,886; 5,770,196; 5,821,123; and 5,869,619; and PCT Publication WO 93/11794.

A composite human antibody can be generated using, for example, Composite Human Antibody™ technology (Antitope Ltd., Cambridge, United Kingdom). To generate composite human antibodies, variable region sequences are designed from fragments of multiple human antibody variable region sequences in a manner that avoids T cell epitopes, thereby minimizing the immunogenicity of the resulting antibody.

A deimmunized antibody is an antibody in which T-cell epitopes have been removed. Methods for making deimmunized antibodies have been described. See, e.g., Jones et al., Methods Mol Biol. 525:405-23 (2009), xiv, and De Groot et al., Cell. Immunol. 244:148-153(2006)). Deimmunized antibodies comprise T-cell epitope-depleted variable regions and human constant regions. Briefly, variable regions of an antibody are cloned and T-cell epitopes are subsequently identified by testing overlapping peptides derived from the variable regions of the antibody in a T cell proliferation assay. T cell epitopes are identified via in silico methods to identify peptide binding to human MHC class II. Mutations are introduced in the variable regions to abrogate binding to human MHC class II. Mutated variable regions are then utilized to generate the deimmunized antibody.

5.2.6. Preparation of Single Domain Antibodies

Single domain antibodies (such as VHHs) provided herein may be obtained using methods known in the art such as by immunizing a Camelid species (such as camel or llama) and obtaining hybridomas therefrom, or by cloning a library of single domain antibodies using molecular biology techniques known in the art and subsequent selection by ELISA with individual clones of unselected libraries or by using phage display. For example, methods of preparing single domain antibodies have been described in, e.g., Els Pardon et al, *Nature Protocol,* 9(3): 674 (2014).

Single domain antibodies provided herein may be produced by culturing cells transformed or transfected with a vector containing a single domain antibody-encoding nucleic acids. Polynucleotide sequences encoding polypeptide components of the antibody of the present disclosure can be obtained using standard recombinant techniques. Desired polynucleotide sequences may be isolated and sequenced from antibody producing cells such as hybridomas cells or B cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in host cells. Many vectors that are available and known in the art can be used for the purpose of the present disclosure. Selection of an appropriate vector will depend mainly on the size of the nucleic acids to be inserted into the vector and the particular host cell to be transformed with the vector. Host cells suitable for expressing antibodies of the present disclosure include prokaryotes such as Archaebacteria and Eubacteria, including Gram-negative or Gram-positive organisms, eukaryotic microbes such as filamentous fungi or yeast, invertebrate cells such as insect or plant cells, and vertebrate cells such as mammalian host cell lines. Host cells are transformed with the above-described expression vectors and cultured in conventional nutrient media modified as appropriate for inducing promoters, selecting transformants, or amplifying the genes encoding the desired sequences. Antibodies produced by the host cells are purified using standard protein purification methods as known in the art.

Methods for antibody production including vector construction, expression, and purification are further described in Plückthun et al., *Antibody Engineering: Producing antibodies in Escherichia coli: From PCR to fermentation* 203-52 (McCafferty et al. eds., 1996); Kwong and Rader, *E. coli Expression and Purification of Fab Antibody Fragments, in Current Protocols in Protein Science* (2009); Tachibana and Takekoshi, *Production of Antibody Fab Fragments in Escherichia coli, in Antibody Expression and Production* (Al-Rubeai ed., 2011); and *Therapeutic Monoclonal Antibodies: From Bench to Clinic* (An ed., 2009).

It is, of course, contemplated that alternative methods, which are well known in the art, may be employed to prepare anti-GUCY2C single domain antibodies. For instance, the appropriate amino acid sequence, or portions thereof, may be produced by direct peptide synthesis using solid-phase techniques (see, e.g., Stewart et al., *Solid-Phase Peptide Synthesis* (1969); and Merrifield, J. Am. Chem. Soc. 85:2149-54 (1963)). In vitro protein synthesis may be performed using manual techniques or by automation. Various portions of the anti-GUCY2C antibody may be chemically synthesized separately and combined using chemical or enzymatic methods to produce the desired anti-GUCY2C antibody. Alternatively, antibodies may be purified from cells or bodily fluids, such as milk, of a transgenic animal engineered to express the antibody, as disclosed, for example, in U.S. Pat. Nos. 5,545,807 and 5,827,690.

Specifically, the single domain antibodies, or other GUCY2C binders provided herein, can be generated by immunizing llamas, performing single B-cell sorting, undertaking V-gene extraction, cloning the GUCY2C binders, such as VHH-Fc fusions, and then performing small scale expression and purification. Additional screening of the single domain antibodies and other molecules that bind to GUCY2C can be performed, including one or more of selecting for ELISA-positive, BLI-positive, and $K_D$ less than 100 nM. These selection criteria can be combined as described in Section 6 below. Additionally, individual VHH binders (and other molecules that bind to GUCY2C) can be assayed for their ability to bind to cells expressing GUCY2C. Such assay can be performed using FACS analysis with cells expressing GUCY2C, and measuring the mean fluorescence intensity (MFI) of fluorescently-labeled VHH molecules. Various aspects mentioned above are described in more details below.

Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

For example, the animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant cell culture as protein fusions. Also, aggregating agents such as alum are suitable to enhance the immune response.

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies. For example, the monoclonal antibodies may be made using the hybridoma method first described by Kohler el al., *Nature,* 256:495 (1975), or may be made by recombinant DNA methods (U.S. Pat. No. 4,816,567).

In the hybridoma method, an appropriate host animal is immunized to elicit lymphocytes that produce or are capable of producing antibodies that will specifically bind the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986).

The immunizing agent will typically include the antigenic protein or a fusion variant thereof. Goding, *Monoclonal Antibodies: Principles and Practice*, Academic Press (1986), pp. 59-103, Immortalized cell lines are usually transformed mammalian cells. The hybridoma cells thus prepared are seeded and grown in a suitable culture medium that preferably contains one or more substances that inhibit the growth or survival of the unfused, parental myeloma cells. Preferred immortalized myeloma cells are those that fuse efficiently, support stable high-level production of antibody by the selected antibody-producing cells, and are sensitive to a medium such as HAT medium.

Culture medium in which hybridoma cells are growing is assayed for production of monoclonal antibodies directed against the antigen. The culture medium in which the hybridoma cells are cultured can be assayed for the presence of monoclonal antibodies directed against the desired antigen, Such techniques and assays are known in the in art. For example, binding affinity may be determined by the Scatchard analysis of Munson et al., *Anal. Biochem.,* 107:220 (1980).

After hybridoma cells are identified that produce antibodies of the desired specificity, affinity, and/or activity, the clones may be subcloned by limiting dilution procedures and grown by standard methods (Goding, supra), Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Monoclonal antibodies may also be made by recombinant DNA methods, such as those described in U.S. Pat. No. 4,816,567, and as described above. DNA encoding the monoclonal antibodies is readily isolated and sequenced using conventional procedures (e.g, by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., *Curr. Opinion in Immunol.,* 5:256-262 (1993) and Plückthun, *Immunol. Revs.* 130:151-188 (1992).

In a further embodiment, antibodies can be isolated from antibody phage libraries generated using the techniques described in McCafferty et al., *Nature,* 348:552-554 (1990). Clackson el al., *Nature,* 352:624-628 (1991) and Marks et al., *J. Mol. Biol.,* 222:581-597 (1991). Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nucl. Acids Res.,* 21:2265-2266 (1993)). Thus, these techniques are viable alternatives to traditional monoclonal antibody hybridoma techniques for isolation of monoclonal antibodies.

The DNA also may be modified, for example, by substituting the coding sequence (U.S. Pat. No. 4,816,567; Morrison, et al., *Proc. Natl Acad. Sci. USA,* 81:6851 (1984)), or by covalently joining to the coding sequence all or part of the coding sequence for a non-immunoglobulin polypeptide. Such non-immunoglobulin polypeptides can be substituted to create a chimeric bivalent antibody comprising one antigen-combining site having specificity for an antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

For eukaryotic expression, the vector components generally include, but are not limited to, one or more of the following, a signal sequence, an origin of replication, one or more marker genes, and enhancer element, a promoter, and a transcription termination sequence.

A vector for use in a eukaryotic host may also an insert that encodes a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available. The DNA for such precursor region can be ligated in reading frame to DNA encoding the antibodies of the present application.

Generally, the origin of replication component is not needed for mammalian expression vectors (the SV40 origin may typically be used only because it contains the early promoter).

Expression and cloning vectors may contain a selection gene, also termed a selectable marker. Selection genes may encode proteins that confer resistance to antibiotics or other toxins, e.g., ampicillin, neomycin, methotrexate, or tetracycline; complement auxotrophic deficiencies; or supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up nucleic acid encoding the antibodies of the present application. For example, cells transformed with the DHFR selection gene are first identified by culturing all of the transformants in a culture medium that contains methotrexate (Mtx), a competitive antagonist of DHFR. An exemplary appropriate host cell when wild-type DHFR is employed is the Chinese hamster ovary (CHO) cell line deficient in DHFR activity. Alternatively, host cells (particularly wild-type hosts that contain endogenous DHFR) transformed or co-transformed with the polypeptide encoding-DNA sequences, wild-type DHFR protein, and another selectable marker such as aminoglycoside 3'-phosphotransferase (APH) can be selected by cell growth in medium containing a selection agent for the selectable marker such as an aminoglycosidic antibiotic.

Expression and cloning vectors usually contain a promoter that is recognized by the host organism and is operably linked to the nucleic acid encoding the desired polypeptide sequences. Eukaryotic genes have an AT-rich region located approximately 25 to 30 based upstream from the site where transcription is initiated. Another sequence found 70 to 80 bases upstream from the start of the transcription of many genes may be included. The 3' end of most eukaryotic may be the signal for addition of the poly A tail to the 3' end of the coding sequence. All of these sequences may be inserted into eukaryotic expression vectors.

Polypeptide transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

Transcription of a DNA encoding the antibodies of the present disclosure by higher eukaryotes is often increased by inserting an enhancer sequence into the vector. Many enhancer sequences are now known from mammalian genes (globin, elastase, albumin, α-fetoprotein, and insulin). Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the polypeptide encoding sequence, but is preferably located at a site 5' from the promoter.

Expression vectors used in eukaryotic host cells (yeast, fungi, insect, plant, animal, human, or nucleated cells from other multicellular organisms) also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the polypeptide-encoding mRNA. One useful transcription termination component is the bovine growth hormone polyadenylation region.

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/−DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2).

Host cells can be transformed with the above-described expression or cloning vectors for antibodies production and cultured in conventional nutrient media modified as appropriate for inducing promoters, selecting transformants, or amplifying the genes encoding the desired sequences.

The host cells used to produce the antibodies of the present application may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255

(1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibodies can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The protein composition prepared from the cells can be purified using, for example, hydroxylapatite chromatography, gel electrophoresis, dialysis, and affinity chromatography, with affinity chromatography being the preferred purification technique. The matrix to which the affinity ligand is attached is most often agarose, but other matrices are available. Mechanically stable matrices such as controlled pore glass or poly (styrene-divinyl) benzene allow for faster flow rates and shorter processing times than can be achieved with agarose. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered. Following any preliminary purification step(s), the mixture comprising the antibody of interest and contaminants may be subjected to low pH hydrophobic interaction chromatography.

Polynucleic acid sequences encoding the antibodies of the present disclosure can be obtained using standard recombinant techniques. Desired polynucleic acid sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present disclosure. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to, an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as GEM™-11 may be utilized in making a recombinant vector which can be used to transform susceptible host cells such as *E. coli* LE392.

The expression vector of the present application may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the present antibody by removing the promoter from the source DNA via restriction enzyme digestion and inserting the isolated promoter sequence into the vector of the present application. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the—galactanase and lactose promoter systems, a tryptophan (trp) promoter system and hybrid promoters such as the tac or the trc promoter. However, other promoters that are functional in bacteria (such as other known bacterial or phage promoters) are suitable as well. Their nucleic acid sequences have been published, thereby enabling a skilled worker operably to ligate them to cistrons encoding the target peptide (Siebenlist et al. *Cell* 20: 269 (1980)) using linkers or adaptors to supply any required restriction sites.

In one aspect, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence can be substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP.

In some embodiments, the production of the antibodies according to the present disclosure can occur in the cytoplasm of the host cell, and therefore does not require the presence of secretion signal sequences within each cistron. Certain host strains (e.g., the *E. coli* $trxB^-$ strains) provide cytoplasm conditions that are favorable for disulfide bond formation, thereby permitting proper folding and assembly of expressed protein subunits.

Prokaryotic host cells suitable for expressing the antibodies of the present disclosure include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla*, or *Paracoccus*. In some embodiments, gram-negative cells are used. In one embodiment, *E. coli* cells are used as hosts. Examples of *E. coli* strains include strain W3110 (Bachmann, *Cellular and Molecular Biology*, vol. 2 (Washington, D.C.: American Society for Microbiology, 1987), pp. 1190-1219; ATCC Deposit No. 27,325) and derivatives thereof, including strain 33D3 having genotype W3110 AfhuA (AtonA) ptr3 lac Iq lacL8 AompT A(nmpc-fepE) degP41 $kan^R$ (U.S. Pat. No. 5,639,635). Other strains and derivatives thereof, such as *E. coli* 294 (ATCC 31,446), *E. coli* B, *E. coli* 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli, Serratia*, or *Salmonella* species can be suitably used as the host when well known plasmids such as pBR322, pBR325, pACYC177, or pKN410 are used to supply the replicon.

Typically the host cell should secrete minimal amounts of proteolytic enzymes, and additional protease inhibitors may desirably be incorporated in the cell culture.

Host cells are transformed with the above-described expression vectors and cultured in conventional nutrient media modified as appropriate for inducing promoters, selecting transformants, or amplifying the genes encoding the desired sequences. Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the antibodies of the present application are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol. The prokaryotic host cells are cultured at suitable temperatures and pHs.

If an inducible promoter is used in the expression vector of the present application, protein expression is induced under conditions suitable for the activation of the promoter. In one aspect of the present application, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., *J. Immunol. Methods* 263:133-147 (2002)). A variety of other inducers may be used, according to the vector construct employed, as is known in the art.

The expressed antibodies of the present disclosure are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Alternatively, protein production is conducted in large quantity by a fermentation process. Various large-scale fed-batch fermentation procedures are available for production of recombinant proteins. To improve the production yield and quality of the antibodies of the present disclosure, various fermentation conditions can be modified. For example, the chaperone proteins have been demonstrated to facilitate the proper folding and solubility of heterologous proteins produced in bacterial host cells. Chen et al. *J Bio Chem* 274:19601-19605 (1999); U.S. Pat. Nos. 6,083,715; 6,027,888; Bothmann and Pluckthun, J. Biol. Chem. 275:17100-17105 (2000); Ramm and Pluckthun, J. Biol. Chem. 275:17106-17113 (2000); Arie et al., *Mol. Microbiol.* 39:199-210 (2001).

To minimize proteolysis of expressed heterologous proteins (especially those that are proteolytically sensitive), certain host strains deficient for proteolytic enzymes can be used for the present invention, as described in, for example, U.S. Pat. Nos. 5,264,365; 5,508,192; Hara et al., *Microbial Drug Resistance,* 2:63-72 (1996). *E. coli* strains deficient for proteolytic enzymes and transformed with plasmids overexpressing one or more chaperone proteins may be used as host cells in the expression system encoding the antibodies of the present application.

The antibodies produced herein can be further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75. Protein A immobilized on a solid phase for example can be used in some embodiments for immunoaffinity purification of binding molecules of the present disclosure. The solid phase to which Protein A is immobilized is preferably a column comprising a glass or silica surface, more preferably a controlled pore glass column or a silicic acid column. In some embodiments, the column has been coated with a reagent, such as glycerol, in an attempt to prevent nonspecific adherence of contaminants. The solid phase is then washed to remove contaminants non-specifically bound to the solid phase. Finally the antibodies of interest is recovered from the solid phase by elution.

5.2.7. Binding Molecules Comprising the Single Domain Antibodies

In another aspect, provided herein is a binding molecule comprising a single domain antibody (e.g., a VHH domain against GUCY2C) provided herein. In addition to chimeric antigen receptors (CARs) provided herein as described in Section 5.3 below, in some embodiments, a single domain antibody against GUCY2C provided herein is part of other binding molecules. Exemplary binding molecules of the present disclosure such as fusion proteins and immunoconjugates are described herein.

In various embodiments, the single domain antibody provided herein can be genetically fused or chemically conjugated to another agent, for example, protein-based entities. The single domain antibody may be chemically-conjugated to the agent, or otherwise non-covalently conjugated to the agent. The agent can be a peptide or antibody (or a fragment thereof).

Thus, in some embodiments, provided herein are single domain antibodies (e.g., VHH domains) that are recombinantly fused or chemically conjugated (covalent or non-covalent conjugations) to a heterologous protein or polypeptide (or fragment thereof, for example, to a polypeptide of about 10, about 20, about 30, about 40, about 50, about 60, about 70, about 80, about 90, about 100, about 150, about 200, about 250, about 300, about 350, about 400, about 450 or about 500 amino acids, or over 500 amino acids) to generate fusion proteins, as well as uses thereof. In particular, provided herein are fusion proteins comprising an antigen-binding fragment of the single domain antibody provided herein (e.g., CDR1, CDR2, and/or CDR3) and a heterologous protein, polypeptide, or peptide.

Moreover, antibodies provided herein can be fused to marker or "tag" sequences, such as a peptide, to facilitate purification. In specific embodiments, the marker or tag amino acid sequence is a hexa-histidine peptide, hemagglutinin ("HA") tag, and "FLAG" tag.

Methods for fusing or conjugating moieties (including polypeptides) to antibodies are known (see, e.g., Arnon et al., Monoclonal Antibodies for Immunotargeting of Drugs in Cancer Therapy, in Monoclonal Antibodies and Cancer Therapy 243-56 (Reisfeld et al. eds., 1985); Hellstrom et al., Antibodies for Drug Delivery, in Controlled Drug Delivery 623-53 (Robinson et al. eds., 2d ed. 1987); Thorpe, Antibody Carriers of Cytotoxic Agents in Cancer Therapy: A Review, in Monoclonal Antibodies: Biological and Clinical Applications 475-506 (Pinchera et al. eds., 1985); Analysis, Results, and Future Prospective of the Therapeutic Use of Radiolabeled Antibody in Cancer Therapy, in Monoclonal Antibodies for Cancer Detection and Therapy 303-16 (Baldwin et al. eds., 1985); Thorpe et al., Immunol. Rev. 62:119-58 (1982); U.S. Pat. Nos. 5,336,603; 5,622,929; 5,359,046; 5,349,053; 5,447,851; 5,723,125; 5,783,181; 5,908,626; 5,844,095; and 5,112,946; EP 307,434; EP 367,166; EP 394,827; PCT publications WO 91/06570, WO 96/04388, WO 96/22024, WO 97/34631, and WO 99/04813; Ashkenazi et al., Proc. Natl. Acad. Sci. USA, 88: 10535-39 (1991); Traunecker et al., Nature, 331:84-86 (1988); Zheng et al., J. Immunol. 154:5590-600 (1995); and Vil et al., Proc. Natl. Acad. Sci. USA 89:11337-41 (1992)).

Fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of the single domain antibodies as provided herein, including, for example, antibodies with higher affinities and lower dissociation rates (see, e.g., U.S. Pat. Nos. 5,605,793; 5,811,238; 5,830,721; 5,834,252; and 5,837,458; Patten et al., Curr. Opinion Biotechnol. 8:724-33 (1997); Harayama, Trends Biotechnol. 16(2):76-82 (1998); Hansson et al., J. Mol. Biol. 287:265-76 (1999); and Lorenzo and Blasco, Biotechniques 24(2):308-13 (1998)). Antibodies, or the encoded antibodies, may be altered by being subjected to random mutagenesis by error-prone PCR, random nucleotide insertion, or other methods prior to recombination. A polynucleotide encoding an antibody provided herein may be recombined with one or more components, motifs, sections, parts, domains, fragments, etc. of one or more heterologous molecules.

In some embodiments, a single domain antibody provided herein (e.g., VHH domain) is conjugated to a second antibody to form an antibody heteroconjugate.

In various embodiments, the single domain antibody is genetically fused to the agent. Genetic fusion may be accomplished by placing a linker (e.g., a polypeptide) between the single domain antibody and the agent. The linker may be a flexible linker.

In various embodiments, the single domain antibody is genetically conjugated to a therapeutic molecule, with a hinge region linking the single domain antibody to the therapeutic molecule.

Also provided herein are methods for making the various fusion proteins provided herein. The various methods described in Section 5.2.6 above may also be utilized to make the fusion proteins provided herein.

In a specific embodiment, the fusion protein provided herein is recombinantly expressed. Recombinant expression of a fusion protein provided herein may require construction of an expression vector containing a polynucleotide that encodes the protein or a fragment thereof. Once a polynucleotide encoding a protein provided herein or a fragment thereof has been obtained, the vector for the production of the molecule may be produced by recombinant DNA technology using techniques well-known in the art. Thus, methods for preparing a protein by expressing a polynucleotide containing an encoding nucleotide sequence are described herein. Methods which are well known to those skilled in the art can be used to construct expression vectors containing coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding a fusion protein provided herein, or a fragment thereof, or a CDR, operably linked to a promoter.

The expression vector can be transferred to a host cell by conventional techniques and the transfected cells are then cultured by conventional techniques to produce a fusion protein provided herein. Thus, also provided herein are host cells containing a polynucleotide encoding a fusion protein provided herein or fragments thereof operably linked to a heterologous promoter.

A variety of host-expression vector systems may be utilized to express the fusion protein provided herein. Such host-expression systems represent vehicles by which the coding sequences of interest may be produced and subsequently purified, but also represent cells which may, when transformed or transfected with the appropriate nucleotide coding sequences, express a fusion protein provided herein in situ. These include but are not limited to microorganisms such as bacteria (e.g., *E. coli* and *B. subtilis*) transformed with recombinant bacteriophage DNA, plasmid DNA or cosmid DNA expression vectors containing coding sequences; yeast (e.g., *Saccharomyces* pichia) transformed with recombinant yeast expression vectors containing coding sequences; insect cell systems infected with recombinant virus expression vectors (e.g., baculovirus) containing coding sequences; plant cell systems infected with recombinant virus expression vectors (e.g., cauliflower mosaic virus, CaMV, tobacco mosaic virus, TMV) or transformed with recombinant plasmid expression vectors (e.g., Ti plasmid) containing coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Bacterial cells such as *Escherichia coli*, or, eukaryotic cells, especially for the expression of whole recombinant antibody molecule, can be used for the expression of a recombinant fusion protein. For example, mammalian cells such as Chinese hamster ovary cells (CHO), in conjunction with a vector such as the major intermediate early gene promoter element from human cytomegalovirus is an effective expression system for antibodies or variants thereof. In a specific embodiment, the expression of nucleotide sequences encoding the fusion proteins provided herein is regulated by a constitutive promoter, inducible promoter or tissue specific promoter.

In bacterial systems, a number of expression vectors may be advantageously selected depending upon the use intended for the fusion protein being expressed. For example, when a large quantity of such a fusion protein is to be produced, for the generation of pharmaceutical compositions of a fusion protein, vectors which direct the expression of high levels of fusion protein products that are readily purified may be desirable. Such vectors include, but are not limited to, the *E. coli* expression vector pUR278 (Ruther et al., EMBO 12:1791 (1983)), in which the coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the fusion protein in infected hosts (e.g., see Logan & Shenk, Proc. Natl. Acad. Sci. USA 8 1:355-359 (1984)). Specific initiation signals may also be required for efficient translation of inserted coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any immunoglobulin chains), CRL7O3O and HsS78Bst cells.

For long-term, high-yield production of recombinant proteins, stable expression can be utilized. For example, cell lines which stably express the fusion proteins may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the fusion protein. Such engineered cell lines may be particularly useful in screening and evaluation of compositions that interact directly or indirectly with the binding molecule.

A number of selection systems may be used, including but not limited to, the herpes simplex virus thymidine kinase (Wigler et al., Cell 11:223 (1977)), hypoxanthineguanine phosphoribosyltransferase (Szybalska & Szybalski, Proc. Natl. Acad. Sci. USA 48:202 (1992)), and adenine phosphoribosyltransferase (Lowy et al., Cell 22:8-17 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIB TECH 11(5):155-2 15 (1993)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), *Current Protocols in Molecular Biology*, John Wiley & Sons, N Y (1993); Kriegler, *Gene Transfer and Expression*, A Laboratory Manual, Stockton Press, N Y (1990); and in Chapters 12 and 13, Dracopoli et al. (eds.), *Current Protocols in Human Genetics*, John Wiley & Sons, N Y (1994); Colberre-Garapin et al., J. Mol. Biol. 150:1 (1981), which are incorporated by reference herein in their entireties.

The expression level of a fusion protein can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing a fusion protein is amplifiable, increase in the level of inhibitor present in culture of host cell will increase the number of copies of the marker gene. Since the amplified region is associated with the fusion protein gene, production of the fusion protein will also increase (Crouse et al., Mol. Cell. Biol. 3:257 (1983)).

The host cell may be co-transfected with multiple expression vectors provided herein. The vectors may contain identical selectable markers which enable equal expression of respective encoding polypeptides. Alternatively, a single vector may be used which encodes, and is capable of expressing multiple polypeptides. The coding sequences may comprise cDNA or genomic DNA.

Once a fusion protein provided herein has been produced by recombinant expression, it may be purified by any method known in the art for purification of a polypeptide (e.g., an immunoglobulin molecule), for example, by chromatography (e.g., ion exchange, affinity, particularly by affinity for the specific antigen after Protein A, sizing column chromatography, and Kappa select affinity chromatography), centrifugation, differential solubility, or by any other standard technique for the purification of proteins. Further, the fusion protein molecules provided herein can be fused to heterologous polypeptide sequences described herein or otherwise known in the art to facilitate purification.

In some embodiments, the present disclosure also provides immunoconjugates comprising any of the antibodies (such as anti-GUCY2C single domain antibodies) described herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In some embodiments, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In some embodiments, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In some embodiments, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or 1123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

The linker may be a "cleavable linker" facilitating release of the conjugated agent in the cell, but non-cleavable linkers are also contemplated herein. Linkers for use in the conjugates of the present disclosure include, without limitation, acid labile linkers (e.g., hydrazone linkers), disulfide-containing linkers, peptidase-sensitive linkers (e.g., peptide linkers comprising amino acids, for example, valine and/or citrulline such as citrulline-valine or phenylalanine-lysine), photolabile linkers, dimethyl linkers, thioether linkers, or hydrophilic linkers designed to evade multidrug transporter-mediated resistance.

The immunuoconjugates or ADCs herein contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A).

In other embodiments, antibodies provided herein are conjugated or recombinantly fused, e.g., to a diagnostic molecule. Such diagnosis and detection can be accomplished, for example, by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin or avidin/biotin; fluorescent materials, such as, but not limited to, umbelliferone, fluorescein, fluorescein isothiocynate, rhodamine, dichlorotriazinylamine fluorescein, dansyl chloride, or phycoerythrin; luminescent materials, such as, but not limited to, luminol; bioluminescent materials, such as, but not limited to, luciferase, luciferin, or aequorin; chemiluminescent material, such as, 225Acγ-emitting, Auger-emitting, β-emitting, an alpha-emitting or positron-emitting radioactive isotope.

5.3. Chimeric Antigen Receptors

In another aspect, provided herein is a chimeric antigen receptor (CAR) comprising an extracellular antigen binding domain comprising at least one single domain antibody (e.g., VHH) provided herein that binds to GUCY2C. Exemplary CARs comprising the present VHH domains (i.e., VHH-based CARs) are illustrated and their superior effects are demonstrated as described in Section 6 below.

In some embodiments, the chimeric antigen receptor (CAR) provided herein comprises a polypeptide comprising: (a) an extracellular antigen binding domain comprising at least one single domain antibody (sdAb) specifically binding to GUCY2C as provided herein, and optionally one or more additional binding domain(s); (b) a transmembrane domain; and (c) an intracellular signaling domain. Each components and additional regions are described in more detail below.

5.3.1. Extracellular Antigen Binding Domain

The extracellular antigen binding domain of the CARs described herein comprises one or more (such as any one of 1, 2, 3, 4, 5, 6 or more) single domain antibodies. The single domain antibodies can be fused to each other directly via peptide bonds, or via peptide linkers.

Single Domain Antibodies

The CARs of the present disclosure comprise an extracellular antigen binding domain comprising one or more single domain antibodies. The sdAbs may be of the same or different origins, and of the same or different sizes. Exemplary sdAbs include, but are not limited to, heavy chain variable domains from heavy-chain only antibodies (e.g., VHH or VNAR), binding molecules naturally devoid of light chains, single domains (such as VH or VL) derived from conventional 4-chain antibodies, humanized heavy-chain only antibodies, human single domain antibodies produced by transgenic mice or rats expressing human heavy chain segments, and engineered domains and single domain scaffolds other than those derived from antibodies. Any sdAbs known in the art or developed by the present disclosure, including the single domain antibodies described above in the present disclosure, may be used to construct the CARs described herein. The sdAbs may be derived from any species including, but not limited to mouse, rat, human, camel, llama, lamprey, fish, shark, goat, rabbit, and bovine. Single domain antibodies contemplated herein also include naturally occurring single domain antibody molecules from species other than Camelidae and sharks.

In some embodiments, the sdAb is derived from a naturally occurring single domain antigen binding molecule known as heavy chain antibody devoid of light chains (also referred herein as "heavy chain only antibodies"). Such single domain molecules are disclosed in WO 94/04678 and Hamers-Casterman, C. et al., *Nature* 363:446-448 (1993), for example. For clarity reasons, the variable domain derived from a heavy chain molecule naturally devoid of light chain is known herein as a VHH to distinguish it from the conventional VH of four chain immunoglobulins. Such a VHH molecule can be derived from antibodies raised in Camelidae species, for example, camel, llama, vicuna, dromedary, alpaca and guanaco. Other species besides Camelidae may produce heavy chain molecules naturally devoid of light chain, and such VHHs are within the scope of the present disclosure. In addition, humanized versions of VHHs as well as other modifications and variants are also contemplated and within the scope of the present disclosure.

VHH molecules from Camelids are about 10 times smaller than IgG molecules. They are single polypeptides and can be very stable, resisting extreme pH and temperature conditions. Moreover, they can be resistant to the action of proteases which is not the case for conventional 4-chain antibodies. Furthermore, in vitro expression of VHHs produces high yield, properly folded functional VHHs. In addition, antibodies generated in Camelids can recognize epitopes other than those recognized by antibodies generated in vitro through the use of antibody libraries or via immunization of mammals other than Camelids (see, for example, WO9749805). As such, multispecific or multivalent CARs comprising one or more VHH domains may interact more efficiently with targets than multispecific or multivalent CARs comprising antigen binding fragments derived from conventional 4-chain antibodies. Since VHHs are known to bind into "unusual" epitopes such as cavities or grooves, the affinity of CARs comprising such VHHs may be more suitable for therapeutic treatment than conventional multispecific polypeptides.

In some embodiments, the sdAb is derived from a variable region of the immunoglobulin found in cartilaginous fish. For example, the sdAb can be derived from the immunoglobulin isotype known as Novel Antigen Receptor (NAR) found in the serum of shark. Methods of producing single domain molecules derived from a variable region of NAR ("IgNARs") are described in WO 03/014161 and Streltsov, *Protein Sci.* 14:2901-2909 (2005).

In some embodiments, the sdAb is recombinant, CDR-grafted, humanized, camelized, de-immunized and/or in vitro generated (e.g., selected by phage display). In some embodiments, the amino acid sequence of the framework regions may be altered by "camelization" of specific amino acid residues in the framework regions. Camelization refers to the replacing or substitution of one or more amino acid residues in the amino acid sequence of a (naturally occurring) VH domain from a conventional 4-chain antibody by one or more of the amino acid residues that occur at the corresponding position(s) in a VHH domain of a heavy chain antibody. This can be performed in a manner known in the field, which will be clear to the skilled person. Such "camelizing" substitutions are preferably inserted at amino acid positions that form and/or are present at the $V_H$-$V_L$ interface, and/or at the so-called Camelidae hallmark residues, as defined herein (see for example WO 94/04678, Davies and Riechmann FEBS Letters 339: 285-290 (1994); Davies and Riechmann, Protein Engineering 9 (6): 531-537 (1996); Riechmann, J. Mol. Biol. 259: 957-969 (1996); and Riechmann and Muyldermans, J. Immunol. Meth. 231: 25-38 (1999)).

In some embodiments, the sdAb is a human single domain antibody produced by transgenic mice or rats expressing human heavy chain segments. See, e.g., US20090307787, U.S. Pat. No. 8,754,287, US20150289489, US20100122358, and WO2004049794. In some embodiments, the sdAb is affinity matured.

In some embodiments, naturally occurring VHH domains against a particular antigen or target, can be obtained from (naïve or immune) libraries of Camelid VHHsequences. Such methods may or may not involve screening such a library using said antigen or target, or at least one part, fragment, antigenic determinant or epitope thereof using one or more screening techniques known in the field. Alternatively, improved synthetic or semi-synthetic libraries derived from (naïve or immune) VHHlibraries may be used, such as VHHlibraries obtained from (naïve or immune) VHHlibraries by techniques such as random mutagenesis and/or CDR shuffling.

In some embodiments, the single domain antibodies are generated from conventional four-chain antibodies. See, for example, EP 0 368 684; Ward et al., Nature, 341 (6242): 544-6 (1989); Holt et al., Trends Biotechnol., 21(11):484-490 (2003); WO 06/030220; and WO 06/003388.

In some embodiments, the extracellular antigen binding domain provided herein comprises at least one binding domain, and the at least one binding domain comprises a single domain antibody that binds to GUCY2C as provided herein, e.g., the anti-GUCY2C single domain antibodies described in Section 5.2 above.

In some embodiments, provided herein is a CAR comprising a polypeptide comprising: (a) an extracellular antigen binding domain comprising an anti-GUCY2C sdAb; (b) a transmembrane domain; and (c) an intracellular signaling domain, wherein the anti-GUCY2C sdAb is an anti-GUCY2C sdAb as described in Section 5.2 above, including, e.g., the VHH domains in Table 7 and those having one, two or all three CDRs in any of those VHH domains in Table 7. In some embodiments, the anti-GUCY2C sdAb is camelid, chimeric, human, or humanized.

In some embodiments, provided herein is a CAR comprising a polypeptide comprising: (a) an extracellular antigen binding domain comprising an anti-GUCY2C sdAb; (b) a transmembrane domain; and (c) an intracellular signaling domain, wherein the anti-GUCY2C sdAb comprises the amino acid sequence of SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In other embodiments, provided herein is a CAR comprising a polypeptide comprising: (a) an extracellular antigen binding domain comprising an anti-GUCY2C sdAb; (b) a transmembrane domain; and (c) an intracellular signaling domain, wherein the anti-GUCY2C sdAb comprises an amino acid sequence having at least 75%, 80%, 85%, 86%, 87%, 88%, 89%, 90%, 91%, 92%, 93%, 94%, 95%, 96%, 97%, 98%, 99%, or 100% sequence identify to the amino acid sequence of SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

In other embodiments, the extracellular antigen binding domain comprises two or more antigen binding domains. Among these two or more antigen binding domains, at least one is a VHH that binds to GUCY2C as provided herein. In some embodiments, the one or more additional binding domain(s) is/are also VHH(s) that bind(s) to GUCY2C. In other embodiments, the one or more additional binding domain(s) bind(s) to one or more additional different antigen (s), e.g., 1, 2, 3, 4 or more additional single domain antibody binding regions (sdAbs) targeting one or more additional different antigen(s).

In some embodiments, provided herein is a multivalent (such as bivalent and trivalent) CAR comprising a polypeptide comprising: (a) an extracellular antigen binding domain comprising two or more single domain antibodies (sdAbs) specifically binding to GUCY2C; (b) a transmembrane domain; and (c) an intracellular signaling domain. In some embodiments, the extracellular antigen binding domain comprises two single domain antibodies (sdAbs) specifically binding to GUCY2C provided herein. In other embodiments, the extracellular antigen binding domain comprises three single domain antibodies (sdAbs) specifically binding to GUCY2C provided herein. In some embodiments, the two or more anti-GUCY2C sdAbs are selected from those anti-GUCY2C sdAbs described in Section 5.2 above, including, e.g., the VHH domains in Table 7 and those having one, two or all three CDRs in any of those VHH domains in Table 7. In some embodiments, the anti-GUCY2CsdAb is camelid, chimeric, human, or humanized. In some embodiments, the two or more anti-GUCY2C sdAbs are each independently selected from anti-GUCY2C sdAbs comprising an amino acid sequence having at least 75%, 80%, 85%, 86%, 87%, 88%, 89%, 90%, 91%, 92%, 93%, 94%, 95%, 96%, 97%, 98%, 99%, or 100% sequence identify to the amino acid sequence of SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

In other embodiments, provided herein is a multispecific (such as bispecific and trispecific) CAR comprising a polypeptide comprising: (a) an extracellular antigen binding domain comprising a first single domain antibody (sdAb) specifically binding to GUCY2C; (b) a transmembrane domain; and (c) an intracellular signaling domain. In some embodiments, the CAR further comprises a second single domain antibody (sdAb) specifically binding to a second antigen (such as a second tumor antigen). In some embodiments, the CAR further comprises a second single domain antibody (sdAb) specifically binding to a second antigen (such as a second tumor antigen); and a third single domain antibody (sdAb) specifically binding to a third antigen (such as a third tumor antigen).

In some embodiments, the additional antigen(s) targeted by the CARs of the present disclosure are cell surface molecules. The single domain antibodies may be chosen to recognize an antigen that acts as a cell surface marker on target cells associated with a special disease state. In some embodiments, the antigen is a tumor antigen. Tumors express a number of proteins that can serve as a target antigen for an immune response, particularly T cell mediated immune responses. The antigens targeted by the CAR may be antigens on a single diseased cell or antigens that are expressed on different cells that each contribute to the disease. The antigens targeted by the CAR may be directly or indirectly involved in the diseases. In some embodiments, the tumor antigen comprises one or more antigenic cancer epitopes associated with a malignant tumor. In some embodiments, the tumor antigen is a tumor-specific antigen (TSA) or a tumor-associated antigen (TAA). A TSA is unique to tumor cells and does not occur on other cells in the body. A TAA associated antigen is not unique to a tumor cell, and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development, when the immune system is immature, and unable to respond or they may be antigens that are normally present at extremely low levels on normal cells, but which are expressed at much higher levels on tumor cells.

In addition to the one or more antigen binding domain(s) provided herein, the CAR provided herein may further comprise one or more of the following: a linker (e.g., a peptide linker), a transmembrane domain, a hinge region, a signal peptide, an intracellular signaling domain, a co-stimulatory signaling domain, each of which is described in more detail below.

For example, in some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, ligands of CD83 and combinations thereof. In some embodiments, the co-stimulatory signaling domain is derived from CD137. In some embodiments, the GUCY2C CAR further comprises a hinge domain (such as a CD8α hinge domain) located between the C-terminus of the extracellular antigen binding domain and the N-terminus of the transmembrane domain. In some embodiments, the GUCY2C CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen-binding domain, a CD8α hinge domain, a CD8α transmembrane domain, a co-stimulatory signaling domain derived from CD137 (4-1BB), and a primary intracellular signaling domain derived from CD3ζ. In some specific embodiments, the CAR provided herein comprises from N terminus to C terminus: a CD8 signal peptide comprising the amino acid sequence of SEQ ID NO: 47, an extracellular antigen binding domain comprising one or more sdAb(s) provided herein, a CD8 hinge comprising the amino acid sequence of SEQ ID NO: 43, a CD8 transmembrane region comprising the amino acid sequence of SEQ ID NO: 44, a 4-1BB co-stimulatory signaling domain comprising the amino acid sequence of SEQ ID NO: 44, and a CD3z intracellular signaling domain comprising the amino acid sequence of SEQ ID NO: 46. In some embodiments, the GUCY2C CAR is monospecific. In some embodiments, the GUCY2C CAR is monovalent. In other embodiments, the GUCY2C CAR is multivalent.

5.3.2. Signal Peptide

The CARs of the present disclosure may comprise a signal peptide (also known as a signal sequence) at the N-terminus of the polypeptide. In general, signal peptides are peptide sequences that target a polypeptide to the desired site in a cell. In some embodiments, the signal peptide targets the effector molecule to the secretory pathway of the cell and will allow for integration and anchoring of the effector molecule into the lipid bilayer. Signal peptides including signal sequences of naturally occurring proteins or synthetic, non-naturally occurring signal sequences, which are compatible for use in the CARs described herein will be evident to one of skill in the art. In some embodiments, the signal peptide is derived from a molecule selected from the group consisting of CD8α, GM-CSF receptor a, and IgG1 heavy chain. In some embodiments, the signal peptide is derived from CD8α. In some embodiments, the signal peptide of CD8α comprises the amino acid sequence of SEQ ID NO: 47.

5.3.3. Hinge Region

The CARs of the present disclosure may comprise a hinge domain that is located between the extracellular antigen binding domain and the transmembrane domain. A hinge domain is an amino acid segment that is generally found between two domains of a protein and may allow for flexibility of the protein and movement of one or both of the domains relative to one another. Any amino acid sequence that provides such flexibility and movement of the extracellular antigen binding domain relative to the transmembrane domain of the effector molecule can be used.

The hinge domain may contain about 10-100 amino acids, e.g., about any one of 15-75 amino acids, 20-50 amino acids, or 30-60 amino acids. In some embodiments, the hinge domain may be at least about any one of 10, 11, 12, 13, 14, 15, 16, 17, 18, 19, 20, 21, 22, 23, 24, 25, 26, 27, 28, 29, 30, 35, 40, 45, 50, 55, 60, 65, 70, or 75 amino acids in length.

In some embodiments, the hinge domain is a hinge domain of a naturally occurring protein. Hinge domains of any protein known in the art to comprise a hinge domain are compatible for use in the chimeric receptors described herein. In some embodiments, the hinge domain is at least a portion of a hinge domain of a naturally occurring protein and confers flexibility to the chimeric receptor. In some embodiments, the hinge domain is derived from CD8α. In some embodiments, the hinge domain is a portion of the hinge domain of CD8α, e.g., a fragment containing at least 15 (e.g., 20, 25, 30, 35, or 40) consecutive amino acids of the hinge domain of CD8α. In some embodiments, the hinge domain of CD8α comprises the amino acid sequence of SEQ ID NO: 43.

Hinge domains of antibodies, such as an IgG, IgA, IgM, IgE, or IgD antibodies, are also compatible for use in the pH-dependent chimeric receptor systems described herein. In some embodiments, the hinge domain is the hinge domain that joins the constant domains CH1 and CH2 of an antibody. In some embodiments, the hinge domain is of an antibody and comprises the hinge domain of the antibody and one or more constant regions of the antibody. In some embodiments, the hinge domain comprises the hinge domain of an antibody and the CH3 constant region of the antibody. In some embodiments, the hinge domain comprises the hinge domain of an antibody and the CH2 and CH3 constant regions of the antibody. In some embodiments, the antibody is an IgG, IgA, IgM, IgE, or IgD antibody. In some embodiments, the antibody is an IgG antibody. In some embodiments, the antibody is an IgG1, IgG2, IgG3, or IgG4 antibody. In some embodiments, the hinge region comprises the hinge region and the CH2 and CH3 constant regions of an IgG1 antibody. In some embodiments, the hinge region comprises the hinge region and the CH3 constant region of an IgG1 antibody.

Non-naturally occurring peptides may also be used as hinge domains for the chimeric receptors described herein. In some embodiments, the hinge domain between the C-terminus of the extracellular ligand-binding domain of an Fc receptor and the N-terminus of the transmembrane domain is a peptide linker, such as a (G×S)n linker, wherein x and n, independently can be an integer between 3 and 12, including 3, 4, 5, 6, 7, 8, 9, 10, 11, 12, or more.

5.3.4. Transmembrane Domain

The CARs of the present disclosure comprise a transmembrane domain that can be directly or indirectly fused to the extracellular antigen binding domain. The transmembrane domain may be derived either from a natural or from a synthetic source. As used herein, a "transmembrane domain" refers to any protein structure that is thermodynamically stable in a cell membrane, preferably an eukaryotic cell membrane. Transmembrane domains compatible for use in the CARs described herein may be obtained from a naturally occurring protein. Alternatively, it can be a synthetic, non-naturally occurring protein segment, e.g., a hydrophobic protein segment that is thermodynamically stable in a cell membrane.

Transmembrane domains are classified based on the three dimensional structure of the transmembrane domain. For example, transmembrane domains may form an alpha helix, a complex of more than one alpha helix, a beta-barrel, or any other stable structure capable of spanning the phospholipid bilayer of a cell. Furthermore, transmembrane domains may also or alternatively be classified based on the transmembrane domain topology, including the number of passes that the transmembrane domain makes across the membrane and the orientation of the protein. For example, single-pass membrane proteins cross the cell membrane once, and multi-pass membrane proteins cross the cell membrane at least twice (e.g., 2, 3, 4, 5, 6, 7 or more times). Membrane proteins may be defined as Type I, Type II or Type III depending upon the topology of their termini and membrane-passing segment(s) relative to the inside and outside of the cell. Type I membrane proteins have a single membrane-spanning region and are oriented such that the N-terminus of the protein is present on the extracellular side of the lipid bilayer of the cell and the C-terminus of the protein is present on the cytoplasmic side. Type II membrane proteins also have a single membrane-spanning region but are oriented such that the C-terminus of the protein is present on the extracellular side of the lipid bilayer of the cell and the N-terminus of the protein is present on the cytoplasmic side. Type III membrane proteins have multiple membrane-spanning segments and may be further sub-classified based on the number of transmembrane segments and the location of N- and C-termini.

In some embodiments, the transmembrane domain of the CAR described herein is derived from a Type I single-pass membrane protein. In some embodiments, transmembrane domains from multi-pass membrane proteins may also be compatible for use in the CARs described herein. Multi-pass membrane proteins may comprise a complex (at least 2, 3, 4, 5, 6, 7 or more) alpha helices or a beta sheet structure. In some embodiments, the N-terminus and the C-terminus of a multi-pass membrane protein are present on opposing sides of the lipid bilayer, e.g., the N-terminus of the protein is present on the cytoplasmic side of the lipid bilayer and the C-terminus of the protein is present on the extracellular side.

In some embodiments, the transmembrane domain of the CAR comprises a transmembrane domain chosen from the transmembrane domain of an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL-2R beta, IL-2R gamma, IL-7R a, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRT AM, Ly9 (CD229), CD160 (BY55), PSGL1, CDIOO (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C. In some embodiments, the transmembrane domain is derived from a molecule selected from the group consisting of CD8α, CD4, CD28, CD137, CD80, CD86, CD152 and PD1.

In some specific embodiments, the transmembrane domain is derived from CD8α. In some embodiments, the transmembrane domain is a transmembrane domain of CD8α comprising the amino acid sequence of SEQ ID NO: 44.

Transmembrane domains for use in the CARs described herein can also comprise at least a portion of a synthetic, non-naturally occurring protein segment. In some embodiments, the transmembrane domain is a synthetic, non-naturally occurring alpha helix or beta sheet. In some embodiments, the protein segment is at least approximately 20 amino acids, e.g., at least 18, 19, 20, 21, 22, 23, 24, 25, 26, 27, 28, 29, 30, or more amino acids. Examples of synthetic transmembrane domains are known in the art, for example in U.S. Pat. No. 7,052,906 and PCT Publication No. WO 2000/032776, the relevant disclosures of which are incorporated by reference herein.

The transmembrane domain provided herein may comprise a transmembrane region and a cytoplasmic region located at the C-terminal side of the transmembrane domain. The cytoplasmic region of the transmembrane domain may comprise three or more amino acids and, in some embodiments, helps to orient the transmembrane domain in the lipid bilayer. In some embodiments, one or more cysteine residues are present in the transmembrane region of the transmembrane domain. In some embodiments, one or more cysteine residues are present in the cytoplasmic region of the transmembrane domain. In some embodiments, the cytoplasmic region of the transmembrane domain comprises positively charged amino acids. In some embodiments, the cytoplasmic region of the transmembrane domain comprises the amino acids arginine, serine, and lysine.

In some embodiments, the transmembrane region of the transmembrane domain comprises hydrophobic amino acid residues. In some embodiments, the transmembrane domain of the CAR provided herein comprises an artificial hydrophobic sequence. For example, a triplet of phenylalanine, tryptophan and valine may be present at the C terminus of the transmembrane domain. In some embodiments, the transmembrane region comprises mostly hydrophobic amino acid residues, such as alanine, leucine, isoleucine, methionine, phenylalanine, tryptophan, or valine. In some embodiments, the transmembrane region is hydrophobic. In some embodiments, the transmembrane region comprises a poly-leucine-alanine sequence. The hydropathy, or hydrophobic or hydrophilic characteristics of a protein or protein segment, can be assessed by any method known in the art, for example the Kyte and Doolittle hydropathy analysis.

5.3.5. Intracellular Signaling Domain

The CARs of the present disclosure comprise an intracellular signaling domain. The intracellular signaling domain is responsible for activation of at least one of the normal effector functions of the immune effector cell expressing the CARs. The term "effector function" refers to a specialized function of a cell. Effector function of a T cell, for example, may be cytolytic activity or helper activity including the secretion of cytokines. Thus the term "cytoplasmic signaling domain" refers to the portion of a protein which transduces the effector function signal and directs the cell to perform a specialized function. While usually the entire cytoplasmic signaling domain can be employed, in many cases it is not necessary to use the entire chain. To the extent that a truncated portion of the cytoplasmic signaling domain is used, such truncated portion may be used in place of the intact chain as long as it transduces the effector function signal. The term cytoplasmic signaling domain is thus meant to include any truncated portion of the cytoplasmic signaling domain sufficient to transduce the effector function signal.

In some embodiments, the intracellular signaling domain comprises a primary intracellular signaling domain of an immune effector cell. In some embodiments, the CAR comprises an intracellular signaling domain consisting essentially of a primary intracellular signaling domain of an immune effector cell. "Primary intracellular signaling domain" refers to cytoplasmic signaling sequence that acts in a stimulatory manner to induce immune effector functions. In some embodiments, the primary intracellular signaling domain contains a signaling motif known as immunoreceptor tyrosine-based activation motif, or ITAM. An "ITAM," as used herein, is a conserved protein motif that is generally present in the tail portion of signaling molecules expressed in many immune cells. The motif may comprises two repeats of the amino acid sequence YxxL/I separated by 6-8 amino acids, wherein each x is independently any amino acid, producing the conserved motif YxxL/Ix(6-8)YxxL/I. ITAMs within signaling molecules are important for signal transduction within the cell, which is mediated at least in part by phosphorylation of tyrosine residues in the ITAM following activation of the signaling molecule. ITAMs may also function as docking sites for other proteins involved in signaling pathways. Exemplary ITAM-containing primary cytoplasmic signaling sequences include those derived from CD3ζ, FcR gamma (FCER1G), FcR beta (Fc Epsilon Rib), CD3 gamma, CD3 delta, CD3 epsilon, CD5, CD22, CD79a, CD79b, and CD66d.

In some embodiments, the primary intracellular signaling domain is derived from CD3ζ. In some embodiments, the intracellular signaling domain consists of the cytoplasmic signaling domain of CD3ζ. In some embodiments, the primary intracellular signaling domain is a cytoplasmic signaling domain of wild-type CD3ζ. In some embodiments, the primary intracellular signaling domain of CD3ζ comprises the amino acid sequence of SEQ ID NO: 46. In some embodiments, the primary intracellular signaling domain of wild-type CD3ζ. In some embodiments, the primary intracellular signaling domain is a functional mutant of the cytoplasmic signaling domain of CD3ζ containing one or more mutations, such as Q65K.

5.3.6. Co-Stimulatory Signaling Domain

Many immune effector cells require co-stimulation, in addition to stimulation of an antigen-specific signal, to promote cell proliferation, differentiation and survival, as well as to activate effector functions of the cell. In some embodiments, the CAR comprises at least one co-stimulatory signaling domain. The term "co-stimulatory signaling domain," as used herein, refers to at least a portion of a protein that mediates signal transduction within a cell to induce an immune response such as an effector function. The co-stimulatory signaling domain of the chimeric receptor described herein can be a cytoplasmic signaling domain from a co-stimulatory protein, which transduces a signal and modulates responses mediated by immune cells, such as T cells, NK cells, macrophages, neutrophils, or eosinophils. "Co-stimulatory signaling domain" can be the cytoplasmic portion of a co-stimulatory molecule. The term "co-stimulatory molecule" refers to a cognate binding partner on an immune cell (such as T cell) that specifically binds with a co-stimulatory ligand, thereby mediating a co-stimulatory response by the immune cell, such as, but not limited to, proliferation and survival.

In some embodiments, the intracellular signaling domain comprises a single co-stimulatory signaling domain. In some embodiments, the intracellular signaling domain comprises two or more (such as about any of 2, 3, 4, or more) co-stimulatory signaling domains. In some embodiments, the intracellular signaling domain comprises two or more of the same co-stimulatory signaling domains. In some embodiments, the intracellular signaling domain comprises two or more co-stimulatory signaling domains from different co-stimulatory proteins, such as any two or more co-stimulatory proteins described herein. In some embodiments, the intracellular signaling domain comprises a primary intracellular signaling domain (such as cytoplasmic signaling domain of CD3ζ) and one or more co-stimulatory signaling domains. In some embodiments, the one or more co-stimulatory signaling domains and the primary intracellular signaling domain (such as cytoplasmic signaling domain of CD3ζ) are fused to each other via optional peptide linkers. The primary intracellular signaling domain, and the one or more co-stimulatory signaling domains may be arranged in any suitable order. In some embodiments, the one or more co-stimulatory signaling domains are located between the transmembrane domain and the primary intracellular signaling domain (such as cytoplasmic signaling domain of CD3ζ). Multiple co-stimulatory signaling domains may provide additive or synergistic stimulatory effects.

Activation of a co-stimulatory signaling domain in a host cell (e.g., an immune cell) may induce the cell to increase or decrease the production and secretion of cytokines, phagocytic properties, proliferation, differentiation, survival, and/or cytotoxicity. The co-stimulatory signaling domain of any co-stimulatory molecule may be compatible for use in the CARs described herein. The type(s) of co-stimulatory signaling domain is selected based on factors such as the type of the immune effector cells in which the effector molecules would be expressed (e.g., T cells, NK cells, macrophages, neutrophils, or eosinophils) and the desired immune effector function (e.g., ADCC effect). Examples of co-stimulatory signaling domains for use in the CARs can be the cytoplasmic signaling domain of co-stimulatory proteins, including, without limitation, members of the B7/CD28 family (e.g., B7-1/CD80, B7-2/CD86, B7-H1/PD-L1, B7-H2, B7-H3, B7-H4, B7-H6, B7-H7, BTLA/CD272, CD28, CTLA-4, Gi24/VISTA/B7-H5, ICOS/CD278, PD-1, PD-L2/B7-DC, and PDCD6); members of the TNF superfamily (e.g., 4-1BB/TNFSF9/CD137, 4-1BB Ligand/TNFSF9, BAFF/BLyS/TNFSF13B, BAFF R/TNFRSF13C, CD27/TNFRSF7, CD27 Ligand/TNFSF7, CD30/TNFRSF8, CD30 Ligand/TNFSF8, CD40/TNFRSF5, CD40/TNFSF5, CD40 Ligand/TNFSF5, DR3/TNFRSF25, GITR/TNFRSF18, GITR Ligand/TNFSF18, HVEM/TNFRSF14, LIGHT/TNFSF14, Lymphotoxin-alpha/TNF-beta, OX40/TN- FRSF4, OX40 Ligand/TNF SF4, RELT/TNFRSF19L, TACI/TNFRSF13B, TL1A/TNFSF15, TNF-alpha, and TNF RII/TNFRSF1B); members of the SLAM family (e.g., 2B4/CD244/SLAMF4, BLAME/SLAMF8, CD2, CD2F-10/SLAMF9, CD48/SLAMF2, CD58/LFA-3, CD84/SLAMF5, CD229/SLAMF3, CRACC/SLAMF7, NTB-A/SLAMF6, and SLAM/CD150); and any other co-stimulatory molecules, such as CD2, CD7, CD53, CD82/Kai-1, CD90/Thy1, CD96, CD160, GUCY2CO, CD300a/LMIR1, HLA Class I, HLA-DR, Ikaros, Integrin alpha 4/CD49d, Integrin alpha 4 beta 1, Integrin alpha 4 beta 7/LPAM-1, LAG-3, TCL1A, TCL1B, CRTAM, DAP12, Dectin-1/CLEC7A, DPPIV/CD26, EphB6, TIM-1/KIM-1/HAVCR, TIM-4, TSLP, TSLP R, lymphocyte function associated antigen-1 (LFA-1), and NKG2C.

In some embodiments, the one or more co-stimulatory signaling domains are selected from the group consisting of CD27, CD28, CD137, OX40, CD30, CD40, CD3, lymphocyte function-associated antigen-1 (LFA-1), CD2, CD7, LIGHT, NKG2C, B7-H3 and ligands that specially bind to CD83.

In some embodiments, the intracellular signaling domain in the CAR of the present disclosure comprises a co-stimulatory signaling domain derived from CD137 (i.e., 4-1BB). In some embodiments, the intracellular signaling domain comprises a cytoplasmic signaling domain of CD3ζ and a co-stimulatory signaling domain of CD137. In some embodiments, the intracellular signaling domain comprises a co-stimulatory signaling domain of CD137 comprising the amino acid sequence of SEQ ID NO: 45.

Also within the scope of the present disclosure are variants of any of the co-stimulatory signaling domains described herein, such that the co-stimulatory signaling domain is capable of modulating the immune response of the immune cell. In some embodiments, the co-stimulatory signaling domains comprises up to 10 amino acid residue variations (e.g., 1, 2, 3, 4, 5, or 8) as compared to a wild-type counterpart. Such co-stimulatory signaling domains comprising one or more amino acid variations may be referred to as variants. Mutation of amino acid residues of the co-stimulatory signaling domain may result in an increase in signaling transduction and enhanced stimulation of immune responses relative to co-stimulatory signaling domains that do not comprise the mutation. Mutation of amino acid residues of the co-stimulatory signaling domain may result in a decrease in signaling transduction and reduced stimulation of immune responses relative to co-stimulatory signaling domains that do not comprise the mutation.

5.3.7. Peptide Linkers

The various single domain antibodies in the multispecific or multivalent CARs described herein may be fused to each other via peptide linkers. In some embodiments, the single domain antibodies are directly fused to each other without any peptide linkers. The peptide linkers connecting different single domain antibodies (e.g., VHH) may be the same or different. Different domains of the CARs may also be fused to each other via peptide linkers.

Each peptide linker in a CAR may have the same or different length and/or sequence depending on the structural and/or functional features of the single domain antibodies and/or the various domains. Each peptide linker may be selected and optimized independently. The length, the degree of flexibility and/or other properties of the peptide linker(s) used in the CARs may have some influence on properties, including but not limited to the affinity, specificity or avidity for one or more particular antigens or epitopes. For example, longer peptide linkers may be selected to ensure that two adjacent domains do not sterically interfere with one another. In some embodiments, a short peptide linker may be disposed between the transmembrane domain and the intracellular signaling domain of a CAR. In some embodiment, a peptide linker comprises flexible residues (such as glycine and serine) so that the adjacent domains are free to move relative to each other. For example, a glycine-serine doublet can be a suitable peptide linker.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 25, 30, 35, 40, 50, 75, 100 or more amino acids long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 amino acid to about 10 amino acids, about 1 amino acids to about 20 amino acids, about 1 amino acid to about 30 amino acids, about 5 amino acids to about 15 amino acids, about 10 amino acids to about 25 amino acids, about 5 amino acids to about 30 amino acids, about 10 amino acids to about 30 amino acids long, about 30 amino acids to about 50 amino acids, about 50 amino acids to about 100 amino acids, or about 1 amino acid to about 100 amino acids.

The peptide linker may have a naturally occurring sequence, or a non-naturally occurring sequence. For example, a sequence derived from the hinge region of heavy chain only antibodies may be used as the linker. See, for example, WO1996/34103. In some embodiments, the peptide linker is a flexible linker. Exemplary flexible linkers include but not limited to glycine polymers, glycine-serine polymers, glycine-alanine polymers, alanine-serine polymers, and other flexible linkers known in the art.

Other linkers known in the art, for example, as described in WO2016014789, WO2015158671, WO2016102965, US20150299317, WO2018067992, U.S. Pat. No. 7,741,465, Colcher et al., *J. Nat. Cancer Inst.* 82:1191-1197 (1990), and Bird et al., *Science* 242:423-426 (1988) may also be included in the CARs provided herein, the disclosure of each of which is incorporated herein by reference.

5.3.8. Exemplary CARs

Exemplary monovalent CARs are generated as shown in Section 6 below, such as C8-CAR, C12-CAR, C13-CAR, C15-CAR, C21-CAR, C27-CAR, C30-CAR and C31-CAR.

In some embodiments, provided herein is a CAR comprising or consisting of the amino acid sequence of SEQ ID NO: 48.

In some embodiments, provided herein is a CAR comprising or consisting of the amino acid sequence of SEQ ID NO: 49.

In some embodiments, provided herein is a CAR comprising or consisting of the amino acid sequence of SEQ ID NO: 50.

In some embodiments, provided herein is a CAR comprising or consisting of the amino acid sequence of SEQ ID NO: 51.

In some embodiments, provided herein is a CAR comprising or consisting of the amino acid sequence of SEQ ID NO: 52.

In some embodiments, provided herein is a CAR comprising or consisting of the amino acid sequence of SEQ ID NO: 53.

In some embodiments, provided herein is a CAR comprising or consisting of the amino acid sequence of SEQ ID NO: 54.

In some embodiments, provided herein is a CAR comprising or consisting of the amino acid sequence of SEQ ID NO: 55.

In certain embodiments, the CAR provided herein comprises amino acid sequences with certain percent identity relative to any one of the CARs exemplified in the Section 6 below.

In some embodiments, provided herein is a GUCY2C CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 48.

In some embodiments, provided herein is a GUCY2C CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 49.

In some embodiments, provided herein is a GUCY2C CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 50.

In some embodiments, provided herein is a GUCY2C CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 51.

In some embodiments, provided herein is a GUCY2C CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 52.

In some embodiments, provided herein is a GUCY2C CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 53.

In some embodiments, provided herein is a GUCY2C CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 54.

In some embodiments, provided herein is a GUCY2C CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 55.

In some embodiments, provided herein is an isolated nucleic acid encoding any of the GUCY2C CARs provided herein. More detailed description regarding nucleic acid sequences and vectors are provided below.

5.4. Engineered Immune Effector Cells

In yet another aspect, provided herein are host cells (such as immune effector cells) comprising any one of the CARs described herein.

Thus, in some embodiments, provided herein is an engineered immune effector cell (such as T cell) comprising a CAR which comprises a polypeptide comprising: (a) an extracellular antigen binding domain comprising one or more anti-GUCY2C sdAb(s); (b) a transmembrane domain; and (c) an intracellular signaling domain, wherein the anti-GUCY2C sdAb is an anti-GUCY2C sdAb as described in Section 5.2 above, including, e.g., the VHH domains in Table 7 and those having one, two or all three CDRs in any of those VHH domains in Table 7. Specifically, in some embodiments, the anti-GUCY2C sdAb in the CAR of the engineered immune effector cell provided herein comprises (i) a CDR1 comprising the amino acid sequence of SEQ ID NO: 19; a CDR2 comprising the amino acid sequence of SEQ ID NO: 27; and a CDR3 comprising the amino acid sequence of SEQ ID NO: 35; (ii) a CDR1 comprising the amino acid sequence of SEQ ID NO: 20; a CDR2 comprising the amino acid sequence of SEQ ID NO: 28; and a CDR3 comprising the amino acid sequence of SEQ ID NO: 36; (iii) a CDR1 comprising the amino acid sequence of SEQ ID NO: 21; a CDR2 comprising the amino acid sequence of SEQ ID NO: 29; and a CDR3 comprising the amino acid sequence of SEQ ID NO: 37; (iv) a CDR1 comprising the amino acid sequence of SEQ ID NO: 22; a CDR2 comprising the amino acid sequence of SEQ ID NO: 30; and a CDR3 comprising the amino acid sequence of SEQ ID NO: 38; (v) a CDR1 comprising the amino acid sequence of SEQ ID NO: 23; a CDR2 comprising the amino acid sequence of SEQ ID NO: 31; and a CDR3 comprising the amino acid sequence of SEQ ID NO: 39; (vi) a CDR1 comprising the amino acid sequence of SEQ ID NO: 24; a CDR2 comprising the amino acid sequence of SEQ ID NO: 32; and a CDR3 comprising the amino acid sequence of SEQ ID NO: 40; (vii) a CDR1 comprising the amino acid sequence of SEQ ID NO: 25; a CDR2 comprising the amino acid sequence of SEQ ID NO: 33; and a CDR3 comprising the amino acid sequence of SEQ ID NO: 41; or (viii) a CDR1 comprising the amino acid sequence of SEQ ID NO: 26; a CDR2 comprising the amino acid sequence of SEQ ID NO: 34; and a CDR3 comprising the amino acid sequence of SEQ ID NO: 42. In some embodiments, the anti-GUCY2C sdAb is camelid, chimeric, human, or humanized. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, ligands of CD83 and combinations thereof. In some embodiments, the CAR further comprises a hinge domain (such as a CD8α hinge domain) located between the C-terminus of the extracellular antigen binding domain and the N-terminus of the transmembrane domain. In some embodiments, the CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ.

In some embodiments, provided herein is an engineered immune effector cell (such as T cell) comprising a CAR which comprises a polypeptide comprising: (a) an extracellular antigen binding domain comprising one or more anti-GUCY2C sdAb(s); (b) a transmembrane domain; and (c) an intracellular signaling domain, wherein the anti-GUCY2C sdAb comprises the amino acid sequence of SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In some embodiments, provided herein is an engineered immune effector cell (such as T cell) comprising a CAR which comprises a polypeptide comprising: (a) an extracellular antigen binding domain comprising one or more anti-GUCY2C sdAb(s); (b) a transmembrane domain; and (c) an intracellular signaling domain, wherein the anti-GUCY2C sdAb comprises an amino acid sequence having at least 75%, 80%, 85%, 86%, 87%, 88%, 89%, 90%, 91%, 92%, 93%, 94%, 95%, 96%, 97%, 98%, 99%, or 100% sequence identify to the amino acid sequence of SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, ligands of CD83 and combinations thereof. In some embodiments, the CAR further comprises a hinge domain (such as a CD8α hinge domain) located between the C-terminus of the extracellular antigen binding domain and the N-terminus of the transmembrane domain. In some embodiments, the CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ.

In some embodiments, provided herein is an engineered immune effector cell (such as T cell) comprising a CAR which comprises an amino acid sequence selected from the group consisting of SEQ ID NO: 48, SEQ ID NO: 49, SEQ ID NO: 50, SEQ ID NO: 51, SEQ ID NO: 52, SEQ ID NO: 53, SEQ ID NO: 54, and SEQ ID NO: 55. In some embodiments, provided herein is an engineered immune effector cell (such as T cell) comprising a CAR which comprises a polypeptide having at least 75%, 80%, 85%, 86%, 87%, 88%, 89%, 90%, 91%, 92%, 93%, 94%, 95%, 96%, 97%, 98%, 99%, or 100% sequence identity to an amino acid sequence selected from the group consisting of SEQ ID NO: 48, SEQ ID NO: 49, SEQ ID NO: 50, SEQ ID NO: 51, SEQ ID NO: 52, SEQ ID NO: 53, SEQ ID NO: 54, and SEQ ID NO: 55.

In other embodiments, there is provided an engineered immune effector cell (such as T cell) comprising a multispecific (such as bispecific or trispecific) chimeric antigen receptor (CAR) comprising a polypeptide comprising: (a) an extracellular antigen binding domain comprising a first single domain antibody (sdAb) specifically binding to GUCY2C and one or more additional antigen binding domain(s); (b) a transmembrane domain; and (c) an intracellular signaling domain. In some embodiments, the first sdAb and/or the additional sdAb is camelid, chimeric, human, or humanized. In some embodiments, the first single domain antibody and the additional single domain antibody are fused to each other via a peptide bond or a peptide linker. In some embodiments, the peptide linker is no more than about 50 (such as no more than about any one of 35, 25, 20, 15, 10, or 5) amino acids long. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, ligands of CD83 and combinations thereof. In some embodiments, the multispecific CAR further comprises a hinge domain (such as a CD8α hinge domain) located between the C-terminus of the extracellular antigen binding domain and the N-terminus of the transmembrane domain. In some embodiments, the multispecific CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ.

In some embodiments, the engineered immune effector cell is a T cell, an NK cell, a peripheral blood mononuclear cell (PBMC), a hematopoietic stem cell, a pluripotent stem cell, or an embryonic stem cell. In some embodiments, the engineered immune effector cell is autologous. In some embodiments, the engineered immune effector cell is allogenic.

Also provided are engineered immune effector cells comprising (or expressing) two or more different CARs. Any two or more of the CARs described herein may be expressed in combination. The CARs may target different antigens, thereby providing synergistic or additive effects. The two or more CARs may be encoded on the same vector or different vectors.

The engineered immune effector cell may further express one or more therapeutic proteins and/or immunomodulators, such as immune checkpoint inhibitors. See, e.g., International Patent Application NOs. PCT/CN2016/073489 and PCT/CN2016/087855, which are incorporated herein by reference in their entirety.

5.4.1. Vectors

The present disclosure provides vectors for cloning and expressing any one of the CARs described herein. In some embodiments, the vector is suitable for replication and integration in eukaryotic cells, such as mammalian cells. In some embodiments, the vector is a viral vector. Examples of viral vectors include, but are not limited to, adenoviral vectors, adeno-associated virus vectors, lentiviral vector, retroviral vectors, vaccinia vector, herpes simplex viral vector, and derivatives thereof. Viral vector technology is well known in the art and is described, for example, in Sambrook et al. (2001, Molecular Cloning: A Laboratory Manual, Cold Spring Harbor Laboratory, New York), and in other virology and molecular biology manuals.

A number of viral based systems have been developed for gene transfer into mammalian cells. For example, retroviruses provide a convenient platform for gene delivery systems. The heterologous nucleic acid can be inserted into a vector and packaged in retroviral particles using techniques known in the art. The recombinant virus can then be isolated and delivered to the engineered mammalian cell in vitro or ex vivo. A number of retroviral systems are known in the art. In some embodiments, adenovirus vectors are used. A number of adenovirus vectors are known in the art. In some embodiments, lentivirus vectors are used. In some embodiments, self-inactivating lentiviral vectors are used. For example, self-inactivating lentiviral vectors carrying the immunomodulator (such as immune checkpoint inhibitor) coding sequence and/or self-inactivating lentiviral vectors carrying chimeric antigen receptors can be packaged with protocols known in the art. The resulting lentiviral vectors can be used to transduce a mammalian cell (such as primary human T cells) using methods known in the art. Vectors derived from retroviruses such as lentivirus are suitable tools to achieve long-term gene transfer, because they allow long-term, stable integration of a transgene and its propagation in progeny cells. Lentiviral vectors also have low immunogenicity, and can transduce non-proliferating cells.

In some embodiments, the vector comprises any one of the nucleic acids encoding a CAR described herein. The nucleic acid can be cloned into the vector using any known molecular cloning methods in the art, including, for example, using restriction endonuclease sites and one or more selectable markers. In some embodiments, the nucleic acid is operably linked to a promoter. Varieties of promoters have been explored for gene expression in mammalian cells, and any of the promoters known in the art may be used in the present disclosure. Promoters may be roughly categorized as constitutive promoters or regulated promoters, such as inducible promoters.

In some embodiments, the nucleic acid encoding the CAR is operably linked to a constitutive promoter. Constitutive promoters allow heterologous genes (also referred to as transgenes) to be expressed constitutively in the host cells. Exemplary constitutive promoters contemplated herein include, but are not limited to, Cytomegalovirus (CMV) promoters, human elongation factors-1 alpha (hEF1α), ubiquitin C promoter (UbiC), phosphoglycerokinase promoter (PGK), simian virus 40 early promoter (SV40), and chicken β-Actin promoter coupled with CMV early enhancer (CAGG). The efficiencies of such constitutive promoters on driving transgene expression have been widely compared in a huge number of studies. For example, Michael C. Milone et al compared the efficiencies of CMV, hEF1α, UbiC and PGK to drive chimeric antigen receptor expression in primary human T cells, and concluded that hEF1α promoter not only induced the highest level of transgene expression, but was also optimally maintained in the CD4 and CD8 human T cells (Molecular Therapy, 17(8): 1453-1464 (2009)). In some embodiments, the nucleic acid encoding the CAR is operably linked to a hEF1α promoter.

In some embodiments, the nucleic acid encoding the CAR is operably linked to an inducible promoter. Inducible promoters belong to the category of regulated promoters. The inducible promoter can be induced by one or more conditions, such as a physical condition, microenvironment of the engineered immune effector cell, or the physiological state of the engineered immune effector cell, an inducer (i.e., an inducing agent), or a combination thereof.

In some embodiments, the inducing condition does not induce the expression of endogenous genes in the engineered mammalian cell, and/or in the subject that receives the pharmaceutical composition. In some embodiments, the inducing condition is selected from the group consisting of: inducer, irradiation (such as ionizing radiation, light), temperature (such as heat), redox state, tumor environment, and the activation state of the engineered mammalian cell.

In some embodiments, the vector also contains a selectable marker gene or a reporter gene to select cells expressing the CAR from the population of host cells transfected through lentiviral vectors. Both selectable markers and reporter genes may be flanked by appropriate regulatory sequences to enable expression in the host cells. For example, the vector may contain transcription and translation terminators, initiation sequences, and promoters useful for regulation of the expression of the nucleic acid sequences.

In some embodiments, the vector comprises more than one nucleic acid encoding CARs. In some embodiments, the vector comprises a nucleic acid comprising a first nucleic acid sequence encoding a first CAR and a second nucleic acid sequence encoding a second CAR, wherein the first nucleic acid is operably linked to the second nucleic acid via a third nucleic acid sequence encoding a self-cleaving peptide. In some embodiments, the self-cleaving peptide is selected from the group consisting of T2A, P2A and F2A.

5.4.2. Immune Effector Cells

"Immune effector cells" are immune cells that can perform immune effector functions. In some embodiments, the immune effector cells express at least FcγRIII and perform ADCC effector function. Examples of immune effector cells which mediate ADCC include peripheral blood mononuclear cells (PBMC), natural killer (NK) cells, monocytes, cytotoxic T cells, neutrophils, and eosinophils.

In some embodiments, the immune effector cells are T cells. In some embodiments, the T cells are CD4+/CD8−, CD4−/CD8+, CD4+/CD8+, CD4−/CD8−, or combinations thereof. In some embodiments, the T cells produce IL-2, TFN, and/or TNF upon expressing the CAR and binding to the target cells, such as GUCY2C+ tumor cells. In some embodiments, the CD8+ T cells lyse antigen-specific target cells upon expressing the CAR and binding to the target cells.

In some embodiments, the immune effector cells are NK cells. In other embodiments, the immune effector cells can be established cell lines, for example, NK-92 cells.

In some embodiments, the immune effector cells are differentiated from a stem cell, such as a hematopoietic stem cell, a pluripotent stem cell, an iPS, or an embryonic stem cell.

The engineered immune effector cells are prepared by introducing the CARs into the immune effector cells, such as T cells. In some embodiments, the CAR is introduced to the immune effector cells by transfecting any one of the isolated nucleic acids or any one of the vectors described above. In some embodiments, the CAR is introduced to the immune effector cells by inserting proteins into the cell membrane while passing cells through a microfluidic system, such as CELL SQUEEZE® (see, e.g. U.S. Patent Application Publication No. 20140287509).

Methods of introducing vectors or isolated nucleic acids into a mammalian cell are known in the art. The vectors described can be transferred into an immune effector cell by physical, chemical, or biological methods.

Physical methods for introducing the vector into an immune effector cell include calcium phosphate precipitation, lipofection, particle bombardment, microinjection, electroporation, and the like. Methods for producing cells comprising vectors and/or exogenous nucleic acids are well-known in the art. See, e.g., Sambrook et al. (2001) Molecular Cloning: A Laboratory Manual, Cold Spring Harbor Laboratory, New York. In some embodiments, the vector is introduced into the cell by electroporation.

Biological methods for introducing the vector into an immune effector cell include the use of DNA and RNA vectors. Viral vectors have become the most widely used method for inserting genes into mammalian, e.g., human cells.

Chemical means for introducing the vector into an immune effector cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro is a liposome (e.g., an artificial membrane vesicle).

In some embodiments, RNA molecules encoding any of the CARs described herein may be prepared by a conventional method (e.g., in vitro transcription) and then introduced into the immune effector cells via known methods such as mRNA electroporation. See, e.g., Rabinovich et al., Human Gene Therapy 17:1027-1035 (2006).

In some embodiments, the transduced or transfected immune effector cell is propagated ex vivo after introduction of the vector or isolated nucleic acid. In some embodiments, the transduced or transfected immune effector cell is cultured to propagate for at least about any of 1 day, 2 days, 3 days, 4 days, 5 days, 6 days, 7 days, 10 days, 12 days, or 14 days. In some embodiments, the transduced or transfected immune effector cell is further evaluated or screened to select the engineered mammalian cell.

Reporter genes may be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al. FEBS Letters 479: 79-82 (2000)). Suitable expression systems are well known and may be prepared using known techniques or obtained commercially.

Other methods to confirm the presence of the nucleic acid encoding the CARs in the engineered immune effector cell, include, for example, molecular biological assays well known to those of skill in the art, such as Southern and Northern blotting, RT-PCR and PCR; biochemical assays, such as detecting the presence or absence of a particular peptide, e.g., by immunological methods (such as ELISAs and Western blots).

5.4.3. Sources of T Cells

In some embodiments, prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments, any number of T cell lines available in the art, may be used. In some embodiments, T cells can be obtained from a unit of blood collected from a subject using any number of techniques known to the skilled artisan, such as Ficoll™ separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In some embodiments, the wash solution lacks calcium and may lack magnesium or may lack many if not all divalent cations. Initial activation steps in the absence of calcium may lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In some embodiments, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+T cells, can be further isolated by positive or negative selection techniques. For example, in some embodiments, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In some embodiments, the time period is about 30 minutes. In a further embodiment, the time period ranges from 30 minutes to 36 hours or longer and all integer values there between. In a further embodiment, the time period is at least 1, 2, 3, 4, 5, or 6 hours. In some embodiments, the time period is 10 to 24 hours. In some embodiments, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, in some embodiments, by simply shortening or lengthening the time T cells are allowed to bind to the CD3/CD28 beads and/or by increasing or decreasing the ratio of beads to T cells, subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used. In some embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, GUCY2C, CD11b, CD16, HLA-DR, and CD8. In certain embodiments, it may be desirable to enrich for or positively select for regulatory T cells which typically express CD4+, CD25+, CD62Lhi, GITR+, and FoxP3+. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations may result in increased cell yield, cell activation, and cell expansion. Further, use of high cell concentrations may allow more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. In some embodiments, using high concentration of cells allows more efficient selection of CD8+ T cells that normally have weaker CD28 expression.

In some embodiments, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In some embodiments, the concentration of cells used is $5\times10^6$/ml. In some embodiments, the concentration used can be from about $1\times10^5$/ml to $1\times10^6$/ml, and any integer value in between.

In some embodiments, the cells may be incubated on a rotator for varying lengths of time at varying speeds at either 2-10° C., or at room temperature.

T cells for stimulation can also be frozen after a washing step. Without being bound by theory, the freeze and subsequent thaw step may provide a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% dextran 40 and 5% dextrose, 20% human serum albumin and 7.5% DMSO, or 31.25% plasmalyte-A, 31.25% dextrose 5%, 0.45% NaCl, 10% dextran 40 and 5% dextrose, 20% human serum albumin, and 7.5% DMSO or other suitable cell freezing media containing for example, Hespan and PlasmaLyte A. The cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In some embodiments, cryopreserved cells are thawed and washed as described herein and allowed to rest for one hour at room temperature prior to activation.

Also contemplated in the present disclosure is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment, a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815 (1991); Henderson et al., Immun 73:316-321 (1991); Bierer et al., Curr. Opin. Immun. 5:763-773 (1993)). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with GUCY2C, e.g., Rituxan.

In some embodiments, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present disclosure to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

5.4.4. Activation and Expansion of T Cells

In some embodiments, prior to or after genetic modification of the T cells with the CARs described herein, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, T cells can be expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD3 antibody include UCHT1, OKT3, HIT3a (BioLegend, San Diego, US) can be used as can other methods commonly known in the art (Graves J, et al., J. Immunol. 146:2102 (1991); Li B, et al., Immunology 116:487 (2005); Rivollier A, et al., Blood 104:4029 (2004)). Examples of an anti-CD28 antibody include 9.3, B-T3, XR-CD28 (Diaclone, Besancon, France) can be used as can other methods commonly known in the art (Berg et al., Transplant Proc. 30(8):3975-3977 (1998); Haanen et al., J. Exp. Med. 190 (9):13191328 (1999); Garland et al., J. Immunol Meth. 227(1-2):53-63 (1999)).

In some embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in certain embodiments in the present disclosure.

In some embodiments, the T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment, the cells (for example, $10^4$ to $4\times10^8$ T cells) and beads (for example, anti-CD3/CD28 MACSiBead particles a at a recommended titer of 1:100) are combined in a buffer, preferably PBS (without divalent cations such as, calcium and magnesium). Those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present disclosure. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/mL is used. In another embodiment, greater than 100 million cells/mL is used. In a further embodiment, a concentration of cells of 10, 15, 20, 25, 30, 35, 40, 45, or 50 million cells/mL is used. In yet another embodiment, a concentration of cells from 75, 80, 85, 90, 95, or 100 million cells/mL is used. In further embodiments, concentrations of 125 or 150 million cells/mL can be used. Using high concentrations may result in increased cell yield, cell activation, and cell expansion. Further, use of high cell concentrations may allow more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In some embodiments, the mixture may be cultured for several hours (about 3 hours) to about 14 days or any hourly integer value in between. In another embodiment, the mixture may be cultured for 21 days. In one embodiment, the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$). T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

5.5. Polynucleotides

In certain embodiments, the disclosure provides polynucleotides that encode the single domain antibodies that bind to GUCY2C and fusion proteins comprising the single domain antibodies that bind to GUCY2C described herein. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand. In some embodiments, the polynucleotide is in the form of cDNA. In some embodiments, the polynucleotide is a synthetic polynucleotide.

In exemplary embodiments, the nucleic acid molecule provided herein comprises a sequence that encodes the single domain antibody having the sequence of SEQ ID NO: 3, such as a nucleic acid having SEQ ID NO: 11.

In exemplary embodiments, the nucleic acid molecule provided herein comprises a sequence that encodes the single domain antibody having the sequence of SEQ ID NO: 4, such as a nucleic acid having SEQ ID NO: 12.

In exemplary embodiments, the nucleic acid molecule provided herein comprises a sequence that encodes the single domain antibody having the sequence of SEQ ID NO: 5, such as a nucleic acid having SEQ ID NO: 13.

In exemplary embodiments, the nucleic acid molecule provided herein comprises a sequence that encodes the single domain antibody having the sequence of SEQ ID NO: 6, such as a nucleic acid having SEQ ID NO: 14.

In exemplary embodiments, the nucleic acid molecule provided herein comprises a sequence that encodes the single domain antibody having the sequence of SEQ ID NO: 7, such as a nucleic acid having SEQ ID NO: 15.

In exemplary embodiments, the nucleic acid molecule provided herein comprises a sequence that encodes the single domain antibody having the sequence of SEQ ID NO: 8, such as a nucleic acid having SEQ ID NO: 16.

In exemplary embodiments, the nucleic acid molecule provided herein comprises a sequence that encodes the single domain antibody having the sequence of SEQ ID NO: 9, such as a nucleic acid having SEQ ID NO: 17.

In exemplary embodiments, the nucleic acid molecule provided herein comprises a sequence that encodes the single domain antibody having the sequence of SEQ ID NO: 10, such as a nucleic acid having SEQ ID NO: 18.

In certain embodiments, the disclosure provides polynucleotides that encode the GUCY2C CAR provided herein. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand. In some embodiments, the polynucleotide is in the form of cDNA. In some embodiments, the polynucleotide is a synthetic polynucleotide.

In exemplary embodiments, the nucleic acid molecule provided herein comprises a sequence that encodes the CAR having the sequence of SEQ ID NO: 48, such as a nucleic acid having SEQ ID NO: 56.

In exemplary embodiments, the nucleic acid molecule provided herein comprises a sequence that encodes the CAR having the sequence of SEQ ID NO: 49, such as a nucleic acid having SEQ ID NO: 57.

In exemplary embodiments, the nucleic acid molecule provided herein comprises a sequence that encodes the CAR having the sequence of SEQ ID NO: 50, such as a nucleic acid having SEQ ID NO: 58.

In exemplary embodiments, the nucleic acid molecule provided herein comprises a sequence that encodes the CAR having the sequence of SEQ ID NO: 51, such as a nucleic acid having SEQ ID NO: 59.

In exemplary embodiments, the nucleic acid molecule provided herein comprises a sequence that encodes the CAR having the sequence of SEQ ID NO: 52, such as a nucleic acid having SEQ ID NO: 60.

In exemplary embodiments, the nucleic acid molecule provided herein comprises a sequence that encodes the CAR having the sequence of SEQ ID NO: 53, such as a nucleic acid having SEQ ID NO: 61.

In exemplary embodiments, the nucleic acid molecule provided herein comprises a sequence that encodes the CAR having the sequence of SEQ ID NO: 54, such as a nucleic acid having SEQ ID NO: 62.

In exemplary embodiments, the nucleic acid molecule provided herein comprises a sequence that encodes the CAR having the sequence of SEQ ID NO: 55, such as a nucleic acid having SEQ ID NO: 63.

The present disclosure further relates to variants of the polynucleotides described herein, wherein the variant encodes, for example, fragments, analogs, and/or derivatives of the single domain antibody or CAR that binds GUCY2C of the disclosure. In certain embodiments, the present disclosure provides a polynucleotide comprising a polynucleotide having a nucleotide sequence at least about 75% identical, at least about 80% identical, at least about 85% identical, at least about 90% identical, at least about 95% identical, and in some embodiments, at least about 96%, 97%, 98% or 99% identical to a polynucleotide encoding the single domain antibody or CAR that binds GUCY2C of the disclosure. As used herein, the phrase "a polynucleotide having a nucleotide sequence at least, for example, 95% "identical" to a reference nucleotide sequence" is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations which produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). Polynucleotide variants can be produced for a variety of reasons, for example, to optimize codon expression for a particular host (i.e., change codons in the human mRNA to those preferred by a bacterial host such as *E. coli*). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

Also provided are vectors comprising the nucleic acid molecules described herein. In an embodiment, the nucleic acid molecules can be incorporated into a recombinant expression vector. The present disclosure provides recombinant expression vectors comprising any of the nucleic acids of the disclosure. As used herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors described herein are not naturally-occurring as a whole; however, parts of the vectors can be naturally-occurring. The described recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. The non-naturally occurring or altered nucleotides or internucleotide linkages do not hinder the transcription or replication of the vector.

In an embodiment, the recombinant expression vector of the disclosure can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λEMBL4, and λNM1149, λZapII (Stratagene) can be used. Examples of plant expression vectors include pBI01, pBI01.2, pBI121, pBI101.3, and pBIN19 (Clontech). Examples of animal expression vectors include pEUK-C1, pMAM, and pMAMneo (Clontech). The recombinant expression vector may be a viral vector, e.g., a retroviral vector, e.g., a gamma retroviral vector.

In an embodiment, the recombinant expression vectors are prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, SV40, 2μ plasmid, λ, bovine papilloma virus, and the like.

The recombinant expression vector may comprise regulatory sequences, such as transcription and translation initiation and termination codons, which are specific to the type of host (e.g., bacterium, plant, fungus, or animal) into which the vector is to be introduced, as appropriate, and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the described expression vectors include, for instance, neomycin/G418 resistance genes, histidinol×resistance genes, histidinol resistance genes, tetracycline resistance genes, and ampicillin resistance genes.

The recombinant expression vector can comprise a native or normative promoter operably linked to the nucleotide sequence of the disclosure. The selection of promoters, e.g., strong, weak, tissue-specific, inducible and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an RSV promoter, an SV40 promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine deaminase, purine nucleoside phosphorylase, and nitroreductase.

In certain embodiments, a polynucleotide is isolated. In certain embodiments, a polynucleotide is substantially pure.

Also provided are host cells comprising the nucleic acid molecules described herein. The host cell may be any cell that contains a heterologous nucleic acid. The heterologous nucleic acid can be a vector (e.g., an expression vector). For example, a host cell can be a cell from any organism that is selected, modified, transformed, grown, used or manipulated in any way, for the production of a substance by the cell, for example the expression by the cell of a gene, a DNA or RNA sequence, a protein or an enzyme. An appropriate host may be determined. For example, the host cell may be selected based on the vector backbone and the desired result. By way of example, a plasmid or cosmid can be introduced into a prokaryote host cell for replication of several types of vectors. Bacterial cells such as, but not limited to DH5α, JM109, and KCB, SURE® Competent Cells, and SOLO-PACK Gold Cells, can be used as host cells for vector replication and/or expression. Additionally, bacterial cells such as *E. coli* LE392 could be used as host cells for phage viruses. Eukaryotic cells that can be used as host cells include, but are not limited to yeast (e.g., YPH499, YPH500 and YPH501), insects and mammals. Examples of mammalian eukaryotic host cells for replication and/or expression of a vector include, but are not limited to, HeLa, NIH3T3, Jurkat, 293, COS, Saos, PC12, SP2/0 (American Type Culture Collection (ATCC), Manassas, VA, CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATCC CRL-TIB-196). Other useful cell lines include those derived from Chinese Hamster Ovary (CHO) cells such as CHO-K1 SV (Lonza Biologics, Walkersville, MD), CHO-K1 (ATCC CRL-61) or DG44.

5.6. Pharmaceutical Compositions

In one aspect, the present disclosure further provides pharmaceutical compositions comprising a single domain antibody, a binding molecule or therapeutic molecule comprising a single domain antibody, or an engineered immune effector cell of the present disclosure. In some embodiments, a pharmaceutical composition comprises a therapeutically effective amount of the single domain antibody, the binding molecule or therapeutic molecule comprising the single domain antibody, or the engineered immune effector cell of the present disclosure and a pharmaceutically acceptable excipient.

In some embodiments, provided herein is a pharmaceutical composition comprising a therapeutically effective amount of the single domain antibody provided herein and a pharmaceutically acceptable excipient.

In some embodiments, provided herein is a pharmaceutical composition comprising a therapeutically effective amount of the therapeutic molecule (such as a fusion protein, immunoconjugate, and a multispecific binding molecule) comprising the single domain antibody provided herein and a pharmaceutically acceptable excipient.

In other embodiments, provided herein is a pharmaceutical composition comprising a therapeutically effective amount of CAR comprising the single domain antibody provided herein and a pharmaceutically acceptable excipient.

In other embodiments, provided herein is a pharmaceutical composition comprising a therapeutically effective amount of engineered immune effector cells provided herein and a pharmaceutically acceptable excipient.

In other embodiments, provided herein is a pharmaceutical composition comprising a therapeutically effective amount of a nucleic acid provided herein, e.g., in a vector, and a pharmaceutically acceptable excipient, e.g., suitable for gene therapy.

In a specific embodiment, the term "excipient" can also refer to a diluent, adjuvant (e.g., Freunds' adjuvant (complete or incomplete), carrier or vehicle. Pharmaceutical excipients can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid excipients. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical excipients are described in *Remington's Pharmaceutical Sciences* (1990) Mack Publishing Co., Easton, PA. Such compositions will contain a prophylactically or therapeutically effective amount of the active ingredient provided herein, such as in purified form, together with a suitable amount of excipient so as to provide the form for proper administration to the patient. The formulation should suit the mode of administration.

In some embodiments, the choice of excipient is determined in part by the particular cell, binding molecule, and/or antibody, and/or by the method of administration. Accordingly, there are a variety of suitable formulations.

Typically, acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers, stabilizers, metal complexes (e.g. Zn-protein complexes); chelating agents such as EDTA and/or non-ionic surfactants.

Buffers may be used to control the pH in a range which optimizes the therapeutic effectiveness, especially if stability is pH dependent. Suitable buffering agents for use with the present disclosure include both organic and inorganic acids and salts thereof. For example, citrate, phosphate, succinate, tartrate, fumarate, gluconate, oxalate, lactate, acetate. Additionally, buffers may comprise histidine and trimethylamine salts such as Tris.

Preservatives may be added to retard microbial growth. Suitable preservatives for use with the present disclosure include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" can be present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Exemplary tonicity agents include polyhydric sugar alcohols, trihydric or higher sugar alcohols, such as glycerin, erythritol, arabitol, xylitol, sorbitol and mannitol.

Additional exemplary excipients include: (1) bulking agents, (2) solubility enhancers, (3) stabilizers and (4) agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") may be present to help solubilize the therapeutic agent as well as to protect the therapeutic protein against agitation-induced aggregation, which also permits the formulation to be exposed to shear surface stress without causing denaturation of the active therapeutic protein or antibody. Suitable non-ionic surfactants include, e.g., polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the pharmaceutical compositions to be used for in vivo administration, they are preferably sterile. The pharmaceutical composition may be rendered sterile by filtration through sterile filtration membranes. The pharmaceutical compositions herein generally can be placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

In another embodiment, a pharmaceutical composition can be provided as a controlled release or sustained release system. In one embodiment, a pump may be used to achieve controlled or sustained release (see, e.g., Sefton, Crit. Ref. Biomed. Eng. 14:201-40 (1987); Buchwald et al., Surgery 88:507-16 (1980); and Saudek et al., N. Engl. J. Med. 321:569-74 (1989)). In another embodiment, polymeric materials can be used to achieve controlled or sustained release of a prophylactic or therapeutic agent (e.g., a fusion protein as described herein) or a composition provided herein (see, e.g., *Medical Applications of Controlled Release* (Langer and Wise eds., 1974); *Controlled Drug Bioavailability, Drug Product Design and Performance* (Smolen and Ball eds., 1984); Ranger and Peppas, J. Macromol. Sci. Rev. Macromol. Chem. 23:61-126 (1983); Levy et al., Science 228:190-92 (1985); During et al., Ann. Neurol. 25:351-56 (1989); Howard et al., J. Neurosurg. 71:105-12 (1989); U.S. Pat. Nos. 5,679,377; 5,916,597; 5,912,015; 5,989,463; and 5,128,326; PCT Publication Nos. WO 99/15154 and WO 99/20253). Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable. In yet another embodiment, a controlled or sustained release system can be placed in proximity of a particular target tissue, for example, the nasal passages or lungs, thus requiring only a fraction of the systemic dose (see, e.g., Goodson, *Medical Applications of Controlled Release* Vol. 2, 115-38 (1984)). Controlled release systems are discussed, for example, by Langer, Science 249:1527-33 (1990). Any technique known to one of skill in the art can be used to produce sustained release formulations comprising one or more agents as described herein (see, e.g., U.S. Pat. No. 4,526,938, PCT publication Nos. WO 91/05548 and WO 96/20698, Ning et al., Radiotherapy & Oncology 39:179-89 (1996); Song et al., PDA J. of Pharma. Sci. & Tech. 50:372-97 (1995); Cleek et al., Pro. Int'l. Symp. Control. Rel. Bioact. Mater. 24:853-54 (1997); and Lam et al., Proc. Int'l. Symp. Control Rel. Bioact. Mater. 24:759-60 (1997)).

The pharmaceutical compositions described herein may also contain more than one active compound or agent as necessary for the particular indication being treated. Alternatively, or in addition, the composition may comprise a cytotoxic agent, chemotherapeutic agent, cytokine, immunosuppressive agent, or growth inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition.

Various compositions and delivery systems are known and can be used with the therapeutic agents provided herein, including, but not limited to, encapsulation in liposomes, microparticles, microcapsules, recombinant cells capable of expressing the single domain antibody or therapeutic molecule provided herein, construction of a nucleic acid as part of a retroviral or other vector, etc.

In some embodiments, the pharmaceutical composition provided herein contains the binding molecules and/or cells in amounts effective to treat or prevent the disease or disorder, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined.

5.7. Methods and Uses

In another aspect, provided herein are methods for using and uses of the GUCY2C binding molecules provided herein, including the anti-GUCY2C VHH, chimeric antigen receptors (CARs), and/or engineered cells expressing the recombinant receptors.

5.7.1. Therapeutic Methods and Uses

Such methods and uses include therapeutic methods and uses, for example, involving administration of the molecules, cells, or compositions containing the same, to a subject having a disease, condition, or disorder expressing or associated with GUCY2C expression, and/or in which cells or tissues express GUCY2C. In some embodiments, the molecule, cell, and/or composition is administered in an effective amount to effect treatment of the disease or disorder. Uses include uses of the antibodies and cells in such methods and treatments, and in the preparation of a medicament in order to carry out such therapeutic methods. In some embodiments, the methods are carried out by administering the antibodies or cells, or compositions comprising the same, to the subject having or suspected of having the disease or condition. In some embodiments, the methods thereby treat the disease or disorder in the subject.

In some embodiments, the treatment provided herein cause complete or partial amelioration or reduction of a disease or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms include, but do not imply, complete curing of a disease or complete elimination of any symptom or effect(s) on all symptoms or outcomes.

As used herein, in some embodiments, the treatment provided herein delay development of a disease or disorder, e.g., defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease or disorder. For example, a late stage cancer, such as development of metastasis, may be delayed. In other embodiments, the method or the use provided herein prevents a disease or disorder.

In some embodiments, the disease or disorder is a GUCY2C associated disease or disorder. In some embodiments, the disease or disorder is cancer. In some embodiments, the cancer is colorectal cancer, gastric cancer or esophageal cancer.

In some embodiments, the methods include adoptive cell therapy, whereby genetically engineered cells expressing the provided GUCY2C-targeted CARs are administered to a subject. Such administration can promote activation of the cells (e.g., T cell activation) in a GUCY2C-targeted manner, such that the cells of the disease or disorder are targeted for destruction.

In some embodiments, the methods include administration of the cells or a composition containing the cells to a subject, tissue, or cell, such as one having, at risk for, or suspected of having the disease or disorder. In some embodiments, the cells, populations, and compositions are administered to a subject having the particular disease or disorder to be treated, e.g., via adoptive cell therapy, such as adoptive T cell therapy. In some embodiments, the cells or compositions are administered to the subject, such as a subject having or at risk for the disease or disorder. In some embodiments, the methods thereby treat, e.g., ameliorate one or more symptom of the disease or disorder, such as by lessening tumor burden in a GUCY2C-expressing cancer.

Methods for administration of cells for adoptive cell therapy are known, as described, e.g., in US Patent Application Publication No. 2003/0170238; U.S. Pat. No. 4,690,915; Rosenberg, *Nat Rev Clin Oncol.* 8 (10):577-85 (2011); Themeli et al., Nat Biotechnol. 31(10): 928-933 (2013); Tsukahara et al., Biochem Biophys Res Commun 438(1): 84-9 (2013); and Davila et al., PLoS ONE 8(4): e61338 (2013). These methods may be used in connection with the methods and compositions provided herein.

In some embodiments, the cell therapy (e.g., adoptive T cell therapy) is carried out by autologous transfer, in which the cells are isolated and/or otherwise prepared from the subject who is to receive the cell therapy, or from a sample derived from such a subject. Thus, in some aspects, the cells are derived from a subject in need of a treatment and the cells, following isolation and processing are administered to the same subject. In other embodiments, the cell therapy (e.g., adoptive T cell therapy) is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject, to whom the cells, cell populations, or compositions are administered is a primate, such as a human. The subject can be male or female and can be any suitable age, including infant, juvenile, adolescent, adult, and geriatric subjects. In some examples, the subject is a validated animal model for disease, adoptive cell therapy, and/or for assessing toxic outcomes.

The GUCY2C-binding molecules, such as VHHs and chimeric receptors containing the VHHs and cells expressing the same, can be administered by any suitable means, for example, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration.

The amount of a prophylactic or therapeutic agent provided herein that will be effective in the prevention and/or treatment of a disease or condition can be determined by standard clinical techniques. Effective doses may be extrapolated from dose-response curves derived from in vitro or animal model test systems. For the prevention or treatment of disease, the appropriate dosage of the binding molecule or cell may depend on the type of disease or disorder to be treated, the type of binding molecule, the severity and course of the disease or disorder, whether the therapeutic agent is administered for preventive or therapeutic purposes, previous therapy, the patient's clinical history and response to the agent, and the discretion of the attending physician. The compositions, molecules and cells are in some embodiments suitably administered to the patient at one time or over a series of treatments.

For example, depending on the type and severity of the disease, dosages of antibodies may include about 10 ug/kg to 100 mg/kg or more. Multiple doses may be administered intermittently. An initial higher loading dose, followed by one or more lower doses may be administered. In some embodiments, wherein the pharmaceutical composition comprises any one of the single domain antibodies described herein, the pharmaceutical composition is administered at a dosage of about 10 ng/kg up to about 100 mg/kg of body weight of the individual or more per day, for example, at about 1 mg/kg/day to 10 mg/kg/day, depending upon the route of administration. Guidance as to particular dosages and methods of delivery is provided in the literature (see, e.g. U.S. Pat. Nos. 4,657,760; 5,206,344; and 5,225,212).

In the context of genetically engineered cells containing the binding molecules, in some embodiments, a subject may be administered the range of about one million to about 100 billion cells and/or that amount of cells per kilogram of body weight. In some embodiments, wherein the pharmaceutical composition comprises any one of the engineered immune cells described herein, the pharmaceutical composition is administered at a dosage of about $10^4$ to $10^9$ cells/kg of body weight of the individual. Dosages may vary depending on attributes particular to the disease or disorder and/or patient and/or other treatments.

In some embodiments, the pharmaceutical composition is administered for a single time. In some embodiments, the pharmaceutical composition is administered for multiple times (such as any of 2, 3, 4, 5, 6, or more times). In some embodiments, the pharmaceutical composition is administered once or multiple times during a dosing cycle. A dosing cycle can be, e.g., 1, 2, 3, 4, 5 or more week(s), or 1, 2, 3, 4, 5, or more month(s). The optimal dosage and treatment regime for a particular patient can be determined by one skilled in the art of medicine by monitoring the patient for signs of disease and adjusting the treatment accordingly.

In some embodiments, the cells or antibodies are administered as part of a combination treatment, such as simultaneously with or sequentially with, in any order, another therapeutic intervention, such as another antibody or engineered cell or receptor or agent, such as a cytotoxic or therapeutic agent.

In some embodiments, the cells or antibodies are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells or antibodies are administered prior to the one or more additional therapeutic agents. In some embodiments, the cells or antibodies are administered after to the one or more additional therapeutic agents.

In certain embodiments, once the cells are administered to a mammal (e.g., a human), the biological activity of the engineered cell populations and/or antibodies is measured by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285 (1): 25-40 (2004). In certain embodiments, the biological activity of the cells also can be measured by assaying expression and/or secretion of certain cytokines, such as CD107a, IFNγ, IL-2, and TNF. In some aspects the biological activity is measured by assessing clinical outcome, such as reduction in tumor burden or load.

In some specific embodiments, provided herein is a method for treating a disease or disorder in a subject comprising administering to the subject a binding molecule comprising a single domain antibody that binds to GUCY2C as described in Section 5.2 above, including, e.g., those with CDRs in Table 7, such as the anti-GUCY2C sdAb comprises (i) a CDR1 comprising the amino acid sequence of SEQ ID NO: 19; a CDR2 comprising the amino acid sequence of SEQ ID NO: 27; and a CDR3 comprising the amino acid sequence of SEQ ID NO: 35; (ii) a CDR1 comprising the amino acid sequence of SEQ ID NO: 20; a CDR2 comprising the amino acid sequence of SEQ ID NO: 28; and a CDR3 comprising the amino acid sequence of SEQ ID NO: 36; (iii) a CDR1 comprising the amino acid sequence of SEQ ID NO: 21; a CDR2 comprising the amino acid sequence of SEQ ID NO: 29; and a CDR3 comprising the amino acid sequence of SEQ ID NO: 37; (iv) a CDR1 comprising the amino acid sequence of SEQ ID NO: 22; a CDR2 comprising the amino acid sequence of SEQ ID NO: 30; and a CDR3 comprising the amino acid sequence of SEQ ID NO: 38; (v) a CDR1 comprising the amino acid sequence of SEQ ID NO: 23; a CDR2 comprising the amino acid sequence of SEQ ID NO: 31; and a CDR3 comprising the amino acid sequence of SEQ ID NO: 39; (vi) a CDR1 comprising the amino acid sequence of SEQ ID NO: 24; a CDR2 comprising the amino acid sequence of SEQ ID NO: 32; and a CDR3 comprising the amino acid sequence of SEQ ID NO: 40; (vii) a CDR1 comprising the amino acid sequence of SEQ ID NO: 25; a CDR2 comprising the amino acid sequence of SEQ ID NO: 33; and a CDR3 comprising the amino acid sequence of SEQ ID NO: 41; or (viii) a CDR1 comprising the amino acid sequence of SEQ ID NO: 26; a CDR2 comprising the amino acid sequence of SEQ ID NO: 34; and a CDR3 comprising the amino acid sequence of SEQ ID NO: 42. In some embodiments, the adAb comprises an amino acid sequence of SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10, or an amino acid sequence having at least 75%, 80%, 85%, 90%, 91%, 92%, 93%, 94%, 95%, 96%, 97%, 98%, or 99% sequence identify to SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In some embodiments, the disease or disorder is a GUCY2C associated disease or disorder. In some embodiments, the disease or disorder is cancer. In some embodiments, the cancer is colorectal cancer, gastric cancer or esophageal cancer.

In other embodiments, provided herein is a method for treating a disease or disorder comprising administering to the subject an engineered immune effector cell (such as T cell) as provided in Section 5.4, including, e.g., the cells comprising a CAR provided in Section 5.3. In some embodiments, the engineered immune cell administered to the subject comprises a CAR comprising a polypeptide comprising: (a) an extracellular antigen binding domain comprising one or more anti-GUCY2C sdAb(s); (b) a transmembrane domain; and (c) an intracellular signaling domain, wherein the anti-GUCY2C sdAb is as described in Section 5.2 above, including e.g., those with CDRs in Table 7, such as the anti-GUCY2C sdAb comprises (i) a CDR1 comprising the amino acid sequence of SEQ ID NO: 19; a CDR2 comprising the amino acid sequence of SEQ ID NO: 27; and a CDR3 comprising the amino acid sequence of SEQ ID NO: 35; (ii) a CDR1 comprising the amino acid sequence of SEQ ID NO: 20; a CDR2 comprising the amino acid sequence of SEQ ID NO: 28; and a CDR3 comprising the amino acid sequence of SEQ ID NO: 36; (iii) a CDR1 comprising the amino acid sequence of SEQ ID NO: 21; a CDR2 comprising the amino acid sequence of SEQ ID NO: 29; and a CDR3 comprising the amino acid sequence of SEQ ID NO: 37; (iv) a CDR1 comprising the amino acid sequence of SEQ ID NO: 22; a CDR2 comprising the amino acid sequence of SEQ ID NO: 30; and a CDR3 comprising the amino acid sequence of SEQ ID NO: 38; (v) a CDR1 comprising the amino acid sequence of SEQ ID NO: 23; a CDR2 comprising the amino acid sequence of SEQ ID NO: 31; and a CDR3 comprising the amino acid sequence of SEQ ID NO: 39; (vi) a CDR1 comprising the amino acid sequence of SEQ ID NO: 24; a CDR2 comprising the amino acid sequence of SEQ ID NO: 32; and a CDR3 comprising the amino acid sequence of SEQ ID NO: 40; (vii) a CDR1 comprising the amino acid sequence of SEQ ID NO: 25; a CDR2 comprising the amino acid sequence of SEQ ID NO: 33; and a CDR3 comprising the amino acid sequence of SEQ ID NO: 41; or (viii) a CDR1 comprising the amino acid sequence of SEQ ID NO: 26; a CDR2 comprising the amino acid sequence of SEQ ID NO: 34; and a CDR3 comprising the amino acid sequence of SEQ ID NO: 42. The sdAbs in the CARs of the present engineered cells also include those comprising the amino acid sequence of SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, and those comprising an amino acid sequence having at least 75%, 80%, 85%, 90%, 91%, 92%, 93%, 94%, 95%, 96%, 97%, 98%, or 99% sequence identify to SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10. In some embodiments, the engineered immune cell administered to the subject comprises a CAR comprising an amino acid sequence selected from the group consisting of SEQ ID NO: 48, SEQ ID NO: 49, SEQ ID NO: 50, SEQ ID NO: 51, SEQ ID NO: 52, SEQ ID NO: 53, SEQ ID NO: 54, and SEQ ID NO: 55, or comprising a polypeptide having at least 75%, 80%, 85%, 86%, 87%, 88%, 89%, 90%, 91%, 92%, 93%, 94%, 95%, 96%, 97%, 98%, or 99% sequence identity to an amino acid sequence selected from the group consisting of SEQ ID NO: 48, SEQ ID NO: 49, SEQ ID NO: 50, SEQ ID NO: 51, SEQ ID NO: 52, SEQ ID NO: 53, SEQ ID NO: 54, and SEQ ID NO: 55. In some embodiments, the disease or disorder is a GUCY2C associated disease or disorder. In some embodiments, the disease or disorder is cancer. In some embodiments, the cancer is colorectal cancer, gastric cancer or esophageal cancer.

5.7.2. Diagnostic and Detection Methods and Uses

In another aspect, provided herein are methods involving use of the binding molecules provided herein, e.g., VHHs that binds GUCY2C and molecules (such as conjugates and complexes) containing such VHHs, for detection, prognosis, diagnosis, staging, determining binding of a particular treatment to one or more tissues or cell types, and/or informing treatment decisions in a subject, such as by the detection of GUCY2C and/or the presence of an epitope thereof recognized by the antibody.

In some embodiments, an anti-GUCY2C antibody (such as any one of the anti-GUCY2C single domain antibodies described herein) for use in a method of diagnosis or detection is provided. In a further aspect, a method of detecting the presence of GUCY2C in a biological sample is provided. In certain embodiments, the method comprises detecting the presence of GUCY2C protein in a biological sample. In certain embodiments, GUCY2C is human GUCY2C. In some embodiments, the methods are diagnostic and/or prognostic methods in association with a GUCY2C-expressing disease or disorder. The methods in some embodiments include incubating and/or probing a biological sample with the antibody and/or administering the antibody to a subject. In certain embodiments, a biological sample includes a cell or tissue or portion thereof, such as tumor or cancer tissue or biopsy or section thereof. In certain embodiments, the contacting is under conditions permissive for binding of the anti-GUCY2C antibody to GUCY2C present in the sample. In some embodiments, the methods further include detecting whether a complex is formed between the anti-GUCY2C antibody and GUCY2C in the sample, such as detecting the presence or absence or level of such binding. Such a method may be an in vitro or in vivo method. In one embodiment, an anti-GUCY2C antibody is used to select subjects eligible for therapy with an anti-GUCY2C antibody or engineered antigen receptor, e.g., where GUCY2C is a biomarker for selection of patients.

In some embodiments, a sample, such as a cell, tissue sample, lysate, composition, or other sample derived therefrom is contacted with the anti-GUCY2C antibody and binding or formation of a complex between the antibody and the sample (e.g., GUCY2C in the sample) is determined or detected. When binding in the test sample is demonstrated or detected as compared to a reference cell of the same tissue type, it may indicate the presence of an associated disease or disorder, and/or that a therapeutic containing the antibody will specifically bind to a tissue or cell that is the same as or is of the same type as the tissue or cell or other biological material from which the sample is derived. In some embodiments, the sample is from human tissues and may be from diseased and/or normal tissue, e.g., from a subject having the disease or disorder to be treated and/or from a subject of the same species as such subject but that does not have the disease or disorder to be treated. In some cases, the normal tissue or cell is from a subject having the disease or disorder to be treated but is not itself a diseased cell or tissue, such as a normal tissue from the same or a different organ than a cancer that is present in a given subject.

Various methods known in the art for detecting specific antibody-antigen binding can be used. Exemplary immunoassays include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be used so as to meet the needs of various uses of the method which are often dictated by the availability of assay equipment and compatible immunoassay procedures. Exemplary labels include radionuclides (e.g. $^{125}I$, $^{131}I$, $^{35}S$, $^{3}H$, or $^{32}P$ and/or chromium ($^{51}Cr$), cobalt ($^{57}Co$), fluorine ($^{18}$F), gadolinium ($^{153}$Gd, $^{159}$Gd), germanium ($^{68}$Ge), holmium ($^{166}$Ho), indium ($^{115}$In, $^{113}$In, $^{112}$In, $^{111}$In), iodine ($^{125}$I, $^{123}$I, $^{121}$I), lanthanium ($^{140}$La) lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium (186Re, 188Re), rhodium (105Rh), rutheroium (97Ru), samarium ($^{153}$Sm), scandium ($^{47}$Sc), selenium ($^{75}$Se), ($^{85}$Sr), sulphur ($^{35}$S), technetium ($^{99}$Tc), thallium ($^{201}$Ti) tin ($^{113}$Sn, $^{117}$Sn), tritium (3H), xenon ($^{133}$Xe), ytterbium ($^{169}$Yb, $^{175}$Yb) yttrium ($^{90}$Y), enzymes (e.g., alkaline phosphatase, horseradish peroxidase, luciferase, or β-galactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). Various general techniques to be used in performing the various immunoassays noted above are known.

In certain embodiments, labeled antibodies (such as anti-GUCY2C single domain antibodies) are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. In other embodiments, antibodies are not labeled, and the presence thereof can be detected using a labeled antibody which binds to any of the antibodies.

5.8. Kits and Articles of Manufacture

Further provided are kits, unit dosages, and articles of manufacture comprising any of the single domain antibodies, the chimeric antigen receptors, or the engineered immune effector cells described herein. In some embodiments, a kit is provided which contains any one of the pharmaceutical compositions described herein and preferably provides instructions for its use.

The kits of the present application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder (such as cancer) described herein, and may have a sterile access port (for example the container may be an intravenous solution bag or a vial having a stopper pierceable by a hypodermic injection needle). The label or package insert indicates that the composition is used for treating the particular condition in an individual. The label or package insert will further comprise instructions for administering the composition to the individual. The label may indicate directions for reconstitution and/or use. The container holding the pharmaceutical composition may be a multi-use vial, which allows for repeat administrations (e.g. from 2-6 administrations) of the reconstituted formulation. Package insert refers to instructions customarily included in commercial packages of therapeutic products that contain information about the indications, usage, dosage, administration, contraindications and/or warnings concerning the use of such therapeutic products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or article of manufacture may include multiple unit doses of the pharmaceutical composition and instructions for use, packaged in quantities sufficient for storage and use in pharmacies, for example, hospital pharmacies and compounding pharmacies.

For the sake of conciseness, certain abbreviations are used herein. One example is the single letter abbreviation to represent amino acid residues. The amino acids and their corresponding three letter and single letter abbreviations are as follows:

| Amino acid | Three letter | One letter |
|---|---|---|
| alanine | Ala | (A) |
| arginine | Arg | (R) |
| asparagine | Asn | (N) |
| aspartic acid | Asp | (D) |
| cysteine | Cys | (C) |
| glutamic acid | Glu | (E) |
| glutamine | Gln | (Q) |
| glycine | Gly | (G) |
| histidine | His | (H) |
| isoleucine | Ile | (I) |
| leucine | Leu | (L) |
| lysine | Lys | (K) |
| methionine | Met | (M) |
| phenylalanine | Phe | (F) |
| proline | Pro | (P) |
| serine | Ser | (S) |
| threonine | Thr | (T) |
| tryptophan | Trp | (W) |
| tyrosine | Tyr | (Y) |
| valine | Val | (V) |

The disclosure is generally disclosed herein using affirmative language to describe the numerous embodiments. The disclosure also specifically includes embodiments in which particular subject matter is excluded, in full or in part, such as substances or materials, method steps and conditions, protocols, procedures, assays or analysis. Thus, even though the disclosure is generally not expressed herein in terms of what the disclosure does not include, aspects that are not expressly included in the disclosure are nevertheless disclosed herein.

A number of embodiments of the disclosure have been described. Nevertheless, it will be understood that various modifications may be made without departing from the spirit and scope of the disclosure. Accordingly, the following examples are intended to illustrate but not limit the scope of disclosure described in the claims.

6. EXAMPLES

The following is a description of various methods and materials used in the studies, and are put forth so as to provide those of ordinary skill in the art with a complete disclosure and description of how to make and use the present disclosure, and are not intended to limit the scope of what the inventors regard as their disclosure nor are they intended to represent that the experiments below were performed and are all of the experiments that may be performed. It is to be understood that exemplary descriptions written in the present tense were not necessarily performed, but rather that the descriptions can be performed to generate the data and the like associated with the teachings of the present disclosure. Efforts have been made to ensure accuracy with respect to numbers used (e.g., amounts, percentages, etc.), but some experimental errors and deviations should be accounted for.

6.1. Example 1—Preparation of Anti-GUCY2C VHH

Immunization of Alpaca

The extracellular region of the artificially synthesized GUCY2C protein was synthesized by Nanjing GenScript Biotechnology Co., Ltd. (sequence UniProtKB: P25092, Ser24-G1n430) for immunized with alpaca. It comprises the nucleic acid sequence of SEQ ID NO: 1 and the amino acid sequence of SEQ ID NO: 2 (see Table 1). Each time 100 ug of GUCY2C protein was mixed with the adjuvant in equal volume. The Freund's complete adjuvant was used only in the primary immunization, while the others use Freund's incomplete adjuvants. The alpaca was immunized seven times on weekly basis for stimulating B cells to express antigen-specific Nanobodies. During the period of immunization, a small amount of alpaca's peripheral blood was drawn for antibody titer testing. After immunization, 200 ml of alpaca's peripheral blood was drawn and total RNA was extracted with Trizol.

TABLE 1

GUCY2C Peptide Sequences

| Description | Sequence | SEQ ID NO. |
|---|---|---|
| GUCY2C protein (Ser24-Gln430) (Nucleic acid) | TCTCAAGTGTCCCAGAACTGCCACAACGGCAGCTA CGAGATCAGCGTGCTGATGATGGGCAACAGCGCC TTTGCCGAGCCTCTGAAGAACCTGGAAGATGCCGT GAACGAAGGCCTGGAAATCGTGCGAGGCAGACTG CAGAATGCCGGCCTGAACGTGACCGTGAACGCCA CCTTTATGTACAGCGACGGCCTGATCCACAACAGC GGCGACTGTAGAAGCAGCACCTGTGAAGGACTGG ACCTGCTGCGGAAGATCAGCAACGCCCAGAGAAT GGGCTGTGTGCTGATCGGCCCTAGCTGCACCTACA GCACCTTCCAGATGTACCTGGACACCGAGCTGAGC TACCCCATGATCAGCGCCGGATCTTTCGGCCTGAG CTGCGACTACAAAGAGACACTGACCCGGCTGATG AGCCCCGCCAGAAAGCTGATGTACTTCCTGGTCAA CTTCTGGAAAACGAACGACCTGCCTTTCAAGACCT ACAGCTGGTCCACCAGCTACGTGTACAAGAACGG CACCGAGACAGAGGACTGCTTCTGGTATCTGAACG CCCTGGAAGCCAGCGTGTCCTACTTTTCTCACGAG CTGGGCTTCAAGGTGGTGCTGCGGCAGGACAAAG AGTTCCAGGACATCCTGATGGACCACAACCGGAA GTCCAACGTGATCATCATGTGCGGCGGACCCGAGT TCCTGTACAAGCTGAAAGGCGATAGAGCCGTGGC CGAGGACATCGTGATCATTCTGGTGGATCTGTTCA ACGACCAGTACTTCGAGGACAATGTGACAGCCCCT GACTACATGAAGAACGTGCTGGTGCTGACACTGA GCCCCGGCAACAGTCTGCTGAACAGCAGCTTCAGC CGGAATCTGAGCCCCACCAAGAGAGATTTCGCCCT GGCCTACCTGAACGGCATCCTGCTGTTTGGCCACA TGCTGAAGATCTTTCTCGAAAACGGCGAGAACATC ACGACCCCTAAGTTCGCCCACGCCTTCCGGAACCT GACCTTCGAGGGATATGACGGCCCCGTGACACTG GATGACTGGGGAGATGTGGACAGCACAATGGTGC TGCTGTACACCAGCGTGGACACCAAAAAGTACAA AGTGCTGCTGACCTACGACACCCACGTGAACAAG ACATACCCCGTGGACATGAGCCCTACCTTCACATG GAAGAACAGCAAGCTGCCCAACGACATCACCGGC AGAGGACCTCAG | SEQ ID NO: 1 |
| GUCY2Cprotein (Ser24-Gln430) (Amino acid) | SQVSQNCHNGSYEISVLMMGNSAFAEPLKNLEDAV NEGLEIVRGRLQNAGLNVTVNATFMYSDGLIHNSGD CRSSTCEGLDLLRKISNAQRMGCVLIGPSCTYSTFQM YLDTELSYPMISAGSFGLSCDYKETLTRLMSPARKL MYFLVNFWKTNDLPFKTYSWSTSYVYKNGTETEDC FWYLNALEASVSYFSHELGFKVVLRQDKEFQDILMD HNRKSNVIIMCGGPEFLYKLKGDRAVAEDIVIILVDL FNDQYFEDNVTAPDYMKNVLVLTLSPGNSLLNSSFS RNLSPTKRDFALAYLNGILLFGHMLKIFLENGENITTP KFAHAFRNLTFEGYDGPVTLDDWGDVDSTMVLLYT SVDTKKYKVLLTYDTHVNKTYPVDMSPTFTWKNSK LPNDITGRGPQ | SEQ ID NO: 2 |

Construction of Nanobody Phage Library

The extracted total RNA was used to synthesize cDNA by the reverse transcription kit PrimeScript II 1st Strand cDNA Synthesis Kit (Takara), and the VHH chain was amplified by a two-step PCRs. The heavy chain antibody gene was obtained by the first PCR. Using cDNA as a PCR template, the upstream and downstream primers covering immunoglobulin IgG were added to the PCR system to amplify different subtypes of IgG, and then IgG2 and IgG3 genes were recovered by TaKaRa MiniBEST Agarose Gel DNA Extraction Kit. The VHH gene with the restriction site was obtained by the second PCR. The gene fragment recovered by the first PCR was used as a template. The primers covering the VHH sequence of the IgG2 and IgG3 heavy chain regions with Sac1 and Spe1 restriction sites were added to the PCR system to amplify a large amount of DNA of VHH for phage library. Lastly, the PCR products were purified with DNA purification kit.

Figure 1:
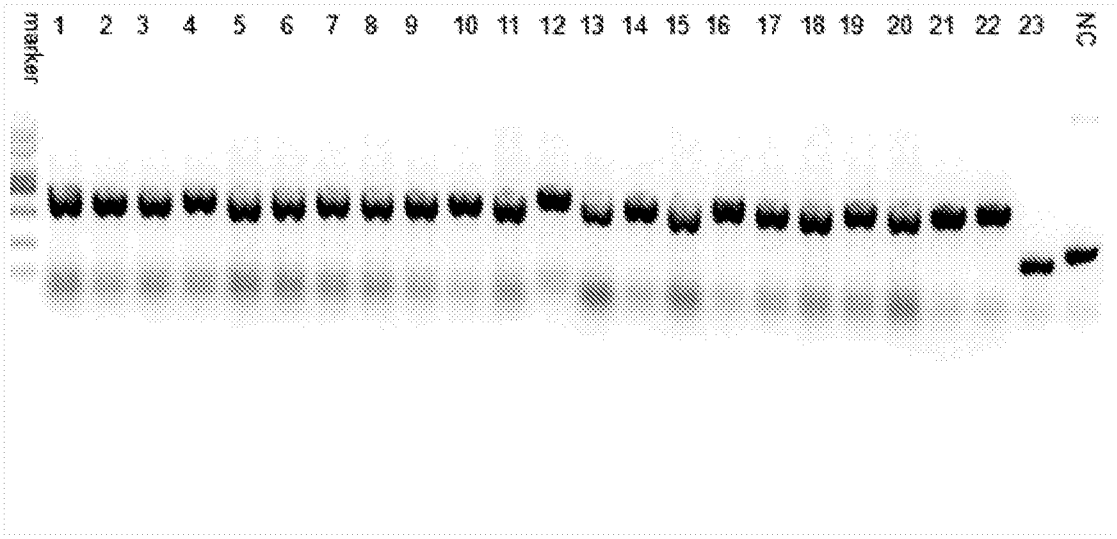

Restriction Digestion, Ligation, Electrotransformation and Phage Library Identification of VHH Gene and pComb3XSS The VHH gene sequence obtained in the second PCR and the phasmid pComb3XSS (addgene) was digested with restriction enzymes Sac1 (NEB) and Spe1 (NEB), and placed in a 37° C. water baths for 4 hours. After purification and recovery, the samples were incubated overnight at 4° C. with T4 DNA ligase. 200 ug of recombinant plasmid was then added into TG1 *E. coli* competent cells and electroporate with electroporator. Then SOC medium was added and the mixture was rotated in the 37° C. incubator for 1 h. 200 μL the bacteria solution was taken with 10 time gradient dilutions to scrape 2×YT solid plates, and the bacteria were cultured overnight in a 37° C. incubator. The next day, the capacity of the library was calculated to be $1\times10^8$ CFU based on the number of colonies on the plate. Twenty-three clones were randomly selected, and the upstream and downstream primers designed for pComb3XSS were added to the PCR reaction system for colony PCR reaction. The insertion rate of the phage library was determined to be above 95% (FIG. 1). Random 100 clones were selected and sent to Anhui Generalbio Co., Ltd. for sequencing. The effective insertion rate was greater than 90%, proving that the library was successfully constructed.

Nanobody Screening for GUCY2C Protein

Protein GUCY2C was dissolved in 0.1 mM pH7.2 PBS, 5 ug protein was coated on a high-affinity ELISA plate, and was incubated at 4° C. overnight. The coating protein was removed the next day, and 5% BSA was added to seal the ELISA plate at room temperature for 2 hours. The blocking solution was removed, and then $1\times10^{11}$ CFU phage were added to ELISA plate and incubated at room temperature for 1 hour. Unbound phages were washed with PBST (PBS+ 0.05% Tween20) for 8 times. The bound phages were eluted with 0.1M pH2.0 Glycine for 8 minutes, and 2M Tris was added for stopping the reaction. The eluting phages were infected with TG1 bacteria in the logarithmic growth phase, and the phages were amplified and purified from TG1 bacteria for the next round of screening. The same screening method was repeated 3 times, and the continuously screening phages were utilized to detect positive clones by Elisa.

Figure 2:
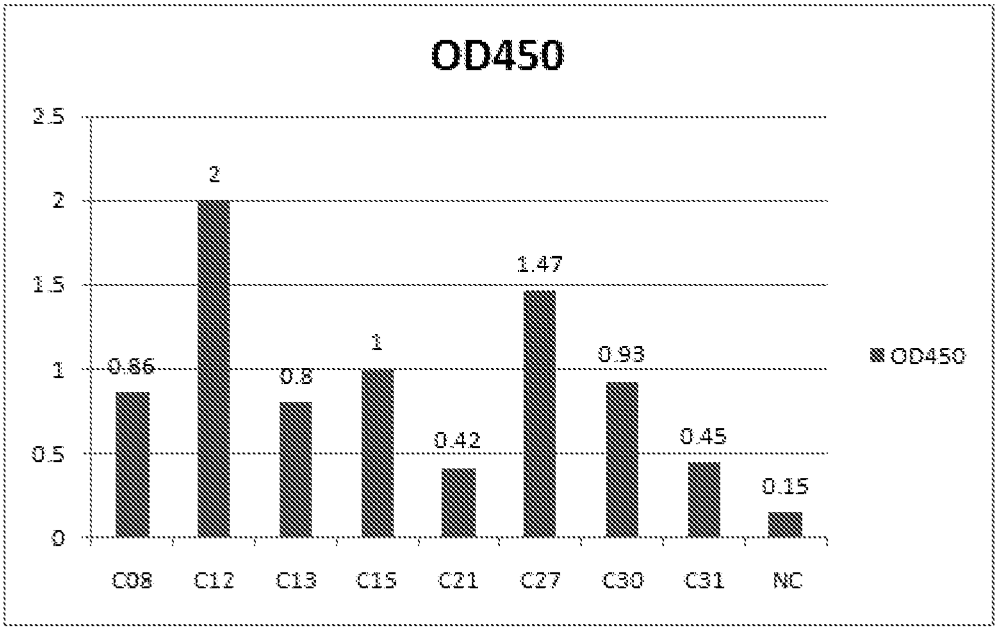
FIG. 2 shows the OD450 values of VHH clones during antibody screening.

The phages of 3 rounds screening were transfected into HB2151 bacteria, and 100 ul of infected HB2151 bacteria were taken to scrape on the surface of 2×YT-AG solid culture dish. 96 single clones were picked and added into 2×YT medium, then cultured in a 96 deep-well plate. 0.8 mM IPTG was added into the medium when the bacteria grew to logarithmic phase and were cultured overnight at 25° C. The supernatant of medium was added to the 1 ug/ml GUCY2C coated ELISA plate which was contained in two control wells. After incubating for 2 hours at 37° C., the plate was washed 3 times with PBST. Peroxidase AffiniPure Goat anti-Alpaca IgG, VHH domain (Jackson Immumo Research) was added into the Elisa plate, incubated at 37° C. for 1 hour and washed 3 times with PBST. TMB solution was added for 20 minutes, then the reaction was stopped with 2M sulfuric acid. The absorbance value at 450 nm wavelength was read on the microplate reader (FIG. 2). Clones with an absorbance value 2.1 times higher than the negative control were considered positive clones and were sent to sequencing.

Figure 3:
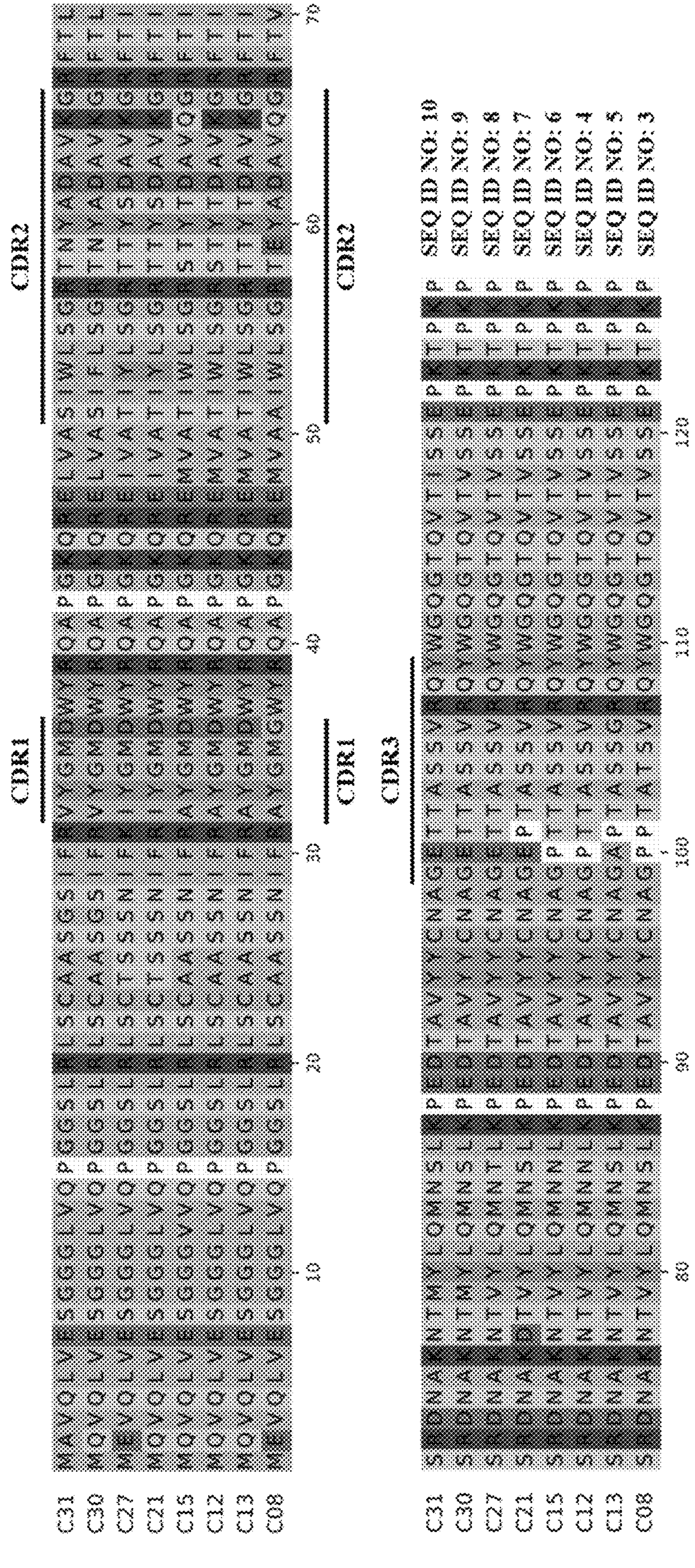
FIG. 3 shows the alignment of the exemplary VHH domains provided herein. SEQ ID NOS: 3-10.

The amino acid and nucleic acid sequences of the exemplary VHH domains are shown in Table 2, and the exemplary CDR sequences (according to Kabat numbering system) of these exemplary VHH domains are shown in Table 3 below. The alignment of these exemplary VHH domains is shown in FIG. 3, which shows high percentage of shared amino acids among these full sequences as well as CDR regions. CDR1 has a consensus sequence of $X_1YGMX_2$, wherein $X_1$ is A, I or V, and $X_2$ is D or G (SEQ ID NO: 64). CDR2 has a consensus sequence of $X_3IX_4LSGRX_5X_6YX_7DAVX_8G$, wherein $X_3$ is A, S or T; $X_4$ is F, W or Y; $X_5$ is S or T; $X_6$ is E, N or T; $X_7$ is A, S or T; and $X_8$ is K or Q (SEQ ID NO: 65). CDR3 has a consensus sequence of $GX_9X_{10}TAX_{11}SX_{12}RQY$, wherein $X_9$ is A, E or P; $X_{10}$ is P or T; $X_{11}$ is S or T; and $X_{12}$ is G or V (SEQ ID NO: 66).

TABLE 2

Nucleic Acid and Amino Acid Sequences of Exemplary VHH Domains

| Description | Sequence | SEQ ID NO. |
|---|---|---|
| C08(amino acid) | MEVQLVESGGGLVQPGGSLRLSCAASSNIFRAYGMG WYRQAPGKQREMVAAIWLSGRTEYADAVQGRFTVSR DNAKNTVYLQMNSLKPEDTAVYYCNAGPPTATSVRQ YWGQGTQVTVSSEPKTPKP | SEQ ID NO: 3 |
| C12(amino acid) | MQVQLVESGGGLVQPGGSLRLSCAASSNIFRAYGMD WYRQAPGKQREMVATIWLSGRSTYTDAVKGRFTISRD NAKNTVYLQMNNLKPEDTAVYYCNAGPTTASSVRQY WGQGTQVTVSSEPKTPKP | SEQ ID NO: 4 |
| C13(amino acid) | MQVQLVESGGGLVQPGGSLRLSCAASSNIFRAYGMD WYRQAPGKQREMVATIWLSGRTTYTDAVKGRFTISRD NAKNTVYLQMNSLKPEDTAVYYCNAGAPTASSGRQY WGQGTQVTVSSEPKTPKP | SEQ ID NO: 5 |

TABLE 2-continued

Nucleic Acid and Amino Acid Sequences of Exemplary VHH Domains

| Description | Sequence | SEQ ID NO. |
|---|---|---|
| C15(amino acid) | MQVQLVESGGGVVQPGGSLRLSCAASSNIFRAYGMD WYRQAPGKQREMVATIWLSGRSTYTDAVQGRFTISRD NAKNTVYLQMNNLKPEDTAVYYCNAGPTTASSVRQY WGQGTQVTVSSEPKTPKP | SEQ ID NO: 6 |
| C21(amino acid) | MQVQLVESGGGLVQPGGSLRLSCTSSSNIFRIYGMDW YRQAPGKQREIVATIYLSGRTTYSDAVKGRFTISRDNA KDTVYLQMNSLKPEDTAVYYCNAGEPTASSVRQYWG QGTQVTVSSEPKTPKP | SEQ ID NO: 7 |
| C27(amino acid) | MEVQLVESGGGLVQPGGSLRLSCTSSSNIFKIYGMDW YRQAPGKQREIVATIYLSGRTTYSDAVKGRFTISRDNA KNTVYLQMNTLKPEDTAVYYCNAGETTASSVRQYWG QGTQVTVSSEPKTPKP | SEQ ID NO: 8 |
| C30(amino acid) | MQVQLVESGGGLVQPGGSLRLSCAASGSIFRVYGMD WYRQAPGKQRELVASIFLSGRTNYADAVKGRFTLSRD NAKNTMYLQMNSLKPEDTAVYYCNAGETTASSVRQY WGQGTQVTVSSEPKTPKP | SEQ ID NO: 9 |
| C31(amino acid) | MAVQLVESGGGLVQPGGSLRLSCAASGSIFRVYGMD WYRQAPGKQRELVASIWLSGRTNYADAVKGRFTLSR DNAKNTMYLQMNSLKPEDTAVYYCNAGETTASSVRQ YWGQGTQVTISSEPKTPKP | SEQ ID NO: 10 |
| C08 (nucleic acid) | ATGGAGGTGCAGCTGGTGGAGTCTGGGGGAGGTTTG GTGCAACCTGGGGGGTCTCTGAGACTCTCCTGTGCA GCCTCTTCAAACATCTTCAGAGCCTATGGCATGGGG TGGTACCGCCAGGCTCCAGGGAAGCAGCGCGAAAT GGTCGCGGCTATTTGGCTCAGTGGTCGCACAGAGTA TGCTGACGCCGTGCAGGGCCGATTCACCGTCTCCAG AGACAACGCCAAGAACACGGTGTATCTGCAAATGA ACAGCCTGAAACCTGAGGACACGGCCGTCTATTACT GTAATGCAGGTCCCCCTACAGCAACTTCCGTCCGTC AATACTGGGGCCAGGGGACCCAGGTCACCGTCTCCT CAGAACCCAAGACACCAAAACCA | SEQ ID NO: 11 |
| C12 (nucleic acid) | ATGCAGGTACAGCTGGTGGAGTCTGGGGGAGGTTTG GTGCAACCTGGGGGGTCTCTGAGACTCTCCTGTGCA GCCTCTTCAAACATCTTCAGAGCCTATGGCATGGAT TGGTACCGCCAGGCTCCAGGAAAGCAGCGCGAAAT GGTCGCGACTATCTGGCTGAGTGGTCGCTCAACGTA TACTGACGCCGTGAAGGGCCGATTCACCATCTCCAG AGACAACGCCAAGAACACGGTGTATCTGCAAATGA ACAACCTGAAACCTGAGGACACGGCCGTCTATTACT GTAATGCAGGTCCCACTACGGCAAGTTCCGTCCGTC AATACTGGGGCCAGGGGACCCAGGTCACCGTCTCCT CAGAACCCAAGACACCAAAACCA | SEQ ID NO: 12 |
| C13(nucleic acid) | ATGCAGGTGCAGCTGGTGGAGTCTGGGGGAGGTTTG GTGCAACCTGGGGGGTCTCTGAGACTCTCCTGTGCA GCCTCTTCAAACATCTTCAGAGCCTATGGCATGGAC TGGTACCGCCAGGCTCCAGGGAAGCAGCGCGAAAT GGTCGCGACTATCTGGCTTAGTGGTCGCACAACGTA TACTGACGCCGTGAAGGGCCGATTCACCATCTCCAG AGACAACGCCAAGAACACGGTGTATCTGCAAATGA ACAGCCTGAAACCTGAGGACACGGCCGTCTATTACT GTAATGCAGGTGCCCCTACGGCAAGTTCCGGCCGTC AATACTGGGGCCAGGGGACCCAGGTCACCGTCTCCT CAGAACCCAAGACACCAAAACCA | SEQ ID NO: 12 |
| C15(nucleic acid) | ATGCAGGTGCAGCTGGTGGAGTCTGGGGGAGGGGT GGTGCAACCTGGGGGGTCTCTGAGACTCTCCTGTGC AGCCTCTTCAAATATCTTTAGAGCCTATGGCATGGA TTGGTACCGCCAGGCTCCAGGAAAGCAGCGCGAAA TGGTCGCGACTATCTGGCTGAGTGGTCGCTCAACGT ATACTGACGCCGTACAGGGCCGATTCACCATCTCCA GAGACAACGCCAAGAACACGGTGTATCTGCAAATG AACAACCTGAAACCTGAGGACACGGCCGTCTATTAC TGTAATGCAGGTCCCACTACGGCAAGTTCCGTCCGT CAATACTGGGGCCAGGGGACCCAGGTCACCGTCTCC TCAGAACCCAAGACACCAAAACCA | SEQ ID NO: 14 |
| C21(nucleic acid) | ATGCAGGTACAGCTGGTGGAGTCTGGGGGAGGTTTG GTGCAACCTGGGGGGTCTCTGAGACTCTCCTGTACA AGCTCTTCAAACATCTTCAGAATCTATGGCATGGAC | SEQ ID NO: 15 |

TABLE 2-continued

| Nucleic Acid and Amino Acid Sequences of Exemplary VHH Domains | | |
|---|---|---|
| Description | Sequence | SEQ ID NO. |
| | TGGTACCGCCAGGCTCCAGGGAAGCAGCGCGAAAT AGTCGCGACTATCTATCTTAGTGGTCGCACAACGTA TAGTGACGCCGTGAAGGGCCGATTCACCATCTCCAG AGACAACGCCAAGGACACGGTGTATCTGCAAATGA ACAGCCTGAAACCTGAGGACACGGCCGTCTATTACT GTAATGCAGGTGAACCTACGGCAAGTTCCGTCCGTC AGTACTGGGGCCAGGGGACCCAGGTCACCGTCTCCT CAGAACCCAAGACACCAAAACCA | |
| C27(nucleic acid) | ATGGAGGTGCAGCTGGTGGAGTCTGGGGGAGGTTTG GTGCAACCTGGGGGGTCTCTGAGACTCTCCTGTACA AGCTCTTCAAACATCTTCAAAATCTATGGCATGGAC TGGTACCGCCAGGCTCCAGGGAAACAGCGCGAAAT AGTCGCGACTATCTATCTTAGTGGTCGCACAACGTA TAGTGACGCCGTGAAGGGCCGATTCACCATCTCCAG AGACAACGCCAAGAACACGGTGTATCTGCAAATGA ACACCCTGAAACCTGAGGACACGGCCGTCTATTACT GTAATGCAGGTGAAACTACGGCAAGTTCCGTCCGTC AATACTGGGGCCAGGGGACCCAGGTCACCGTCTCCT CAGAACCCAAGACACCAAAACCA | SEQ ID NO: 16 |
| C30(nucleic acid) | ATGCAGGTGCAGCTGGTGGAGTCTGGGGGAGGCTTG GTGCAGCCTGGGGGGTCTCTGAGACTCTCCTGTGCA GCCTCTGGAAGCATCTTCAGAGTCTATGGCATGGAC TGGTACCGCCAGGCTCCAGGGAAGCAGCGCGAGTT GGTCGCGTCTATTTTTCTTAGTGGTAGGACAAACTAT GCAGACGCCGTGAAGGGCCGATTCACGCTCTCCAGA GATAACGCCAAGAATACTATGTATCTGCAAATGAAC AGCCTGAAACCTGAGGACACGGCCGTCTATTATTGT AATGCAGGTGAAACTACGGCAAGTTCCGTCCGTCAA TACTGGGGCCAGGGGACCCAGGTCACCGTCTCCTCA GAACCCAAGACACCAAAACCA | SEQ ID NO: 17 |
| C31(nucleic acid) | ATGGCGGTGCAGCTGGTGGAGTCTGGGGGAGGCTTG GTGCAGCCTGGGGGGTCTCTGAGACTCTCCTGTGCA GCCTCTGGAAGCATCTTCAGAGTCTATGGCATGGAC TGGTACCGCCAGGCTCCAGGGAAGCAGCGCGAGTT GGTCGCGTCTATTTGGCTTAGTGGTAGGACAAACTA TGCAGACGCCGTGAAGGGCCGATTCACGCTCTCCAG AGATAACGCCAAGAATACGATGTATCTGCAAATGA ACAGCCTGAAACCTGAGGACACGGCCGTCTATTATT GTAATGCAGGTGAAACTACGGCAAGTTCCGTCCGTC AATACTGGGGCCAGGGGACCCAGGTCACCATCTCCT CGGAACCCAAGACACCAAAACCA | SEQ ID NO: 18 |

TABLE 3

| CDR Amino Acid Sequences of Exemplary VHH Domains | | |
|---|---|---|
| Description | Sequence | SEQ ID NO. |
| C08-CDR1 | AYGMG | SEQ ID NO: 19 |
| C12-CDR1 | AYGMD | SEQ ID NO: 20 |
| C13-CDR1 | AYGMD | SEQ ID NO: 21 |
| C15-CDR1 | AYGMD | SEQ ID NO: 22 |
| C21-CDR1 | IYGMD | SEQ ID NO: 23 |
| C27-CDR1 | IYGMD | SEQ ID NO: 24 |
| C30-CDR1 | VYGMD | SEQ ID NO: 25 |
| C31-CDR1 | VYGMD | SEQ ID NO: 26 |
| C08-CDR2 | AIWLSGRTEYADAVQG | SEQ ID NO: 27 |
| C12-CDR2 | TIWLSGRSTYTDAVKG | SEQ ID NO: 28 |
| C13-CDR2 | TIWLSGRTTYTDAVKG | SEQ ID NO: 29 |

TABLE 3-continued

| CDR Amino Acid Sequences of Exemplary VHH Domains | | |
|---|---|---|
| Description | Sequence | SEQ ID NO. |
| C15-CDR2 | TIWLSGRSTYTDAVQG | SEQ ID NO: 30 |
| C21-CDR2 | TIYLSGRTTYSDAVKG | SEQ ID NO: 31 |
| C27-CDR2 | TIYLSGRTTYSDAVKG | SEQ ID NO: 32 |
| C30-CDR2 | SIFLSGRTNYADAVKG | SEQ ID NO: 33 |
| C31-CDR2 | SIWLSGRTNYADAVKG | SEQ ID NO: 34 |
| C08-CDR3 | GPPTATSVRQY | SEQ ID NO: 35 |
| C12-CDR3 | GPTTASSVRQY | SEQ ID NO: 36 |
| C13-CDR3 | GAPTASSGRQY | SEQ ID NO: 37 |
| C15-CDR3 | GPTTASSVRQY | SEQ ID NO: 38 |
| C21-CDR3 | GEPTASSVRQY | SEQ ID NO: 39 |
| C27-CDR3 | GETTASSVRQY | SEQ ID NO: 40 |

TABLE 3-continued

CDR Amino Acid Sequences of Exemplary VHH Domains

| Description | Sequence | SEQ ID NO. |
|---|---|---|
| C30-CDR3 | GETTASSVRQY | SEQ ID NO: 41 |
| C31-CDR3 | GETTASSVRQY | SEQ ID NO: 42 |

6.2. Example 2—Construction of Chimeric Antigen Receptor

Figure 4A:
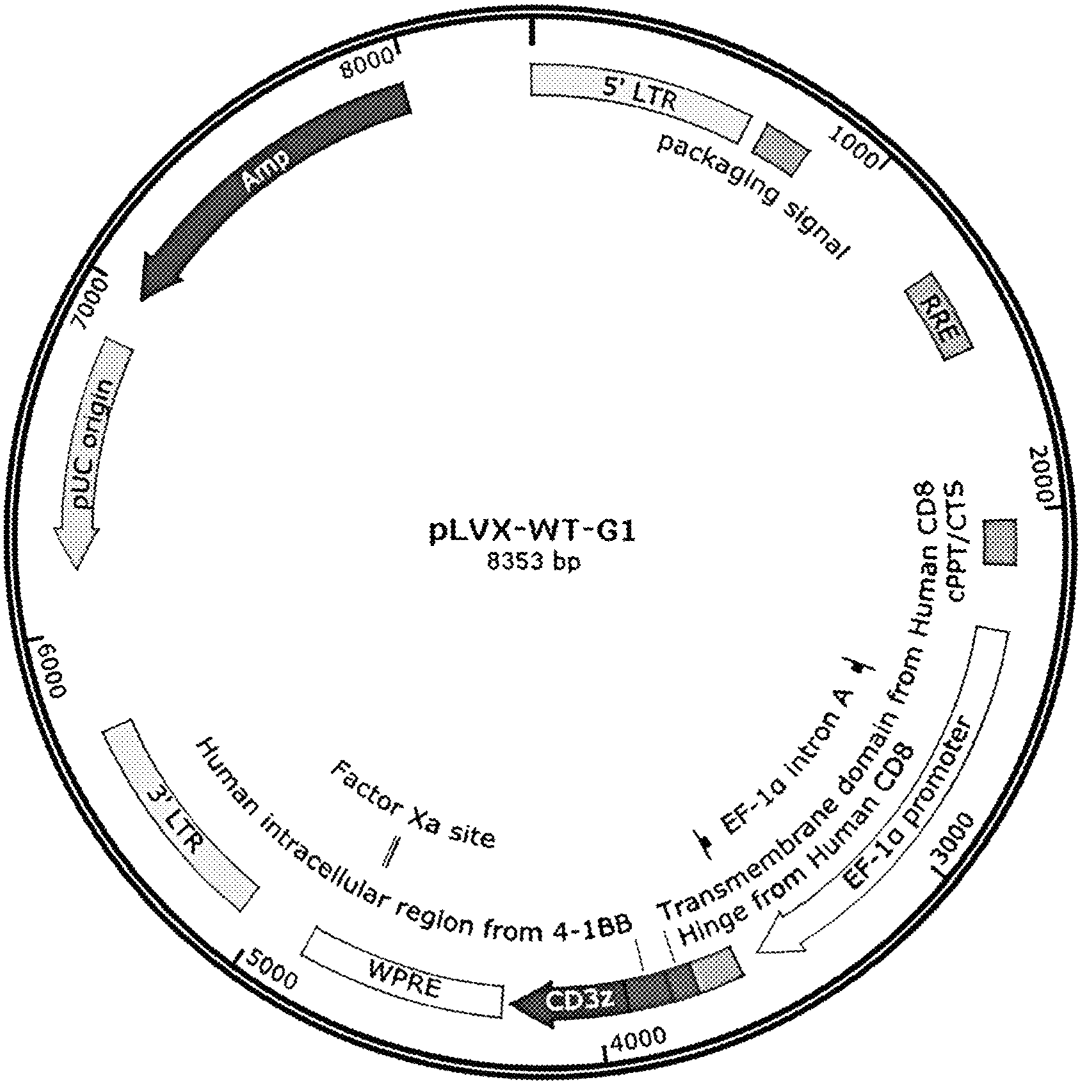
FIG. 4A shows the schematic diagram of the transformed vector pLVX-WT-G1. The CMV promoter of the pLVX-Puro is replaced with the EF-1a promoter, and the CD8 hinge, CD8 transmembrane domain, 4-1BB and CD3z are added following the EF-1a promoter.

The vector pL VX-WT-G1 was modified using the pL VX-Puro vector as a template, in which the CMV promoter in the pLVX-Puro vector was transformed into the EF1a promoter, and the partial sequence of the chimeric antigen receptor was inserted into EF1a following the promoter. The sequence consists of CD8 hinge, CD8 transmembrane region, 4-1BB and CD3z, which amino acid sequences are SEQ ID NO: 43, SEQ ID NO: 44, SEQ ID NO: 45 and SEQ ID NO: 46, respectively, as shown in Table 4 below. The transformed vector is shown in FIG. 4A. The optimized sequence of contained the CD8 signal peptide and anti-GUCY2C VHHs were inserted following the CD8 hinge of the pLVX-WT-G1 vector by ligation to construct the anti-GUCY2C VHH based chimeric antigen receptor vector pL VX-WT-G1-VHH-CAR. The CD8 signal peptide comprises the amino acid sequence of SEQ ID NO: 47 (see Table 4).

The amino acid and nucleic acid sequences of the exemplary constructed chimeric antigen receptor are shown in Table 5.

TABLE 4

Sequences of Regions in Exempary CARs

| Description | Sequence | SEQ ID NO. |
|---|---|---|
| CD8 hinge | TTTPAPRPPTPAPTIASQPLSLRPEACRPAAGGAVHTR GLDFACD | SEQ ID NO: 43 |
| CD8 TM | IYIWAPLAGTCGVLLLSLVITLYC | SEQ ID NO: 44 |
| 4-1BB | KRGRKKLLYIFKQPFMRPVQTTQEEDGCSCRFPEEEE GGCEL | SEQ ID NO: 45 |
| CD3z | RVKFSRSADAPAYQQGQNQLYNELNLGRREEYDVL DKRRGRDPEMGGKPRRKNPQEGLYNELQKDKMAE AYSEIGMKGERRRGKGHDGLYQGLSTATKDTYDAL HMQALPPR | SEQ ID NO: 46 |
| CD8 single peptide | MALPVTALLLPLALLLHAARP | SEQ ID NO: 47 |

TABLE 5

| Description | Sequence | SEQ ID NO. |
|---|---|---|
| C08-CAR (amino acid) | MALPVTALLLPLALLLHAARPEVQLVESGGGLVQP GGSLRLSCAASSNIFRAYGMGWYRQAPGKQREMV AAIWLSGRTEYADAVQGRFTVSRDNAKNTVYLQM NSLKPEDTAVYYCNAGPPTATSVRQYWGQGTQVT VSSEPKTPKPTSTTTPAPRPPTPAPTIASQPLSLRPEA CRPAAGGAVHTRGLDFACDIYIWAPLAGTCGVLLL SLVITLYCKRGRKKLLYIFKQPFMRPVQTTQEEDGC SCRFPEEEEGGCELRVKFSRSADAPAYQQGQNQLY NELNLGRREEYDVLDKRRGRDPEMGGKPRRKNPQ EGLYNELQKDKMAEAYSEIGMKGERRRGKGHDGL YQGLSTATKDTYDALHMQALPPR | SEQ ID NO: 48 |
| C12-CAR (amino acid) | MALPVTALLLPLALLLHAARPQVQLVESGGGLVQP GGSLRLSCAASSNIFRAYGMDWYRQAPGKQREMV ATIWLSGRSTYTDAVKGRFTISRDNAKNTVYLQMN NLKPEDTAVYYCNAGPTTASSVRQYWGQGTQVTV SSEPKTPKPTSTTTPAPRPPTPAPTIASQPLSLRPEAC RPAAGGAVHTRGLDFACDIYIWAPLAGTCGVLLLS LVITLYCKRGRKKLLYIFKQPFMRPVQTTQEEDGCS CRFPEEEEGGCELRVKFSRSADAPAYQQGQNQLYN ELNLGRREEYDVLDKRRGRDPEMGGKPRRKNPQE GLYNELQKDKMAEAYSEIGMKGERRRGKGHDGLY QGLSTATKDTYDALHMQALPPR | SEQ ID NO: 49 |
| C13-CAR (amino acid) | MALPVTALLLPLALLLHAARPQVQLVESGGGLVQP GGSLRLSCAASSNIFRAYGMDWYRQAPGKQREMV ATIWLSGRTTYTDAVKGRFTISRDNAKNTVYLQMN SLKPEDTAVYYCNAGAPTASSGRQYWGQGTQVTV SSEPKTPKPTSTTTPAPRPPTPAPTIASQPLSLRPEAC RPAAGGAVHTRGLDFACDIYIWAPLAGTCGVLLLS | SEQ ID NO: 50 |

TABLE 5-continued

| Description | Sequence | SEQ ID NO. |
|---|---|---|
| | LVITLYCKRGRKKLLYIFKQPFMRPVQTTQEEDGCS CRFPEEEEGGCELRVKFSRSADAPAYQQGQNQLYN ELNLGRREEYDVLDKRRGRDPEMGGKPRRKNPQE GLYNELQKDKMAEAYSEIGMKGERRRGKGHDGLY QGLSTATKDTYDALHMQALPPR | |
| C15-CAR (amino acid) | MALPVTALLLPLALLLHAARPQVQLVESGGGVVQP GGSLRLSCAASSNIFRAYGMDWYRQAPGKQREMV ATIWLSGRSTYTDAVQGRFTISRDNAKNTVYLQMN NLKPEDTAVYYCNAGPTTASSVRQYWGQGTQVTV SSEPKTPKPTSTTTPAPRPPTPAPTIASQPLSLRPEAC RPAAGGAVHTRGLDFACDIYIWAPLAGTCGVLLLS LVITLYCKRGRKKLLYIFKQPFMRPVQTTQEEDGCS CRFPEEEEGGCELRVKFSRSADAPAYQQGQNQLYN ELNLGRREEYDVLDKRRGRDPEMGGKPRRKNPQE GLYNELQKDKMAEAYSEIGMKGERRRGKGHDGLY QGLSTATKDTYDALHMQALPPR | SEQ ID NO: 51 |
| C21-CAR (amino acid) | MALPVTALLLPLALLLHAARPQVQLVESGGGLVQP GGSLRLSCTSSSNIFRIYGMDWYRQAPGKQREIVATI YLSGRTTYSDAVKGRFTISRDNAKDTVYLQMNSLK PEDTAVYYCNAGEPTASSVRQYWGQGTQVTVSSEP KTPKPTSTTTPAPRPPTPAPTIASQPLSLRPEACRPAA GGAVHTRGLDFACDIYIWAPLAGTCGVLLLSLVITL YCKRGRKKLLYIFKQPFMRPVQTTQEEDGCSCRFPE EEEGGCELRVKFSRSADAPAYQQGQNQLYNELNLG RREEYDVLDKRRGRDPEMGGKPRRKNPQEGLYNE LQKDKMAEAYSEIGMKGERRRGKGHDGLYQGLST ATKDTYDALHMQALPPR | SEQ ID NO: 52 |
| C27-CAR (amino acid) | MALPVTALLLPLALLLHAARPEVQLVESGGGLVQP GGSLRLSCTSSSNIFKIYGMDWYRQAPGKQREIVATI YLSGRTTYSDAVKGRFTISRDNAKNTVYLQMNTLK PEDTAVYYCNAGETTASSVRQYWGQGTQVTVSSEP KTPKPTSTTTPAPRPPTPAPTIASQPLSLRPEACRPAA GGAVHTRGLDFACDIYIWAPLAGTCGVLLLSLVITL YCKRGRKKLLYIFKQPFMRPVQTTQEEDGCSCRFPE EEEGGCELRVKFSRSADAPAYQQGQNQLYNELNLG RREEYDVLDKRRGRDPEMGGKPRRKNPQEGLYNE LQKDKMAEAYSEIGMKGERRRGKGHDGLYQGLST ATKDTYDALHMQALPPR | SEQ ID NO: 53 |
| C30-CAR (amino acid) | MALPVTALLLPLALLLHAARPQVQLVESGGGLVQP GGSLRLSCAASGSIFRVYGMDWYRQAPGKQRELVA SIFLSGRTNYADAVKGRFTLSRDNAKNTMYLQMNS LKPEDTAVYYCNAGETTASSVRQYWGQGTQVTVS SEPKTPKPTSTTTPAPRPPTPAPTIASQPLSLRPEACR PAAGGAVHTRGLDFACDIYIWAPLAGTCGVLLLSL VITLYCKRGRKKLLYIFKQPFMRPVQTTQEEDGCSC RFPEEEEGGCELRVKFSRSADAPAYQQGQNQLYNE LNLGRREEYDVLDKRRGRDPEMGGKPRRKNPQEG LYNELQKDKMAEAYSEIGMKGERRRGKGHDGLYQ GLSTATKDTYDALHMQALPPR | SEQ ID NO: 54 |
| C31-CAR (amino acid) | MALPVTALLLPLALLLHAARPAVQLVESGGGLVQP GGSLRLSCAASGSIFRVYGMDWYRQAPGKQRELVA SIWLSGRTNYADAVKGRFTLSRDNAKNTMYLQMN SLKPEDTAVYYCNAGETTASSVRQYWGQGTQVTIS SEPKTPKPTSTTTPAPRPPTPAPTIASQPLSLRPEACR PAAGGAVHTRGLDFACDIYIWAPLAGTCGVLLLSL VITLYCKRGRKKLLYIFKQPFMRPVQTTQEEDGCSC RFPEEEEGGCELRVKFSRSADAPAYQQGQNQLYNE LNLGRREEYDVLDKRRGRDPEMGGKPRRKNPQEG LYNELQKDKMAEAYSEIGMKGERRRGKGHDGLYQ GLSTATKDTYDALHMQALPPR | SEQ ID NO: 55 |
| C08-CAR (nucleic acid) | ATGGCCTTACCAGTGACCGCCTTGCTCCTGCCGCT GGCCTTGCTGCTCCACGCCGCCAGGCCGGAGGTG CAGCTGGTGGAGTCTGGGGGAGGTTTGGTGCAAC CTGGGGGGTCTCTGAGACTCTCCTGTGCAGCCTCT TCAAACATCTTCAGAGCCTATGGCATGGGGTGGT ACCGCCAGGCTCCAGGGAAGCAGCGCGAAATGG TCGCGGCTATTTGGCTCAGTGGTCGCACAGAGTA TGCTGACGCCGTGCAGGGCCGATTCACCGTCTCC AGAGACAACGCCAAGAACACGGTGTATCTGCAA ATGAACAGCCTGAAACCTGAGGACACGGCCGTCT ATTACTGTAATGCAGGTCCCCCTACAGCAACTTCC GTCCGTCAATACTGGGGCCAGGGGACCCAGGTCA | SEQ ID NO: 56 |

TABLE 5-continued

| Description | Sequence | SEQ ID NO. |
|---|---|---|
| | CCGTCTCCTCAGAACCCAAGACACCAAAACCAAC<br>TAGTACCACGACGCCAGCGCCGCGACCACCAACA<br>CCGGCGCCCACCATCGCGTCGCAGCCCCTGTCCC<br>TGCGCCCAGAGGCGTGCCGGCCAGCGGCGGGGG<br>GCGCAGTGCACACGAGGGGGCTGGACTTCGCCTG<br>TGATATCTACATCTGGGCGCCCTTGGCCGGGACTT<br>GTGGGGTCCTTCTCCTGTCACTGGTTATCACCCTT<br>TACTGCAAACGGGGCAGAAAGAAACTCCTGTATA<br>TATTCAAACAACCATTTATGAGACCAGTACAAAC<br>TACTCAAGAGGAAGATGGCTGTAGCTGCCGATTT<br>CCAGAAGAAGAAGAAGGAGGATGTGAACTGAGA<br>GTGAAGTTCAGCAGGAGCGCAGACGCCCCCGCGT<br>ACCAGCAGGGCCAGAACCAGCTCTATAACGAGCT<br>CAATCTAGGACGAAGAGAGGAGTACGATGTTTTG<br>GACAAGAGACGTGGCCGGGACCCTGAGATGGGG<br>GGAAAGCCGAGAAGGAAGAACCCTCAAGAAGGC<br>CTGTACAATGAACTGCAGAAAGATAAGATGGCGG<br>AGGCCTACAGTGAGATTGGGATGAAAGGCGAGC<br>GCCGGAGGGGCAAGGGGCACGATGGCCTTTACCA<br>GGGTCTCAGTACAGCCACCAAGGACACCTACGAC<br>GCCCTTCACATGCAGGCCCTGCCCCCTCGCTAA | |
| C12-CAR<br>(nucleic acid) | ATGGCCTTACCAGTGACCGCCTTGCTCCTGCCGCT<br>GGCCTTGCTGCTCCACGCCGCCAGGCCGCAGGTA<br>CAGCTGGTGGAGTCTGGGGGAGGTTTGGTGCAAC<br>CTGGGGGGTCTCTGAGACTCTCCTGTGCAGCCTCT<br>TCAAACATCTTCAGAGCCTATGGCATGGATTGGT<br>ACCGCCAGGCTCCAGGAAAGCAGCGCGAAATGG<br>TCGCGACTATCTGGCTGAGTGGTCGCTCAACGTA<br>TACTGACGCCGTGAAGGGCCGATTCACCATCTCC<br>AGAGACAACGCCAAGAACACGGTGTATCTGCAA<br>ATGAACAACCTGAAACCTGAGGACACGGCCGTCT<br>ATTACTGTAATGCAGGTCCCACTACGGCAAGTTC<br>CGTCCGTCAATACTGGGGCCAGGGGACCCAGGTC<br>ACCGTCTCCTCAGAACCCAAGACACCAAAACCAA<br>CTAGTACCACGACGCCAGCGCCGCGACCACCAAC<br>ACCGGCGCCCACCATCGCGTCGCAGCCCCTGTCC<br>CTGCGCCCAGAGGCGTGCCGGCCAGCGGCGGGG<br>GGCGCAGTGCACACGAGGGGGCTGGACTTCGCCT<br>GTGATATCTACATCTGGGCGCCCTTGGCCGGGAC<br>TTGTGGGGTCCTTCTCCTGTCACTGGTTATCACCC<br>TTTACTGCAAACGGGGCAGAAAGAAACTCCTGTA<br>TATATTCAAACAACCATTTATGAGACCAGTACAA<br>ACTACTCAAGAGGAAGATGGCTGTAGCTGCCGAT<br>TTCCAGAAGAAGAAGAAGGAGGATGTGAACTGA<br>GAGTGAAGTTCAGCAGGAGCGCAGACGCCCCCGC<br>GTACCAGCAGGGCCAGAACCAGCTCTATAACGAG<br>CTCAATCTAGGACGAAGAGAGGAGTACGATGTTT<br>TGGACAAGAGACGTGGCCGGGACCCTGAGATGG<br>GGGGAAAGCCGAGAAGGAAGAACCCTCAAGAAG<br>GCCTGTACAATGAACTGCAGAAAGATAAGATGGC<br>GGAGGCCTACAGTGAGATTGGGATGAAAGGCGA<br>GCGCCGGAGGGGCAAGGGGCACGATGGCCTTTAC<br>CAGGGTCTCAGTACAGCCACCAAGGACACCTACG<br>ACGCCCTTCACATGCAGGCCCTGCCCCCTCGCTA<br>A | SEQ ID NO: 57 |
| C13-CAR<br>(nucleic acid) | ATGGCCTTACCAGTGACCGCCTTGCTCCTGCCGCT<br>GGCCTTGCTGCTCCACGCCGCCAGGCCGCAGGTG<br>CAGCTGGTGGAGTCTGGGGGAGGTTTGGTGCAAC<br>CTGGGGGGTCTCTGAGACTCTCCTGTGCAGCCTCT<br>TCAAACATCTTCAGAGCCTATGGCATGGACTGGT<br>ACCGCCAGGCTCCAGGGAAGCAGCGCGAAATGG<br>TCGCGACTATCTGGCTTAGTGGTCGCACAACGTA<br>TACTGACGCCGTGAAGGGCCGATTCACCATCTCC<br>AGAGACAACGCCAAGAACACGGTGTATCTGCAA<br>ATGAACAGCCTGAAACCTGAGGACACGGCCGTCT<br>ATTACTGTAATGCAGGTGCCCCTACGGCAAGTTC<br>CGGCCGTCAATACTGGGGCCAGGGGACCCAGGTC<br>ACCGTCTCCTCAGAACCCAAGACACCAAAACCAA<br>CTAGTACCACGACGCCAGCGCCGCGACCACCAAC<br>ACCGGCGCCCACCATCGCGTCGCAGCCCCTGTCC<br>CTGCGCCCAGAGGCGTGCCGGCCAGCGGCGGGG<br>GGCGCAGTGCACACGAGGGGGCTGGACTTCGCCT<br>GTGATATCTACATCTGGGCGCCCTTGGCCGGGAC<br>TTGTGGGGTCCTTCTCCTGTCACTGGTTATCACCC<br>TTTACTGCAAACGGGGCAGAAAGAAACTCCTGTA<br>TATATTCAAACAACCATTTATGAGACCAGTACAA | SEQ ID NO: 58 |

TABLE 5-continued

| Description | Sequence | SEQ ID NO. |
|---|---|---|
| | ACTACTCAAGAGGAAGATGGCTGTAGCTGCCGAT TTCCAGAAGAAGAAGAAGGAGGATGTGAACTGA GAGTGAAGTTCAGCAGGAGCGCAGACGCCCCCGC GTACCAGCAGGGCCAGAACCAGCTCTATAACGAG CTCAATCTAGGACGAAGAGAGGAGTACGATGTTT TGGACAAGAGACGTGGCCGGGACCCTGAGATGG GGGGAAAGCCGAGAAGGAAGAACCCTCAAGAAG GCCTGTACAATGAACTGCAGAAAGATAAGATGGC GGAGGCCTACAGTGAGATTGGGATGAAAGGCGA GCGCCGGAGGGGCAAGGGGCACGATGGCCTTTAC CAGGGTCTCAGTACAGCCACCAAGGACACCTACG ACGCCCTTCACATGCAGGCCCTGCCCCCTCGCTA A | |
| C15-CAR (nucleic acid) | ATGGCCTTACCAGTGACCGCCTTGCTCCTGCCGCT GGCCTTGCTGCTCCACGCCGCCAGGCCGCAGGTG CAGCTGGTGGAGTCTGGGGGAGGGGTGGTGCAAC CTGGGGGGTCTCTGAGACTCTCCTGTGCAGCCTCT TCAAATATCTTTAGAGCCTATGGCATGGATTGGT ACCGCCAGGCTCCAGGAAAGCAGCGCGAAATGG TCGCGACTATCTGGCTGAGTGGTCGCTCAACGTA TACTGACGCCGTACAGGGCCGATTCACCATCTCC AGAGACAACGCCAAGAACACGGTGTATCTGCAA ATGAACAACCTGAAACCTGAGGACACGGCCGTCT ATTACTGTAATGCAGGTCCCACTACGGCAAGTTC CGTCCGTCAATACTGGGGCCAGGGGACCCAGGTC ACCGTCTCCTCAGAACCCAAGACACCAAAACCAA CTAGTACCACGACGCCAGCGCCGCGACCACCAAC ACCGGCGCCCACCATCGCGTCGCAGCCCCTGTCC CTGCGCCCAGAGGCGTGCCGGCCAGCGGCGGGG GGCGCAGTGCACACGAGGGGGCTGGACTTCGCCT GTGATATCTACATCTGGGCGCCCTTGGCCGGGAC TTGTGGGGTCCTTCTCCTGTCACTGGTTATCACCC TTTACTGCAAACGGGGCAGAAAGAAACTCCTGTA TATATTCAAACAACCATTTATGAGACCAGTACAA ACTACTCAAGAGGAAGATGGCTGTAGCTGCCGAT TTCCAGAAGAAGAAGAAGGAGGATGTGAACTGA GAGTGAAGTTCAGCAGGAGCGCAGACGCCCCCGC GTACCAGCAGGGCCAGAACCAGCTCTATAACGAG CTCAATCTAGGACGAAGAGAGGAGTACGATGTTT TGGACAAGAGACGTGGCCGGGACCCTGAGATGG GGGGAAAGCCGAGAAGGAAGAACCCTCAAGAAG GCCTGTACAATGAACTGCAGAAAGATAAGATGGC GGAGGCCTACAGTGAGATTGGGATGAAAGGCGA GCGCCGGAGGGGCAAGGGGCACGATGGCCTTTAC CAGGGTCTCAGTACAGCCACCAAGGACACCTACG ACGCCCTTCACATGCAGGCCCTGCCCCCTCGCTA A | SEQ ID NO: 59 |
| C21-CAR (nucleic acid) | ATGGCCTTACCAGTGACCGCCTTGCTCCTGCCGCT GGCCTTGCTGCTCCACGCCGCCAGGCCGCAGGTA CAGCTGGTGGAGTCTGGGGGAGGTTTGGTGCAAC CTGGGGGGTCTCTGAGACTCTCCTGTACAAGCTCT TCAAACATCTTCAGAATCTATGGCATGGACTGGT ACCGCCAGGCTCCAGGGAAGCAGCGCGAAATAG TCGCGACTATCTATCTTAGTGGTCGCACAACGTAT AGTGACGCCGTGAAGGGCCGATTCACCATCTCCA GAGACAACGCCAAGGACACGGTGTATCTGCAAAT GAACAGCCTGAAACCTGAGGACACGGCCGTCTAT TACTGTAATGCAGGTGAACCTACGGCAAGTTCCG TCCGTCAGTACTGGGGCCAGGGGACCCAGGTCAC CGTCTCCTCAGAACCCAAGACACCAAAACCAACT AGTACCACGACGCCAGCGCCGCGACCACCAACAC CGGCGCCCACCATCGCGTCGCAGCCCCTGTCCCT GCGCCCAGAGGCGTGCCGGCCAGCGGCGGGGGG CGCAGTGCACACGAGGGGGCTGGACTTCGCCTGT GATATCTACATCTGGGCGCCCTTGGCCGGGACTT GTGGGGTCCTTCTCCTGTCACTGGTTATCACCCTT TACTGCAAACGGGGCAGAAAGAAACTCCTGTATA TATTCAAACAACCATTTATGAGACCAGTACAAAC TACTCAAGAGGAAGATGGCTGTAGCTGCCGATTT CCAGAAGAAGAAGAAGGAGGATGTGAACTGAGA GTGAAGTTCAGCAGGAGCGCAGACGCCCCCGCGT ACCAGCAGGGCCAGAACCAGCTCTATAACGAGCT CAATCTAGGACGAAGAGAGGAGTACGATGTTTTG GACAAGAGACGTGGCCGGGACCCTGAGATGGGG GGAAAGCCGAGAAGGAAGAACCCTCAAGAAGGC CTGTACAATGAACTGCAGAAAGATAAGATGGCGG | SEQ ID NO: 60 |

TABLE 5-continued

| Description | Sequence | SEQ ID NO. |
|---|---|---|
| | AGGCCTACAGTGAGATTGGGATGAAAGGCGAGC GCCGGAGGGGCAAGGGGCACGATGGCCTTTACCA GGGTCTCAGTACAGCCACCAAGGACACCTACGAC GCCCTTCACATGCAGGCCCTGCCCCCTCGCTAA | |
| C27-CAR (nucleic acid) | ATGGCCTTACCAGTGACCGCCTTGCTCCTGCCGCT GGCCTTGCTGCTCCACGCCGCCAGGCCGGAGGTG CAGCTGGTGGAGTCTGGGGGAGGTTTGGTGCAAC CTGGGGGGTCTCTGAGACTCTCCTGTACAAGCTCT TCAAACATCTTCAAAATCTATGGCATGGACTGGT ACCGCCAGGCTCCAGGGAAACAGCGCGAAATAG TCGCGACTATCTATCTTAGTGGTCGCACAACGTAT AGTGACGCCGTGAAGGGCCGATTCACCATCTCCA GAGACAACGCCAAGAACACGGTGTATCTGCAAAT GAACACCCTGAAACCTGAGGACACGGCCGTCTAT TACTGTAATGCAGGTGAAACTACGGCAAGTTCCG TCCGTCAATACTGGGGCCAGGGGACCCAGGTCAC CGTCTCCTCAGAACCCAAGACACCAAAACCAACT AGTACCACGACGCCAGCGCCGCGACCACCAACAC CGGCGCCCACCATCGCGTCGCAGCCCCTGTCCCT GCGCCCAGAGGCGTGCCGGCCAGCGGCGGGGGG CGCAGTGCACACGAGGGGGCTGGACTTCGCCTGT GATATCTACATCTGGGCGCCCTTGGCCGGGACTT GTGGGGTCCTTCTCCTGTCACTGGTTATCACCCTT TACTGCAAACGGGGCAGAAAGAAACTCCTGTATA TATTCAAACAACCATTTATGAGACCAGTACAAAC TACTCAAGAGGAAGATGGCTGTAGCTGCCGATTT CCAGAAGAAGAAGAAGGAGGATGTGAACTGAGA GTGAAGTTCAGCAGGAGCGCAGACGCCCCCGCGT ACCAGCAGGGCCAGAACCAGCTCTATAACGAGCT CAATCTAGGACGAAGAGAGGAGTACGATGTTTTG GACAAGAGACGTGGCCGGGACCCTGAGATGGGG GGAAAGCCGAGAAGGAAGAACCCTCAAGAAGGC CTGTACAATGAACTGCAGAAAGATAAGATGGCGG AGGCCTACAGTGAGATTGGGATGAAAGGCGAGC GCCGGAGGGGCAAGGGGCACGATGGCCTTTACCA GGGTCTCAGTACAGCCACCAAGGACACCTACGAC GCCCTTCACATGCAGGCCCTGCCCCCTCGCTAA ATGGCCTTACCAGTGACCGCCTTGCTCCTGCCGCT GGCCTTGCTGCTCCACGCCGCCAGGCCGCAGGTG CAGCTGGTGGAGTCTGGGGGAGGCTTGGTGCAGC CTGGGGGGTCTCTGAGACTCTCCTGTGCAGCCTCT GGAAGCATCTTCAGAGTCTATGGCATGGACTGGT ACCGCCAGGCTCCAGGGAAGCAGCGCGAGTTGGT | SEQ ID NO: 61 |
| C30-CAR (nucleic acid) | CGCGTCTATTTTTCTTAGTGGTAGGACAAACTATG CAGACGCCGTGAAGGGCCGATTCACGCTCTCCAG AGATAACGCCAAGAATACTATGTATCTGCAAATG AACAGCCTGAAACCTGAGGACACGGCCGTCTATT ATTGTAATGCAGGTGAAACTACGGCAAGTTCCGT CCGTCAATACTGGGGCCAGGGGACCCAGGTCACC GTCTCCTCAGAACCCAAGACACCAAAACCAACTA GTACCACGACGCCAGCGCCGCGACCACCAACACC GGCGCCCACCATCGCGTCGCAGCCCCTGTCCCTG CGCCCAGAGGCGTGCCGGCCAGCGGCGGGGGGC GCAGTGCACACGAGGGGGCTGGACTTCGCCTGTG ATATCTACATCTGGGCGCCCTTGGCCGGGACTTGT GGGGTCCTTCTCCTGTCACTGGTTATCACCCTTTA CTGCAAACGGGGCAGAAAGAAACTCCTGTATATA TTCAAACAACCATTTATGAGACCAGTACAAACTA CTCAAGAGGAAGATGGCTGTAGCTGCCGATTTCC AGAAGAAGAAGAAGGAGGATGTGAACTGAGAGT GAAGTTCAGCAGGAGCGCAGACGCCCCCGCGTAC CAGCAGGGCCAGAACCAGCTCTATAACGAGCTCA ATCTAGGACGAAGAGAGGAGTACGATGTTTTGGA CAAGAGACGTGGCCGGGACCCTGAGATGGGGGG AAAGCCGAGAAGGAAGAACCCTCAAGAAGGCCT GTACAATGAACTGCAGAAAGATAAGATGGCGGA GGCCTACAGTGAGATTGGGATGAAAGGCGAGCG CCGGAGGGGCAAGGGGCACGATGGCCTTTACCAG GGTCTCAGTACAGCCACCAAGGACACCTACGACG CCCTTCACATGCAGGCCCTGCCCCCTCGCTAA | SEQ ID NO: 62 |
| C31-CAR (nucleic acid) | ATGGCCTTACCAGTGACCGCCTTGCTCCTGCCGCT GGCCTTGCTGCTCCACGCCGCCAGGCCGGCGGTG CAGCTGGTGGAGTCTGGGGGAGGCTTGGTGCAGC CTGGGGGGTCTCTGAGACTCTCCTGTGCAGCCTCT GGAAGCATCTTCAGAGTCTATGGCATGGACTGGT | SEQ ID NO: 63 |

TABLE 5-continued

| Description | Sequence | SEQ ID NO. |
|---|---|---|
| | ACCGCCAGGCTCCAGGGAAGCAGCGCGAGTTGGT<br>CGCGTCTATTTGGCTTAGTGGTAGGACAAACTAT<br>GCAGACGCCGTGAAGGGCCGATTCACGCTCTCCA<br>GAGATAACGCCAAGAATACGATGTATCTGCAAAT<br>GAACAGCCTGAAACCTGAGGACACGGCCGTCTAT<br>TATTGTAATGCAGGTGAAACTACGGCAAGTTCCG<br>TCCGTCAATACTGGGGCCAGGGGACCCAGGTCAC<br>CATCTCCTCGGAACCCAAGACACCAAAACCAACT<br>AGTACCACGACGCCAGCGCCGCGACCACCAACAC<br>CGGCGCCCACCATCGCGTCGCAGCCCCTGTCCCT<br>GCGCCCAGAGGCGTGCCGGCCAGCGGCGGGGGG<br>CGCAGTGCACACGAGGGGGCTGGACTTCGCCTGT<br>GATATCTACATCTGGGCGCCCTTGGCCGGGACTT<br>GTGGGGTCCTTCTCCTGTCACTGGTTATCACCCTT<br>TACTGCAAACGGGGCAGAAAGAAACTCCTGTATA<br>TATTCAAACAACCATTTATGAGACCAGTACAAAC<br>TACTCAAGAGGAAGATGGCTGTAGCTGCCGATTT<br>CCAGAAGAAGAAGAAGGAGGATGTGAACTGAGA<br>GTGAAGTTCAGCAGGAGCGCAGACGCCCCCGCGT<br>ACCAGCAGGGCCAGAACCAGCTCTATAACGAGCT<br>CAATCTAGGACGAAGAGAGGAGTACGATGTTTTG<br>GACAAGAGACGTGGCCGGGACCCTGAGATGGGG<br>GGAAAGCCGAGAAGGAAGAACCCTCAAGAAGGC<br>CTGTACAATGAACTGCAGAAAGATAAGATGGCGG<br>AGGCCTACAGTGAGATTGGGATGAAAGGCGAGC<br>GCCGGAGGGGCAAGGGGCACGATGGCCTTTACCA<br>GGGTCTCAGTACAGCCACCAAGGACACCTACGAC<br>GCCCTTCACATGCAGGCCCTGCCCCCTCGCTAA | |

Lentivirus Packaging

The 293T cells were recovered with DMEM/10% FBS as the medium and cultured in a 37° C., 5% CO2 incubator. On the day before the virus was packaged, the cells were digested and cultured in a 25 cm 2 flasks at 50% confluency. When infecting cells, the vector pLVX-WT-G1-VHH-CAR was mixed with the helper vector VSVG and GAG-pol in proportion, and incubated at room temperature for 5 minutes. The infection reagent PEI MAX and the plasmid mixture were mixed and incubated at room temperature for 20 minutes to form a DNA-infection reagent compound which was added to the 293T cell culture medium. After 6 hours incubated in a 37° C., 5% CO2 incubator, the supernatant was replaced with complete medium, and incubated in a 37° C., 5% CO2 incubator. After 48 hours and 72 hours, the virus was harvested once. Then, the virus was concentrated by centrifugation and used to test the virus titer.

CAR-T Cell Preparation

Mononuclear cells were extracted from human peripheral blood using Ficoll reagent and CD3+ cells were sorted with EasySep™ Human T Cell Isolation Kit (stemcell). The cells were adjusted to a maximum of 5×10$^7$ cell/ml, 0.5 ml/tube, and 25 ul RapidSpheres was added to each tube. After mixing at room temperature, the sample was inserted into the magnetic rack and incubated 3 minutes at room temperature. The effluent was collected and centrifuged to obtain CD3+ cells. The sorted CD3+ cells were incubated after resuspended with x-vivo15 medium. The cells were cultured into a 24-well plate at 0.5-1×10 6 cells/well, and x-vivo15 medium up to 0.5 ml was added. CD3/CD28 beads were added to the sorting cells at a ratio of 1:1, and supplemented with IL2 to a final concentration of 100 IU/ml, then incubated overnight in a 37° C., 5% CO2 incubator.

Fresh medium was then used and 1×10$^6$ T cells were cultured in a 96-well plate for overnight. The next day, concentrated VHH-CAR virus was added into T cells and co-cultured for 6 hours. Fresh x-vivo15 medium was replaced with after centrifugation and supplemented with IL2 to a final concentration of 100 IU/ml, then was continued to culture in a 37° C., 5% CO2 incubator. After several subculture, the positive rate of CAR-T cells was detected using flow cytometry.

Positive Detection Rate of CAR-T Cells

Figure 4B:
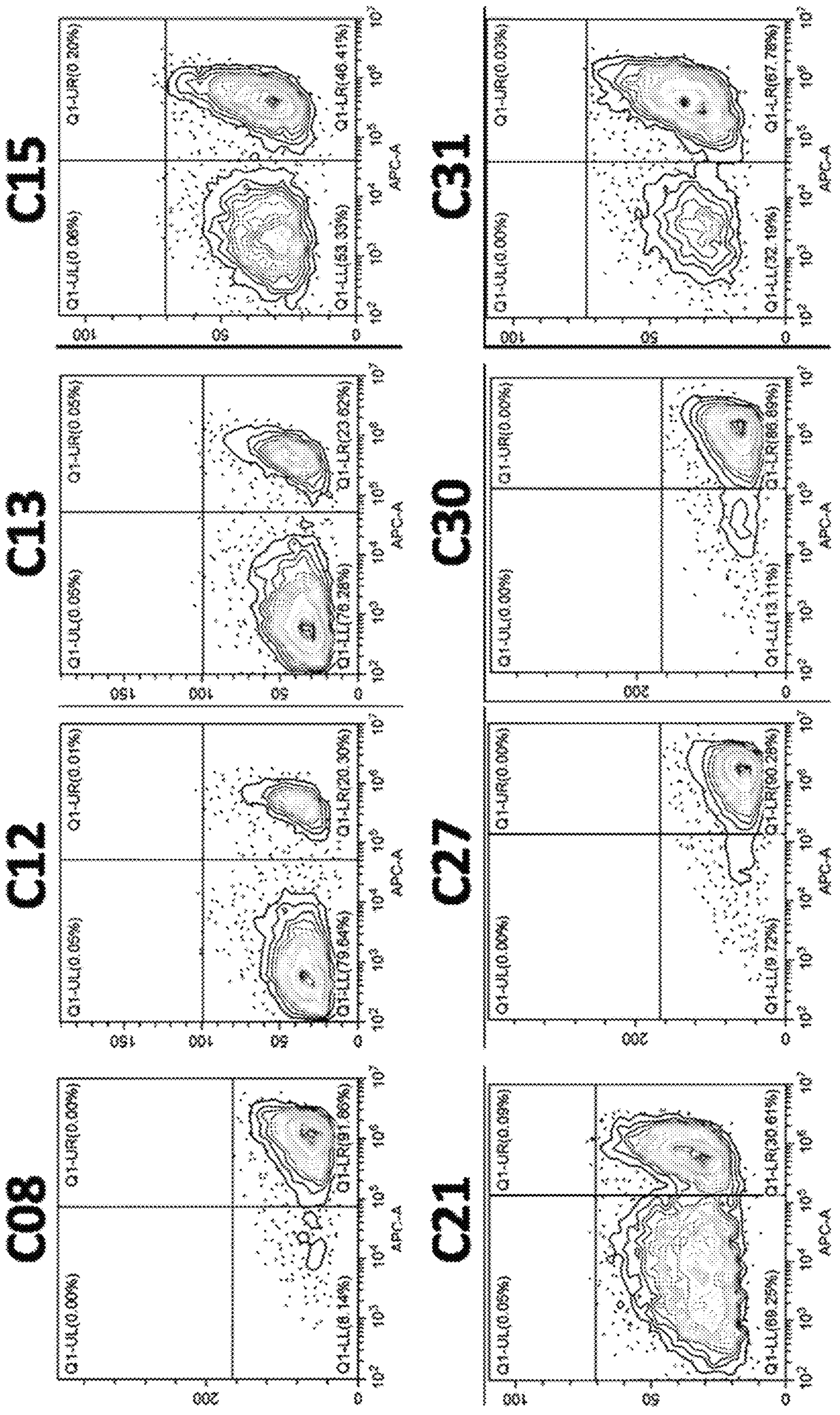
FIG. 4B shows flow cytometry analysis for the positive rates of CAR-T cells stained with anti-Alpaca IgG, VHH domain secondary antibody.

The various CAR-T cells after collecting and counting were resuspended in PBS. After washing twice with PBS, 1:1000 diluted Alexa Fluor 647-conjugated AffiniPure Goat anti-Alpaca IgG, VHH Domain (Jackson ImmumoResearch) secondary antibody was added into the reaction system and incubate at room temperature for 1 hour, washed twice with PBS, and then detected with flow cytometry (see FIG. 4B). As shown, the positive rates of C08, C12, C13, C15, C21, C27, C30 and C31 were 91.86%, 20.32%, 23.62%, 46.41%, 30.61%, 90.28%, 86.89% and 67.78%, respectively.

T84-Luci-eGFP Cells Preparation

1×10$^5$ cell/100 μl T84 cells were plated into a 24-well plate. Next day, 100 ul pLVX-Luci-eGFP virus (virus titer: 0.5-1×10$^8$ TU/ml) was into T84 cells when the cells grew to 60%-70% in each well. Then 300 ul complete medium was added and the cells grew in a 37° C., 5% CO2 incubator. The cell density was observed every day and the cells were subcultured when the cell density reached 80%-90%. When the positive rate reaches more than 95%, T84 cells were used for cytotoxicity assays and animal experiment.

6.3. Example 3—CAR-T Cell Cytotoxicity Assays

1×10$^5$/ml the target cells were plated into a 96-well plate and grown overnight in a 37° C., 5% CO2 incubator. T cells (negative control) and various CAR-T cells were mixed with the target cell with E:T (effector cell:target cell)=2:1. The volume of the cell culture medium was made up to 200 μl/well, then incubated for 24 h in a 37° C., 5% CO2 incubator. The cell culture medium was disgarded and cells were washed with PBS one time. 100 μl Bright-Glo Luciferase substrate was added into each well, incubated at room temperature for 5 min. 100 ul supernatant which was transferred to the white plate was detected with a microplate reader (see FIG. 5 and FIG. 6). The results demonstrated cytotoxicity for all the tested CAR-T cells expressing C8-CAR, C12-CAR, C13-CAR, C15-CAR, C21-CAR, C27-CAR, C30-CAR and C31-CAR.

6.4. Example 4—In Vivo Activity of CAR-T Cells

The ability of anti-GUCY2C CAR-T cells to eliminate colon cancer was tested in vivo using a NCG mouse model. T84-Luci-eGFP cells in good growth condition were prepared to a concentration of $1\times10^8$ cells/ml and injected subcutaneously into the armpit of the right forelimb of NCG female mice. Each mouse was injected with $5\times10^6$ cells and the injection volume was 0.05 ml. About 2 weeks after the injection of cells, the tumor volume was about 100-150 $mm^3$. Each mouse was injected with $3\times10^6$ CAR-T cells through the tail vein. The tumor size was measured with a caliper every 2 to 3 days. In vivo fluorescence imaging of mice was performed once a week. 0.1 ml of Luciferin substrate was injected into the subcutaneous part of the abdomen of the mouse, and the mouse was anesthetized 8 minutes later. The anesthetized mice were put into the PerkinElmer small animal in vivo optical imaging system (IVIS Lumina LT) for photographing detection. After the CAR-T cells injection, 100 ul of mouse blood was drawn every week, and the residual CAR-T cells in the mouse were monitored by flow cytometry and qPCR. Results are shown in FIGS. 7A-7C, as shown the tested exemplary CAR-T cells provided herein expressing C8-CAR, C12-CAR, C13-CAR, C15-CAR and C21-CAR demonstrated superior in vivo anti-cancer activities.

The teachings of all patents, published applications and references cited herein are incorporated by reference in their entirety. While example embodiments have been particularly shown and described, it will be understood by those skilled in the art that various changes in form and details may be made therein without departing from the scope of the embodiments encompassed by the appended claims.

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

What is claimed:

1. An anti-GUCY2C single domain antibody (sdAb) comprising:

(i) a CDR1, a CDR2, and a CDR3 having the amino acid sequences of the CDR1, CDR2, and CDR3, respectively, as set forth in SEQ ID NO: 3;

(ii) a CDR1, a CDR2, and a CDR3 having the amino acid sequences of the CDR1, CDR2, and CDR3, respectively, as set forth in SEQ ID NO: 4;

(iii) a CDR1, a CDR2, and a CDR3 having the amino acid sequences of the CDR1, CDR2, and CDR3, respectively, as set forth in SEQ ID NO: 5;

(iv) a CDR1, a CDR2, and a CDR3 having the amino acid sequences of the CDR1, CDR2, and CDR3, respectively, as set forth in SEQ ID NO: 6;
(v) a CDR1, a CDR2, and a CDR3 having the amino acid sequences of the CDR1, CDR2, and CDR3, respectively, as set forth in SEQ ID NO: 7;
(vi) a CDR1, a CDR2, and a CDR3 having the amino acid sequences of the CDR1, CDR2, and CDR3, respectively, as set forth in SEQ ID NO: 8;
(vii) a CDR1, a CDR2, and a CDR3 having the amino acid sequences of the CDR1, CDR2, and CDR3, respectively, as set forth in SEQ ID NO: 9; or
(viii) a CDR1, a CDR2, and a CDR3 having the amino acid sequences of the CDR1, CDR2, and CDR3, respectively, as set forth in SEQ ID NO: 10,
wherein the CDR1, CDR2 and CDR3 are determined according to the Kabat numbering scheme, the IMGT numbering scheme, the AbM numbering scheme, the Chothia numbering scheme, or the Contact numbering scheme.

2. The anti-GUCY2C sdAb of claim 1, comprising:
(i) a CDR1 comprising the amino acid sequence of SEQ ID NO: 19; a CDR2 comprising the amino acid sequence of SEQ ID NO: 27; and a CDR3 comprising the amino acid sequence of SEQ ID NO: 35;
(ii) a CDR1 comprising the amino acid sequence of SEQ ID NO: 20; a CDR2 comprising the amino acid sequence of SEQ ID NO: 28; and a CDR3 comprising the amino acid sequence of SEQ ID NO: 36;
(iii) a CDR1 comprising the amino acid sequence of SEQ ID NO: 21; a CDR2 comprising the amino acid sequence of SEQ ID NO: 29; and a CDR3 comprising the amino acid sequence of SEQ ID NO: 37;
(iv) a CDR1 comprising the amino acid sequence of SEQ ID NO: 22; a CDR2 comprising the amino acid sequence of SEQ ID NO: 30; and a CDR3 comprising the amino acid sequence of SEQ ID NO: 38;
(v) a CDR1 comprising the amino acid sequence of SEQ ID NO: 23; a CDR2 comprising the amino acid sequence of SEQ ID NO: 31; and a CDR3 comprising the amino acid sequence of SEQ ID NO: 39;
(vi) a CDR1 comprising the amino acid sequence of SEQ ID NO: 24; a CDR2 comprising the amino acid sequence of SEQ ID NO: 32; and a CDR3 comprising the amino acid sequence of SEQ ID NO: 40;
(vii) a CDR1 comprising the amino acid sequence of SEQ ID NO: 25; a CDR2 comprising the amino acid sequence of SEQ ID NO: 33; and a CDR3 comprising the amino acid sequence of SEQ ID NO: 41; or
(viii) a CDR1 comprising the amino acid sequence of SEQ ID NO: 26; a CDR2 comprising the amino acid sequence of SEQ ID NO: 34; and a CDR3 comprising the amino acid sequence of SEQ ID NO: 42;
wherein the CDR1, CDR2 and CDR3 are determined according to the Kabat numbering scheme.

3. The anti-GUCY2C sdAb of claim 1, further comprising one or more FR regions as set forth in any one of SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, or comprising the amino acid sequence of any one of SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

4. The anti-GUCY2C sdAb of claim 1, wherein anti-GUCY2C sdAb comprises or consists of an amino acid sequence having at least 75%, 80%, 85%, 90%, 95%, 96%, 97%, 98%, 99%, or more sequence identity with the sequence of any one of SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

5. The anti-GUCY2C sdAb of claim 1, wherein anti-GUCY2C sdAb is a camelid sdAb, or a humanized sdAb.

6. The anti-GUCY2C sdAb of claim 1, wherein the anti-GUCY2C sdAb is genetically fused or chemically conjugated to an agent.

7. An isolated nucleic acid comprising a nucleic acid sequence encoding the anti-GUCY2C sdAb of claim 1.

8. The isolated nucleic acid of claim 7, wherein the isolated nucleic acid comprises a nucleic acid sequence selected from the group consisting of SEQ ID NOs: 11 to 18.

9. A vector comprising the nucleic acid of claim 7.

10. A pharmaceutical composition, comprising the anti-GUCY2C sdAb of claim 1, and a pharmaceutically acceptable excipient.

11. A method of treating a disease or disorder in a subject, comprising administering to the subject an effective amount of the anti-GUCY2C sdAb of claim 1.

12. The method of claim 11, wherein the disease or disorder is a GUCY2C associated disease or disorder.

13. The method of claim 11, wherein the disease or disorder is cancer.

14. The method of claim 11, wherein the disease or disorder is colorectal cancer, gastric cancer, or escophageal cancer.

15. A chimeric antigen receptor (CAR), comprising:
(a) an extracellular antigen binding domain comprising the anti-GUCY2C sdAb of claim 4;
(b) a transmembrane domain; and
(c) an intracellular signaling domain.

16. The CAR of claim 15, wherein the extracellular antigen binding domain further comprises one or more additional antigen binding domain(s).

17. The CAR of claim 15, wherein the transmembrane domain is derived from a molecule selected from a group consisting of CD8α, CD4, CD28, CD137, CD80, CD86, CD152, and PD1.

18. The CAR of claim 15, wherein the intracellular signaling domain comprises a primary intracellular signaling domain of an immune effector cell.

19. The CAR of claim 18, wherein the primary intracellular signaling domain is derived from CD3ζ.

20. The CAR of claim 18, wherein the intracellular signaling domain further comprises a co-stimulatory signaling domain.

21. The CAR of claim 20, wherein the co-stimulatory signaling domain is derived from a co-stimulatory molecule selected from the group consisting of CD27, CD28, CD137 (4-1BB), OX40, CD30, CD40, CD3, LFA-1, CD2, CD7, LIGHT, NKG2C, B7-H3, ligands of CD83 and combinations thereof.

22. The CAR of claim 15, further comprising a hinge domain located between the C-terminus of the extracellular antigen binding domain and the N-terminus of the transmembrane domain.

23. The CAR of claim 22, wherein the hinge domain is derived from CD8α.

24. The CAR of claim 15, further comprising a signal peptide located at the N-terminus of the extracellular antigen binding domain.

25. The CAR of claim 24, wherein the signal peptide is derived from CD8α.

26. The CAR of claim 15, comprising (i) an amino acid sequence selected from the group consisting of SEQ ID NO: 48, SEQ ID NO: 49, SEQ ID NO: 50, SEQ ID NO: 51, SEQ ID NO: 52, SEQ ID NO: 53, SEQ ID NO: 54, and SEQ ID NO: 55; or (ii) an amino acid sequence having at least 75%, 80%, 85%, 90%, 95%, 96%, 97%, 98%, 99%, or more sequence identity with the sequence of any one of SEQ ID NO: 48, SEQ ID NO: 49, SEQ ID NO: 50, SEQ ID NO: 51, SEQ ID NO: 52, SEQ ID NO: 53, SEQ ID NO: 54, and SEQ ID NO: 55.

27. An isolated nucleic acid comprising a nucleic acid sequence encoding the CAR of claim 15.

28. The isolated nucleic acid of claim 27, wherein the isolated nucleic acid comprises a nucleic acid sequence selected from the group consisting of SEQ ID NOs: 56 to 63.

29. A vector comprising the nucleic acid of claim 27.

30. An engineered immune effector cell, comprising the CAR of claim 15.

31. The engineered immune effector cell of claim 30, wherein the immune effector cell is a T cell.

* * * * *

SEQUENCE LISTING

```
<160> NUMBER OF SEQ ID NOS: 66

<210> SEQ ID NO 1
<211> LENGTH: 1221
<212> TYPE: DNA
<213> ORGANISM: Artificial Sequence
<220> FEATURE:
<223> OTHER INFORMATION: GUCY2C protein peptide (Ser24-Gln430) (Nucleic
      acid)

<400> SEQUENCE: 1

tctcaagtgt cccagaactg ccacaacggc agctacgaga tcagcgtgct gatgatgggc     60

aacagcgcct ttgccgagcc tctgaagaac ctggaagatg ccgtgaacga aggcctggaa    120

atcgtgcgag gcagactgca gaatgccggc ctgaacgtga ccgtgaacgc cacctttatg    180

tacagcgacg gcctgatcca caacagcggc gactgtagaa gcagcacctg tgaaggactg    240

gacctgctgc ggaagatcag caacgcccag agaatgggct gtgtgctgat cggccctagc    300

tgcacctaca gcaccttcca gatgtacctg gacaccgagc tgagctaccc catgatcagc    360

gccggatctt tcggcctgag ctgcgactac aaagagacac tgacccggct gatgagcccc    420

gccagaaagc tgatgtactt cctggtcaac ttctggaaaa cgaacgacct gcctttcaag    480

acctacagct ggtccaccag ctacgtgtac aagaacggca ccgagacaga ggactgcttc    540

tggtatctga acgccctgga agccagcgtg tcctactttt ctcacgagct gggcttcaag    600

gtggtgctgc ggcaggacaa agagttccag gacatcctga tggaccacaa ccggaagtcc    660

aacgtgatca tcatgtgcgg cggacccgag ttcctgtaca agctgaaagg cgatagagcc    720

gtggccgagg acatcgtgat cattctggtg gatctgttca acgaccagta cttcgaggac    780

aatgtgacag cccctgacta catgaagaac gtgctggtgc tgacactgag ccccggcaac    840

agtctgctga acagcagctt cagccggaat ctgagcccca ccaagagaga tttcgccctg    900

gcctacctga acggcatcct gctgtttggc cacatgctga agatctttct cgaaaacggc    960

gagaacatca cgacccctaa gttcgcccac gccttccgga acctgacctt cgagggatat   1020

gacggccccg tgacactgga tgactgggga gatgtggaca gcacaatggt gctgctgtac   1080
```

```
accagcgtgg acaccaaaaa gtacaaagtg ctgctgacct acgacaccca cgtgaacaag   1140

acataccccg tggacatgag ccctaccttc acatggaaga acagcaagct gcccaacgac   1200

atcaccggca gaggacctca g                                             1221


<210> SEQ ID NO 2
<211> LENGTH: 407
<212> TYPE: PRT
<213> ORGANISM: Artificial Sequence
<220> FEATURE:
<223> OTHER INFORMATION: GUCY2C protein peptide (Ser24-Gln430) (Amino
      acid)

<400> SEQUENCE: 2

Ser Gln Val Ser Gln Asn Cys His Asn Gly Ser Tyr Glu Ile Ser Val
1               5                   10                  15

Leu Met Met Gly Asn Ser Ala Phe Ala Glu Pro Leu Lys Asn Leu Glu
            20                  25                  30

Asp Ala Val Asn Glu Gly Leu Glu Ile Val Arg Gly Arg Leu Gln Asn
        35                  40                  45

Ala Gly Leu Asn Val Thr Val Asn Ala Thr Phe Met Tyr Ser Asp Gly
    50                  55                  60

Leu Ile His Asn Ser Gly Asp Cys Arg Ser Ser Thr Cys Glu Gly Leu
65                  70                  75                  80

Asp Leu Leu Arg Lys Ile Ser Asn Ala Gln Arg Met Gly Cys Val Leu
                85                  90                  95

Ile Gly Pro Ser Cys Thr Tyr Ser Thr Phe Gln Met Tyr Leu Asp Thr
            100                 105                 110

Glu Leu Ser Tyr Pro Met Ile Ser Ala Gly Ser Phe Gly Leu Ser Cys
        115                 120                 125

Asp Tyr Lys Glu Thr Leu Thr Arg Leu Met Ser Pro Ala Arg Lys Leu
    130                 135                 140

Met Tyr Phe Leu Val Asn Phe Trp Lys Thr Asn Asp Leu Pro Phe Lys
145                 150                 155                 160

Thr Tyr Ser Trp Ser Thr Ser Tyr Val Tyr Lys Asn Gly Thr Glu Thr
                165                 170                 175

Glu Asp Cys Phe Trp Tyr Leu Asn Ala Leu Glu Ala Ser Val Ser Tyr
            180                 185                 190

Phe Ser His Glu Leu Gly Phe Lys Val Val Leu Arg Gln Asp Lys Glu
        195                 200                 205

Phe Gln Asp Ile Leu Met Asp His Asn Arg Lys Ser Asn Val Ile Ile
    210                 215                 220

Met Cys Gly Gly Pro Glu Phe Leu Tyr Lys Leu Lys Gly Asp Arg Ala
225                 230                 235                 240

Val Ala Glu Asp Ile Val Ile Ile Leu Val Asp Leu Phe Asn Asp Gln
                245                 250                 255

Tyr Phe Glu Asp Asn Val Thr Ala Pro Asp Tyr Met Lys Asn Val Leu
            260                 265                 270

Val Leu Thr Leu Ser Pro Gly Asn Ser Leu Leu Asn Ser Ser Phe Ser
        275                 280                 285

Arg Asn Leu Ser Pro Thr Lys Arg Asp Phe Ala Leu Ala Tyr Leu Asn
    290                 295                 300

Gly Ile Leu Leu Phe Gly His Met Leu Lys Ile Phe Leu Glu Asn Gly
305                 310                 315                 320

Glu Asn Ile Thr Thr Pro Lys Phe Ala His Ala Phe Arg Asn Leu Thr
                325                 330                 335
```

```
Phe Glu Gly Tyr Asp Gly Pro Val Thr Leu Asp Asp Trp Gly Asp Val
            340                 345                 350

Asp Ser Thr Met Val Leu Leu Tyr Thr Ser Val Asp Thr Lys Lys Tyr
        355                 360                 365

Lys Val Leu Leu Thr Tyr Asp Thr His Val Asn Lys Thr Tyr Pro Val
    370                 375                 380

Asp Met Ser Pro Thr Phe Thr Trp Lys Asn Ser Lys Leu Pro Asn Asp
385                 390                 395                 400

Ile Thr Gly Arg Gly Pro Gln
                405


<210> SEQ ID NO 3
<211> LENGTH: 127
<212> TYPE: PRT
<213> ORGANISM: Artificial Sequence
<220> FEATURE:
<223> OTHER INFORMATION: Exemplary VHH Domain - C08 (amino acid)

<400> SEQUENCE: 3

Met Glu Val Gln Leu Val Glu Ser Gly Gly Gly Leu Val Gln Pro Gly
1               5                   10                  15

Gly Ser Leu Arg Leu Ser Cys Ala Ala Ser Ser Asn Ile Phe Arg Ala
            20                  25                  30

Tyr Gly Met Gly Trp Tyr Arg Gln Ala Pro Gly Lys Gln Arg Glu Met
        35                  40                  45

Val Ala Ala Ile Trp Leu Ser Gly Arg Thr Glu Tyr Ala Asp Ala Val
    50                  55                  60

Gln Gly Arg Phe Thr Val Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Ala Gly Pro Pro Thr Ala Thr Ser Val Arg Gln Tyr Trp Gly Gln
            100                 105                 110

Gly Thr Gln Val Thr Val Ser Ser Glu Pro Lys Thr Pro Lys Pro
        115                 120                 125


<210> SEQ ID NO 4
<211> LENGTH: 127
<212> TYPE: PRT
<213> ORGANISM: Artificial Sequence
<220> FEATURE:
<223> OTHER INFORMATION: Exemplary VHH Domain - C12 (amino acid)

<400> SEQUENCE: 4

Met Gln Val Gln Leu Val Glu Ser Gly Gly Gly Leu Val Gln Pro Gly
1               5                   10                  15

Gly Ser Leu Arg Leu Ser Cys Ala Ala Ser Ser Asn Ile Phe Arg Ala
            20                  25                  30

Tyr Gly Met Asp Trp Tyr Arg Gln Ala Pro Gly Lys Gln Arg Glu Met
        35                  40                  45

Val Ala Thr Ile Trp Leu Ser Gly Arg Ser Thr Tyr Thr Asp Ala Val
    50                  55                  60

Lys Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Asn Ala Gly Pro Thr Thr Ala Ser Ser Val Arg Gln Tyr Trp Gly Gln
```

```
            100                 105                 110

Gly Thr Gln Val Thr Val Ser Ser Glu Pro Lys Thr Pro Lys Pro
        115                 120                 125


<210> SEQ ID NO 5
<211> LENGTH: 127
<212> TYPE: PRT
<213> ORGANISM: Artificial Sequence
<220> FEATURE:
<223> OTHER INFORMATION: Exemplary VHH Domain - C13 (amino acid)

<400> SEQUENCE: 5

Met Gln Val Gln Leu Val Glu Ser Gly Gly Gly Leu Val Gln Pro Gly
1               5                   10                  15

Gly Ser Leu Arg Leu Ser Cys Ala Ala Ser Ser Asn Ile Phe Arg Ala
            20                  25                  30

Tyr Gly Met Asp Trp Tyr Arg Gln Ala Pro Gly Lys Gln Arg Glu Met
        35                  40                  45

Val Ala Thr Ile Trp Leu Ser Gly Arg Thr Thr Tyr Thr Asp Ala Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Ala Gly Ala Pro Thr Ala Ser Ser Gly Arg Gln Tyr Trp Gly Gln
            100                 105                 110

Gly Thr Gln Val Thr Val Ser Ser Glu Pro Lys Thr Pro Lys Pro
        115                 120                 125


<210> SEQ ID NO 6
<211> LENGTH: 127
<212> TYPE: PRT
<213> ORGANISM: Artificial Sequence
<220> FEATURE:
<223> OTHER INFORMATION: Exemplary VHH Domain - C15 (amino acid)

<400> SEQUENCE: 6

Met Gln Val Gln Leu Val Glu Ser Gly Gly Gly Val Val Gln Pro Gly
1               5                   10                  15

Gly Ser Leu Arg Leu Ser Cys Ala Ala Ser Ser Asn Ile Phe Arg Ala
            20                  25                  30

Tyr Gly Met Asp Trp Tyr Arg Gln Ala Pro Gly Lys Gln Arg Glu Met
        35                  40                  45

Val Ala Thr Ile Trp Leu Ser Gly Arg Ser Thr Tyr Thr Asp Ala Val
    50                  55                  60

Gln Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Asn Ala Gly Pro Thr Thr Ala Ser Ser Val Arg Gln Tyr Trp Gly Gln
            100                 105                 110

Gly Thr Gln Val Thr Val Ser Ser Glu Pro Lys Thr Pro Lys Pro
        115                 120                 125


<210> SEQ ID NO 7
<211> LENGTH: 127
<212> TYPE: PRT
<213> ORGANISM: Artificial Sequence
<220> FEATURE:
```

<223> OTHER INFORMATION: Exemplary VHH Domain - C21 (amino acid)

<400> SEQUENCE: 7

Met Gln Val Gln Leu Val Glu Ser Gly Gly Gly Leu Val Gln Pro Gly
1 5 10 15

Gly Ser Leu Arg Leu Ser Cys Thr Ser Ser Ser Asn Ile Phe Arg Ile
20 25 30

Tyr Gly Met Asp Trp Tyr Arg Gln Ala Pro Gly Lys Gln Arg Glu Ile
35 40 45

Val Ala Thr Ile Tyr Leu Ser Gly Arg Thr Thr Tyr Ser Asp Ala Val
50 55 60

Lys Gly Arg Phe Thr Ile Ser Arg Asp Asn Ala Lys Asp Thr Val Tyr
65 70 75 80

Leu Gln Met Asn Ser Leu Lys Pro Glu Asp Thr Ala Val Tyr Tyr Cys
85 90 95

Asn Ala Gly Glu Pro Thr Ala Ser Ser Val Arg Gln Tyr Trp Gly Gln
100 105 110

Gly Thr Gln Val Thr Val Ser Ser Glu Pro Lys Thr Pro Lys Pro
115 120 125

<210> SEQ ID NO 8
<211> LENGTH: 127
<212> TYPE: PRT
<213> ORGANISM: Artificial Sequence
<220> FEATURE:
<223> OTHER INFORMATION: Exemplary VHH Domain - C27 (amino acid)

<400> SEQUENCE: 8

Met Glu Val Gln Leu Val Glu Ser Gly Gly Gly Leu Val Gln Pro Gly
1 5 10 15

Gly Ser Leu Arg Leu Ser Cys Thr Ser Ser Ser Asn Ile Phe Lys Ile
20 25 30

Tyr Gly Met Asp Trp Tyr Arg Gln Ala Pro Gly Lys Gln Arg Glu Ile
35 40 45

Val Ala Thr Ile Tyr Leu Ser Gly Arg Thr Thr Tyr Ser Asp Ala Val
50 55 60

Lys Gly Arg Phe Thr Ile Ser Arg Asp Asn Ala Lys Asn Thr Val Tyr
65 70 75 80

Leu Gln Met Asn Thr Leu Lys Pro Glu Asp Thr Ala Val Tyr Tyr Cys
85 90 95

Asn Ala Gly Glu Thr Thr Ala Ser Ser Val Arg Gln Tyr Trp Gly Gln
100 105 110

Gly Thr Gln Val Thr Val Ser Ser Glu Pro Lys Thr Pro Lys Pro
115 120 125

<210> SEQ ID NO 9
<211> LENGTH: 127
<212> TYPE: PRT
<213> ORGANISM: Artificial Sequence
<220> FEATURE:
<223> OTHER INFORMATION: Exemplary VHH Domain - C30 (amino acid)

<400> SEQUENCE: 9

Met Gln Val Gln Leu Val Glu Ser Gly Gly Gly Leu Val Gln Pro Gly
1 5 10 15

Gly Ser Leu Arg Leu Ser Cys Ala Ala Ser Gly Ser Ile Phe Arg Val
20 25 30

Tyr Gly Met Asp Trp Tyr Arg Gln Ala Pro Gly Lys Gln Arg Glu Leu

```
        35                  40                  45

Val Ala Ser Ile Phe Leu Ser Gly Arg Thr Asn Tyr Ala Asp Ala Val
    50                  55                  60

Lys Gly Arg Phe Thr Leu Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Asn Ala Gly Glu Thr Thr Ala Ser Ser Val Arg Gln Tyr Trp Gly Gln
            100                 105                 110

Gly Thr Gln Val Thr Val Ser Ser Glu Pro Lys Thr Pro Lys Pro
        115                 120                 125


<210> SEQ ID NO 10
<211> LENGTH: 127
<212> TYPE: PRT
<213> ORGANISM: Artificial Sequence
<220> FEATURE:
<223> OTHER INFORMATION: Exemplary VHH Domain - C31 (amino acid)

<400> SEQUENCE: 10

Met Ala Val Gln Leu Val Glu Ser Gly Gly Gly Leu Val Gln Pro Gly
1               5                   10                  15

Gly Ser Leu Arg Leu Ser Cys Ala Ala Ser Gly Ser Ile Phe Arg Val
            20                  25                  30

Tyr Gly Met Asp Trp Tyr Arg Gln Ala Pro Gly Lys Gln Arg Glu Leu
        35                  40                  45

Val Ala Ser Ile Trp Leu Ser Gly Arg Thr Asn Tyr Ala Asp Ala Val
    50                  55                  60

Lys Gly Arg Phe Thr Leu Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Asn Ala Gly Glu Thr Thr Ala Ser Ser Val Arg Gln Tyr Trp Gly Gln
            100                 105                 110

Gly Thr Gln Val Thr Ile Ser Ser Glu Pro Lys Thr Pro Lys Pro
        115                 120                 125


<210> SEQ ID NO 11
<211> LENGTH: 381
<212> TYPE: DNA
<213> ORGANISM: Artificial Sequence
<220> FEATURE:
<223> OTHER INFORMATION: Exemplary VHH Domain - C08 (nucleic acid)

<400> SEQUENCE: 11

atggaggtgc agctggtgga gtctggggga ggtttggtgc aacctggggg gtctctgaga      60

ctctcctgtg cagcctcttc aaacatcttc agagcctatg gcatggggtg gtaccgccag     120

gctccaggga agcagcgcga aatggtcgcg gctatttggc tcagtggtcg cacagagtat     180

gctgacgccg tgcagggccg attcaccgtc tccagagaca acgccaagaa cacggtgtat     240

ctgcaaatga acagcctgaa acctgaggac acggccgtct attactgtaa tgcaggtccc     300

cctacagcaa cttccgtccg tcaatactgg ggccagggga cccaggtcac cgtctcctca     360

gaacccaaga caccaaaacc a                                               381


<210> SEQ ID NO 12
<211> LENGTH: 381
<212> TYPE: DNA
```

```
<213> ORGANISM: Artificial Sequence
<220> FEATURE:
<223> OTHER INFORMATION: Exemplary VHH Domain - C12 (nucleic acid)

<400> SEQUENCE: 12

atgcaggtac agctggtgga gtctggggga ggtttggtgc aacctggggg gtctctgaga     60

ctctcctgtg cagcctcttc aaacatcttc agagcctatg gcatggattg gtaccgccag    120

gctccaggaa agcagcgcga aatggtcgcg actatctggc tgagtggtcg ctcaacgtat    180

actgacgccg tgaagggccg attcaccatc tccagagaca acgccaagaa cacggtgtat    240

ctgcaaatga acaacctgaa acctgaggac acggccgtct attactgtaa tgcaggtccc    300

actacggcaa gttccgtccg tcaatactgg ggccagggga cccaggtcac cgtctcctca    360

gaacccaaga caccaaaacc a                                              381


<210> SEQ ID NO 13
<211> LENGTH: 381
<212> TYPE: DNA
<213> ORGANISM: Artificial Sequence
<220> FEATURE:
<223> OTHER INFORMATION: Exemplary VHH Domain - C13 (nucleic acid)

<400> SEQUENCE: 13

atgcaggtgc agctggtgga gtctggggga ggtttggtgc aacctggggg gtctctgaga     60

ctctcctgtg cagcctcttc aaacatcttc agagcctatg gcatggactg gtaccgccag    120

gctccaggga agcagcgcga aatggtcgcg actatctggc ttagtggtcg cacaacgtat    180

actgacgccg tgaagggccg attcaccatc tccagagaca acgccaagaa cacggtgtat    240

ctgcaaatga acagcctgaa acctgaggac acggccgtct attactgtaa tgcaggtgcc    300

cctacggcaa gttccggccg tcaatactgg ggccagggga cccaggtcac cgtctcctca    360

gaacccaaga caccaaaacc a                                              381


<210> SEQ ID NO 14
<211> LENGTH: 381
<212> TYPE: DNA
<213> ORGANISM: Artificial Sequence
<220> FEATURE:
<223> OTHER INFORMATION: Exemplary VHH Domain - C15 (nucleic acid)

<400> SEQUENCE: 14

atgcaggtgc agctggtgga gtctggggga ggggtggtgc aacctggggg gtctctgaga     60

ctctcctgtg cagcctcttc aaatatcttt agagcctatg gcatggattg gtaccgccag    120

gctccaggaa agcagcgcga aatggtcgcg actatctggc tgagtggtcg ctcaacgtat    180

actgacgccg tacagggccg attcaccatc tccagagaca acgccaagaa cacggtgtat    240

ctgcaaatga acaacctgaa acctgaggac acggccgtct attactgtaa tgcaggtccc    300

actacggcaa gttccgtccg tcaatactgg ggccagggga cccaggtcac cgtctcctca    360

gaacccaaga caccaaaacc a                                              381


<210> SEQ ID NO 15
<211> LENGTH: 381
<212> TYPE: DNA
<213> ORGANISM: Artificial Sequence
<220> FEATURE:
<223> OTHER INFORMATION: Exemplary VHH Domain - C21 (nucleic acid)

<400> SEQUENCE: 15

atgcaggtac agctggtgga gtctggggga ggtttggtgc aacctggggg gtctctgaga     60
```

```
ctctcctgta caagctcttc aaacatcttc agaatctatg gcatggactg gtaccgccag    120

gctccaggga agcagcgcga aatagtcgcg actatctatc ttagtggtcg cacaacgtat    180

agtgacgccg tgaagggccg attcaccatc tccagagaca acgccaagga cacggtgtat    240

ctgcaaatga acagcctgaa acctgaggac acggccgtct attactgtaa tgcaggtgaa    300

cctacggcaa gttccgtccg tcagtactgg ggccagggga cccaggtcac cgtctcctca    360

gaacccaaga caccaaaacc a                                               381
```

<210> SEQ ID NO 16
<211> LENGTH: 381
<212> TYPE: DNA
<213> ORGANISM: Artificial Sequence
<220> FEATURE:
<223> OTHER INFORMATION: Exemplary VHH Domain - C27 (nucleic acid)

<400> SEQUENCE: 16

```
atggaggtgc agctggtgga gtctggggga ggtttggtgc aacctggggg gtctctgaga     60

ctctcctgta caagctcttc aaacatcttc aaaatctatg gcatggactg gtaccgccag    120

gctccaggga aacagcgcga aatagtcgcg actatctatc ttagtggtcg cacaacgtat    180

agtgacgccg tgaagggccg attcaccatc tccagagaca acgccaagaa cacggtgtat    240

ctgcaaatga acaccctgaa acctgaggac acggccgtct attactgtaa tgcaggtgaa    300

actacggcaa gttccgtccg tcaatactgg ggccagggga cccaggtcac cgtctcctca    360

gaacccaaga caccaaaacc a                                               381
```

<210> SEQ ID NO 17
<211> LENGTH: 381
<212> TYPE: DNA
<213> ORGANISM: Artificial Sequence
<220> FEATURE:
<223> OTHER INFORMATION: Exemplary VHH Domain - C30 (nucleic acid)

<400> SEQUENCE: 17

```
atgcaggtgc agctggtgga gtctggggga ggcttggtgc agcctggggg gtctctgaga     60

ctctcctgtg cagcctctgg aagcatcttc agagtctatg gcatggactg gtaccgccag    120

gctccaggga agcagcgcga gttggtcgcg tctatttttc ttagtggtag gacaaactat    180

gcagacgccg tgaagggccg attcacgctc tccagagata acgccaagaa tactatgtat    240

ctgcaaatga acagcctgaa acctgaggac acggccgtct attattgtaa tgcaggtgaa    300

actacggcaa gttccgtccg tcaatactgg ggccagggga cccaggtcac cgtctcctca    360

gaacccaaga caccaaaacc a                                               381
```

<210> SEQ ID NO 18
<211> LENGTH: 381
<212> TYPE: DNA
<213> ORGANISM: Artificial Sequence
<220> FEATURE:
<223> OTHER INFORMATION: Exemplary VHH Domain - C31 (nucleic acid)

<400> SEQUENCE: 18

```
atggcggtgc agctggtgga gtctggggga ggcttggtgc agcctggggg gtctctgaga     60

ctctcctgtg cagcctctgg aagcatcttc agagtctatg gcatggactg gtaccgccag    120

gctccaggga agcagcgcga gttggtcgcg tctatttggc ttagtggtag gacaaactat    180

gcagacgccg tgaagggccg attcacgctc tccagagata acgccaagaa tacgatgtat    240
```

ctgcaaatga acagcctgaa acctgaggac acggccgtct attattgtaa tgcaggtgaa 300
actacggcaa gttccgtccg tcaatactgg ggccagggga cccaggtcac catctcctcg 360
gaacccaaga caccaaaacc a 381

<210> SEQ ID NO 19
<211> LENGTH: 5
<212> TYPE: PRT
<213> ORGANISM: Artificial Sequence
<220> FEATURE:
<223> OTHER INFORMATION: CDR Amino Acid Sequence of Exemplary VHH Domain - C08-CDR1

<400> SEQUENCE: 19

Ala Tyr Gly Met Gly
1 5

<210> SEQ ID NO 20
<211> LENGTH: 5
<212> TYPE: PRT
<213> ORGANISM: Artificial Sequence
<220> FEATURE:
<223> OTHER INFORMATION: CDR Amino Acid Sequence of Exemplary VHH Domain - C12-CDR1

<400> SEQUENCE: 20

Ala Tyr Gly Met Asp
1 5

<210> SEQ ID NO 21
<211> LENGTH: 5
<212> TYPE: PRT
<213> ORGANISM: Artificial Sequence
<220> FEATURE:
<223> OTHER INFORMATION: CDR Amino Acid Sequence of Exemplary VHH Domain - C13-CDR1

<400> SEQUENCE: 21

Ala Tyr Gly Met Asp
1 5

<210> SEQ ID NO 22
<211> LENGTH: 5
<212> TYPE: PRT
<213> ORGANISM: Artificial Sequence
<220> FEATURE:
<223> OTHER INFORMATION: CDR Amino Acid Sequence of Exemplary VHH Domain - C15-CDR1

<400> SEQUENCE: 22

Ala Tyr Gly Met Asp
1 5

<210> SEQ ID NO 23
<211> LENGTH: 5
<212> TYPE: PRT
<213> ORGANISM: Artificial Sequence
<220> FEATURE:
<223> OTHER INFORMATION: CDR Amino Acid Sequence of Exemplary VHH Domain - C21-CDR1

<400> SEQUENCE: 23

Ile Tyr Gly Met Asp
1 5

<210> SEQ ID NO 24
<211> LENGTH: 5

```
<212> TYPE: PRT
<213> ORGANISM: Artificial Sequence
<220> FEATURE:
<223> OTHER INFORMATION: CDR Amino Acid Sequence of Exemplary VHH
      Domain - C27-CDR1

<400> SEQUENCE: 24

Ile Tyr Gly Met Asp
1               5


<210> SEQ ID NO 25
<211> LENGTH: 5
<212> TYPE: PRT
<213> ORGANISM: Artificial Sequence
<220> FEATURE:
<223> OTHER INFORMATION: CDR Amino Acid Sequence of Exemplary VHH
      Domain - C30-CDR1

<400> SEQUENCE: 25

Val Tyr Gly Met Asp
1               5


<210> SEQ ID NO 26
<211> LENGTH: 5
<212> TYPE: PRT
<213> ORGANISM: Artificial Sequence
<220> FEATURE:
<223> OTHER INFORMATION: CDR Amino Acid Sequence of Exemplary VHH
      Domain - C31-CDR1

<400> SEQUENCE: 26

Val Tyr Gly Met Asp
1               5


<210> SEQ ID NO 27
<211> LENGTH: 16
<212> TYPE: PRT
<213> ORGANISM: Artificial Sequence
<220> FEATURE:
<223> OTHER INFORMATION: CDR Amino Acid Sequence of Exemplary VHH
      Domain - C08-CDR2

<400> SEQUENCE: 27

Ala Ile Trp Leu Ser Gly Arg Thr Glu Tyr Ala Asp Ala Val Gln Gly
1               5                   10                  15


<210> SEQ ID NO 28
<211> LENGTH: 16
<212> TYPE: PRT
<213> ORGANISM: Artificial Sequence
<220> FEATURE:
<223> OTHER INFORMATION: CDR Amino Acid Sequence of Exemplary VHH
      Domain - C12-CDR2

<400> SEQUENCE: 28

Thr Ile Trp Leu Ser Gly Arg Ser Thr Tyr Thr Asp Ala Val Lys Gly
1               5                   10                  15


<210> SEQ ID NO 29
<211> LENGTH: 16
<212> TYPE: PRT
<213> ORGANISM: Artificial Sequence
<220> FEATURE:
<223> OTHER INFORMATION: CDR Amino Acid Sequence of Exemplary VHH
      Domain - C13-CDR2

<400> SEQUENCE: 29

Thr Ile Trp Leu Ser Gly Arg Thr Thr Tyr Thr Asp Ala Val Lys Gly
```

1 5 10 15

<210> SEQ ID NO 30
<211> LENGTH: 16
<212> TYPE: PRT
<213> ORGANISM: Artificial Sequence
<220> FEATURE:
<223> OTHER INFORMATION: CDR Amino Acid Sequence of Exemplary VHH Domain - C15-CDR2

<400> SEQUENCE: 30

Thr Ile Trp Leu Ser Gly Arg Ser Thr Tyr Thr Asp Ala Val Gln Gly
1 5 10 15

<210> SEQ ID NO 31
<211> LENGTH: 16
<212> TYPE: PRT
<213> ORGANISM: Artificial Sequence
<220> FEATURE:
<223> OTHER INFORMATION: CDR Amino Acid Sequence of Exemplary VHH Domain - C21-CDR2

<400> SEQUENCE: 31

Thr Ile Tyr Leu Ser Gly Arg Thr Thr Tyr Ser Asp Ala Val Lys Gly
1 5 10 15

<210> SEQ ID NO 32
<211> LENGTH: 16
<212> TYPE: PRT
<213> ORGANISM: Artificial Sequence
<220> FEATURE:
<223> OTHER INFORMATION: CDR Amino Acid Sequence of Exemplary VHH Domain - C27-CDR2

<400> SEQUENCE: 32

Thr Ile Tyr Leu Ser Gly Arg Thr Thr Tyr Ser Asp Ala Val Lys Gly
1 5 10 15

<210> SEQ ID NO 33
<211> LENGTH: 16
<212> TYPE: PRT
<213> ORGANISM: Artificial Sequence
<220> FEATURE:
<223> OTHER INFORMATION: CDR Amino Acid Sequence of Exemplary VHH Domain - C30-CDR2

<400> SEQUENCE: 33

Ser Ile Phe Leu Ser Gly Arg Thr Asn Tyr Ala Asp Ala Val Lys Gly
1 5 10 15

<210> SEQ ID NO 34
<211> LENGTH: 16
<212> TYPE: PRT
<213> ORGANISM: Artificial Sequence
<220> FEATURE:
<223> OTHER INFORMATION: CDR Amino Acid Sequence of Exemplary VHH Domain - C31-CDR2

<400> SEQUENCE: 34

Ser Ile Trp Leu Ser Gly Arg Thr Asn Tyr Ala Asp Ala Val Lys Gly
1 5 10 15

<210> SEQ ID NO 35
<211> LENGTH: 11
<212> TYPE: PRT
<213> ORGANISM: Artificial Sequence
<220> FEATURE:
<223> OTHER INFORMATION: CDR Amino Acid Sequence of Exemplary VHH Domain - C08-CDR3

<400> SEQUENCE: 35

Gly Pro Pro Thr Ala Thr Ser Val Arg Gln Tyr
1 5 10

<210> SEQ ID NO 36
<211> LENGTH: 11
<212> TYPE: PRT
<213> ORGANISM: Artificial Sequence
<220> FEATURE:
<223> OTHER INFORMATION: CDR Amino Acid Sequence of Exemplary VHH Domain - C12-CDR3

<400> SEQUENCE: 36

Gly Pro Thr Thr Ala Ser Ser Val Arg Gln Tyr
1 5 10

<210> SEQ ID NO 37
<211> LENGTH: 11
<212> TYPE: PRT
<213> ORGANISM: Artificial Sequence
<220> FEATURE:
<223> OTHER INFORMATION: CDR Amino Acid Sequence of Exemplary VHH Domain - C13-CDR3

<400> SEQUENCE: 37

Gly Ala Pro Thr Ala Ser Ser Gly Arg Gln Tyr
1 5 10

<210> SEQ ID NO 38
<211> LENGTH: 11
<212> TYPE: PRT
<213> ORGANISM: Artificial Sequence
<220> FEATURE:
<223> OTHER INFORMATION: CDR Amino Acid Sequence of Exemplary VHH Domain - C15-CDR3

<400> SEQUENCE: 38

Gly Pro Thr Thr Ala Ser Ser Val Arg Gln Tyr
1 5 10

<210> SEQ ID NO 39
<211> LENGTH: 11
<212> TYPE: PRT
<213> ORGANISM: Artificial Sequence
<220> FEATURE:
<223> OTHER INFORMATION: CDR Amino Acid Sequence of Exemplary VHH Domain - C21-CDR3

<400> SEQUENCE: 39

Gly Glu Pro Thr Ala Ser Ser Val Arg Gln Tyr
1 5 10

<210> SEQ ID NO 40
<211> LENGTH: 11
<212> TYPE: PRT
<213> ORGANISM: Artificial Sequence
<220> FEATURE:
<223> OTHER INFORMATION: CDR Amino Acid Sequence of Exemplary VHH Domain - C27-CDR3

<400> SEQUENCE: 40

Gly Glu Thr Thr Ala Ser Ser Val Arg Gln Tyr
1 5 10

<210> SEQ ID NO 41

```
<211> LENGTH: 11
<212> TYPE: PRT
<213> ORGANISM: Artificial Sequence
<220> FEATURE:
<223> OTHER INFORMATION: CDR Amino Acid Sequence of Exemplary VHH
      Domain - C30-CDR3

<400> SEQUENCE: 41

Gly Glu Thr Thr Ala Ser Ser Val Arg Gln Tyr
1               5                   10


<210> SEQ ID NO 42
<211> LENGTH: 11
<212> TYPE: PRT
<213> ORGANISM: Artificial Sequence
<220> FEATURE:
<223> OTHER INFORMATION: CDR Amino Acid Sequence of Exemplary VHH
      Domain - C31-CDR3

<400> SEQUENCE: 42

Gly Glu Thr Thr Ala Ser Ser Val Arg Gln Tyr
1               5                   10


<210> SEQ ID NO 43
<211> LENGTH: 45
<212> TYPE: PRT
<213> ORGANISM: Artificial Sequence
<220> FEATURE:
<223> OTHER INFORMATION: CD8 hinge

<400> SEQUENCE: 43

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45


<210> SEQ ID NO 44
<211> LENGTH: 24
<212> TYPE: PRT
<213> ORGANISM: Artificial Sequence
<220> FEATURE:
<223> OTHER INFORMATION: CD8 TM

<400> SEQUENCE: 44

Ile Tyr Ile Trp Ala Pro Leu Ala Gly Thr Cys Gly Val Leu Leu Leu
1               5                   10                  15

Ser Leu Val Ile Thr Leu Tyr Cys
            20


<210> SEQ ID NO 45
<211> LENGTH: 42
<212> TYPE: PRT
<213> ORGANISM: Artificial Sequence
<220> FEATURE:
<223> OTHER INFORMATION: 4-1BB

<400> SEQUENCE: 45

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 46
<211> LENGTH: 112
<212> TYPE: PRT
<213> ORGANISM: Artificial Sequence
<220> FEATURE:
<223> OTHER INFORMATION: CD3z

<400> SEQUENCE: 46

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 47
<211> LENGTH: 21
<212> TYPE: PRT
<213> ORGANISM: Artificial Sequence
<220> FEATURE:
<223> OTHER INFORMATION: CD8 single peptide

<400> SEQUENCE: 47

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 48
<211> LENGTH: 372
<212> TYPE: PRT
<213> ORGANISM: Artificial Sequence
<220> FEATURE:
<223> OTHER INFORMATION: C08-CAR (amino acid)

<400> SEQUENCE: 48

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Ala Ser Ser Asn
        35                  40                  45

Ile Phe Arg Ala Tyr Gly Met Gly Trp Tyr Arg Gln Ala Pro Gly Lys
    50                  55                  60

Gln Arg Glu Met Val Ala Ala Ile Trp Leu Ser Gly Arg Thr Glu Tyr
65                  70                  75                  80

Ala Asp Ala Val Gln Gly Arg Phe Thr Val Ser Arg Asp Asn Ala Lys
                85                  90                  95

Asn Thr Val Tyr Leu Gln Met Asn Ser Leu Lys Pro Glu Asp Thr Ala
            100                 105                 110
```

Val Tyr Tyr Cys Asn Ala Gly Pro Pro Thr Ala Thr Ser Val Arg Gln
115 120 125

Tyr Trp Gly Gln Gly Thr Gln Val Thr Val Ser Ser Glu Pro Lys Thr
130 135 140

Pro Lys Pro Thr Ser Thr Thr Thr Pro Ala Pro Arg Pro Pro Thr Pro
145 150 155 160

Ala Pro Thr Ile Ala Ser Gln Pro Leu Ser Leu Arg Pro Glu Ala Cys
165 170 175

Arg Pro Ala Ala Gly Gly Ala Val His Thr Arg Gly Leu Asp Phe Ala
180 185 190

Cys Asp Ile Tyr Ile Trp Ala Pro Leu Ala Gly Thr Cys Gly Val Leu
195 200 205

Leu Leu Ser Leu Val Ile Thr Leu Tyr Cys Lys Arg Gly Arg Lys Lys
210 215 220

Leu Leu Tyr Ile Phe Lys Gln Pro Phe Met Arg Pro Val Gln Thr Thr
225 230 235 240

Gln Glu Glu Asp Gly Cys Ser Cys Arg Phe Pro Glu Glu Glu Glu Gly
245 250 255

Gly Cys Glu Leu Arg Val Lys Phe Ser Arg Ser Ala Asp Ala Pro Ala
260 265 270

Tyr Gln Gln Gly Gln Asn Gln Leu Tyr Asn Glu Leu Asn Leu Gly Arg
275 280 285

Arg Glu Glu Tyr Asp Val Leu Asp Lys Arg Arg Gly Arg Asp Pro Glu
290 295 300

Met Gly Gly Lys Pro Arg Arg Lys Asn Pro Gln Glu Gly Leu Tyr Asn
305 310 315 320

Glu Leu Gln Lys Asp Lys Met Ala Glu Ala Tyr Ser Glu Ile Gly Met
325 330 335

Lys Gly Glu Arg Arg Arg Gly Lys Gly His Asp Gly Leu Tyr Gln Gly
340 345 350

Leu Ser Thr Ala Thr Lys Asp Thr Tyr Asp Ala Leu His Met Gln Ala
355 360 365

Leu Pro Pro Arg
370

<210> SEQ ID NO 49
<211> LENGTH: 372
<212> TYPE: PRT
<213> ORGANISM: Artificial Sequence
<220> FEATURE:
<223> OTHER INFORMATION: C12-CAR (amino acid)

<400> SEQUENCE: 49

Met Ala Leu Pro Val Thr Ala Leu Leu Leu Pro Leu Ala Leu Leu Leu
1 5 10 15

His Ala Ala Arg Pro Gln Val Gln Leu Val Glu Ser Gly Gly Gly Leu
20 25 30

Val Gln Pro Gly Gly Ser Leu Arg Leu Ser Cys Ala Ala Ser Ser Asn
35 40 45

Ile Phe Arg Ala Tyr Gly Met Asp Trp Tyr Arg Gln Ala Pro Gly Lys
50 55 60

Gln Arg Glu Met Val Ala Thr Ile Trp Leu Ser Gly Arg Ser Thr Tyr
65 70 75 80

Thr Asp Ala Val Lys Gly Arg Phe Thr Ile Ser Arg Asp Asn Ala Lys
85 90 95

```
Asn Thr Val Tyr Leu Gln Met Asn Asn Leu Lys Pro Glu Asp Thr Ala
            100                 105                 110

Val Tyr Tyr Cys Asn Ala Gly Pro Thr Thr Ala Ser Ser Val Arg Gln
        115                 120                 125

Tyr Trp Gly Gln Gly Thr Gln Val Thr Val Ser Ser Glu Pro Lys Thr
    130                 135                 140

Pro Lys Pro Thr Ser Thr Thr Thr Pro Ala Pro Arg Pro Pro Thr Pro
145                 150                 155                 160

Ala Pro Thr Ile Ala Ser Gln Pro Leu Ser Leu Arg Pro Glu Ala Cys
                165                 170                 175

Arg Pro Ala Ala Gly Gly Ala Val His Thr Arg Gly Leu Asp Phe Ala
            180                 185                 190

Cys Asp Ile Tyr Ile Trp Ala Pro Leu Ala Gly Thr Cys Gly Val Leu
        195                 200                 205

Leu Leu Ser Leu Val Ile Thr Leu Tyr Cys Lys Arg Gly Arg Lys Lys
    210                 215                 220

Leu Leu Tyr Ile Phe Lys Gln Pro Phe Met Arg Pro Val Gln Thr Thr
225                 230                 235                 240

Gln Glu Glu Asp Gly Cys Ser Cys Arg Phe Pro Glu Glu Glu Glu Gly
                245                 250                 255

Gly Cys Glu Leu Arg Val Lys Phe Ser Arg Ser Ala Asp Ala Pro Ala
            260                 265                 270

Tyr Gln Gln Gly Gln Asn Gln Leu Tyr Asn Glu Leu Asn Leu Gly Arg
        275                 280                 285

Arg Glu Glu Tyr Asp Val Leu Asp Lys Arg Arg Gly Arg Asp Pro Glu
    290                 295                 300

Met Gly Gly Lys Pro Arg Arg Lys Asn Pro Gln Glu Gly Leu Tyr Asn
305                 310                 315                 320

Glu Leu Gln Lys Asp Lys Met Ala Glu Ala Tyr Ser Glu Ile Gly Met
                325                 330                 335

Lys Gly Glu Arg Arg Arg Gly Lys Gly His Asp Gly Leu Tyr Gln Gly
            340                 345                 350

Leu Ser Thr Ala Thr Lys Asp Thr Tyr Asp Ala Leu His Met Gln Ala
        355                 360                 365

Leu Pro Pro Arg
    370


<210> SEQ ID NO 50
<211> LENGTH: 372
<212> TYPE: PRT
<213> ORGANISM: Artificial Sequence
<220> FEATURE:
<223> OTHER INFORMATION: C13-CAR (amino acid)

<400> SEQUENCE: 50

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Arg Leu Ser Cys Ala Ala Ser Ser Asn
        35                  40                  45

Ile Phe Arg Ala Tyr Gly Met Asp Trp Tyr Arg Gln Ala Pro Gly Lys
    50                  55                  60

Gln Arg Glu Met Val Ala Thr Ile Trp Leu Ser Gly Arg Thr Thr Tyr
65                  70                  75                  80
```

-continued

Thr Asp Ala Val Lys Gly Arg Phe Thr Ile Ser Arg Asp Asn Ala Lys
85 90 95

Asn Thr Val Tyr Leu Gln Met Asn Ser Leu Lys Pro Glu Asp Thr Ala
100 105 110

Val Tyr Tyr Cys Asn Ala Gly Ala Pro Thr Ala Ser Ser Gly Arg Gln
115 120 125

Tyr Trp Gly Gln Gly Thr Gln Val Thr Val Ser Ser Glu Pro Lys Thr
130 135 140

Pro Lys Pro Thr Ser Thr Thr Thr Pro Ala Pro Arg Pro Pro Thr Pro
145 150 155 160

Ala Pro Thr Ile Ala Ser Gln Pro Leu Ser Leu Arg Pro Glu Ala Cys
165 170 175

Arg Pro Ala Ala Gly Gly Ala Val His Thr Arg Gly Leu Asp Phe Ala
180 185 190

Cys Asp Ile Tyr Ile Trp Ala Pro Leu Ala Gly Thr Cys Gly Val Leu
195 200 205

Leu Leu Ser Leu Val Ile Thr Leu Tyr Cys Lys Arg Gly Arg Lys Lys
210 215 220

Leu Leu Tyr Ile Phe Lys Gln Pro Phe Met Arg Pro Val Gln Thr Thr
225 230 235 240

Gln Glu Glu Asp Gly Cys Ser Cys Arg Phe Pro Glu Glu Glu Glu Gly
245 250 255

Gly Cys Glu Leu Arg Val Lys Phe Ser Arg Ser Ala Asp Ala Pro Ala
260 265 270

Tyr Gln Gln Gly Gln Asn Gln Leu Tyr Asn Glu Leu Asn Leu Gly Arg
275 280 285

Arg Glu Glu Tyr Asp Val Leu Asp Lys Arg Arg Gly Arg Asp Pro Glu
290 295 300

Met Gly Gly Lys Pro Arg Arg Lys Asn Pro Gln Glu Gly Leu Tyr Asn
305 310 315 320

Glu Leu Gln Lys Asp Lys Met Ala Glu Ala Tyr Ser Glu Ile Gly Met
325 330 335

Lys Gly Glu Arg Arg Arg Gly Lys Gly His Asp Gly Leu Tyr Gln Gly
340 345 350

Leu Ser Thr Ala Thr Lys Asp Thr Tyr Asp Ala Leu His Met Gln Ala
355 360 365

Leu Pro Pro Arg
370

<210> SEQ ID NO 51
<211> LENGTH: 372
<212> TYPE: PRT
<213> ORGANISM: Artificial Sequence
<220> FEATURE:
<223> OTHER INFORMATION: C15-CAR (amino acid)

<400> SEQUENCE: 51

Met Ala Leu Pro Val Thr Ala Leu Leu Leu Pro Leu Ala Leu Leu Leu
1 5 10 15

His Ala Ala Arg Pro Gln Val Gln Leu Val Glu Ser Gly Gly Gly Val
20 25 30

Val Gln Pro Gly Gly Ser Leu Arg Leu Ser Cys Ala Ala Ser Ser Asn
35 40 45

Ile Phe Arg Ala Tyr Gly Met Asp Trp Tyr Arg Gln Ala Pro Gly Lys
50 55 60

Gln Arg Glu Met Val Ala Thr Ile Trp Leu Ser Gly Arg Ser Thr Tyr
65 70 75 80

Thr Asp Ala Val Gln Gly Arg Phe Thr Ile Ser Arg Asp Asn Ala Lys
85 90 95

Asn Thr Val Tyr Leu Gln Met Asn Asn Leu Lys Pro Glu Asp Thr Ala
100 105 110

Val Tyr Tyr Cys Asn Ala Gly Pro Thr Thr Ala Ser Ser Val Arg Gln
115 120 125

Tyr Trp Gly Gln Gly Thr Gln Val Thr Val Ser Ser Glu Pro Lys Thr
130 135 140

Pro Lys Pro Thr Ser Thr Thr Thr Pro Ala Pro Arg Pro Pro Thr Pro
145 150 155 160

Ala Pro Thr Ile Ala Ser Gln Pro Leu Ser Leu Arg Pro Glu Ala Cys
165 170 175

Arg Pro Ala Ala Gly Gly Ala Val His Thr Arg Gly Leu Asp Phe Ala
180 185 190

Cys Asp Ile Tyr Ile Trp Ala Pro Leu Ala Gly Thr Cys Gly Val Leu
195 200 205

Leu Leu Ser Leu Val Ile Thr Leu Tyr Cys Lys Arg Gly Arg Lys Lys
210 215 220

Leu Leu Tyr Ile Phe Lys Gln Pro Phe Met Arg Pro Val Gln Thr Thr
225 230 235 240

Gln Glu Glu Asp Gly Cys Ser Cys Arg Phe Pro Glu Glu Glu Glu Gly
245 250 255

Gly Cys Glu Leu Arg Val Lys Phe Ser Arg Ser Ala Asp Ala Pro Ala
260 265 270

Tyr Gln Gln Gly Gln Asn Gln Leu Tyr Asn Glu Leu Asn Leu Gly Arg
275 280 285

Arg Glu Glu Tyr Asp Val Leu Asp Lys Arg Arg Gly Arg Asp Pro Glu
290 295 300

Met Gly Gly Lys Pro Arg Arg Lys Asn Pro Gln Glu Gly Leu Tyr Asn
305 310 315 320

Glu Leu Gln Lys Asp Lys Met Ala Glu Ala Tyr Ser Glu Ile Gly Met
325 330 335

Lys Gly Glu Arg Arg Arg Gly Lys Gly His Asp Gly Leu Tyr Gln Gly
340 345 350

Leu Ser Thr Ala Thr Lys Asp Thr Tyr Asp Ala Leu His Met Gln Ala
355 360 365

Leu Pro Pro Arg
370

<210> SEQ ID NO 52
<211> LENGTH: 372
<212> TYPE: PRT
<213> ORGANISM: Artificial Sequence
<220> FEATURE:
<223> OTHER INFORMATION: C21-CAR (amino acid)

<400> SEQUENCE: 52

Met Ala Leu Pro Val Thr Ala Leu Leu Leu Pro Leu Ala Leu Leu Leu
1 5 10 15

His Ala Ala Arg Pro Gln Val Gln Leu Val Glu Ser Gly Gly Gly Leu
20 25 30

Val Gln Pro Gly Gly Ser Leu Arg Leu Ser Cys Thr Ser Ser Ser Asn
35 40 45

-continued

Ile Phe Arg Ile Tyr Gly Met Asp Trp Tyr Arg Gln Ala Pro Gly Lys
50 55 60

Gln Arg Glu Ile Val Ala Thr Ile Tyr Leu Ser Gly Arg Thr Thr Tyr
65 70 75 80

Ser Asp Ala Val Lys Gly Arg Phe Thr Ile Ser Arg Asp Asn Ala Lys
85 90 95

Asp Thr Val Tyr Leu Gln Met Asn Ser Leu Lys Pro Glu Asp Thr Ala
100 105 110

Val Tyr Tyr Cys Asn Ala Gly Glu Pro Thr Ala Ser Ser Val Arg Gln
115 120 125

Tyr Trp Gly Gln Gly Thr Gln Val Thr Val Ser Ser Glu Pro Lys Thr
130 135 140

Pro Lys Pro Thr Ser Thr Thr Thr Pro Ala Pro Arg Pro Pro Thr Pro
145 150 155 160

Ala Pro Thr Ile Ala Ser Gln Pro Leu Ser Leu Arg Pro Glu Ala Cys
165 170 175

Arg Pro Ala Ala Gly Gly Ala Val His Thr Arg Gly Leu Asp Phe Ala
180 185 190

Cys Asp Ile Tyr Ile Trp Ala Pro Leu Ala Gly Thr Cys Gly Val Leu
195 200 205

Leu Leu Ser Leu Val Ile Thr Leu Tyr Cys Lys Arg Gly Arg Lys Lys
210 215 220

Leu Leu Tyr Ile Phe Lys Gln Pro Phe Met Arg Pro Val Gln Thr Thr
225 230 235 240

Gln Glu Glu Asp Gly Cys Ser Cys Arg Phe Pro Glu Glu Glu Glu Gly
245 250 255

Gly Cys Glu Leu Arg Val Lys Phe Ser Arg Ser Ala Asp Ala Pro Ala
260 265 270

Tyr Gln Gln Gly Gln Asn Gln Leu Tyr Asn Glu Leu Asn Leu Gly Arg
275 280 285

Arg Glu Glu Tyr Asp Val Leu Asp Lys Arg Arg Gly Arg Asp Pro Glu
290 295 300

Met Gly Gly Lys Pro Arg Arg Lys Asn Pro Gln Glu Gly Leu Tyr Asn
305 310 315 320

Glu Leu Gln Lys Asp Lys Met Ala Glu Ala Tyr Ser Glu Ile Gly Met
325 330 335

Lys Gly Glu Arg Arg Arg Gly Lys Gly His Asp Gly Leu Tyr Gln Gly
340 345 350

Leu Ser Thr Ala Thr Lys Asp Thr Tyr Asp Ala Leu His Met Gln Ala
355 360 365

Leu Pro Pro Arg
370

<210> SEQ ID NO 53
<211> LENGTH: 372
<212> TYPE: PRT
<213> ORGANISM: Artificial Sequence
<220> FEATURE:
<223> OTHER INFORMATION: C27-CAR (amino acid)

<400> SEQUENCE: 53

Met Ala Leu Pro Val Thr Ala Leu Leu Leu Pro Leu Ala Leu Leu Leu
1 5 10 15

His Ala Ala Arg Pro Glu Val Gln Leu Val Glu Ser Gly Gly Gly Leu
20 25 30

Val Gln Pro Gly Gly Ser Leu Arg Leu Ser Cys Thr Ser Ser Ser Asn
35 40 45

Ile Phe Lys Ile Tyr Gly Met Asp Trp Tyr Arg Gln Ala Pro Gly Lys
50 55 60

Gln Arg Glu Ile Val Ala Thr Ile Tyr Leu Ser Gly Arg Thr Thr Tyr
65 70 75 80

Ser Asp Ala Val Lys Gly Arg Phe Thr Ile Ser Arg Asp Asn Ala Lys
85 90 95

Asn Thr Val Tyr Leu Gln Met Asn Thr Leu Lys Pro Glu Asp Thr Ala
100 105 110

Val Tyr Tyr Cys Asn Ala Gly Glu Thr Thr Ala Ser Ser Val Arg Gln
115 120 125

Tyr Trp Gly Gln Gly Thr Gln Val Thr Val Ser Ser Glu Pro Lys Thr
130 135 140

Pro Lys Pro Thr Ser Thr Thr Thr Pro Ala Pro Arg Pro Pro Thr Pro
145 150 155 160

Ala Pro Thr Ile Ala Ser Gln Pro Leu Ser Leu Arg Pro Glu Ala Cys
165 170 175

Arg Pro Ala Ala Gly Gly Ala Val His Thr Arg Gly Leu Asp Phe Ala
180 185 190

Cys Asp Ile Tyr Ile Trp Ala Pro Leu Ala Gly Thr Cys Gly Val Leu
195 200 205

Leu Leu Ser Leu Val Ile Thr Leu Tyr Cys Lys Arg Gly Arg Lys Lys
210 215 220

Leu Leu Tyr Ile Phe Lys Gln Pro Phe Met Arg Pro Val Gln Thr Thr
225 230 235 240

Gln Glu Glu Asp Gly Cys Ser Cys Arg Phe Pro Glu Glu Glu Glu Gly
245 250 255

Gly Cys Glu Leu Arg Val Lys Phe Ser Arg Ser Ala Asp Ala Pro Ala
260 265 270

Tyr Gln Gln Gly Gln Asn Gln Leu Tyr Asn Glu Leu Asn Leu Gly Arg
275 280 285

Arg Glu Glu Tyr Asp Val Leu Asp Lys Arg Arg Gly Arg Asp Pro Glu
290 295 300

Met Gly Gly Lys Pro Arg Arg Lys Asn Pro Gln Glu Gly Leu Tyr Asn
305 310 315 320

Glu Leu Gln Lys Asp Lys Met Ala Glu Ala Tyr Ser Glu Ile Gly Met
325 330 335

Lys Gly Glu Arg Arg Arg Gly Lys Gly His Asp Gly Leu Tyr Gln Gly
340 345 350

Leu Ser Thr Ala Thr Lys Asp Thr Tyr Asp Ala Leu His Met Gln Ala
355 360 365

Leu Pro Pro Arg
370

<210> SEQ ID NO 54
<211> LENGTH: 372
<212> TYPE: PRT
<213> ORGANISM: Artificial Sequence
<220> FEATURE:
<223> OTHER INFORMATION: C30-CAR (amino acid)

<400> SEQUENCE: 54

Met Ala Leu Pro Val Thr Ala Leu Leu Leu Pro Leu Ala Leu Leu Leu
1 5 10 15

```
His Ala Ala Arg Pro Gln Val Gln Leu Val Glu Ser Gly Gly Gly Leu
            20                  25                  30

Val Gln Pro Gly Gly Ser Leu Arg Leu Ser Cys Ala Ala Ser Gly Ser
        35                  40                  45

Ile Phe Arg Val Tyr Gly Met Asp Trp Tyr Arg Gln Ala Pro Gly Lys
    50                  55                  60

Gln Arg Glu Leu Val Ala Ser Ile Phe Leu Ser Gly Arg Thr Asn Tyr
65                  70                  75                  80

Ala Asp Ala Val Lys Gly Arg Phe Thr Leu Ser Arg Asp Asn Ala Lys
                85                  90                  95

Asn Thr Met Tyr Leu Gln Met Asn Ser Leu Lys Pro Glu Asp Thr Ala
            100                 105                 110

Val Tyr Tyr Cys Asn Ala Gly Glu Thr Thr Ala Ser Ser Val Arg Gln
        115                 120                 125

Tyr Trp Gly Gln Gly Thr Gln Val Thr Val Ser Ser Glu Pro Lys Thr
    130                 135                 140

Pro Lys Pro Thr Ser Thr Thr Thr Pro Ala Pro Arg Pro Pro Thr Pro
145                 150                 155                 160

Ala Pro Thr Ile Ala Ser Gln Pro Leu Ser Leu Arg Pro Glu Ala Cys
                165                 170                 175

Arg Pro Ala Ala Gly Gly Ala Val His Thr Arg Gly Leu Asp Phe Ala
            180                 185                 190

Cys Asp Ile Tyr Ile Trp Ala Pro Leu Ala Gly Thr Cys Gly Val Leu
        195                 200                 205

Leu Leu Ser Leu Val Ile Thr Leu Tyr Cys Lys Arg Gly Arg Lys Lys
    210                 215                 220

Leu Leu Tyr Ile Phe Lys Gln Pro Phe Met Arg Pro Val Gln Thr Thr
225                 230                 235                 240

Gln Glu Glu Asp Gly Cys Ser Cys Arg Phe Pro Glu Glu Glu Glu Gly
                245                 250                 255

Gly Cys Glu Leu Arg Val Lys Phe Ser Arg Ser Ala Asp Ala Pro Ala
            260                 265                 270

Tyr Gln Gln Gly Gln Asn Gln Leu Tyr Asn Glu Leu Asn Leu Gly Arg
        275                 280                 285

Arg Glu Glu Tyr Asp Val Leu Asp Lys Arg Arg Gly Arg Asp Pro Glu
    290                 295                 300

Met Gly Gly Lys Pro Arg Arg Lys Asn Pro Gln Glu Gly Leu Tyr Asn
305                 310                 315                 320

Glu Leu Gln Lys Asp Lys Met Ala Glu Ala Tyr Ser Glu Ile Gly Met
                325                 330                 335

Lys Gly Glu Arg Arg Arg Gly Lys Gly His Asp Gly Leu Tyr Gln Gly
            340                 345                 350

Leu Ser Thr Ala Thr Lys Asp Thr Tyr Asp Ala Leu His Met Gln Ala
        355                 360                 365

Leu Pro Pro Arg
    370
```

<210> SEQ ID NO 55
<211> LENGTH: 372
<212> TYPE: PRT
<213> ORGANISM: Artificial Sequence
<220> FEATURE:
<223> OTHER INFORMATION: C31-CAR (amino acid)

<400> SEQUENCE: 55

```
Met Ala Leu Pro Val Thr Ala Leu Leu Leu Pro Leu Ala Leu Leu Leu
1               5                   10                  15

His Ala Ala Arg Pro Ala Val Gln Leu Val Glu Ser Gly Gly Gly Leu
            20                  25                  30

Val Gln Pro Gly Gly Ser Leu Arg Leu Ser Cys Ala Ala Ser Gly Ser
        35                  40                  45

Ile Phe Arg Val Tyr Gly Met Asp Trp Tyr Arg Gln Ala Pro Gly Lys
    50                  55                  60

Gln Arg Glu Leu Val Ala Ser Ile Trp Leu Ser Gly Arg Thr Asn Tyr
65                  70                  75                  80

Ala Asp Ala Val Lys Gly Arg Phe Thr Leu Ser Arg Asp Asn Ala Lys
                85                  90                  95

Asn Thr Met Tyr Leu Gln Met Asn Ser Leu Lys Pro Glu Asp Thr Ala
            100                 105                 110

Val Tyr Tyr Cys Asn Ala Gly Glu Thr Thr Ala Ser Ser Val Arg Gln
        115                 120                 125

Tyr Trp Gly Gln Gly Thr Gln Val Thr Ile Ser Ser Glu Pro Lys Thr
    130                 135                 140

Pro Lys Pro Thr Ser Thr Thr Thr Pro Ala Pro Arg Pro Pro Thr Pro
145                 150                 155                 160

Ala Pro Thr Ile Ala Ser Gln Pro Leu Ser Leu Arg Pro Glu Ala Cys
                165                 170                 175

Arg Pro Ala Ala Gly Gly Ala Val His Thr Arg Gly Leu Asp Phe Ala
            180                 185                 190

Cys Asp Ile Tyr Ile Trp Ala Pro Leu Ala Gly Thr Cys Gly Val Leu
        195                 200                 205

Leu Leu Ser Leu Val Ile Thr Leu Tyr Cys Lys Arg Gly Arg Lys Lys
    210                 215                 220

Leu Leu Tyr Ile Phe Lys Gln Pro Phe Met Arg Pro Val Gln Thr Thr
225                 230                 235                 240

Gln Glu Glu Asp Gly Cys Ser Cys Arg Phe Pro Glu Glu Glu Glu Gly
                245                 250                 255

Gly Cys Glu Leu Arg Val Lys Phe Ser Arg Ser Ala Asp Ala Pro Ala
            260                 265                 270

Tyr Gln Gln Gly Gln Asn Gln Leu Tyr Asn Glu Leu Asn Leu Gly Arg
        275                 280                 285

Arg Glu Glu Tyr Asp Val Leu Asp Lys Arg Arg Gly Arg Asp Pro Glu
    290                 295                 300

Met Gly Gly Lys Pro Arg Arg Lys Asn Pro Gln Glu Gly Leu Tyr Asn
305                 310                 315                 320

Glu Leu Gln Lys Asp Lys Met Ala Glu Ala Tyr Ser Glu Ile Gly Met
                325                 330                 335

Lys Gly Glu Arg Arg Arg Gly Lys Gly His Asp Gly Leu Tyr Gln Gly
            340                 345                 350

Leu Ser Thr Ala Thr Lys Asp Thr Tyr Asp Ala Leu His Met Gln Ala
        355                 360                 365

Leu Pro Pro Arg
    370
```

<210> SEQ ID NO 56
<211> LENGTH: 1119
<212> TYPE: DNA
<213> ORGANISM: Artificial Sequence
<220> FEATURE:
<223> OTHER INFORMATION: C08-CAR (nucleic acid)

<400> SEQUENCE: 56

```
atggccttac cagtgaccgc cttgctcctg ccgctggcct tgctgctcca cgccgccagg     60
ccggaggtgc agctggtgga gtctggggga ggtttggtgc aacctggggg gtctctgaga    120
ctctcctgtg cagcctcttc aaacatcttc agagcctatg gcatggggtg gtaccgccag    180
gctccaggga agcagcgcga aatggtcgcg gctatttggc tcagtggtcg cacagagtat    240
gctgacgccg tgcagggccg attcaccgtc tccagagaca acgccaagaa cacggtgtat    300
ctgcaaatga acagcctgaa acctgaggac acggccgtct attactgtaa tgcaggtccc    360
cctacagcaa cttccgtccg tcaatactgg ggccagggga cccaggtcac cgtctcctca    420
gaacccaaga caccaaaacc aactagtacc acgacgccag cgccgcgacc accaacaccg    480
gcgcccacca tcgcgtcgca gcccctgtcc ctgcgcccag aggcgtgccg gccagcggcg    540
gggggcgcag tgcacacgag ggggctggac ttcgcctgtg atatctacat ctgggcgccc    600
ttggccggga cttgtggggt ccttctcctg tcactggtta tcacccttta ctgcaaacgg    660
ggcagaaaga aactcctgta tatattcaaa caaccattta tgagaccagt acaaactact    720
caagaggaag atggctgtag ctgccgattt ccagaagaag aagaaggagg atgtgaactg    780
agagtgaagt tcagcaggag cgcagacgcc cccgcgtacc agcagggcca gaaccagctc    840
tataacgagc tcaatctagg acgaagagag gagtacgatg ttttggacaa gagacgtggc    900
cgggaccctg agatgggggg aaagccgaga aggaagaacc ctcaagaagg cctgtacaat    960
gaactgcaga aagataagat ggcggaggcc tacagtgaga ttgggatgaa aggcgagcgc   1020
cggaggggca aggggcacga tggcctttac cagggtctca gtacagccac caaggacacc   1080
tacgacgccc ttcacatgca ggccctgccc cctcgctaa                          1119
```

<210> SEQ ID NO 57
<211> LENGTH: 1119
<212> TYPE: DNA
<213> ORGANISM: Artificial Sequence
<220> FEATURE:
<223> OTHER INFORMATION: C12-CAR (nucleic acid)

<400> SEQUENCE: 57

```
atggccttac cagtgaccgc cttgctcctg ccgctggcct tgctgctcca cgccgccagg     60
ccgcaggtac agctggtgga gtctggggga ggtttggtgc aacctggggg gtctctgaga    120
ctctcctgtg cagcctcttc aaacatcttc agagcctatg gcatggattg gtaccgccag    180
gctccaggaa agcagcgcga aatggtcgcg actatctggc tgagtggtcg ctcaacgtat    240
actgacgccg tgaagggccg attcaccatc tccagagaca acgccaagaa cacggtgtat    300
ctgcaaatga acaacctgaa acctgaggac acggccgtct attactgtaa tgcaggtccc    360
actacggcaa gttccgtccg tcaatactgg ggccagggga cccaggtcac cgtctcctca    420
gaacccaaga caccaaaacc aactagtacc acgacgccag cgccgcgacc accaacaccg    480
gcgcccacca tcgcgtcgca gcccctgtcc ctgcgcccag aggcgtgccg gccagcggcg    540
gggggcgcag tgcacacgag ggggctggac ttcgcctgtg atatctacat ctgggcgccc    600
ttggccggga cttgtggggt ccttctcctg tcactggtta tcacccttta ctgcaaacgg    660
ggcagaaaga aactcctgta tatattcaaa caaccattta tgagaccagt acaaactact    720
caagaggaag atggctgtag ctgccgattt ccagaagaag aagaaggagg atgtgaactg    780
agagtgaagt tcagcaggag cgcagacgcc cccgcgtacc agcagggcca gaaccagctc    840
```

```
tataacgagc tcaatctagg acgaagagag gagtacgatg ttttggacaa gagacgtggc    900

cgggaccctg agatgggggg aaagccgaga aggaagaacc ctcaagaagg cctgtacaat    960

gaactgcaga aagataagat ggcggaggcc tacagtgaga ttgggatgaa aggcgagcgc   1020

cggaggggca aggggcacga tggcctttac cagggtctca gtacagccac caaggacacc   1080

tacgacgccc ttcacatgca ggccctgccc cctcgctaa                          1119
```

```
<210> SEQ ID NO 58
<211> LENGTH: 1119
<212> TYPE: DNA
<213> ORGANISM: Artificial Sequence
<220> FEATURE:
<223> OTHER INFORMATION: C13-CAR (nucleic acid)

<400> SEQUENCE: 58

atggccttac cagtgaccgc cttgctcctg ccgctggcct tgctgctcca cgccgccagg     60

ccgcaggtgc agctggtgga gtctggggga ggtttggtgc aacctggggg gtctctgaga    120

ctctcctgtg cagcctcttc aaacatcttc agagcctatg gcatggactg gtaccgccag    180

gctccaggga agcagcgcga aatggtcgcg actatctggc ttagtggtcg cacaacgtat    240

actgacgccg tgaagggccg attcaccatc tccagagaca acgccaagaa cacggtgtat    300

ctgcaaatga acagcctgaa acctgaggac acggccgtct attactgtaa tgcaggtgcc    360

cctacggcaa gttccggccg tcaatactgg ggccagggga cccaggtcac cgtctcctca    420

gaacccaaga caccaaaacc aactagtacc acgacgccag cgccgcgacc accaacaccg    480

gcgcccacca tcgcgtcgca gcccctgtcc ctgcgcccag aggcgtgccg gccagcggcg    540

gggggcgcag tgcacacgag ggggctggac ttcgcctgtg atatctacat ctgggcgccc    600

ttggccggga cttgtggggt ccttctcctg tcactggtta tcacccttta ctgcaaacgg    660

ggcagaaaga aactcctgta tatattcaaa caaccattta tgagaccagt acaaactact    720

caagaggaag atggctgtag ctgccgattt ccagaagaag aagaaggagg atgtgaactg    780

agagtgaagt tcagcaggag cgcagacgcc cccgcgtacc agcagggcca gaaccagctc    840

tataacgagc tcaatctagg acgaagagag gagtacgatg ttttggacaa gagacgtggc    900

cgggaccctg agatgggggg aaagccgaga aggaagaacc ctcaagaagg cctgtacaat    960

gaactgcaga aagataagat ggcggaggcc tacagtgaga ttgggatgaa aggcgagcgc   1020

cggaggggca aggggcacga tggcctttac cagggtctca gtacagccac caaggacacc   1080

tacgacgccc ttcacatgca ggccctgccc cctcgctaa                          1119
```

```
<210> SEQ ID NO 59
<211> LENGTH: 1119
<212> TYPE: DNA
<213> ORGANISM: Artificial Sequence
<220> FEATURE:
<223> OTHER INFORMATION: C15-CAR (nucleic acid)

<400> SEQUENCE: 59

atggccttac cagtgaccgc cttgctcctg ccgctggcct tgctgctcca cgccgccagg     60

ccgcaggtgc agctggtgga gtctggggga ggggtggtgc aacctggggg gtctctgaga    120

ctctcctgtg cagcctcttc aaatatcttt agagcctatg gcatggattg gtaccgccag    180

gctccaggaa agcagcgcga aatggtcgcg actatctggc tgagtggtcg ctcaacgtat    240

actgacgccg tacagggccg attcaccatc tccagagaca acgccaagaa cacggtgtat    300

ctgcaaatga acaacctgaa acctgaggac acggccgtct attactgtaa tgcaggtccc    360
```

```
actacggcaa gttccgtccg tcaatactgg ggccagggga cccaggtcac cgtctcctca    420

gaacccaaga caccaaaacc aactagtacc acgacgccag cgccgcgacc accaacaccg    480

gcgcccacca tcgcgtcgca gcccctgtcc ctgcgcccag aggcgtgccg gccagcggcg    540

gggggcgcag tgcacacgag ggggctggac ttcgcctgtg atatctacat ctgggcgccc    600

ttggccggga cttgtggggt ccttctcctg tcactggtta tcacccttta ctgcaaacgg    660

ggcagaaaga aactcctgta tatattcaaa caaccattta tgagaccagt acaaactact    720

caagaggaag atggctgtag ctgccgattt ccagaagaag aagaaggagg atgtgaactg    780

agagtgaagt tcagcaggag cgcagacgcc cccgcgtacc agcagggcca gaaccagctc    840

tataacgagc tcaatctagg acgaagagag gagtacgatg ttttggacaa gagacgtggc    900

cgggaccctg agatgggggg aaagccgaga aggaagaacc ctcaagaagg cctgtacaat    960

gaactgcaga aagataagat ggcggaggcc tacagtgaga ttgggatgaa aggcgagcgc   1020

cggaggggca aggggcacga tggcctttac cagggtctca gtacagccac caaggacacc   1080

tacgacgccc ttcacatgca ggccctgccc cctcgctaa                           1119
```

<210> SEQ ID NO 60
<211> LENGTH: 1119
<212> TYPE: DNA
<213> ORGANISM: Artificial Sequence
<220> FEATURE:
<223> OTHER INFORMATION: C21-CAR (nucleic acid)

<400> SEQUENCE: 60

```
atggccttac cagtgaccgc cttgctcctg ccgctggcct tgctgctcca cgccgccagg     60

ccgcaggtac agctggtgga gtctggggga ggtttggtgc aacctggggg gtctctgaga    120

ctctcctgta caagctcttc aaacatcttc agaatctatg gcatggactg gtaccgccag    180

gctccaggga agcagcgcga aatagtcgcg actatctatc ttagtggtcg cacaacgtat    240

agtgacgccg tgaagggccg attcaccatc tccagagaca acgccaagga cacggtgtat    300

ctgcaaatga acagcctgaa acctgaggac acggccgtct attactgtaa tgcaggtgaa    360

cctacggcaa gttccgtccg tcagtactgg ggccagggga cccaggtcac cgtctcctca    420

gaacccaaga caccaaaacc aactagtacc acgacgccag cgccgcgacc accaacaccg    480

gcgcccacca tcgcgtcgca gcccctgtcc ctgcgcccag aggcgtgccg gccagcggcg    540

gggggcgcag tgcacacgag ggggctggac ttcgcctgtg atatctacat ctgggcgccc    600

ttggccggga cttgtggggt ccttctcctg tcactggtta tcacccttta ctgcaaacgg    660

ggcagaaaga aactcctgta tatattcaaa caaccattta tgagaccagt acaaactact    720

caagaggaag atggctgtag ctgccgattt ccagaagaag aagaaggagg atgtgaactg    780

agagtgaagt tcagcaggag cgcagacgcc cccgcgtacc agcagggcca gaaccagctc    840

tataacgagc tcaatctagg acgaagagag gagtacgatg ttttggacaa gagacgtggc    900

cgggaccctg agatgggggg aaagccgaga aggaagaacc ctcaagaagg cctgtacaat    960

gaactgcaga aagataagat ggcggaggcc tacagtgaga ttgggatgaa aggcgagcgc   1020

cggaggggca aggggcacga tggcctttac cagggtctca gtacagccac caaggacacc   1080

tacgacgccc ttcacatgca ggccctgccc cctcgctaa                           1119
```

<210> SEQ ID NO 61
<211> LENGTH: 1119
<212> TYPE: DNA

<213> ORGANISM: Artificial Sequence
<220> FEATURE:
<223> OTHER INFORMATION: C27-CAR (nucleic acid)

<400> SEQUENCE: 61

```
atggccttac cagtgaccgc cttgctcctg ccgctggcct tgctgctcca cgccgccagg     60

ccggaggtgc agctggtgga gtctggggga ggtttggtgc aacctggggg gtctctgaga    120

ctctcctgta caagctcttc aaacatcttc aaaatctatg gcatggactg gtaccgccag    180

gctccaggga aacagcgcga aatagtcgcg actatctatc ttagtggtcg cacaacgtat    240

agtgacgccg tgaagggccg attcaccatc tccagagaca acgccaagaa cacggtgtat    300

ctgcaaatga acaccctgaa acctgaggac acggccgtct attactgtaa tgcaggtgaa    360

actacggcaa gttccgtccg tcaatactgg ggccagggga cccaggtcac cgtctcctca    420

gaacccaaga caccaaaacc aactagtacc acgacgccag cgccgcgacc accaacaccg    480

gcgcccacca tcgcgtcgca gcccctgtcc ctgcgcccag aggcgtgccg gccagcggcg    540

gggggcgcag tgcacacgag ggggctggac ttcgcctgtg atatctacat ctgggcgccc    600

ttggccggga cttgtggggt ccttctcctg tcactggtta tcacccttta ctgcaaacgg    660

ggcagaaaga aactcctgta tatattcaaa caaccattta tgagaccagt acaaactact    720

caagaggaag atggctgtag ctgccgattt ccagaagaag aagaaggagg atgtgaactg    780

agagtgaagt tcagcaggag cgcagacgcc cccgcgtacc agcagggcca gaaccagctc    840

tataacgagc tcaatctagg acgaagagag gagtacgatg ttttggacaa gagacgtggc    900

cgggaccctg agatgggggg aaagccgaga aggaagaacc ctcaagaagg cctgtacaat    960

gaactgcaga aagataagat ggcggaggcc tacagtgaga ttgggatgaa aggcgagcgc   1020

cggaggggca aggggcacga tggcctttac cagggtctca gtacagccac caaggacacc   1080

tacgacgccc ttcacatgca ggccctgccc cctcgctaa                          1119
```

<210> SEQ ID NO 62
<211> LENGTH: 1119
<212> TYPE: DNA
<213> ORGANISM: Artificial Sequence
<220> FEATURE:
<223> OTHER INFORMATION: C30-CAR (nucleic acid)

<400> SEQUENCE: 62

```
atggccttac cagtgaccgc cttgctcctg ccgctggcct tgctgctcca cgccgccagg     60

ccgcaggtgc agctggtgga gtctggggga ggcttggtgc agcctggggg gtctctgaga    120

ctctcctgtg cagcctctgg aagcatcttc agagtctatg gcatggactg gtaccgccag    180

gctccaggga agcagcgcga gttggtcgcg tctatttttc ttagtggtag gacaaactat    240

gcagacgccg tgaagggccg attcacgctc tccagagata acgccaagaa tactatgtat    300

ctgcaaatga acagcctgaa acctgaggac acggccgtct attattgtaa tgcaggtgaa    360

actacggcaa gttccgtccg tcaatactgg ggccagggga cccaggtcac cgtctcctca    420

gaacccaaga caccaaaacc aactagtacc acgacgccag cgccgcgacc accaacaccg    480

gcgcccacca tcgcgtcgca gcccctgtcc ctgcgcccag aggcgtgccg gccagcggcg    540

gggggcgcag tgcacacgag ggggctggac ttcgcctgtg atatctacat ctgggcgccc    600

ttggccggga cttgtggggt ccttctcctg tcactggtta tcacccttta ctgcaaacgg    660

ggcagaaaga aactcctgta tatattcaaa caaccattta tgagaccagt acaaactact    720

caagaggaag atggctgtag ctgccgattt ccagaagaag aagaaggagg atgtgaactg    780
```

agagtgaagt tcagcaggag cgcagacgcc cccgcgtacc agcagggcca gaaccagctc 840
tataacgagc tcaatctagg acgaagagag gagtacgatg ttttggacaa gagacgtggc 900
cgggaccctg agatgggggg aaagccgaga aggaagaacc ctcaagaagg cctgtacaat 960
gaactgcaga aagataagat ggcggaggcc tacagtgaga ttgggatgaa aggcgagcgc 1020
cggaggggca aggggcacga tggcctttac cagggtctca gtacagccac caaggacacc 1080
tacgacgccc ttcacatgca ggccctgccc cctcgctaa 1119

<210> SEQ ID NO 63
<211> LENGTH: 1119
<212> TYPE: DNA
<213> ORGANISM: Artificial Sequence
<220> FEATURE:
<223> OTHER INFORMATION: C31-CAR (nucleic acid)

<400> SEQUENCE: 63
atggccttac cagtgaccgc cttgctcctg ccgctggcct tgctgctcca cgccgccagg 60
ccggcggtgc agctggtgga gtctggggga ggcttggtgc agcctggggg gtctctgaga 120
ctctcctgtg cagcctctgg aagcatcttc agagtctatg gcatggactg gtaccgccag 180
gctccaggga agcagcgcga gttggtcgcg tctatttggc ttagtggtag gacaaactat 240
gcagacgccg tgaagggccg attcacgctc tccagagata acgccaagaa tacgatgtat 300
ctgcaaatga acagcctgaa acctgaggac acggccgtct attattgtaa tgcaggtgaa 360
actacggcaa gttccgtccg tcaatactgg ggccagggga cccaggtcac catctcctcg 420
gaacccaaga caccaaaacc aactagtacc acgacgccag cgccgcgacc accaacaccg 480
gcgcccacca tcgcgtcgca gcccctgtcc ctgcgcccag aggcgtgccg gccagcggcg 540
gggggcgcag tgcacacgag ggggctggac ttcgcctgtg atatctacat ctgggcgccc 600
ttggccggga cttgtggggt ccttctcctg tcactggtta tcacccttta ctgcaaacgg 660
ggcagaaaga aactcctgta tatattcaaa caaccattta tgagaccagt acaaactact 720
caagaggaag atggctgtag ctgccgattt ccagaagaag aagaaggagg atgtgaactg 780
agagtgaagt tcagcaggag cgcagacgcc cccgcgtacc agcagggcca gaaccagctc 840
tataacgagc tcaatctagg acgaagagag gagtacgatg ttttggacaa gagacgtggc 900
cgggaccctg agatgggggg aaagccgaga aggaagaacc ctcaagaagg cctgtacaat 960
gaactgcaga aagataagat ggcggaggcc tacagtgaga ttgggatgaa aggcgagcgc 1020
cggaggggca aggggcacga tggcctttac cagggtctca gtacagccac caaggacacc 1080
tacgacgccc ttcacatgca ggccctgccc cctcgctaa 1119

<210> SEQ ID NO 64
<211> LENGTH: 5
<212> TYPE: PRT
<213> ORGANISM: Artificial Sequence
<220> FEATURE:
<223> OTHER INFORMATION: anti-GUCY2C single domain antibody (sdAb) -
CDR1
<220> FEATURE:
<221> NAME/KEY: VARIANT
<222> LOCATION: (1)..(1)
<223> OTHER INFORMATION: X is A, I or V
<220> FEATURE:
<221> NAME/KEY: VARIANT
<222> LOCATION: (5)..(5)
<223> OTHER INFORMATION: X is D or G

<400> SEQUENCE: 64

-continued

```
Xaa Tyr Gly Met Xaa
1               5


<210> SEQ ID NO 65
<211> LENGTH: 16
<212> TYPE: PRT
<213> ORGANISM: Artificial Sequence
<220> FEATURE:
<223> OTHER INFORMATION: anti-GUCY2C single domain antibody (sdAb) -
      CDR2
<220> FEATURE:
<221> NAME/KEY: VARIANT
<222> LOCATION: (1)..(1)
<223> OTHER INFORMATION: X is A, S or T
<220> FEATURE:
<221> NAME/KEY: VARIANT
<222> LOCATION: (3)..(3)
<223> OTHER INFORMATION: X is F, W or Y
<220> FEATURE:
<221> NAME/KEY: VARIANT
<222> LOCATION: (8)..(8)
<223> OTHER INFORMATION: X is S or T
<220> FEATURE:
<221> NAME/KEY: VARIANT
<222> LOCATION: (9)..(9)
<223> OTHER INFORMATION: X is E, N or T
<220> FEATURE:
<221> NAME/KEY: VARIANT
<222> LOCATION: (11)..(11)
<223> OTHER INFORMATION: X is A, S or T
<220> FEATURE:
<221> NAME/KEY: VARIANT
<222> LOCATION: (15)..(15)
<223> OTHER INFORMATION: X is K or Q

<400> SEQUENCE: 65

Xaa Ile Xaa Leu Ser Gly Arg Xaa Xaa Tyr Xaa Asp Ala Val Xaa Gly
1               5                   10                  15


<210> SEQ ID NO 66
<211> LENGTH: 11
<212> TYPE: PRT
<213> ORGANISM: Artificial Sequence
<220> FEATURE:
<223> OTHER INFORMATION: anti-GUCY2C single domain antibody (sdAb) -
      CDR3
<220> FEATURE:
<221> NAME/KEY: VARIANT
<222> LOCATION: (2)..(2)
<223> OTHER INFORMATION: X is A, E or P
<220> FEATURE:
<221> NAME/KEY: VARIANT
<222> LOCATION: (3)..(3)
<223> OTHER INFORMATION: X is P or T
<220> FEATURE:
<221> NAME/KEY: VARIANT
<222> LOCATION: (6)..(6)
<223> OTHER INFORMATION: X is S or T
<220> FEATURE:
<221> NAME/KEY: VARIANT
<222> LOCATION: (8)..(8)
<223> OTHER INFORMATION: X is G or V

<400> SEQUENCE: 66

Gly Xaa Xaa Thr Ala Xaa Ser Xaa Arg Gln Tyr
1               5                   10
```